US007671059B2

(12) United States Patent
Machajewski et al.

(10) Patent No.: US 7,671,059 B2
(45) Date of Patent: Mar. 2, 2010

(54) 2-AMINO-7,8-DIHYDRO-6H-PYRIDO[4,3-D] PYRIMIDIN-5-ONES

(75) Inventors: Timothy D. Machajewski, Emeryville, CA (US); Cynthia M. Shafer, Emeryville, CA (US); Christopher McBride, Emeryville, CA (US); William Antonios-McCrea, Emeryville, CA (US); Brandon M. Doughan, Emeryville, CA (US); Barry H. Levine, Emeryville, CA (US); Yi Xia, Emeryville, CA (US); Maureen McKenna, Emeryville, CA (US); X. Michael Wang, Emeryville, CA (US); Kris Mendenhall, Emeryville, CA (US); Yasheen Zhou, Emeryville, CA (US); Kristin Brinner, Emeryville, CA (US); Zhenhai Gao, Emeryville, CA (US); Daniel Poon, Emeryville, CA (US); Paul Barsanti, Emeryville, CA (US); Xiaodong Lin, Emeryville, CA (US); Abran Costales, Emeryville, CA (US); Alice Rico, Emeryville, CA (US); Nathan Brammeier, Emeryville, CA (US); Teresa Pick, Emeryville, CA (US); Paul A. Renhowe, Emeryville, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/541,462

(22) Filed: Sep. 28, 2006

(65) Prior Publication Data

US 2007/0123546 A1 May 31, 2007

Related U.S. Application Data

(60) Provisional application No. 60/722,796, filed on Sep. 30, 2005, provisional application No. 60/836,886, filed on Aug. 9, 2006.

(51) Int. Cl.
*A61K 31/519* (2006.01)
*A61K 31/5355* (2006.01)
*C07D 471/04* (2006.01)
*C07D 487/04* (2006.01)
*C07D 413/06* (2006.01)
*A61P 35/00* (2006.01)

(52) U.S. Cl. .............. 514/255.05; 544/279; 544/117; 514/234.2; 546/220; 546/209; 560/42; 548/204

(58) Field of Classification Search ............ 514/264.11, 514/233.2, 234.2, 255.05; 544/279, 117
See application file for complete search history.

(56) References Cited

U.S. PATENT DOCUMENTS 4,734,418 A 3/1988 Yokoyama et al.

2007/0027150 A1 2/2007 Machajewski et al.
2007/0135458 A1* 6/2007 Chen et al. ............. 514/264.11

FOREIGN PATENT DOCUMENTS

| EP | 0188094 A2 | 7/1986 |
| EP | 0192783 A1 | 9/1986 |
| EP | 0278742 A2 | 8/1988 |
| WO | WO 2005/105797 A1 | 11/2005 |
| WO | WO 2006/045096 A2 | 4/2006 |
| WO | WO 2006/045096 A3 | 4/2006 |
| WO | WO 2006/074293 A2 | 7/2006 |

OTHER PUBLICATIONS

Ujino, et al., Antiviral Research 74 (2007), A62-A63.*
Hu, et al., J. Virol, Dec. 2004, 13122-13131.*
Bagatell, et al., Mol. Cancer Ther., 2004, 3 (8), 1021-1030.*
Ashton, et al. Synthesis of 6-aryl-4-hydroxypiperidin-2-ones and a possible application to the synthesis of a novel HMG-CoA reductase inhibitor. *Heterocycles*, 28(2): 1015-1035 (1989).
Kumar, A. et al. Ketene dithioacetals. Part II. Reaction of 3-cyano-4-methylthio-2(1H)-pyridones with hydrazine and guanidine: synthesis of novel substituted and fused pyrazolo[4,3-c]pyridone and pyrido[4,3-d]pyrimidine derivatives. *Journal of the Chemical Society, Perkin Transactions 1: Organic and Bio-organic Chemistry* (8), 857-62 (1972-1999).
Donovan, et al. Constitutive MEK/MAPK Activation Leads to $p27^{Kip1}$ Deregulation and Antiestrogen Resistance in Human Breast Cancer Cells*. *J. Biol. Chem.* 276:40888, 2001.
Bull, et al. Asymmetric synthesis of β-haloaryl β-amino acid derivatives. *J. Chem. Soc., Perkin Trans. 1*, 2001, (23), 3112.
Carreras, et al. Filter binding assay for the geldanamycin-heat shock protein 90 interaction. *Anal Biochem* (2003) 317(1): 40-46.
Kim, et al. Development of a fluorescence polarization assay for the molecular chaperone HSP90. *J Biomol Screen* (2004) 9(5): 375-381.
Zhou, et al. A time-resolved fluorescence resonance energy transfer-based HTS assay and a surface plasmon resonance-based binding assay for heat shock protein 90 inhibitors. *Anal Biochem* (2004) 331(2): 349-357.
Beliakoff, et al. Hormone-refractory breast cancer remains sensitive to the antitumor activity of heat shock protein 90 inhibitors. *Clin Cancer Res*, (2003) 9, 4961-4971.

(Continued)

*Primary Examiner*—Mark L Berch
*Assistant Examiner*—Cecilia M Jaisle
(74) *Attorney, Agent, or Firm*—Vinit Kathardekar; Hugo Eng; Dennis Shelton

(57) ABSTRACT

Disclosed are 2-amino-7,8-dihydro-6H-pyrido[4,3-d]pyrimidin-5-one compounds, their stereoisomers, tautomers, pharmaceutically acceptable salts, and prodrugs thereof; compositions that include a pharmaceutically acceptable carrier and one or more of the 2-amino-7,8-dihydro-6H-pyrido[4,3-d]pyrimidin-5-one compounds, either alone or in combination with at least one additional therapeutic agent. Disclosed also are methods of using the 2-amino-7,8-dihydro-6H-pyrido[4,3-d]pyrimidin-5-one compounds, either alone or in combination with at least one additional therapeutic agent, in the prophylaxis or treatment of cellular proliferative, viral, autoimmune, cardiovascular, and central nervous system diseases.

26 Claims, No Drawings

OTHER PUBLICATIONS

Smith, et al ErbB2 overexpression in an ovarian cancer cell line confers sensitivity to the HSP90 inhibitor geldanamycin. *Anticancer Res*, (2002) 22, 1993-2000.

Solit, et al. 17-Allylamino-17-demethoxygeldanamycin induces the degradation of androgen receptor and HER-2/neu and inhibits the growth of prostate cancer xenografts. *Clin Cancer Res*, (2002) 8, 986-993.

Blagosklonny, et al. The Hsp90 inhibitor geldanamycin selectively sensitizes Bcr-Abl-expressing leukemia cells to cytotoxic chemotherapy. *Leukemia* , (2001) 15, 1537-1543.

Burger, et al. 17-(Allylamino)-17-demethoxygeldanamycin activity in human melanoma models. *Anticancer Drugs*, (2004) 15, 377-387.

Nakatani, et al. STI571 (Glivec) inhibits the interaction between c-KIT and heat shock protein 90 of the gastrointestinal stromal tumor cell line, GIST-T1. *Cancer Sci*, (2005) 96, 116-119.

Fumo, et al. 17-Allylamino-17-demethoxygeldanamycin (17-AAG) is effective in down-regulating mutated, constitutively activated KIT protein in human mast cells. *Blood*, (2004) 103, 1078-1084.

George, et al. Combination of the histone deacetylase inhibitor LBH589 and the hsp90 inhibitor 17-AAG is highly active against human CML-BC cells and AML cells with activating mutation of FLT-3. *Blood*, (2005) 105, 1768-1776.

George, et al. Cotreatment with 17-allylamino-demethoxygeldanamycin and FLT-3 kinase inhibitor PKC412 is highly effective against human acute myelogenous leukemia cells with mutant FLT-3. *Cancer Res*, (2004) 64, 3645-52.

Heideman, et al. Absence of tpr-met and expression of c-met in human gastric mucosa and carcinoma. *J Pathol*. (2001) 194(4):428-435.

Nguyen, et al. Enhancement of paclitaxel-mediated cytotoxicity in lung cancer cells by 17-allylamino geldanamycin: in vitro and in vivo analysis. *Ann Thorac Surg*, (2001) 72, 371-8; discussion 371-379.

Yin, et al. Potent activity of a novel dimeric heat shock protein 90 inhibitor against head and neck squamous cell carcinoma in vitro and in vivo. *Clin Cancer Res*, (2005) 11, 3889-3896.

Yang, et al. Disruption of the EF-2 kinase/Hsp90 protein complex: a possible mechanism to inhibit glioblastoma by geldanamycin. *Cancer Res*, (2001) 61, 4010-4016.

Chung, et al. Magnetic resonance spectroscopic pharmacodynamic markers of the heat shock protein 90 inhibitor 17-allylamino, 17-demethoxygeldanamycin (17AAG) in human colon cancer models. *J Natl Cancer Inst*. Nov. 5, 2003;95(21):1624-1633.

Park, et al. The heat shock protein 90-binding geldanamycin inhibits cancer cell proliferation, down-regulates oncoproteins, and inhibits epidermal growth factor-induced invasion in thyroid cancer cell lines. *J Clin Endocrinol Metab*. Jul. 2003;88(7):3346-3353.

Mitsiades, et al. Antimyeloma activity of heat shock protein-90 inhibition. *Blood* Feb. 1, 2006;107(3):1092-1100.

Isaacs, et al. Hsp90 regulates a von Hippel Lindau-independent hypoxia-inducible factor-1α-degradative pathway. *J Biol Chem*. Aug. 16, 2002;277(33):29936-29944.

Bonvini, et al. Nucleophosmin-anaplastic lymphoma kinase (NPM-ALK), a novel Hsp90-client tyrosine kinase: down-regulation of NPM-ALK expression and tyrosine phosphorylation in ALK(+) CD30(+) lymphoma cells by the Hsp90 antagonist 17-allylamino, 17-demethoxygeldanamycin. *Cancer Res*. Mar. 1, 2002;62(5):1559-66.

Georgakis, et al. Inhibition of heat shock protein 90 function by 17-allylamino-17-demethoxy-geldanamycin in Hodgkin's lymphoma cells down-regulates Akt kinase, dephosphorylates extracellular signal-regulated kinase, and induces cell cycle arrest and cell death. *Clin. Cancer Res*. Jan. 15, 2006;12(2):584-590.

Neckers, et al. Heat shock protein 90. *Current Opinion in Onclology* Jan. 15, 2003:419-424.

Bagatell, et al. Altered Hsp90 function in cancer: A unique therapeutic opportunity. *Molecular Cancer Therapeutics* 2004 3(8):1021-1030.

Machajewski, et al. AKT kinase and Hsp90 inhibitors as novel anticancer therapeutics. *Annual Reports in Medicinal Chemistry* 2005 40: 263-276.

Gao, et al. Beyond kinases for anticancer discovery: purine-binding enzymes and ATPases. *Annual Reports in Medicinal Chemistry* 2003 38: 194-202.

Davies et al. The conjugate addition of enantiomerically pure lithium amides as homochiral ammonia equivalents: scope, limitations and synthetic applications. Tetrahedron: Asymmetry 16 (2005) 2833-2891.

Staas et al. Asymmetric Synthesis of α,α-Difluoro-β-amino Acid Derivatives from Enantiomerically Pure *N-tert*-Butylsulfinimines. *J. Org. Chem*. 2002, 67, 8276-8279.

Tang et al. The *tert*-Butanesulfinyl Group: An Ideal Chiral Directing Group and Boc-Surrogate for the Asymmetric Synthesis and Applications of β-Amino Acids. *J. Org. Chem*. 1999, 64, 12-13.

Tang et al. Asymmetric Synthesis of β-Amino Acid Derivatives Incorporating a Broad Range of Substitution Patterns by Enolate Additions to *tert*-Butanesulfinyl Imines. *J. Org. Chem*. 2002, 67, 7819-7832.

* cited by examiner

2-AMINO-7,8-DIHYDRO-6H-PYRIDO[4,3-D]PYRIMIDIN-5-ONES

CROSS REFERENCE TO RELATED APPLICATIONS

This application claims the benefit under 35 U.S.C. 119(e) to provisional applications U.S. Ser. No. 60/722,796 filed on Sep. 30, 2005, and U.S. Ser. No. 60/836,886 filed on Aug. 9, 2006, each of which is incorporated herein by reference in its entirety.

FIELD OF THE INVENTION

The present invention relates to new 2-amino-7,8-dihydro-6H-pyrido[4,3-d]pyrimidin-5-one compounds, their stereoisomers, tautomers, pharmaceutically acceptable salts, and prodrugs thereof; compositions of the new compounds, either alone or in combination with at least one additional therapeutic agent, with a pharmaceutically acceptable carrier; and uses of the new compounds and compositions, either alone or in combination with at least one additional therapeutic agent, in the prophylaxis or treatment of cellular proliferative, viral, autoimmune, cardiovascular, and central nervous system diseases.

BACKGROUND OF THE INVENTION

Heat shock or stress dramatically increases cellular production of several classes of highly conserved chaperone proteins, commonly known as heat-shock proteins (HSPs). These chaperones, including the members of the HSP60, HSP70, and HSP90 families, are ATP-dependent molecules that facilitate/ensure proper client protein (e.g. protein that requires interaction with the chaperones for its activity and stability) folding, prevent non-specific aggregations, and maintain active protein conformations.

The HSP90 family, comprised of HSP90 α and β, Grp94 and TRAP-1, represents one of the most abundant cellular proteins, accounting for 1-2% of total protein in a mammalian cell under normal conditions. HSP90 is unique among cellular chaperones in that it is not required for general co-translational protein folding but is instead dedicated to a unique set of cellular proteins, many of which are key signaling molecules critically involved in cell growth, differentiation, and apoptosis. So far over 100 proteins have been documented to associate with HSP90 and this list of client proteins is expanding rapidly.

Crystallographic studies have revealed the existence of an unconventional low affinity ATP binding cleft at their N-terminal domain that is well conserved among the four HSP90 family members. ATP binding and hydrolysis play an essential role in the regulation of chaperone functions. The occupancy of the ATP binding site by the ansamycin antibiotics geldanamycin (GM) and herbimycin A (HA), as well as the structurally unrelated fugal metabolite radicicol, inhibits the intrinsic ATPase activity of HSP90 and blocks the ATP/ADP-regulated association-dissociation cycles between HSP90 and client proteins. Consequently, ATP-competitive HSP90 inhibitors induce destabilization and eventual ubiquitin-dependent degradation of client proteins.

HSP90 has generated tremendous interest as a novel anticancer target following the realization that many of its clients are bona fide oncoproteins that are frequently overexpressed, mutated, or constitutively active in tumor cells. These include well known and established cancer drug targets such as receptor tyrosine kinases (HER-2/neu, epidermal growth factor receptor EGFR, Met and insulin-like growth factor-1 receptor IGF-1R), metastable serine/threonine kinases (Akt and Raf-1), mutated signaling proteins (Flt3, v-Src), chimeric oncoproteins (Bcr-Abl, NPM-ALK), cell-cycle regulators (CDK4 and CDK6), transcription factors (estrogen and androgen receptors ER and AR, hypoxia-inducible factor HIF-1α) and apoptosis regulators (Survivin and Apaf-1). It is notable that HSP90 client proteins functionally contribute to all of the six "hallmarks of cancer", which include (with examples of relevant HSP90 client proteins in parenthesis) 1) self-sufficiency in growth signals (ErbB2, Raf-1), 2) insensitivity to growth suppression signals (Plk, Myt1), 3) evasion of apoptosis (Akt, RIP), 4) acquisition of limitless replicative potential (hTERT), 5) sustained angiogenesis,(HIF-1α, FAK) and 6) invasion and metastasis (Met). The association with HSP90 ensures that these otherwise unstable oncoproteins function properly in multiple signaling pathways that are essential in maintaining the unregulated growth and the malignant phenotypes of tumors.

Inactivation of HSP90 by an ATP-competitive inhibitor will induce simultaneous depletion of multiple oncoproteins and cause concurrent inhibition of various oncogenic signaling pathways. Therefore, by disrupting the function of a single molecular entity HSP90, an HSP90 inhibitor may uniquely provide a combinatorial attack on multistep oncogenesis and block all of the six hallmarks of cancer. Depending on cellular contexts, HSP90 inhibitors effectively cause growth arrest, differentiation, or apoptosis of tumor cells both in vitro and in vivo. In addition, HSP90 itself is overexpressed (about 2-20 fold) in multiple tumor types as a result of oncogenic transformation (e.g. accumulation of mutated proteins) and cellular stress (e.g. low pH and lack of nutrients). Overexpression of Hsp90 has been shown to correlate with poor prognosis in breast cancer.

Cancer cells are highly adaptive to hostile microenvironments and are capable of acquiring drug resistance, in part due to their inherent genetic instability and plasticity. Moreover, most forms of cancer are polygenic and harbor multiple signaling aberrations. HSP90 may be a key component of the very machinery that allows certain cancer cells to escape apoptotic death and evoke alternative or overlapping signaling to efficiently develop resistance to a specific drug treatment. Consequently, inhibition of Hsp90 by concurrently disrupting a wide range of oncogenic pathways may prove to be a very effective approach to combat a variety of hard-to-treat tumor.[20-23] The cancers include, for example, breast cancer[1], ovarian[2], prostate[3], chronic myelogenous leukemia (CML)[4], melanoma[5], gastrointestinal stromal tumors (GISTs)[6], master cell leukemia[7], testicular tumor[7], acute myelogenous leukemia[8,9], gastric tumor[10], lung[11], head and neck[12], glioblastoma[13], colon[14], thyroid[15], stomach, liver, multiple myeloma[16], renal[17], and lymphoma[18,19].

In addition to cancers, Hsp90 inhibitors may also have the potential to treat non-oncological indications where diseased cells show increased expression and usage of HSP90. These include, but are not limited to viral diseases mediated by hepatitis B virus (HBV), hepatitis C virus (HCV) and herpes simplex virus type 1 (HSV-1) as well as autoimmune diseases including those mediated by persistent lymphocyte activation. In all these cases, elevated Hsp90 activity either facilitates virus assembly and replication or is required for aberrant signaling transduction in inappropriately activated lymphocyte. Furthermore, HSP90 inhibitors are also known to induce upregulation of other heat shock proteins (e.g. HSP70), which may offer neuroprotection and cardioprotection against ischemic injury as well as damages caused by protein-aggregation. Therefore, HSP90 inhibitors offer therapeutic potential in treatment of central nervous system (CNS) disorders and cardiovascular diseases.

SUMMARY OF THE INVENTION

In one aspect of the present invention, new 2-amino-7,8-dihydro-6H-pyrido[4,3-d]pyrimidin-5-one compounds, tautomers, and stereoisomers, and the pharmaceutically acceptable salts and prodrugs thereof are provided. The 2-amino-7, 8-dihydro-6H-pyrido[4,3-d]pyrimidin-5-one compounds, pharmaceutically acceptable salts, and prodrugs are HSP90 inhibitors and are useful in treating cellular proliferative, viral, autoimmune, cardiovascular and central nervous system diseases.

In one embodiment, the 2-amino-7,8-dihydro-6H-pyrido[4,3-d]pyrimidin-5-one compounds have the formula (I):

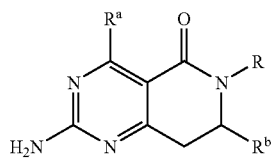

or a stereoisomer, tautomer, pharmaceutically acceptable salt, or prodrug thereof, wherein $R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkylthiol,
(7) substituted or unsubstituted $C_1$-$C_6$ alkyl,
(8) amino or substituted amino,
(9) substituted or unsubstituted aryl,
(10) substituted or unsubstituted heteroaryl, and
(11) substituted or unsubstituted heterocyclyl;

R is selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl;

$R^b$ is selected from the group consisting of
(1) substituted or unsubstituted $C_3$-$C_7$ cycloalkyl,
(2) substituted or unsubstituted $C_5$-$C_7$ cycloalkenyl,
(3) substituted or unsubstituted aryl,
(4) substituted or unsubstituted heteroaryl, and
(5) substituted or unsubstituted heterocyclyl;
with the proviso that when $R^a$ is amino, then $R^b$ is not phenyl, 4-alkyl-phenyl, 4-alkoxy-phenyl, or 4-halo-phenyl.

In another aspect, the present invention provides methods for treating cellular proliferative diseases in a human or animal subject in need of such treatment comprising administering to said subject an amount of a compound of formula (I) effective to reduce or prevent cellular proliferation in the subject.

In another aspect, the present invention provides methods for treating cellular proliferative diseases in a human or animal subject in need of such treatment, comprising administering to said subject an amount of a compound of formula (I) effective to reduce or prevent cellular proliferation in the subject in combination with at least one additional agent for the treatment of cancer.

In other aspects, the present invention provides therapeutic compositions, comprising at least one compound of formula (I) in combination with one or more additional agents for the treatment of cancer, as are commonly employed in cancer therapy.

In one embodiment, provided are compounds, compositions, and methods for treating a condition by modulating HSP90 activity. In some aspects, the condition is a cellular proliferative, viral, autoimmune, cardiovascular, or central nervous system disease.

In one embodiment, provided are compounds, compositions, and methods for treating cancers such as, for example, lung and bronchus; prostate; testicular tumor; breast; pancreas; colon and rectum; thyroid; stomach; liver and intrahepatic bile duct; kidney and renal; pelvis; urinary bladder; uterine corpus; uterine cervix; ovary; multiple myeloma; esophagus; acute myelogenous leukemia; chronic myelogenous leukemia; lymphocytic leukemia; lymphoma; myeloid leukemia; master cell leukemia, brain; oral cavity and pharynx; larynx; head; neck; glioblastoma; small intestine; gastrointestinal stromal tumors (GISTs); gastric tumor; non-hodgkin lymphoma; melanoma; and villous colon adenoma.

In one embodiment, provided are compounds, compositions, and methods for treating a viral disease. Such diseases include, for example, viral diseases mediated by hepatitis B virus (HBV), hepatitis C virus (HCV), or herpes simplex virus type 1 (HSV-1).

In one embodiment, provided are compounds, compositions, and methods for treating an autoimmune disease. In some aspects, the autoimmune disease is mediated by persistent lymphocyte activation.

In one embodiment, provided are compounds, compositions, and methods for treating a cardiovascular or central nervous system disease.

The invention further provides compositions, kits, methods of use, and methods of manufacture and related synthetic intermediates as described in the detailed description of the invention.

DETAILED DESCRIPTION

In one aspect of the present invention, new 2-amino-7,8-dihydro-6H-pyrido[4,3-d]pyrimidin-5-one compounds, stereoisomers, and tautomers, and the pharmaceutically acceptable salts and prodrugs thereof are provided. The 2-amino-7, 8-dihydro-6H-pyrido[4,3-d]pyrimidin-5-one compounds, stereoisomers, and tautomers, and the pharmaceutically acceptable salts and prodrugs thereof are HSP90 inhibitors and are useful in the treating cellular proliferative, viral, autoimmune, cardiovascular and central nervous system diseases.

In one embodiment, the 2-amino-7,8-dihydro-6H-pyrido[4,3-d]pyrimidin-5-one compounds of the invention have the formula (I):

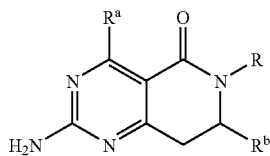

or a stereoisomer, tautomer, pharmaceutically acceptable salt, or prodrug thereof, wherein $R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkylthiol,
(7) substituted or unsubstituted $C_1$-$C_6$ alkyl,
(8) amino or substituted amino,
(9) substituted or unsubstituted aryl,
(10) substituted or unsubstituted heteroaryl, and
(11) substituted or unsubstituted heterocyclyl;

R is selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl;

$R^b$ is selected from the group consisting of
(1) substituted or unsubstituted $C_3$-$C_7$ cycloalkyl,
(2) substituted or unsubstituted $C_5$-$C_7$ cycloalkenyl,
(3) substituted or unsubstituted aryl,
(4) substituted or unsubstituted heteroaryl, and
(5) substituted or unsubstituted heterocyclyl; and
with the proviso that when $R^a$ is amino, then $R^b$ is not phenyl, 4-alkyl-phenyl, 4-alkoxy-phenyl, or 4-halo-phenyl.

Other embodiments provide a compound having formula (Ia)

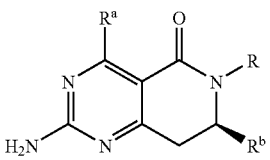

or a tautomer, pharmaceutically acceptable salt, or prodrug thereof, wherein R, $R^a$, and $R^b$ are as previously defined for formula (I) and with the proviso that when $R^a$ is amino, then $R^b$ is not phenyl, 4-alkyl-phenyl, 4-alkoxy-phenyl, or 4-halo-phenyl.

In some embodiments of the compounds of formula (I) or (Ia), $R^a$ is hydrogen.

In other embodiments, $R^a$ is substituted or unsubstituted $C_1$-$C_6$ alkyl.

In some embodiments, $R^a$ is $C_1$-$C_6$ alkyl or halo $C_1$-$C_6$ alkyl. In some such embodiments, $R^a$ is methyl.

In some embodiments, $R^b$ is aryl or heteroaryl. In some such embodiments, $R^b$ is selected from the group consisting of phenyl, pyridyl, pyrimidinyl, pyrazinyl, indolyl, thiazolyl, and thienyl, each of which can be substituted or unsubstituted. In some aspects, the invention provides compounds wherein the aforementioned $R^b$ groups are substituted with substituted or unsubstituted aryl, or substituted or unsubstituted heteroaryl. In other aspects the $R^b$ groups are substituted with halo. In still other aspects the $R^b$ groups are substituted with fluoro. In still other aspects, the $R^b$ groups are substituted with alkyl, haloalkyl, alkoxy, and haloalkoxy. In some aspects, the $R^b$ groups are substituted with methyl. In other aspects, the $R^b$ groups are substituted with methoxy.

In other embodiments, $R^b$ is selected from the group consisting of substituted aryl, substituted heterocyclyl, substituted heteroaryl, substituted $C_3$-$C_7$ cycloalkyl, and substituted $C_5$-$C_7$ cycloalkenyl, wherein said aryl, heterocyclyl, heteroaryl, $C_3$-$C_7$ cycloalkyl, and $C_5$-$C_7$ cycloalkenyl is selected from the group consisting of pyrrolyl, phenyl, pyridyl, pyrazinyl, pyrimidinyl, pyridazinyl, pyrazolyl, imidazolyl, triazolyl, indolyl, oxadiazole, thiadiazole, furanyl, quinolinyl, isoquinolinyl, isoxazolyl, oxazolyl, thiazolyl, morpholino, piperidinyl, pyrrolidinyl, thienyl, cyclohexyl, cyclopentyl, cyclohexenyl, and cyclopentenyl. In some aspects, the aforementioned groups are substituted with one to two substituents selected from the group consisting of halo, alkoxy, alkyl, amino, alkylamino, haloalkyl, and haloalkoxy.

In some embodiments, R is selected from the group consisting of hydrogen, unsubstituted alkyl, and substituted alkyl. In some such embodiments, R is selected from the group consisting of methyl, ethyl, allyl, 3-methyl-butyl, and isobutyl. In other embodiments, R is selected from the group consisting of hydrogen, benzyl, 1-(4-methoxyphenyl)ethyl, methyl, 3-amninopropyl, and 2-methyl-2-morpholinopropyl. In still other embodiment, R is hydrogen.

In another embodiment, the 2-amino-7,8-dihydro-6H-pyrido[4,3-d]pyrimidin-5-one compounds have the formula (II):

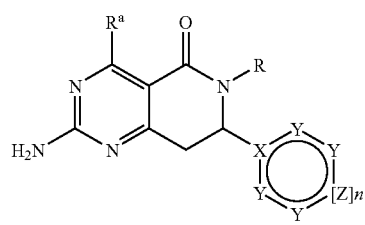

or a stereoisomer, tautomer, pharmaceutically acceptable salt, or prodrug thereof, wherein
n is 0 or 1,
wherein $R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkylthiol,
(7) substituted or unsubstituted $C_1$-$C_6$ alkyl,
(8) amino or substituted amino,
(9) substituted or unsubstituted aryl,
(10) substituted or unsubstituted heteroaryl, and
(11) substituted or unsubstituted heterocyclyl;

wherein R is selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl, wherein when n is 1, X is C, Y is at each position independently selected from $CQ^1$ and N, and Z is selected from $CR^2$ and N with the proviso that no more than 3 Y and Z groups are N, and wherein when n is 0, X is C or N, Y is at each position independently selected from $CQ^1$, N, $NQ^2$, O, and S with the proviso that no more than 4 X and Y groups are N and $NQ^2$ and no more than 1 Y group is S or O;

wherein $Q^1$ is at each position independently selected from the group consisting of
(1) hydrogen,
(2) halogen,
(3) substituted or unsubstituted $C_1$-$C_6$ alkyl,
(4) substituted or unsubstituted $C_2$-$C_6$ alkenyl,
(5) substituted or unsubstituted $C_2$-$C_6$ alkynyl,
(6) substituted or unsubstituted $C_3$-$C_7$ cycloalkyl,
(7) substituted or unsubstituted $C_5$-$C_7$ cycloalkenyl,
(8) substituted or unsubstituted aryl,
(9) substituted or unsubstituted heteroaryl,
(10) substituted or unsubstituted heterocyclyl,
(11) substituted or unsubstituted amino,
(12) —$OR^3$ or —$SR^3$,
(13) —$C(O)R^3$, —$CO_2R^3$, —$C(O)N(R^3)_2$, —$S(O)R^3$, —$SO_2R^3$, or —$SO_2N(R^3)_2$,
(14) —$OC(O)R^3$, —$N(R^3)C(O)R^3$, or —$N(R^3)SO_2R^3$,
(15) —CN, and
(16) —$NO_2$;

wherein $Q^2$ is at each position independently selected from the group consisting of
(1) hydrogen,
(3) substituted or unsubstituted $C_1$-$C_6$ alkyl,
(4) substituted or unsubstituted $C_2$-$C_6$ alkenyl,
(5) substituted or unsubstituted $C_2$-$C_6$ alkynyl,
(6) substituted or unsubstituted $C_3$-$C_7$ cycloalkyl,
(7) substituted or unsubstituted $C_5$-$C_7$ cycloalkenyl,
(8) substituted or unsubstituted aryl,
(9) substituted or unsubstituted heteroaryl, and
(10) substituted or unsubstituted heterocyclyl;

wherein $R^2$ is selected from the group consisting of
(1) hydrogen,
(2) halogen,
(3) substituted or unsubstituted $C_1$-$C_3$ alkyl, and
(4) —$OR^3$, —$SR^3$, or —$NHR^3$;

wherein $R^3$ is at each position independently selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl, with the proviso that when $R^a$ is amino, then X, Y, Z, and n together do not form a phenyl, 4-alkyl-phenyl, 4-alkoxy-phenyl, or 4-halo-phenyl group.

In other embodiments, the 2-amino-7,8-dihydro-6H-pyrido[4,3-d]pyrimidin-5-one compounds have the formula (IIa):

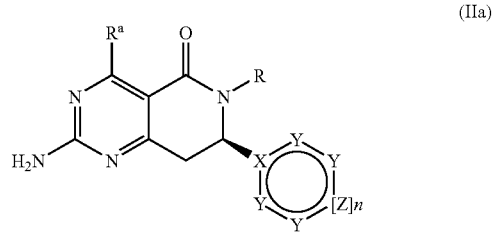

(IIa)

or a tautomer, pharmaceutically acceptable salt, or prodrug thereof, wherein $R^a$, R, X, Y, Z, and n are previously defined for formula (II) and with the proviso that when $R^a$ is amino, then X, Y, Z, and n together do not form a phenyl, 4-alkyl-phenyl, 4-alkoxy-phenyl, or 4-halo-phenyl group.

In some embodiments when n is 0, X is C, and Y adjacent to X is not O.

In some embodiments of the compounds of formula (II) or (IIa), $R^a$ is hydrogen.

In other embodiments, $R^a$ is substituted or unsubstituted $C_1$-$C_6$ alkyl.

In some embodiments, $R^a$ is $C_1$-$C_6$ alkyl or halo $C_1$-$C_6$ alkyl. In some such embodiments, $R^a$ is methyl.

For the compounds of formula (I), (Ia), (II), or (IIa), representative substituted alkyl groups include arylalkyl, heteroarylalkyl, cycloalkylalkyl, heterocyclylalkyl, aminoalkyl, alkylaminoalkyl, dialkylaminoalkyl, and sulfonamidoalkyl groups.

Representative aryl groups include phenyl groups.

Representative heteroaryl groups include pyridyl, pyrazinyl, pyrimidinyl, pyridazinyl, pyrazolyl, indolyl, quinolinyl, isoquinolinyl, furanyl, oxazolyl, thiazolyl, and thienyl groups.

In one embodiment, one of $Q^1$ or $Q^2$ is selected from the group consisting of substituted and unsubstituted phenyl, substituted and unsubstituted pyridyl, substituted and unsubstituted pyrimidinyl, substituted and unsubstituted pyrazinyl, substituted and unsubstituted indolyl, substituted and unsubstituted thiazolyl, and substituted and unsubstituted thienyl.

In one embodiment, one of $Q^1$ or $Q^2$ is selected from the group consisting of piperidinyl, morpholinyl, pyrrolidinonyl, and benzyl amino.

In one embodiment, one of $Q^1$ or $Q^2$ is selected from the group consisting of cyclohexyl and cyclopentyl.

In one embodiment, one of $Q^1$ or $Q^2$ is selected from the group consisting of cyclohexenyl and cyclopentenyl.

In one embodiment, one of $Q^1$ or $Q^2$ is selected from the group consisting of substituted aryl, substituted heterocyclyl, substituted heteroaryl, substituted $C_3$-$C_7$ cycloalkyl, and substituted $C_5$-$C_7$ cycloalkenyl, wherein said aryl, heterocyclyl, heteroaryl, $C_3$-$C_7$ cycloalkyl, and $C_5$-$C_7$ cycloalkenyl is selected from the group consisting of pyrrolyl, phenyl, pyridyl, pyrazinyl, pyrimidinyl, pyridazinyl, pyrazolyl, imidazolyl, triazolyl, indolyl, oxadiazole, thiadiazole, furanyl, quinolinyl, isoquinolinyl, isoxazolyl, oxazolyl, thiazolyl, morpholino, piperidinyl, pyrrolidinyl, thienyl, cyclohexyl, cyclopentyl, cyclohexenyl, and cyclopentenyl. In some aspects, the aforementioned groups are substituted with one to two substituents selected from the group consisting of halo, alkoxy, alkyl, amino, alkylamino, haloalkyl, and haloalkoxy.

In one embodiment, one of $Q^1$ or $Q^2$ is selected from substituted and unsubstituted pyridyl, substituted and unsubstituted pyrazinyl, substituted and unsubstituted phenyl, substituted and unsubstituted isoquinolinyl, substituted and unsubstituted pyrimidinyl, substituted and unsubstituted pyrazolyl, and substituted and unsubstituted furanyl. In some aspects, the aforementioned groups are substituted with one to two substituents selected from the group consisting of halo, alkoxy, alkyl, amino, alkylamino, haloalkyl, and haloalkoxy.

In other embodiments one of $Q^1$ or $Q^2$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol-4-yl, 1-methyl-1H-pyrzol-4-yl, 2-(5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-aminocarbonylphenyl, 2-amino-pyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethyl-phenyl, 2-ethoxy-thiazol-4-yl, 2-fluoro-3-methoxy-phenyl, 2-fluoro-3-methylphenyl, 2-fluoro-4-methyl-phenyl, 2-fluoro-5-methoxy-phenyl, 2-fluoro-5-methylphenyl, 2-fluorophenyl, 2-fluoro-pyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethoxy-phenyl, 3,4-dimethoxy-phenyl, 3,5-dimethyl-isoxazol-4-yl, 3,6-dimethyl-pyrazin-2-yl, 3-acetamidophenyl, 3-aminocarbonylphenyl, 3-bromo-phenyl, 3-chloro-pyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6-methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxy-pyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-6-methoxy-pyridin-2-yl, 5-chloro-4-methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2-yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy)pyrazin-2-yl, and 6-trifluoromethyl-pyridin-2-yl.

In one embodiment $Q^1$ is halo.

In one embodiment $Q^1$ is alkyl. In some aspects, $Q^1$ is methyl.

In one embodiment, $R^2$ is selected from hydrogen and fluoro. In some aspects, $R^2$ is fluoro.

In one embodiment, $R^2$ is selected from alkyl. In some aspects, $R^2$ is methyl.

In one embodiment, $R^2$ is selected from alkoxy. In some aspects, $R^2$ is methoxy.

In one embodiment $Q^1$ is $OR^3$.

In one embodiment, $R^3$ is selected from the group consisting of methyl, ethyl, isopropyl, cyclopentyl, and cyclohexyl.

In one embodiment, $R^3$ is selected from substituted and unsubstituted phenyl, substituted and unsubstituted thiazolyl, substituted and unsubstituted pyridyl, substituted and unsubstituted pyrazinyl, and substituted and unsubstituted pyrimidinyl.

In one embodiment, $R^3$ is selected from the group consisting of 2-aminoethyl, 2-piperidinylethyl, 2-piperazinylethyl, 2-morpholinylethyl, and 2-(N-methylpiperazinyl)ethyl.

In some embodiments, R is selected from the group consisting of hydrogen, unsubstituted alkyl, and substituted alkyl. In some such embodiments, R is selected from the group consisting of methyl, ethyl, allyl, 3-methyl-butyl, and isobutyl. In other embodiments, R is selected from the group consisting of hydrogen, benzyl, 1-(4-methoxyphenyl)ethyl, methyl, 3-aminopropyl, and 2-methyl-2-morpholinopropyl.

In another embodiment of the invention, compounds of formula (III) are provided:

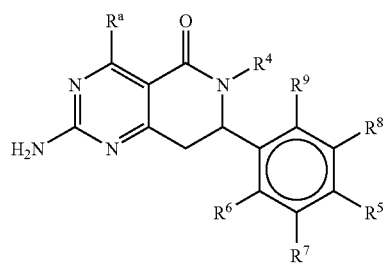

(III)

or a stereoisomer, tautomer, pharmaceutically acceptable salt, or prodrug thereof, wherein
wherein $R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkylthiol,
(7) substituted or unsubstituted $C_1$-$C_6$ alkyl,
(8) amino or substituted amino,
(9) substituted or unsubstituted aryl,
(10) substituted or unsubstituted heteroaryl, and
(11) substituted or unsubstituted heterocyclyl;
$R^4$ is hydrogen or substituted or unsubstituted $C_1$-$C_6$ alkyl;
$R^5$ is hydrogen, alkyl, alkoxy, or halo;
each of $R^6$, $R^7$, $R^8$, and $R^9$ are independently selected from the group consisting of hydrogen, alkyl, alkoxy, halo, substituted or unsubstituted aryl, and substituted or unsubstituted heteroaryl; or
a stereoisomer, tautomer, pharmaceutically acceptable salt, or prodrug thereof, and with the proviso that when $R^a$ is amino and $R^6$, $R^7$, $R^8$, and $R^9$ are hydrogen, then $R^5$ is not hydrogen, alkyl, alkoxy, or halo.

In some embodiments, provided are compounds of formula (IIIa):

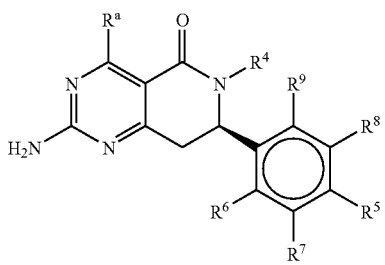

(IIIa)

or a tautomer, pharmaceutically acceptable salt, or prodrug thereof, wherein $R^a$, $R^4$, $R^5$, $R^6$, $R^7$, $R^8$, and $R^9$ are as previously defined for formula (III) and with the proviso that when $R^a$ is amino and $R^6$, $R^7$, $R^8$, and $R^9$ are hydrogen, then $R^5$ is not hydrogen, alkyl, alkoxy, or halo.

In some embodiments, $R^a$ is hydrogen.

In some embodiments, $R^a$ is substituted or unsubstituted $C_1$-$C_6$ alkyl.

In some embodiments, $R^a$ is $C_1$-$C_6$ alkyl or halo $C_1$-$C_6$ alkyl. In some such embodiments, $R^a$ is methyl.

In some embodiments of the invention, $R^4$ is selected from the group consisting of hydrogen, benzyl, 1-(4-methoxyphenyl)ethyl, methyl, 3-aminopropyl, and 2-methyl-2-morpholinopropyl. In other embodiments, R is selected from the group consisting of methyl, ethyl, allyl, 3-methyl-butyl, and isobutyl.

In some embodiments, $R^5$ is hydrogen or fluoro. In some aspects, $R^5$ is fluoro.

In some embodiments, $R^5$ is methyl or methoxy.

In some embodiments, $R^7$, $R^8$, and $R^9$ are each hydrogen.

In some embodiments, $R^6$ is aryl or heteroaryl substituted with one to two substituents selected from the group consisting of halo, alkoxy, alkyl, amino, alkylamino, haloalkyl, and haloalkoxy.

In some embodiments $R^6$ is selected from the group consisting of substituted aryl and substituted heteroaryl, wherein said aryl and heteroaryl is selected from the group consisting of furanyl, pyrrolyl, phenyl, pyridyl, pyrazinyl, pyrimidinyl, pyridazinyl, pyrazolyl, imidazolyl, triazolyl, indolyl, oxadiazole, thiadiazole, quinolinyl, isoquinolinyl, isoxazolyl, oxazolyl, thiazolyl, and thienyl. In some aspects, the aforementioned groups are substituted with one to two substituents selected from the group consisting of halo, alkoxy, alkyl, amino, alkylamino, haloalkyl, and haloalkoxy.

In other embodiments $R^6$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol-4-yl, 2-(5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-aminocarbonylphenyl, 2-amino-pyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethylphenyl, 2-ethoxy-thiazol-4-yl, fluoro-3-methoxy-phenyl, 2-fluoro-3-methylphenyl, 2-fluoro-4-methyl-phenyl, 2-fluoro-5-methoxy-phenyl 2-fluoro-5-methylphenyl, 2-fluorophenyl, 2-fluoro-pyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethoxy-phenyl, 3,4-dimethoxy-phenyl, 3,5-dimethyl-isoxazol-4-yl, 3,6-dimethyl-pyrazin-2-yl, 3-acetamidophenyl, 3-aminocarbonylphenyl, 3-bromo-phenyl, 3-chloro-pyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6-methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxy-pyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-amino6-methoxy-pyridin-2-yl, 5-chloro-4-methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6-ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2-yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy)pyrazin-2-yl, and 6-trifluoromethyl-pyridin-2-yl.

In another embodiment of the invention, compounds of formula (IV) are provided:

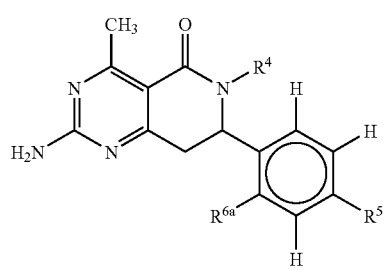

(IV)

or a stereoisomer, tautomer, pharmaceutically acceptable salt, or prodrug thereof, wherein $R^4$ is hydrogen or substituted or unsubstituted $C_1$-$C_6$ alkyl, $R^5$ is hydrogen or halo, $R^{6a}$ is selected from the group consisting of halo, substituted or unsubstituted aryl, and substituted or unsubstituted heteroaryl.

In some embodiments provided are compounds of formula (IVa):

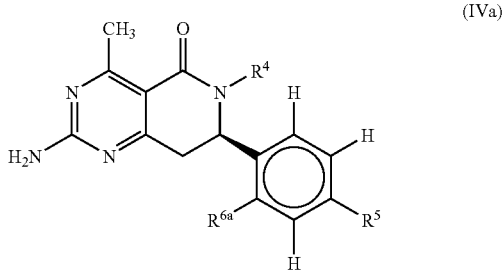

or a tautomer, pharmaceutically acceptable salt, or prodrug thereof, wherein $R^4$, $R^5$, and $R^{6a}$ are as previously defined for formula (IV).

In some embodiments of the compounds of formula (IV) or (IVa), $R^4$ is selected from the group consisting of hydrogen, benzyl, 1-(4-methoxyphenyl)ethyl, methyl, 3-aminopropyl, and 2-methyl-2-morpholinopropyl. In other embodiments, R is selected from the group consisting of methyl, ethyl, allyl, 3-methyl-butyl, and isobutyl.

In some embodiments, $R^5$ is hydrogen or fluoro. In some aspects $R^5$ is fluoro.

In some aspects, $R^{6a}$ is aryl or heteroaryl substituted with one to two substituents selected from the group consisting of halo, alkoxy, alkyl, amino, alkylamino, haloalkyl, and haloalkoxy.

In some embodiments $R^{6a}$ is selected from the group consisting of substituted aryl and substituted heteroaryl, wherein said aryl and heteroaryl is selected from the group consisting of furanyl, pyrrolyl, phenyl, pyridyl, pyrazinyl, pyrimidinyl, pyridazinyl, pyrazolyl, imidazolyl, triazolyl, indolyl, oxadiazole, thiadiazole, quinolinyl, isoquinolinyl, isoxazolyl, oxazolyl, thiazolyl, and thienyl. In some aspects, the aforementioned groups are substituted with one to two substituents selected from the group consisting of halo, alkoxy, alkyl, amino, alkylamino, haloalkyl, and haloalkoxy.

In some embodiments, $R^{6a}$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol-4-yl, (5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-aminocarbonylphenyl, 2-amino-pyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethyl-phenyl, 2-ethoxy-thiazol-4-yl, 2-fluoro-3-methoxy-phenyl, 2-fluoro-3-methylphenyl, 2-fluoro-4-methyl-phenyl, 2-fluoro-5-methoxy-phenyl, 2-fluoro-5-methylphenyl, 2-fluorophenyl, 2-fluoro-pyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethyl-phenyl, 3,4-dimethoxy-phenyl, 3,5-dimethyl-isoxazol-4-yl, 3,6-dimethyl-pyrazin-2-yl, 3-acetamidophenyl, 3-aminocarbonylphenyl, 3-bromo-phenyl, 3-chloro-pyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6-methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxy-pyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-amino6-methoxy-pyridin-2-yl, 5-chloro-4-methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6-ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2-yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy)pyrazin-2-yl, and 6-trifluoromethyl-pyridin-2-yl.

In another embodiment, provided are compounds having formula (V)

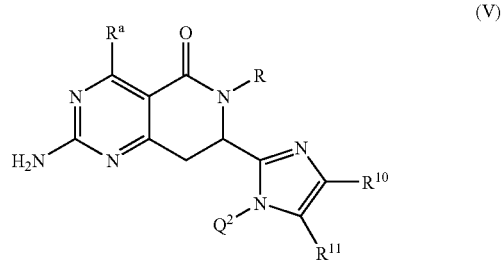

wherein $R^{10}$ and $R^{11}$ are independently $Q^1$, and $R^a$, R, $Q^1$, and $Q^2$ are as previously defined for formula (II).

In another embodiment, 2-amino-quinazolin-5-one compounds have formula (Va)

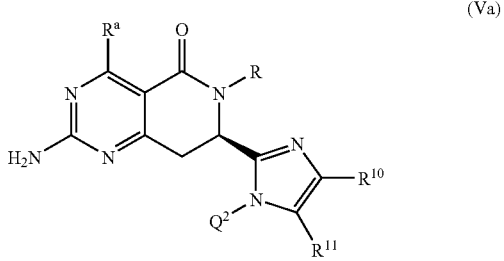

wherein $R^{10}$ and $R^{11}$ are independently $Q^1$, and $R^a$, R, $Q^1$, and $Q^2$ are as previously defined for formula (V).

In some aspects of the compounds of formula (V) and (Va), $R^a$ is methyl.

In other aspects of the compounds of formula (V) and (Va), $R^a$ is hydrogen.

In some aspects of the compounds of formula (V) and (Va), R is selected from the group consisting of hydrogen, benzyl, 1-(4-methoxyphenyl)ethyl, methyl, 3-aminopropyl, and 2-methyl-2-morpholinopropyl. In other aspects, R is selected from the group consisting of methyl, ethyl, allyl, 3-methylbutyl, and isobutyl.

In some aspects of the compounds of formula (V) and (Va), $Q^2$ is selected from the group consisting of substituted or unsubstituted aryl, substituted or unsubstituted heterocyclyl, substituted or unsubstituted heteroaryl, substituted or unsubstituted $C_3$-$C_7$ cycloalkyl, and substituted or unsubstituted $C_5$-$C_7$ cycloalkenyl. In other aspects said aryl, heterocyclyl, heteroaryl, $C_3$-$C_7$ cycloalkyl, and $C_5$-$C_7$ cycloalkenyl is selected from the group consisting of phenyl, pyridyl, pyrazinyl, pyrimidinyl, pyridazinyl, pyrazolyl, imidazolyl, triazolyl, indolyl, oxadiazole, thiadiazole, furanyl, quinolinyl, isoquinolinyl, isoxazolyl, oxazolyl, thiazolyl, morpholino, piperidinyl, pyrrolidinyl, thienyl, cyclohexyl, cyclopentyl, cyclohexenyl, and cyclopentenyl. In some aspects, the aforementioned groups are substituted with one to two substituents selected from the group consisting of halo, alkoxy, alkyl, amino, alkylamino, haloalkyl, and haloalkoxy.

In other aspects of the compounds of formula (V) and (Va), $Q^2$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol4-yl, 2-(5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-amninocarbonylphenyl, 2-amino-pyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethyl-phenyl, 2-ethoxy-thiazol-4-yl, 2-fluoro-3-methoxy-phenyl, 2-fluoro-3-methylphenyl, 2-fluoro-4-methyl-phenyl, 2-fluoro-5-methoxyphenyl, 2-fluoro-5-methylphenyl, 2-fluorophenyl, 2-fluoropyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethoxy-phenyl, 3,4-dimethoxy-phenyl, 3,5-dimethylisoxazol-4-yl, 3,6-dimethyl-pyrazin-2-yl, 3-acetamidophenyl, 3-aminocarbonylphenyl, 3-bromo-phenyl, 3-chloropyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6-methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxypyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-amino-6-methoxy-pyridin-2-yl, 5-chloro-4-methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6-ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2-yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy)pyrazin-2-yl, and 6-trifluoromethyl-pyridin-2-yl.

In one embodiment of the compounds of formula (V) and (Va), $R^9$ and $R^{10}$ are hydrogen. In another aspect one of $R^9$ or $R^{10}$ is hydrogen and the other is halo or $C_1$-$C_6$ alkoxy. In some aspects, one of $R^9$ or $R^{10}$ is fluoro. In other aspects one of $R^9$ or $R^{10}$ is methoxy.

In one embodiment, the present invention provides a compound or a stereoisomer, tautomer, pharmaceutically acceptable salt, or prodrug thereof selected from the group consisting of the compounds in Example 9, Tables 1-5.

In another embodiment, the present invention provides a compound or a stereoisomer, tautomer, pharmaceutically acceptable salt, or prodrug thereof selected from the group consisting of (R)-2-amino-7-[2-(2-fluoro-pyridin-3-yl)-phenyl]-4-methyl-7,8-dihydro-6H-pyrido[4,3-d]pyrimidin-5-one;

(S)-2-amino-6-benzyl-7-[4-fluoro-2-(2-fluoro-pyridin-3-yl)-phenyl]-4-methyl-7,8-dihydro-6H-pyrido[4,3-d]pyrimidin-5-one;

(R)-2-amino-7-[4-fluoro-2-(2-fluoro-pyridin-3-yl)-phenyl]-4-methyl-7,8-dihydro-6H-pyrido[4,3-d]pyrimidin-5-one;

(R)-2-amino-7-(2-bromo-4-fluoro-phenyl)-6-[(S)-1-(4-methoxy-phenyl)-ethyl]-4-methyl-7,8-dihydro-6H-pyrido[4,3-d]pyrimidin-5-one;

(R)-2-amino-7-[2-(6-methoxy-pyridin-2-yl)-phenyl]-4-methyl-7,8-dihydro-6H-pyrido[4,3-d]pyrimidin-5-one;

(R)-2-amino-7-[4-fluoro-2-(6-methoxy-pyridin-2-yl)-phenyl]-4-methyl-7,8-dihydro-6H-pyrido[4,3-d]pyrimidin-5-one;

2-amino-7-[4-fluoro-2-(6-methoxy-pyridin-2-yl)-phenyl]-4,6-dimethyl-7,8-dihydro-6H-pyrido[4,3-d]pyrimidin-5-one;

2-amino-7-[4-fluoro-2-(2-fluoro-pyridin-3-yl)-phenyl]-4,6-dimethyl-7,8-dihydro-6H-pyrido[4,3-d]pyrimidin-5-one;

2-amino-7-[4-fluoro-2-(6-methoxypyridin-2-yl)phenyl]-4-methyl-7,8-dihydropyrido[4,3-d]pyrimidin-5(6H)-one;

2-amino-7-[2-(6-methoxy-pyrazin-2-yl)-phenyl]-4-methyl-7,8-dihydro-6H-pyrido[4,3-d]pyrimidin-5-one;

(R)-2-amino-7-[4-fluoro-2-(6-methoxy-pyrazin-2-yl)-phenyl]-4-methyl-7,8-dihydro-6H-pyrido[4,3-d]pyrimidin-5-one;

2-amino-7-[4-fluoro-2-(6-methoxy-pyrazin-2-yl)-phenyl]-4,6-dimethyl-7,8-dihydro-6H-pyrido[4,3-d]pyrimidin-5-one;

2-amino-7-[2-(2-methoxy-pyridin-3-yl)-phenyl]-4-methyl-7,8-dihydro-6H-pyrido[4,3-d]pyrimidin-5-one;

2-amino-7-(5,2'-difluoro-biphenyl-2-yl)-4-methyl-7,8-dihydro-6H-pyrido[4,3-d]pyrimidin-5-one;
2-amino-7-(5-fluoro-2'-trifluoromethoxy-biphenyl-2-yl)-4-methyl-7,8-dihydro-6H-pyrido[4,3-d]pyrimidin-5-one;
2-amino-7-[2-(2-chloro-pyridin-3-yl)-4-fluoro-phenyl]-4-methyl-7,8-dihydro-6H-pyrido[4,3-d]pyrimidin-5-one;
2-amino-7-[4-fluoro-2-(6-fluoro-pyridin-3-yl)-phenyl]-4-methyl-7,8-dihydro-6H-pyrido[4,3-d]pyrimidin-5-one;
2-amino-7-(4-fluoro-2-isoquinolin-4-yl-phenyl)-4-methyl-7,8-dihydro-6H-pyrido[4,3-d]pyrimidin-5-one;
2-amino-7-(5,3'-difluoro-biphenyl-2-yl)-4-methyl-7,8-dihydro-6H-pyrido[4,3-d]pyrimidin-5-one;
2-amino-7-[2-(4-chloro-pyridin-3-yl)-4-fluoro-phenyl]-4-methyl-7,8-dihydro-6H-pyrido[4,3-d]pyrimidin-5-one;
2-amino-7-(5,2'-difluoro-3'-methoxy-biphenyl-2-yl)-4-methyl-7,8-dihydro-6H-pyrido[4,3-d]pyrimidin-5-one;
2-amino-7-(5,4'-difluoro-2'-methyl-biphenyl-2-yl)-4-methyl-7,8-dihydro-6H-pyrido[4,3-d]pyrimidin-5-one;
2-amino-7-(5-fluoro-2'-methoxy-biphenyl-2-yl)-4-methyl-7,8-dihydro-6H-pyrido[4,3-d]pyrimidin-5-one;
2-amino-7-(4-fluoro-2-pyrimidin-5-yl-phenyl)-4-methyl-7,8-dihydro-6H-pyrido[4,3-d]pyrimidin-5-one;
2-amino-7-[4-fluoro-2-(2-methoxy-pyridin-3-yl)-phenyl]-4-methyl-7,8-dihydro-6H-pyrido[4,3-d]pyrimidin-5-one;
2-amino-7-(5-fluoro-3'-methoxy-biphenyl-2-yl)-4-methyl-7,8-dihydro-6H-pyrido[4,3-d]pyrimidin-5-one;
(R)-2-amino-6-(3-amino-propyl)-7-[4-fluoro-2-(6-methoxy-pyridin-2-yl)-phenyl]-4-methyl-7,8-dihydro-6H-pyrido[4,3-d]pyrimidin-5-one;
2-amino-7-(4-fluoro-2-pyridin-3-yl-phenyl)-4-methyl-7,8-dihydro-6H-pyrido[4,3-d]pyrimidin-5-one;
2-amino-7-(5,2'-difluoro-4'-methyl-biphenyl-2-yl)-4-methyl-7,8-dihydro-6H-pyrido[4,3-d]pyrimidin-5-one;
2-amino-7-[4-fluoro-2-(1-methyl-1H-pyrazol-4-yl)-phenyl]-4-methyl-7,8-dihydro-6H-pyrido[4,3-d]pyrimidin-5-one;
2-amino-7-[4-fluoro-2-(1H-pyrazol-4-yl)-phenyl]-4-methyl-7,8-dihydro-6H-pyrido[4,3-d]pyrimidin-5-one;
2-amino-4-methyl-7-(5,2',3'-trifluoro-biphenyl-2-yl)-7,8-dihydro-6H-pyrido[4,3-d]pyrimidin-5-one;
2-amino-7-(2-bromo-4-fluoro-phenyl)-4-methyl-6-(2-methyl-2-morpholin-4-yl-propyl)-7,8-dihydro-6H-pyrido[4,3-d]pyrimidin-5-one;
2-amino-7-(3'-dimethylamino-5-fluoro-biphenyl-2-yl)-4-methyl-7,8-dihydro-6H-pyrido[4,3-d]pyrimidin-5-one;
2-amino-7-[2-(2,4-dimethoxy-pyrimidin-5-yl)-4-fluoro-phenyl]-4-methyl-7,8-dihydro-6H-pyrido[4,3-d]pyrimidin-5-one;
2-amino-7-[4-fluoro-2-(5-methoxy-pyridin-3-yl)-phenyl]-4-methyl-7,8-dihydro-6H-pyrido[4,3-d]pyrimidin-5-one;
2-amino-7-(4-fluoro-2-pyrimidin-5-yl-phenyl)-4-methyl-6-(2-methyl-2-morpholin-4-yl-propyl)-7,8-dihydro-6H-pyrido[4,3-d]pyrimidin-5-one;
2-amino-7-[4-fluoro-2-(2-methoxy-pyridin-3-yl)-phenyl]-4-methyl-6-(2-methyl-2-morpholin-4-yl-propyl)-7,8-dihydro-6H-pyrido[4,3-d]pyrimidin-5-one;
2-amino-7-(5-fluoro-3'-methoxy-biphenyl-2-yl)-4-methyl-6-(2-methyl-2-morpholin-4-yl-propyl)-7,8-dihydro-6H-pyrido[4,3-d]pyrimidin-5-one;
(R)-2-amino-7-[4-fluoro-2-(4-methoxy-5-methyl-pyrimidin-2-yl)-phenyl]-4-methyl-7,8-dihydro-6H-pyrido[4,3-d]pyrimidin-5-one; and
2-amino-7-(4-fluoro-2-furan-3-yl-phenyl)-4-methyl-7,8-dihydro-6H-pyrido[4,3-d]pyrimidin-5-one.

In another embodiment, the compounds of the present invention exhibit helical asymmetry. More particularly, the compounds of the present invention may be atropisomers, which is a subclass of conformers that can be isolated as separate chemical species and which arise from restricted rotation about a single bond.

In other aspects, the present invention provides methods for manufacture of 2-amino-7,8-dihydro-6H-pyrido[4,3-d]pyrimidin-5-one compounds. Methods of making representative compounds of the invention are described in Examples 1-8. It is further contemplated that, in addition to the compounds of formula (I), intermediates, and their corresponding methods of syntheses are included within the scope of the invention.

In other aspects, the present invention provides compositions that include the HSP90 inhibitors described herein, and methods that utilize the HSP90 inhibitors described herein.

In one aspect, the present invention provides pharmaceutical compositions comprising at least one 2-amino-7,8-dihydro-6H-pyrido[4,3-d]pyrimidin-5-one compound (e.g., a compound of formula (I), (Ia), (II), (IIa), (III), (IIIa), (IV), (IVa), (V), or (Va)) or a stereoisomer, tautomer, or pharmaceutical acceptable salt or prodrug thereof together with a pharmaceutically acceptable carrier suitable for administration to a human or animal subject, either alone or together with other anticancer agents.

A number of suitable anticancer agents to be used as combination therapeutics are contemplated for use in the compositions and methods of the present invention. Suitable anticancer agents to be used in combination with the compounds of the invention include agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g., IFN-a] and interleukins [e.g., IL-2]); adoptive immunotherapy agents; hematopoietic growth factors; agents that induce tumor cell differentiation (e.g., all-trans-retinoic acid); gene therapy reagents; antisense therapy reagents and nucleotides; tumor vaccines; inhibitors of angiogenesis, and the like. Numerous other examples of chemotherapeutic compounds and anticancer therapies suitable for co-administration with the 2-amino-7,8-dihydro-6H-pyrido[4,3-d]pyrimidin-5-one compounds of the invention are known to those skilled in the art.

In certain embodiments, anticancer agents to be used in combination with 2-amino-7,8-dihydro-6H-pyrido[4,3-d]pyrimidin-5-one compounds of the invention comprise agents that induce or stimulate apoptosis. Agents that induce apoptosis include, but are not limited to, radiation; kinase inhibitors (e.g., Epidermal Growth Factor Receptor [EGFR] kinase inhibitor, Vascular Endothelial Growth Factor Receptor [VEGFR] kinase inhibitor, Fibroblast Growth Factor Receptor [FGFR] kinase inhibitor, Platelet-derived Growth Factor Receptor [PGFR] I kinase inhibitor, and Bcr-Abl kinase inhibitors such as STI-571 [Gleevec or Glivec]); antisense molecules; antibodies [e.g., Herceptin and Rituxan]; anti-estrogens [e.g., raloxifene and tamoxifen]; anti-androgens [e.g., flutamide, bicalutamide, finasteride, amino-glutethamide, ketoconazole, and corticosteroids]; cyclooxygenase 2 (COX-2) inhibitors [e.g., Celecoxib, meloxicam, NS-398, and non-steroidal anti-inflammatory drugs (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-16, cisplatinum, 5-FU, Doxrubicin, Taxotere or Taxol]; cellular signaling molecules; ceramides and cytokines; and staurosparine; and the like.

In other aspects, the invention provides methods for using the compounds and compositions described herein. For example, the compounds and compositions described herein can be used in the treatment of cancer. The compounds and compositions described herein can also be used in the manufacture of a medicament for the treatment of cancer.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of an 2-amino-7,8-dihydro-6H-pyrido[4,3-d]pyrimidin-5-one compound or composition (e.g., a compound or composition of formula (I), (Ia), (II), (IIa), (III), (IIIa), (IV), (IVa), (V), or (Va)), either alone or in combination with other anticancer agents.

In another embodiment, the present invention provides methods for treating a cellular proliferative disease in a human or animal subject in need of such treatment comprising, administering to said subject an amount of an 2-amino-7,8-dihydro-6H-pyrido[4,3-d]pyrimidin-5-one compound or composition (e.g., a compound or composition of formula (I)-(V)) effective to reduce or prevent cellular proliferation or tumor growth in the subject.

In another embodiment, the present invention provides methods for treating a cellular proliferative disease in a human or animal subject in need of such treatment comprising administering to said subject an amount of an 2-amino-7,8-dihydro-6H-pyrido[4,3-d]pyrimidin-5-one compound (e.g., a compound of formula (I), (Ia), (II), (IIa), (III), (IIIa), (IV), (IVa), (V), and (Va)) effective to reduce or prevent cellular proliferation in the subject in combination with at least one additional agent for the treatment of cancer.

The present invention provides compounds that are inhibitors of HSP90. The inhibitors are useful in pharmaceutical compositions for human or veterinary use where inhibition of HSP90 is indicated, e.g., in the treatment of cellular proliferative diseases such as tumor and/or cancerous cell growth mediated by HSP90. In particular, the compounds are useful in the treatment of human or animal (e.g., murine) cancers, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-hodgkin lymphoma; melanoma; and villous colon adenoma.

In another embodiment, the invention provides methods of treating an HSP90 mediated disorder. In one method, an effective amount of an 2-amino-7,8-dihydro-6H-pyrido[4,3-d]pyrimidin-5-one compound (e.g, a compound of formula (I), (Ia), (II), (IIa), (III), (IIIa), (IV), (IVa), (V), and (Va)) is administered to a patient (e.g., a human or animal subject) in need thereof to mediate (or modulate) HSP90 activity. In some aspects, the HSP90 mediated disorder is a cellular proliferative, viral, autoimmune, cardiovascular, and central nervous system disorder.

In another embodiment, the invention provides methods of treating a cellular proliferative, viral, autoimmune, cardiovascular, or central nervous system disorder. In one method, an effective amount of a 2-amino-7,8-dihydro-6H-pyrido[4,3-d]pyrimidin-5-one compound (e.g, a compound of formula (I), (Ia), (II), (IIa), (III), (IIIa), (IV), (IVa), (V), and (Va)) is administered to a patient (e.g., a human or animal subject) in need thereof to treat a cellular proliferative, viral, autoimmune, cardiovascular, and central nervous system disorder.

A representative assay for determining HSP90 inhibitory activity is described in Example 10. In a preferred embodiment, the 2-amino-7,8-dihydro-6H-pyrido[4,3-d]pyrimidin-5-one compounds of the invention have an $IC_{50}$ value for inhibiting HSP90 activity less than or equal to 100 µM. In more preferred embodiments, the $IC_{50}$ value is less than or equal to 50 µM, even more preferred with an $IC_{50}$ value less than or equal to 25 µM. Still more preferred embodiment have $IC_{50}$ values less than or equal to 10 µM, and even more preferred embodiments have $IC_{50}$ values less than or equal to 1 µM.

The following definitions are provided to better understand the invention.

"Alkyl" or "unsubstituted alkyl" refers to saturated hydrocarbyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH (CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$) (CH$_2$CH$_3$), —CH$_2$CH$_2$CH(CH$_3$)$_2$, —CH$_2$CH$_2$CH(CH$_3$) (CH$_2$CH$_3$), —CH$_2$CH$_2$CH(CH$_2$CH$_3$)$_2$, —CH$_2$CH$_2$C(CH$_3$)$_3$, CH$_2$CH$_2$C(CH$_2$CH$_3$)$_3$, —CH(CH$_3$)CH$_2$CH(CH$_3$)$_2$, —CH (CH$_3$)CH(CH$_3$)CH(CH$_3$)$_2$, —CH(CH$_2$CH$_3$)CH(CH$_3$)CH (CH$_3$)(CH$_2$CH$_3$), and others. Thus the phrase "alkyl groups" includes primary alkyl groups, secondary alkyl groups, and tertiary alkyl groups. Preferred alkyl groups include straight and branched chain alkyl groups having 1 to 12, 1 to 6, or 1 to 3 carbon atoms.

"Alkylene" or "unsubstituted alkylene" refers to the same residues as noted above for "alkyl," but having two points of attachment. Exemplary alkylene groups include ethylene (—CH$_2$CH$_2$—), propylene (—CH$_2$CH$_2$CH$_2$—), and dimethylpropylene (—CH$_2$C(CH$_3$)$_2$CH$_2$—).

"Alkenyl" or "unsubstituted alkenyl" refers to straight chain and branched, chain hydrocarbyl radicals having one or more carbon-carbon double bonds and from 2 to about 20 carbon atoms. Preferred alkenyl groups include straight chain and branched alkenyl groups having 2 to 12, or 2 to 6 carbon atoms.

"Alkynyl" or "unsubstituted alkynyl" refers to straight chain and branched chain hydrocarbyl radicals having one or more carbon-carbon triple bonds and from 2 to about 20 carbon atoms. Preferred alkynyl groups include straight chain and branched alkynyl groups having 2 to 12, or 2 to 6 carbon atoms.

"Cycloalkyl" or "unsubstituted cycloalkyl" refers to a mono- or polycyclic alkyl substituent. Representative cycloalkyl groups include cyclopropyl, cyclobutyl, cyclopentyl, cyclohexyl, cycloheptyl, and cyclooctyl. Preferred cycloalkyl groups have 3 to 7 carbon atoms.

"Cycloalkenyl" or "unsubstituted cycloalkenyl" refers to a mono- or polycyclic alkyl substituents having at least one ring carbon-carbon double bond. Preferred cycloalkenyl groups have 5 to 7 carbon atoms and include cyclopentenyl and cyclohexenyl.

"Substituted alkyl" refers to an alkyl group as defined above in which one or more bonds to a carbon(s) or hydrogen(s) are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide, sulfone, sulfonyl, and sulfoxide groups; a nitrogen atom in groups such as amino, amido, alkylamino, arylamino, alkylarylamino, diarylamino, N-oxides, imides, and enamines. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; or nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heteroaryl, heterocyclyl, cycloalkyl, or cycloalkenyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amino, or a substituted or unsubstituted alkylamino, arylamino, heterocyclylamino. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —$(CH_2)_3NH_2$, —$(CH_2)_3NH(CH_3)$, —$(CH_2)_3NH(CH_3)_2$, —$CH_2C(=CH_2)CH_2NH_2$, —$CH_2C(=O)CH_2NH_2$, —$CH_2OCH_2NH_2$, —$CH_2CO_2H$. Examples of substituents of substituted alkyl are: —$CH_2OH$, —OH, —$OCH_3$, —$OC_2H_5$, —$OCF_3$, $OC(=O)CH_3$, —$OC(=O)NH_2$, —$OC(=O)N(CH_3)_2$, —CN, —$NO_2$, —$C(=O)CH_3$, —$CO_2H$, —$CO_2CH_3$, —$CONH_2$, —$NH_2$, —$N(CH_3)_2$, —$NHSO_2CH_3$, —$NHCOCH_3$, —$NHC(=O)OCH_3$, —$NHSO_2CH_3$, —$SO_2CH_3$, —$SO_2NH_2$, and halo.

"Substituted alkenyl" has the same meaning with respect to unsubstituted alkenyl groups that substituted alkyl groups has with respect to unsubstituted alkyl groups. A substituted alkenyl group includes alkenyl groups in which a non-carbon or non-hydrogen atom is bonded to a carbon double bonded to another carbon and those in which one of the non-carbon or-non-hydrogen atoms is bonded to a carbon not involved in a double bond to another carbon.

"Substituted alkynyl" has the same meaning with respect to unsubstituted alkynyl groups that substituted alkyl groups has with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Substituted cycloalkyl" has the same meaning with respect to unsubstituted cycloalkyl groups that substituted alkyl groups has with respect to unsubstituted alkyl groups.

"Substituted cycloalkenyl" has the same meaning with respect to unsubstituted cycloalkenyl groups that substituted alkyl groups has with respect to unsubstituted alkyl groups.

"Aryl" or "unsubstituted aryl" refers to monocyclic and polycyclic aromatic groups that do not contain ring heteroatoms. Such groups can contain from 6 to 14 carbon atoms but preferably 6. Exemplary aryl moieties employed as substituents in compounds of the present invention include phenyl, naphthyl, and the like.

"Aralkyl" or "arylalkyl" refers to an alkyl group substituted with an aryl group as defined above. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl and the like. "Heteroarylalkyl" or "heteroaralkyl". refers to an alkyl group substituted with a heteroaryl group as defined above. Typically, heteroarylalkyl groups employed in compounds of the present invention have from 1 to 6 carbon atoms incorporated within the alkyl portion of the aralkyl group. Suitable heteroarylalkyl groups employed in compounds of the present invention include, for example, picolyl and the like.

"Alkoxy" refers to $R^{20}O$— wherein $R^{20}$ is $C_1$-$C_7$ alkyl or substituted alkyl. In some embodiments, $R^{20}$ is $C_1$-$C_6$ alkyl. Representative examples of alkoxy groups include methoxy, ethoxy, t-butoxy, trifluoromethoxy, and the like.

"Amino" refers herein to the group —$NH_2$.

"Substituted amino" refers to the group —$NR^{60}R^{61}$ where $R^{60}$ and $R^{61}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —$SO_2$-alkyl, —$SO_2$-substituted alkyl, and where $R^{60}$ and $R^{61}$ are joined, together with the nitrogen bound thereto to form a heterocyclic or substituted heterocyclic group provided that $R^{60}$ and $R^{61}$ are both not hydrogen. When $R^{60}$ is hydrogen and $R^{61}$ is alkyl, the substituted amino group is sometimes referred to herein as alkylamino. When $R^{60}$ and $R^{61}$ are alkyl, the substituted amino group is sometimes referred to herein as dialkylamno. When referring to a monosubstituted amino, it is meant that either $R^{60}$ and $R^{61}$ is hydrogen but not both. When referring to a disubstituted amino, it is meant that neither $R^{60}$ and $R^{61}$ is hydrogen. The term "alkylamino" refers herein to the group —$NR^{60}R^{61}$ where $R^{60}$ is $C_1$-$C_7$ alkyl and $R^{60}$ is hydrogen or $C_1$-$C_7$ alkyl. The term "dialkylamino" refers to the group —$NR^{60}R^{61}$ where $R^{60}$ and $R^{61}$ are $C_1$-$C_7$ alkyl. The term "arylamino" refers herein to the group —$NR^{60}R^{61}$ where $R^{60}$ is $C_5$-$C_7$ aryl and $R^{61}$ is hydrogen, $C_1$-$C_7$ alkyl, or $C_5$-$C_7$ aryl. The term "aralkylamino" refers herein to the group —$NR^{60}R^{61}$ where $R^{60}$ is aralkyl and $R^{61}$ is hydrogen, $C_1$-$C_7$ alkyl, $C_5$-$C_7$ aryl, or $C_5$-$C_7$ aralkyl.

"Amidino" refers to the moieties $R^{40}$—$C(=N)$—$NR^{41}$— (the radical being at the "$N^1$" nitrogen) and $R^{40}(NR^{41})C=N$— (the radical being at the "$N^2$" nitrogen), where $R^{40}$ and $R^{41}$ can be hydrogen, $C_1$-$C_7$ alkyl, aryl, or $C_5$-$C_7$ aralkyl.

"Alkoxyalkyl" refers to the group -$alk_1$-O-$alk_2$ where $alk_1$ is $C_1$-$C_7$ alkyl, and $alk_2$ is $C_1$-$C_7$ alkyl. The term "aryloxyalkyl" refers to the group —($C_1$-$C_7$ alkyl)-O—($C_5$-$C_7$ aryl).

"Alkoxyalkylamino" refers herein to the group —$NR^{27}$-(alkoxyalkyl), where $R^{27}$ is typically hydrogen, $C_5$-$C_7$ aralkyl, or $C_1$-$C_7$ alkyl.

"Aminocarbonyl" refers herein to the group —C(O)—$NH_2$. "Substituted aminocarbonyl" refers herein to the group —C(O)—$NR^{28}R^{29}$ where $R^{28}$ is $C_1$-$C_7$ alkyl and $R^{29}$ is hydrogen or $C_1$-$C_7$ alkyl. The term "arylaminocarbonyl" refers herein to the group —C(O)—$NR^{30}R^{31}$ where $R^{30}$ is $C_5$-$C_7$ aryl and $R^{31}$ is hydrogen, $C_1$-$C_7$ alkyl or $C_5$-$C_7$ aryl. "Aralkylaminocarbonyl" refers herein to the group —C(O)—$NR^{32}R^{33}$ where $R^{32}$ is $C_5$-$C_7$ aralkyl and $R^{33}$ is hydrogen, $C_1$-$C_7$ alkyl, $C_5$-$C_7$ aryl, or $C_5$-$C_7$ aralkyl.

"Aminosulfonyl" refers herein to the group —$S(O)_2$—$NH_2$. "Substituted aminosulfonyl" refers herein to the group —$S(O)_2$—$NR^{34}R^{35}$ where $R^{34}$ is $C_1$-$C_7$ alkyl and $R^{35}$ is hydrogen or $C_1$-$C_7$ alkyl. The term "aralkylaminosulfonlyaryl" refers herein to the group —($C_5$-$C_7$ aryl)-S(O)$_2$—NH-aralkyl.

"Aryloxy" refers to $R^{50}$O— wherein $R^{50}$ is aryl.

"Carbonyl" refers to the divalent group —C(O)—. "Alkylcarbonyl" refers to the group —C(O)alkyl. "Arylcarbonyl" refers to the group —C(O)aryl. Similarly, the term "heteroarylcarbonyl", "aralkylcarbonyl", and "heteroaralkylcarbonyl" refers to —C(O)—R where R is respectively heteroaryl, aralkyl, and heteroaralkyl.

"Carbonyloxy" refers generally to the group —C(O)—O—. Such groups include esters, —C(O)—O—$R^{36}$, where $R^{36}$ is $C_1$-$C_7$ alkyl, $C_3$-$C_7$ cycloalkyl, aryl, or $C_5$-$C_7$ aralkyl. The term "arylcarbonyloxy" refers herein to the group —C(O)—O-(aryl). The term "aralkylcarbonyloxy" refers herein to the group —C(O)—O—($C_5$-$C_7$ aralkyl).

"Cycloalkylalkyl" refers to an alkyl group substituted with a cyloalkyl group as defined above. Typically, cycloalkylalkyl groups have from 1 to 6 carbon atoms incorporated within the alkyl portion of the cycloalkylalkyl group.

"Carbonylamino" refers to the divalent group —NH—C(O)— in which the hydrogen atom of the amide nitrogen of the carbonylamino group can be replaced $C_1$-$C_7$ alkyl, aryl, or $C_5$-$C_7$ aralkyl group. Carbonylamino groups include moieties such as carbamate esters (—NH—C(O)—O—$R^{28}$) and amido —NH—C(O)—$R^{28}$, where $R^{28}$ is a straight or branched chain $C_1$-$C_7$ alkyl, $C_3$-$C_7$ cycloalkyl, or aryl or $C_5$-$C_7$ aralkyl. The term "alkylcarbonylamino" refers to the group —NH—C(O)—$R^{28'}$ where $R^{28'}$ is alkyl having from 1 to about 7 carbon atoms in its backbone structure. The term "arylcarbonylamino" refers to group —NH—C(O)—$R^{29}$ where $R^{29}$ is $C_5$-$C_7$ aryl. Similarly, the term "aralkylcarbonylamino" refers to carbonylamino where $R^{29}$ is $C_5$-$C_7$ aralkyl.

"Guanidino" or "guanidyl" refers to moieties derived from guanidine, $H_2N$—C(=NH)—$NH_2$. Such moieties include those bonded at the nitrogen atom carrying the formal double bond (the "2"-position of the guanidine, e.g., diaminomethyleneamino, $(H_2N)_2C$=NH—) and those bonded at either of the nitrogen atoms carrying a formal single bond (the "1-" and/or "3"-positions of the guandine, e.g., $H_2N$—C(=NH)—NH—). The hydrogen atoms at any of the nitrogens can be replaced with a suitable substituent, such as $C_1$-$C_7$ alkyl, aryl, or $C_5$-$C_7$ aralkyl.

"Halogen" or "halo" refers to chloro, bromo, fluoro, and iodo groups. The term "haloalkyl" refers to an alkyl radical substituted with one or more halogen atoms. "Haloalkyl" groups include —$CF_3$. The term "haloalkoxy" refers to an alkoxy radical substituted with one or more halogen atoms. "Haloalkoxy" groups include —$OCF_3$ and —$OCH_2CF_3$.

"Hydroxyl" or "hydroxy" refers to the group —OH.

"Heterocyclic" or "unsubstituted heterocyclic group," "heterocycle" or "unsubstituted heterocycle," and "heterocyclyl" or "unsubstituted heterocyclyl," "heterocycloalkyl" or "unsubstituted heterocycloalkyl group," as used herein refers to any non-aromatic monocyclic or polycyclic ring compounds containing a heteroatom selected from nitrogen, oxygen, or sulfur. Examples include 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-1 double bonds and the 6-membered ring has 0-2 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above provided that the point of attachment is through the heterocyclic ring.

Heterocyclic moieties can be, for example monosubstituted or disubstituted with various substituents independently selected from but not limited to hydroxy, alkoxy, halo, oxo (C=O), alkylimino ($R^{31}$N=; wherein $R^{31}$ is alkyl or alkoxy group), amino, alkylamino, acylaminoalkyl, alkoxy, thioalkoxy, polyalkoxy, alkyl, cycloalkyl or haloalkyl.

The heterocyclic groups may be attached at various positions as shown below as will be apparent to those having skill in the organic and medicinal chemistry arts in conjunction with the disclosure herein.

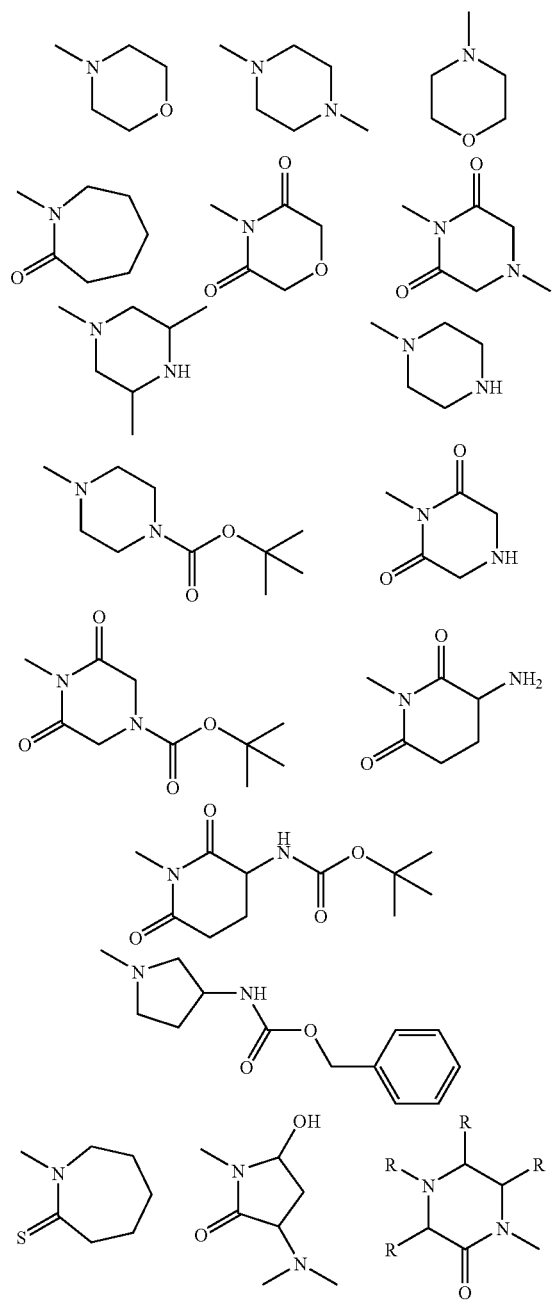

where R is H or a heterocyclic substituent, as described herein.

"Heteroaryl" or "unsubstituted heteroaryl" refers herein to an aromatic group having from 1 to 4 heteroatoms as ring atoms in an aromatic ring with the remainder of the ring atoms being carbon atoms. The term "heteroaryl" includes rings in which nitrogen is the heteroatom as well as partially and fully-saturated rings in which at least one cyclic structure is aromatic, such as, for example, benzodioxozolo (which has a heterocyclic structure fused to a phenyl group, i.e.,

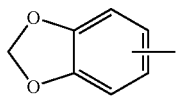

provided that the point of attachment is through the heteroaryl ring. Heteroaryl groups can be further substituted and may be attached at various positions as will be apparent to those having skill in the organic and medicinal chemistry arts in conjunction with the disclosure herein. Representative substituted and unsubstituted heteroaryl groups include, for example, those found in the compounds disclosed in this application and in the examples shown below

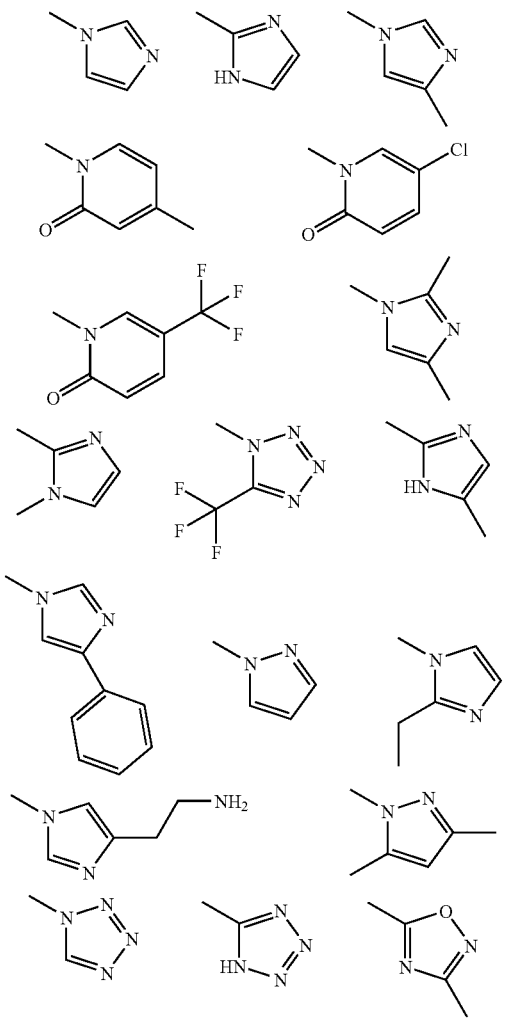

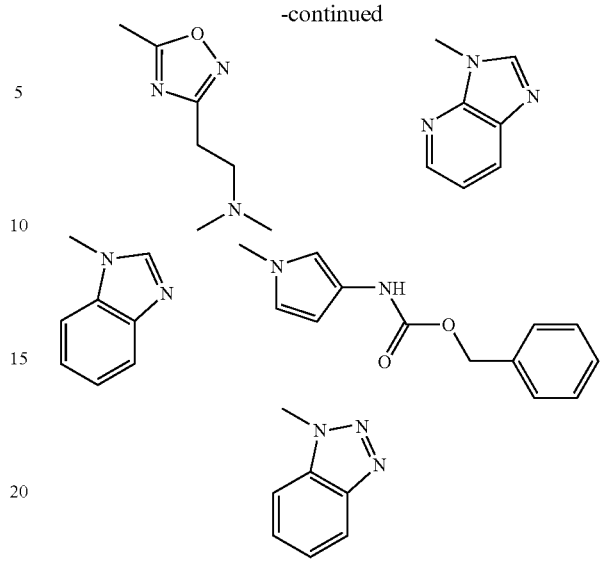

Preferred heterocycles and heteroaryls have 3 to 14 ring atoms and include, for example: diazapinyl, pyrroyl, pyrrolidinyl, pyrazolyl, pyrazolidinyl, imidazoyl, imidazolidinyl, pyridyl, piperidinyl, pyrazinyl, piperazinyl, azetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, quinoxalinyl, phthalazinyl, naphthpyridinyl, indazolyl, and benzothienyl.

"Heteroarylalkyl" or "heteroaralkyl" refers to an alkyl group substituted with a heteroaryl group as defined above. Typically, heteroarylalkyl groups have from 1 to 6 carbon atoms incorporated within the alkyl portion of the heteroarylalkyl group.

"Imino" refers to the group =NH.

"Nitro" refers to the group $NO_2$.

"Sulfonyl" refers herein to the group —$SO_2$—. "Alkylsulfonyl" refers to a substituted sulfonyl of the structure —$SO_2R^{52}$— in which $R^{52}$ is $C_1$-$C_7$ alkyl. Alkylsulfonyl groups employed in compounds of the present invention are typically alkylsulfonyl groups having from 1 to 6 carbon atoms in its backbone structure. Thus, typical alkylsulfonyl groups employed in compounds-of the present invention include, for example, methylsulfonyl (i.e., where $R^{52}$ is methyl), ethylsulfonyl (i.e., where $R^{52}$ is ethyl), propylsulfonyl (i.e., where $R^{52}$ is propyl), and the like. The term "arylsulfonyl" refers herein to the group —$SO_2$-aryl. The term "heterocyclylsulfonyl" refers herein to the group —$SO_2$—heterocyclyl. The term "aralkylsulfonyl" refers herein to the group —$SO_2$-aralkyl. The term "sulfonamido" refers herein to —$SO_2NH_2$. The term "sulfonarnidoalkyl" refers to (alkyl)$SO_2NH_2$—.

"Thio" or "thiol" refers to the group —SH. "Alkylthio" or "alkylthiol" refers to a thio group substituted with an alkyl group such as, for example, a $C_1$-$C_6$ alkyl group.

"Thioamido" refers to the group —C(=S)$NH_2$.

"Optionally substituted" refers to the optional replacement of hydrogen with a monovalent or divalent radical. "Substituted" refers to the replacement of hydrogen with a monovalent or divalent radical. Unless indicated otherwise, suitable substitution groups include, for example, hydroxyl, alkoxy, nitro, amino, imino, cyano, halo, thio, sulfonyl, thioamido, amidino, oxo, oxamidino, methoxamidino, guanidino, sulfonamido, carboxyl, formyl, alkyl, haloalkyl, alkylamino, haloalkylamino, alkoxy, haloalkoxy, alkoxy-alkyl, alkylcarbonyl, aminocarbonyl, arylcarbonyl, aralkylcarbonyl, heteroarylcarbonyl, heteroaralkyl-carbonyl, alkylthio, aminoalkyl, cyanoalkyl, aryl and the like. Other suitable substitution groups include those substituents indicated for substituted alkyl. Examples of various suitable substitution groups are also found in reference to the compounds disclosed throughout this application.

The substitution group can itself be substituted. The group substituted onto the substitution group can be carboxyl, halo, nitro, amino, cyano, hydroxyl, alkyl, alkoxy, aminocarbonyl, —$SR^{42}$, thioamido, —$SO_3H$, —$SO_2R$, or cycloalkyl, where $R^{42}$ is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

Unless indicated otherwise, the nomenclature of substituents that are not explicitly defined herein are arrived at by naming the terminal portion of the finctionality followed by the adjacent functionality toward the point of attachment. For example, the substituent "alkoxyheteroaryl" refers to the group (alkoxy)-(heteroaryl)-.

Preferred compounds of the invention have a total molecular weight less than 1000 Daltons, preferably less than 750 Daltons. Compounds of the invention typically have a minimum molecular weight of at least 150 Daltons. Preferred embodiments of the invention have a molecular weight between 150 and 750 Daltons, more preferred embodiments have a molecular weight between 200 and 500 Daltons. Other embodiments of the invention are compounds with a molecular weight between 300 and 450 Daltons. In another aspect of the invention compounds of the invention have a molecular weight between 350 and 400 Daltons.

Similarly, it is understood that the above definitions are not intended to include impermissible substitution patterns (e.g., methyl substituted with 5 fluoro groups). Such impermissible substitution patterns are well known to the skilled artisan.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of enantiomers, as well as enantiomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the 2-amino-7,8-dihydro-6H-pyrido[4,3-d]pyrimidin-5-one compounds of the invention. These salts can be prepared in situ during the final isolation and purification of the 2-amino-7,8-dihydro-6H-pyrido[4,3-d]pyrimidin-5-one compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, sulfate, tartrate, thiocyanate, p-toluenesulfonate, and undecanoate. Also, the basic nitrogen-containing groups can be quatemized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the 2-amino-7,8-dihydro-6H-pyrido[4,3-d]pyrimidin-5-one compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylaamine, ethylenediamine, ethanolamine, diethanolamine, piperazine, and the like.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in Higuchi, T., and V. Stella, "Pro-drugs as Novel Delivery Systems," *A.C.S. Symposium Series* 14, and in "Bioreversible Carriers in Drug Design," in Edward B. Roche (ed.), *American Pharmaceutical Association*, Pergamon Press, 1987, both of which are incorporated herein by reference.

The term "HSP90 mediated disorder" refers to a disorder that can be beneficially treated by the inhibition of HSP90.

The term "cellular proliferative diseases" refers to diseases including, for example, cancer, tumor, hyperplasia, restenosis, cardiac hypertrophy, immune disorder and inflammation.

The term "cancer" refers to cancer diseases that can be beneficially treated by the inhibition of HSP90, including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to detectably inhibit HSP90 activity by any of the assays described herein, by other HSP90 activity assays known to those having ordinary skill in the art, or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrastemal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

While the compounds of the invention can be administered as the sole active pharmaceutical agent, they can also be used in combination with one or more other agents used in the treatment of cancer. Representative agents useful in combination with the compounds of the invention for the treatment of cancer include, for example, irinotecan, topotecan, gemcitabine, gefitinib, vatalanib, sunitinib, sorafenib, erlotinib, dexrazoxane, gleevec, herceptin, 5-fluorouracil, leucovorin, carboplatin, cisplatin, taxanes, tezacitabine, cyclophosphamide, vinca alkaloids, imatinib, anthracyclines, rituximab, trastuzumab, topoisomerase I inhibitors, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

Antiestrogens, such as tamoxifen, inhibit breast cancer growth through induction of cell cycle arrest, that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to antiestrogen resistance (Donovan, et al, *J. Biol. Chem.* 276:40888, 2001). As reported by Donovan et al., inhibition of MAPK signaling through treatment with MEK inhibitor changed the phosphorylation status of p27 in hormone refactory breast cancer cell lines and in so doing restored hormone sensitivity. Accordingly, in one aspect, the compounds of formula (I), (Ia), (II), (Ia), (III), (IIIa), (IV), (IVa), (V), or (Va) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-ABL tyrosine kinase. The afflicted patients are responsive to gleevec, a small molecule tyrosine kinase inhibitor, as a result of inhibition of Abl kinase activity. However, many patients with advanced stage disease respond to gleevec initially, but then relapse later due to resistance-conferring mutations in the Abl kinase domain. In vitro studies have demonstrated that BCR-Avl employs the Raf kinase pathway to elicit its effects. In addition, inhibiting more than one kinase in the same pathway provides additional protection against resistance-conferring mutations. Accordingly, in another aspect of the invention, the compounds of formula (I), (Ia), (II), (IIa), (III), (IIIa), (IV), (IVa), (V), or (Va) are used in combination with at least one additional agent, such as gleevec, in the treatment of hematological cancers, such as chronic myelogenous leukemia (CML), to reverse or prevent resistance to the at least one additional agent.

In another aspect of the invention, kits that include one or more compounds of the invention are provided. Representative kits include a 2-amino-7,8-dihydro-6H-pyrido[4,3-d]pyrimidin-5-one compound of the invention (e.g., a compound of formula (I), (Ia), (II), (IIa), (III), (IIa), (IV), (IVa), (V), or (Va)) and a package insert or other labeling including directions for treating a cellular proliferative disease by administering an HSP90 inhibitory amount of the compound.

The synthesis of representative 2-amino-7,8-dihydro-6H-pyrido[4,3-d]pyrimidin-5-one compounds are described in Examples 1-8. Representative 2-amino-7,8-dihydro-6H-pyrido[4,3-d]pyrimidin-5-one compounds that were prepared are shown in Tables 1-5 in Example 9.

In one aspect, certain compounds of the invention having a substituted 7-phenyl moiety can be prepared as shown in Scheme 1. Benzyl amine 1-C, prepared from chiral amine 1-A by reductive amination, and cinnamate 1-D, prepared from a Wadsworth Emmons homologation of aldehyde 1-B, are coupled to give the conjugate addition product 1-E (Steven D. Bull, Stephen G. Davies, Santiago Delgado-Ballester, Peter M. Kelly, Luke J. Kotchie, Massimo Gianotti, Mario Laderas and Andrew D. Smith, *J. Chem. Soc., Perkin Trans.* 1, 2001, (23), 3112). Removal of the benzyl group is accomplished using 1.1 eq. of cerric ammonium nitrate in acetonitrile and water. Resulting amine 1-F is acylated with methyl malonyl chloride 1-G to give compound 1-H. Cyclization is effected via a Dieckmann condensation upon treatment with base such as sodium ethoxide. The resulting lactam is then treated with acid such as HCl to effect decarboxylation and afford compound 1-I. O-acylation with acetyl chloride and treatment with catalytic dimethylaminopyridine in boiling solvent such as acetonitrile or toluene to effect migration of the acetate group gives compound I-J. Pyrimidine I-K is formed by treating I-J with guanidine/EtOH and dimethylamine. The para-methoxybenzyl group can be removed at this stage (or after the Suzuki coupling) with cerric ammonium nitrate or trifluoroacetic acid. The phenyl ring of I-K can optionally be functionalized via a Suzuki coupling with a suitable boronic acid to give the biaryl compound I-L. Subsequent deprotection of the para-methoxybenzyl group gives amine I-M.

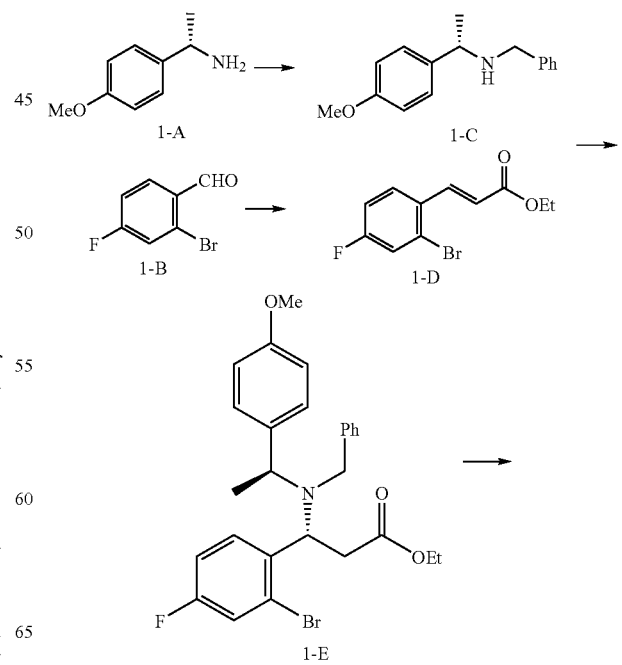

Scheme 1.

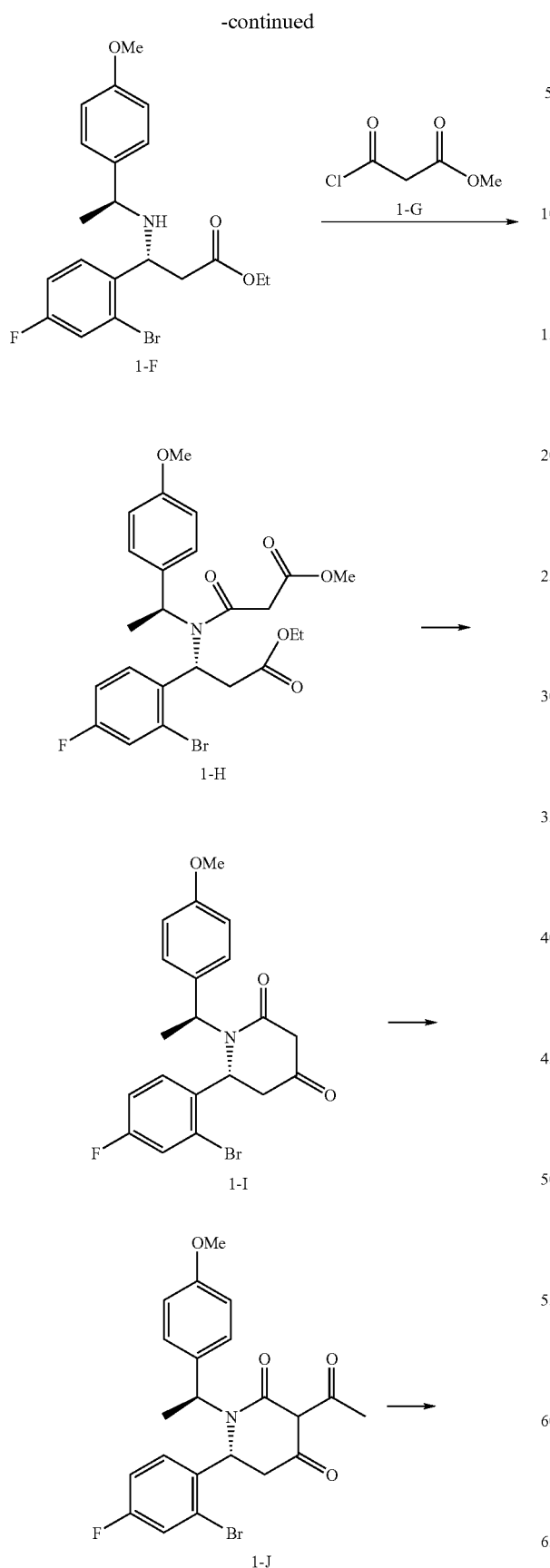
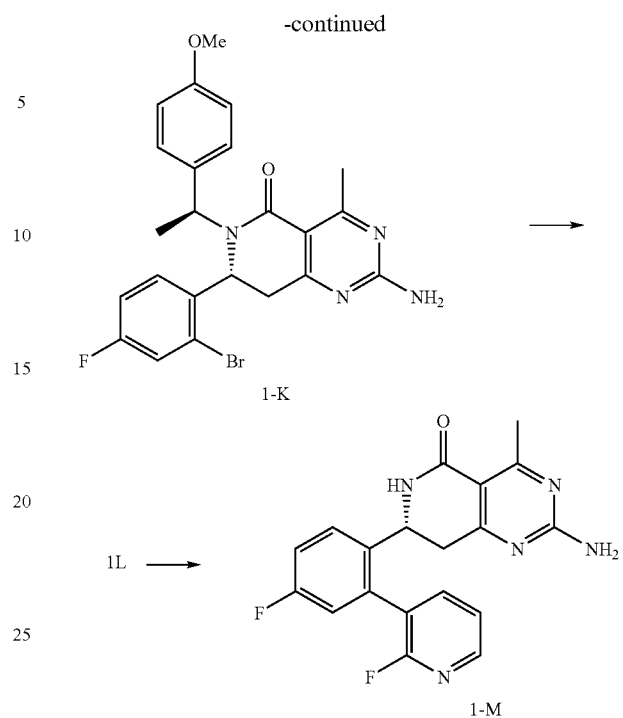

In another aspect, certain compounds of the invention can be prepared as shown in Scheme 2. Condensation of an appropriate amine such as methyl amine with oxalic acid and a desired aldehyde such as 2-A in refluxing ethanol results in formation of acid 2-B, that is next converted to the corresponding ester 2-C under esterification conditions such as with thionyl chloride in an appropriate alcoholic solvent at 0° C. Formation of acetoamide 2-E is accomplished by treatment of the 2-C ester with diketene 2-D. Subsequent cyclization of 2-D in the presence of base such as sodium methoxide and with microwave heating produces lactam 2-F. Aminopyridine formation is accomplished in two steps, the first being formation of an intermediate enamine by heating the lactam in an ethanolic solution of pyrrolidine under microwave conditions and secondly, addition of guanidine-HCl to this solution followed by additional microwave heating. Isolation of the aminopyrimidine 2-G by reverse phase HPLC followed by coupling with an appropriate arylboronic acid under Suzuki conditions and microwave heating gives the biaryl compound 2-H.

Scheme 2.

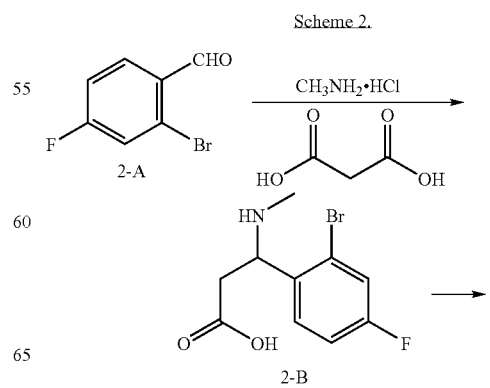

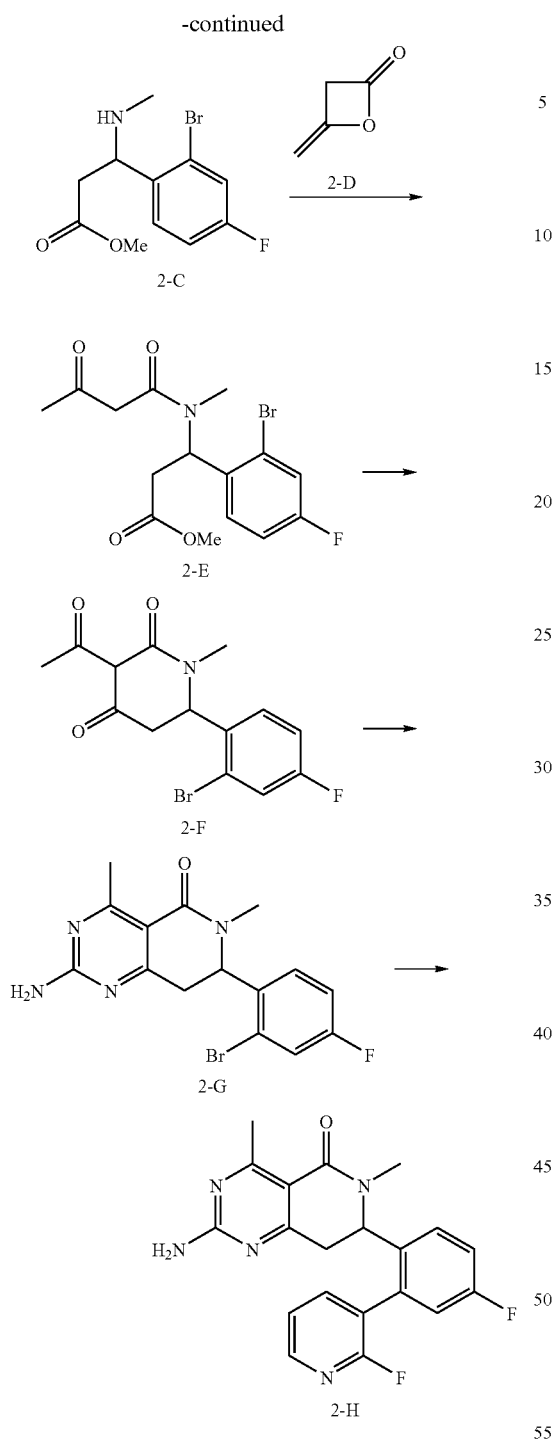
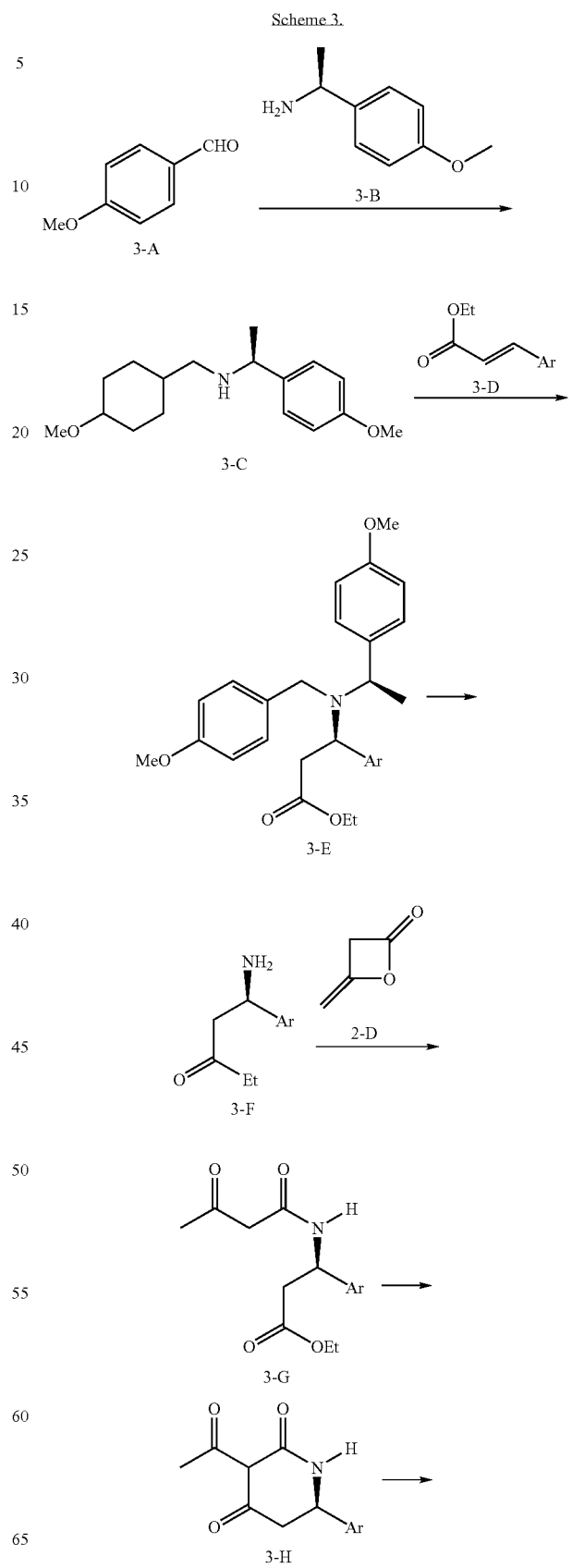

Scheme 3 shows another means for synthesizing certain compounds of the invention. Reductive amination of p-anisole 3-A with (S)-1-(4-methoxyphenyl)ethanamine 3-B and sodium borohydride over molecular sieves gives amine 3-C. Subsequent formation of the amine anion such as by reacting 3-C with n-butyl lithium and treatment with the appropriate cinnamate ester 3-D gives the conjugate addition product 3-E. Deprotection with trifluoroacetic acid gives amine 3-F that can be converted to 3-I following the steps shown in the Scheme 2 and described above.

-continued

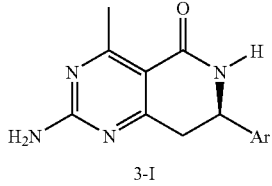

3-I

In one embodiment, provided is a method of preparing a compound of formula (I), comprising
(a) reacting a compound of formula (I) with an acid to form an acid addition salt; or
(b) reacting an acid addition salt of formula (I) to form a free base compound of formula (I); or
(c) reacting an intermediate compound of formula (VI) with guanidine or a guanidine derivative

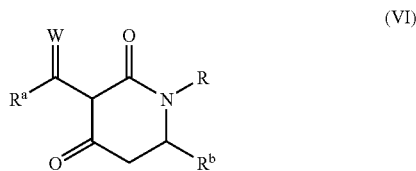
(VI)

wherein $R^a$, R, and $R^b$ are as defined for formula (I) and W is O or NR'R" where R' and R" are independently H or alkyl to form a compound of formula (I).

In one embodiment, provided is an intermediate compound of formula (VI). In one aspect, $R^a$ is methyl. In another aspect, the intermediate compound of formula (VI) is a compound of formula (VII)

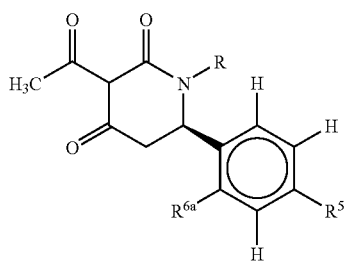
(VII)

wherein
R is as defined for formula (VI);
$R^5$ is hydrogen or halo; and
$R^{6a}$ is selected from the group consisting of halo, substituted or unsubstituted aryl, and substituted or unsubstituted heteroaryl.

In some embodiments of the compounds of formula (VI) or (VII), R is selected from the group consisting of hydrogen, unsubstituted alkyl, and substituted alkyl. In some such embodiments, R is selected from the group consisting of methyl, ethyl, allyl, 3-methyl-butyl, and isobutyl. In other embodiments, R is selected from the group consisting of hydrogen, benzyl, 1-(4-methoxyphenyl)ethyl, methyl, 3-aminopropyl, and 2-methyl-2-morpholinopropyl. In still other embodiment, R is hydrogen.

In some embodiments, $R^5$ is halo. In some aspects $R^5$ is fluoro.
In other embodiments $R^5$ is hydrogen.
In some embodiments, $R^{6a}$ is halo. In some aspects $R^{6a}$ is bromo.
In some embodiments $R^5$ and $R^{6a}$ are both halo. In other embodiments Rs is fluoro and $R^{6a}$ is bromo.
In some embodiments $R^{6a}$ is selected from the group consisting of substituted aryl and substituted heteroaryl wherein said aryl and heteroaryl is selected from the group consisting of furanyl, pyrrolyl, phenyl, pyridyl, pyrazinyl, pyrimidinyl, pyridazinyl, pyrazolyl, imidazolyl, triazolyl, indolyl, oxadiazole, thiadiazole, quinolinyl, isoquinolinyl, isoxazolyl, oxazolyl, thiazolyl, and thienyl.
In some embodiments, $R^{6a}$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol-4-yl, 2-(5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-aminocarbonylphenyl, 2-amino-pyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethylphenyl, 2-ethoxy-thiazol-4-yl, 2-fluoro-3-methoxy-phenyl, 2-fluoro-3-methylphenyl, 2-fluoro-4-methyl-phenyl, 2-fluoro-5-methoxy-phenyl, 2-fluoro-5-methylphenyl, 2-fluorophenyl, 2-fluoro-pyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethoxy-phenyl, 3,4-dimethoxy-phenyl, 3,5-dimethylisoxazol-4-yl, 3,6-dimethyl-pyrazin-2-yl, 3-acetamidophenyl, 3-aminocarbonylphenyl, 3-bromo-phenyl, 3-chloro-pyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6-methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxy-pyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-amino-6-methoxy-pyridin-2-yl, 5-chloro-4-methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6-ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2-yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy) pyrazin-2-yl, and 6-trifluoromethyl-pyridin-2-yl.

In another embodiment the guanidine derivative is acetyl guanidine.

In another embodiment, provided is a use of compound of formula (VI) or (VII) for the manufacture of a compound of formula (I).

The present invention will be understood more readily by reference to the following examples, which are provided by way of illustration and are not intended to be limiting of the present invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LC/MS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 4° C.) or a Hewlett Packard System (Series 1100 HPLC; Column: Eclipse XDB-C18, 2.1×50 mm; solvent system: 1-95% acetonitrile in water with 0.05%TFA; flow rate 0.4 mL/min; molecular weight range 150-850; cone Voltage 50 V; column temperature 3° C.). All masses were reported as those of the protonated parent ions.

GCMS analysis is performed on a Hewlett Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.)

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine, and triethyl amine. Typical solvents employed for the reverse phase HPLC were varying concentrations of acetonitrile and water with 0.1% trifluoroacetic acid.

| The following are abbreviations used in the examples: | |
|---|---|
| aq.: | Aqueous |
| Boc: | tert-Butoxycarbonyl |
| BSA: | bovine serum albumin |
| Celite | Diatomaceous earth |
| DCM: | Dichloromethane |
| eq.: | equivalent |
| $Et_3N$: | Triethylamine |
| EtOAc: | Ethyl acetate |
| GC | Gas Chromatography |
| h: | hour |
| HPLC: | High performance liquid chromatography |
| $IC_{50}$ value: | The concentration of an inhibitor that causes a 50% reduction in a measured activity. |
| L: | liter |
| LC/MS: | Liquid chromatography/mass spectrometry |
| LRMS: | Low resolution mass spectrometry |
| MeOH: | Methanol |
| min: | minute |
| mL: | milliliter |
| mm: | millimeter |
| mM: | millimolar |
| mmol: | millimole |
| nm: | Nanometer |
| NMP: | N-Methylpyrrolidone |
| RP-HPLC: | Reversed-phase high-performance liquid chromatography |
| rt | room temperature |
| sat: | Saturated |
| THF: | Tetrahydrofuran |
| TMS: | Trimethylsilane |
| TLC: | Thin layer chromatography |
| TRF: | Time resolved fluorescence. |

Nomenclature for the compounds disclosed in this application was provided using ACD Name version 5.07 software (Nov. 14, 2001) or ACD Name Batch version 5.04 (May 28, 2002) available from Advanced Chemistry Development, Inc., or by using AutoNom 2000 (Automatic Nomenclature) for ISIS/Base, implementing IUPAC standardized nomenclature. Other compounds, intermediates, and starting materials were named using standard IUPAC nomenclature.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the above disclosure.

The following examples illustrate methods for making representative compounds of the invention.

Example 1

Representative Procedures for Compounds of the Invention

Step A: α,β-Unsaturated Ester

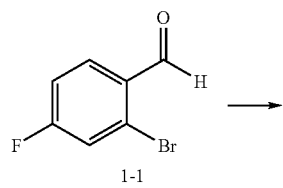

-continued

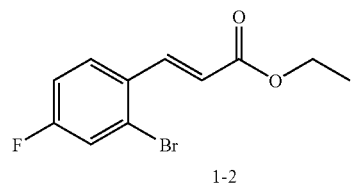

n-Butyllithium (84 mmol) was added dropwise to a stirred solution of triethylphosphono acetate (88 mmol) in dry THF (176 mL) at −78° C. under $N_2$. The solution was left to stir for 30 min. keeping inner temperature below −70° C. The phosphonate solution was transferred via cannula to a solution of 2-bromo-4-fluorobenzaldehyde 1-1 (80 mmol) in THF (160 mL) at −78° C. under $N_2$. The resulting solution was warmed to room temperature over 2 h. The reaction mixture was quenched by adding aqueous $NH_4Cl$ and then extracted with EtOAc (×3). The organics were combined, washed with $H_2O$ (×3), sat. brine (×3), then dried ($Na_2SO_4$), filtered, and evaporated under reduced pressure to give pale yellow oil. White crystals formed after cooling in refrigerator. The crystals were filtered and washed with methanol to provide the pure compound 1-2. The mother liquor was concentrated, cooled and filtered. This process was repeated until most of the theoretical yield of E-ethyl 3-(2-bromo-4-fluorophenyl)acrylate was collected as a white crystals.

Step B: Conjugate Addition of Asymmetric Amine to α,β-Unsaturated Ester

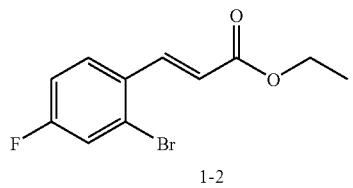

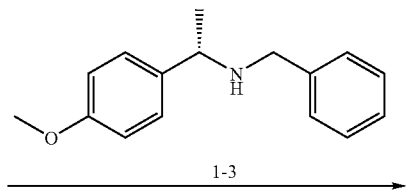

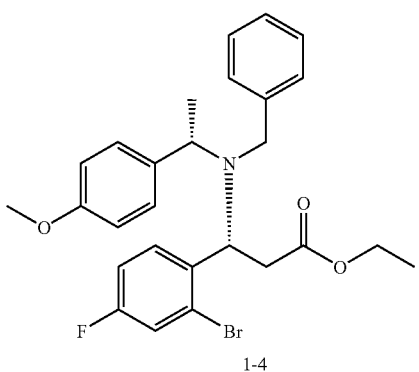

To a stirred solution of (S)-N-benzyl-1-(4-methoxyphenyl) ethanamine 1-3 (58 mmol) in dry THF (116 mL) was added compound 1-2. The reaction was cooled to -78° C., and n-butyl lithium (56.2 mmol) was added dropwise at −78° C. under $N_2$. After addition, the reaction mixture was stirred at −78° C. for 40 min. Then the reaction mixture was partitioned between aqueous $NH_4Cl$, and EtOAc, extracted with EtOAc (×3), the organics separated, then washed with $H_2O$ (×3), sat. brine (×3), then dried ($Na_2SO_4$), filtered, and evaporated under reduced pressure to give crude oil, which was then purified on silica gel column (hexane/EtOAc) to provide compound 1-4.

Step C: CAN (Ceric Ammonium Nitrate) Deprotection

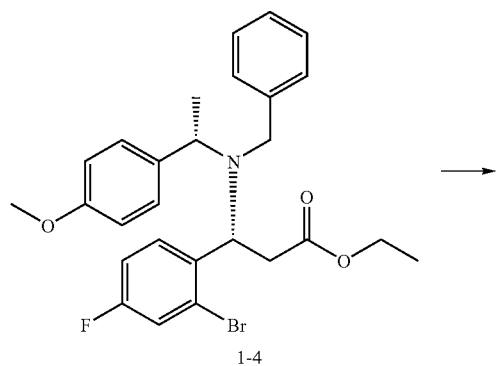

1-4

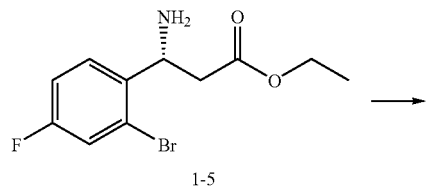

1-5

The starting material 1-4 (81.78 mmol) was dissolved in acetonitrile:water (5:1, 1.6 L). While stirring CAN (490.68 mmol) compound 1-4 was added in three separate portions stirring for 1 h between each addition. The reaction was then allowed to stir overnight at room temperature. Next, the acetonitrile was removed under vacuum, and the remaining aqueous layer was extracted (4×400 mL) with EtOAc. The EtOAc layers were combined, dried over sodium sulfate, filtered, and concentrated to yield the crude product compound 1-5. The crude product was purified using a flash column (5% MeOH in DCM).

Step D: Acylation

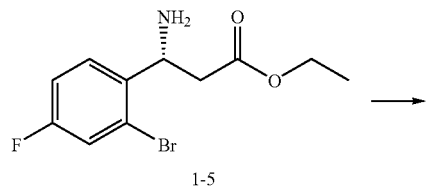

1-5

-continued

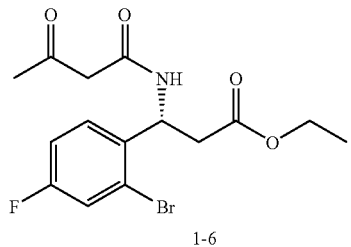

1-6

To a stirred solution of free amine 1-5 (5.27 mmol) in DCM (26 mL) was added triethyl amine (21.08 mmol) and diketene (6.33 mmol) at room temperature. The reaction was stirred until judged complete by LCMS. Then the mixture was partitioned between DCM and aqueous $NaHCO_3$, extracted with DCM (×3), the organic layers were combined, then washed with $H_2O$ (×3), sat. brine (×3), then dried ($Na_2SO_4$), filtered, and evaporated under reduced pressure to give crude oil, which was then purified on silica gel column (hexane/EtOAc) to provide compound 1-6.

Step E: Cyclization

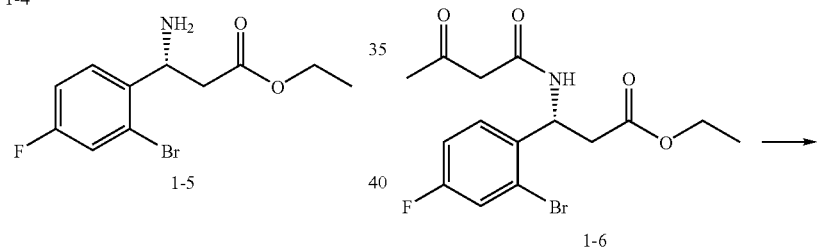

1-6

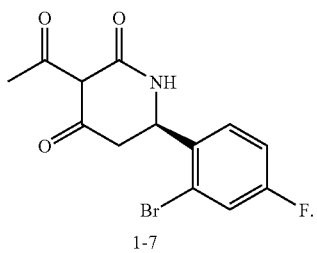

1-7

To the reaction vial containing compound 1-6 (1.1 mmol) in methanol (5 mL) was added 25% NaOMe in MeOH (0.5 mL). The reaction mixture was heated in the microwave at 144° C. for 5 min. After cooling to room temperature, the reaction mixture was diluted with aqueous ammoinium choride, washed with DCM (×3), then washed with $H_2O$ (×3), sat. brine (×3), then dried ($Na_2SO_4$), filtered, and evaporated under reduced pressure to give crude product, piperidine-dione 1-7, which was used directly in the next step.

Step F: Amino-Pyrimidine-Lactam

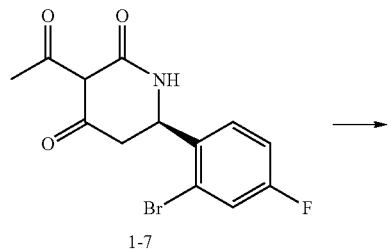

1-7

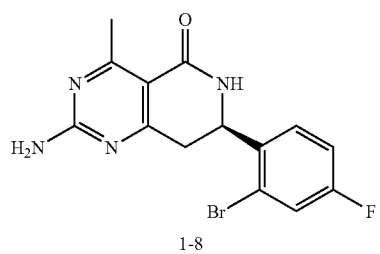

1-8

To the mixture of piperidindione 1-7 (0.915 mmol) and guanidine HCl (4.573 mmol) in ethanol (9 mL) was added pyrrolidine (18.3 mmol). The reaction mixture was treated in microwave (PowerMAX setting) at 160° C. for 10 min. After cooling to room temperature, the reaction mixture was extracted with DCM (×3), then washed with H$_2$O (×3), sat. brine (×3), then dried (Na$_2$SO$_4$), filtered, and evaporated under reduced pressure to give crude product 1-8, which was then purified on silica gel column (EtOAc).

Step G: Suzuki Coupling

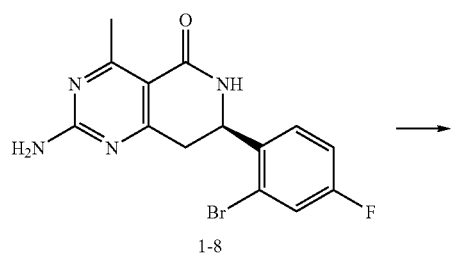

1-8

-continued

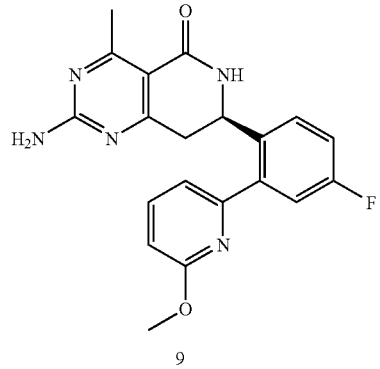

9

To the mixture of amino-pyrimidine-lactam 1-8 (1 eq.), boronic acid or ester (4 eq.) in DMA was added Pd(dppf)$_2$Cl$_2$ (0.4 eq.) and 2 M K$_2$CO$_3$ (8 eq). The reaction mixture was treated in microwave at 120° C. for 15 min. After cooling down to room temperature the reaction mixture was diluted with DCM (×3), washed with H$_2$O (×3), sat. brine (×3), then dried (Na$_2$SO$_4$), filtered, and evaporated under reduced pressure to give crude product, which was then purified reverse-phase prep HPLC to give the pure HSP90 inhibitor.

Example 2

Synthesis of Representative N-Alkylated Compounds of the Invention

Step A: Reductive Amination

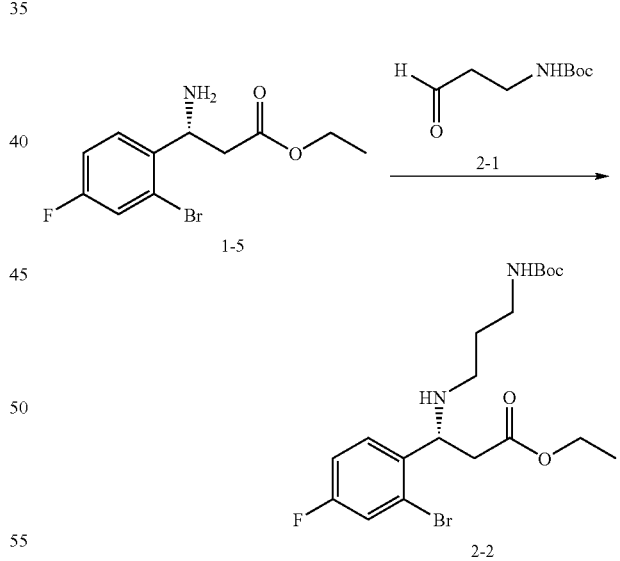

To a stirred solution of free amine 1-5 (1 eq.), aldehyde 2-1 (1 eq.) in DCM was added sodium triacetoxyborohydride (1.1 eq.) at room temperature. The reaction was stirred at room temperature until judged complete by LCMS. Then the mixture was partitioned between DCM and aqueous NaHCO$_3$, extracted with DCM (×3) and the organics combined, then washed with H$_2$O (×3), sat. brine (×3), then dried (Na$_2$SO$_4$), filtered, and evaporated under reduced pressure to give crude product, compound 2-2, which was used directly for the next reaction.

Steps B-E: Acylation, Cyclization, Amino-Pyrimidine-Lactam Formation, Suzuki Coupling

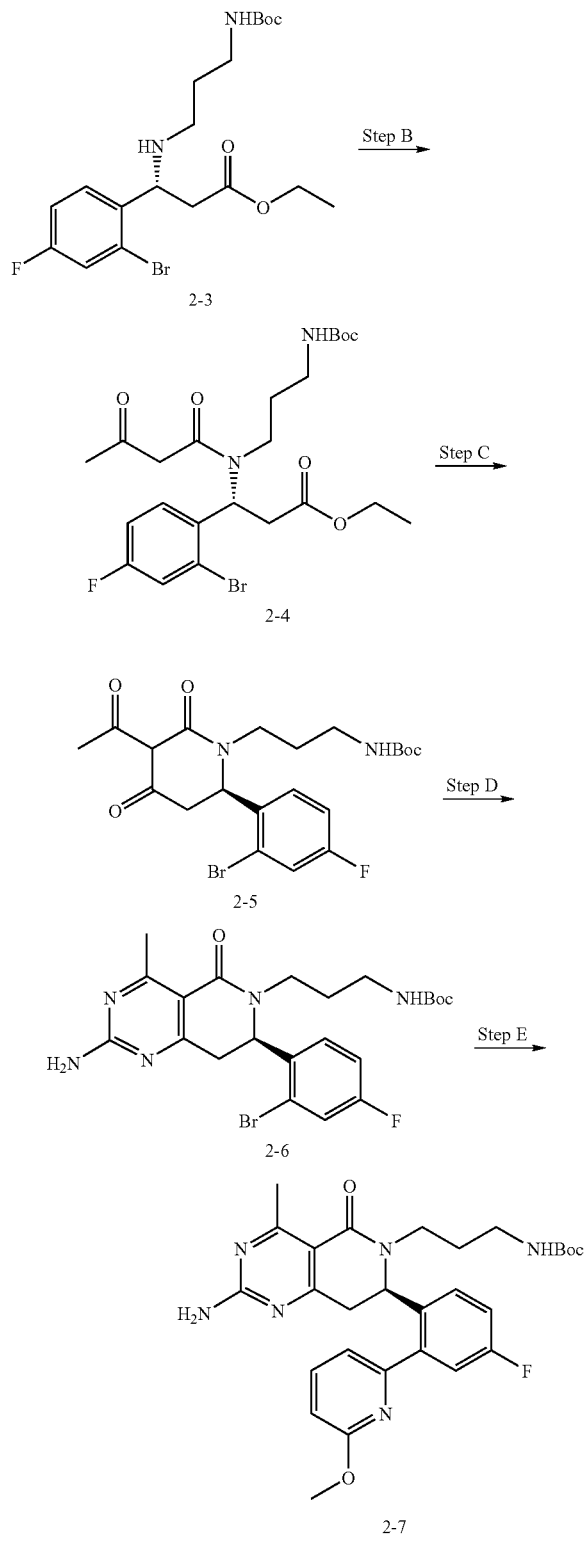

Step B to Step E were the same as Step E to Step G in Example 1.

Step F: Deprotection

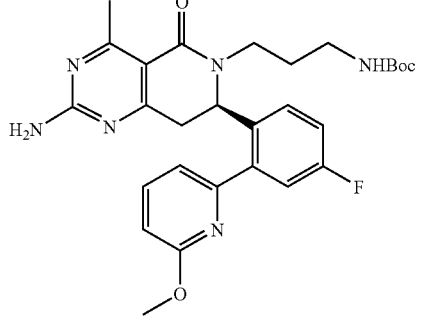

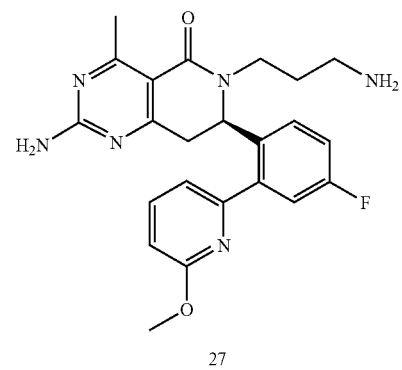

To the solution of Boc-protected N-alkylated lactam in DCM was treated with 50% TFA. The reaction mixture was stirred at room temperature. After completion, the reaction mixture was concentrated and purified on reverse phase prep HPLC to give the pure compound.

Other alkylated amine compounds of the invention were prepared in a similar manner.

Example 3

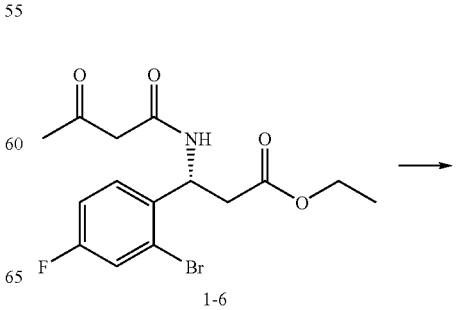

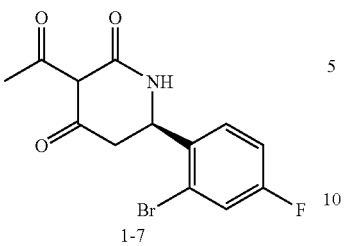

1-7

A mixture of sodium methoxide (25% by wt in methanol, 0.193 mol), methyl acetate (0.0644 mole) and 100 mL anhydrous methanol was stirred at room temperature under nitrogen for one hour. Then, neat amide 1-6 (24.1 g, 0.0644 mol) was added. The reaction was refluxed under nitrogen for one hour and then solvent were distilled out gradually until the internal temperature reached 85° C. The reaction was monitored with HPLC until 1-6 was completely consumed. Reaction was cooled to room temperature and remaining solvent was removed under reduced pressure. The residue was dissolved in 100 mL water and then cooled to 5° C. in an ice/water bath. To this solution was then added 1N HCl until pH=1, during which the internal temperature was maintained below 10° C. The mixture was stirred until a smooth suspension formed and then was filtered. The collected solids were washed with water (100 mL×3) and air-dried overnight to give 20.7 g of lactam 1-7 as a slightly yellowish solid with a yield of 98.1% and purity of 98.3% (HPLC area ratio).

Example 4

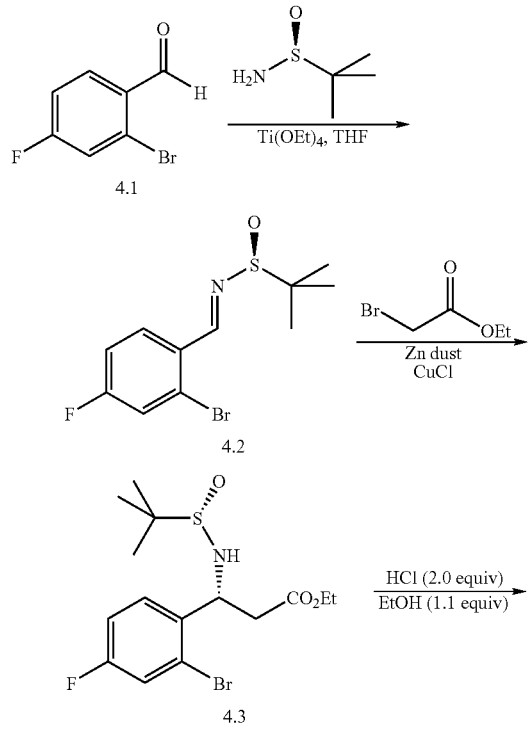

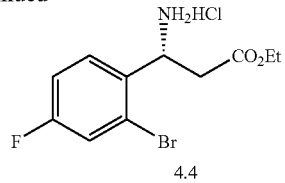

4.4

Step 1:

A 500 mL round-bottom flask was charged with dry THF (50 mL), titanium ethoxide (41 mL), (S)-(−)-tert-butanesulfinamide (Advanced Asymmetrics, 12.0 g, 99.1 mmol, 1.1 equiv), and 2-bromo-4-fluorobenzaldehyde 4.1 (Matrix Scientific, cat. # 011279, 18.2 g, 90.1 mmol, 1.0 equiv). The resulting reaction mixture was stirred under $N_2$ at rt for 4 h. Upon reaction completion as monitored by LCMS, the reaction mixture was diluted with EtOAc (360 mL), and a mixture of brine (200 mL) with celite was added with vigorous stirring. The resulting emulsion was filtered through a pad of celite and washed with EtOAc (200 mL). The filtrate was transferred to a seperatory funnel, and the aqueous layer removed. The organics were washed with brine (200 mL), then dried ($Na_2SO_4$) and concentrated in vacuo to afford 4.2 as a yellowish oil that may solidify upon standing (26.5 g, 86.3 mmol, 96%). $^1$H NMR (300 MHz, $CD_3Cl$) δ 8.86 (s, 1H), 8.03 (m, 1H), 7.35 (m, 1H), 7.11 (m, 1H), 1.11 (s, 9H) LCMS m/z 307.9 (MH$^+$), $t_R$=3.22 min.

Step 2:

A three-necked 100 mL round-bottom flask, reflux condensor, and addition funnel were oven-dried overnight. Upon removal from the oven, they were assembled and put under positive $N_2$ pressure and cooled to room temperature. The flask was charged with Zn dust (21.3 g, 326.0 mmol, 15.0 equiv), CuCl (32.6 g, 32.6 mmol, 1.5 equiv), and dry THF (60 mL). The resulting reaction mixture was heated to reflux temperature (bath temperature approximately 90° C.) and stirred vigorously with an overhead stirrer for 30 min. The reaction was removed from the oil bath (maintaining vigorous stirring) and the addition funnel was then charged with ethylbromoacetate (3.6 mL, 32.6 mmol, 1.5 equiv) and dry THF (30 mL). Addition of the ethylbromoacetate should be done at a rate to maintain gentle refluxing of the reaction mixture. Once addition is complete, the reaction mixture was stirred for an additional 20 min, then heated to 50° C. for 30 min. The reaction mixture was then cooled to 0° C., and the addition funnel charged with 4.2 (6.60 g, 21.5 mmol, 1.0 equiv) and dry THF (20 mL). This solution was then added dropwise to the reaction mixture, which was stirred an additional 4 hours at 0° C. Once the reaction has gone to completion as judged by LCMS, the reaction mixture was filtered through a pad of celite, washing the Zn and the filter pad with $Et_2O$ (2×100 mL). The filtrate was washed with 0.25 M citric acid (200 mL), sat. $NaHCO_{3(aq)}$ (2×200 mL), dried ($Na_2SO_4$), and concentrated in vacuo to afford 4.3 (7.30 g, 18.4 mmol, 86%) as a clear oil.: $^1$H NMR (300 MHz, $CD_3Cl$) δ 7.39 (m, 1H), 7.28 (m, 1H), 7.01 (m, 1H), 5.14 (m, 1H), 4.92 (d, J=5.4, 2H), 4.1 (m, 2H), 2.90 (ddd, $J_1$=, $J_2$=, $J_3$=, 2H), 1.22 (m, 3H, 9H). LCMS m/z 396.0 (MH$^+$), $t_R$=2.96 min. HPLC (frac_10 min_2070% B), $t_R$=4.108 (major diastereomer), $t_R$=3.962 (Claisen condensation byproduct) $t_R$=3.888 (minor diastereomer), 95.5:2.1:2.1. de=96%.

Step 3:

A 500 mL round-bottom flask was charged with 4.3 (7.30 g, 18.4 mmol, 1.0 equiv), Et$_2$O (37 mL), EtOH (1.2 mL, 1.1 equiv) and 4M HCl in Et$_2$O (37 mL, 2.0 equiv). The reaction mixture was stirred at room temperature for 30 minutes. The resulting suspension was filtered and the solids triturated with Et$_2$O (3×40 mL) and hexanes (2×40 mL). The solid was dried under vacuum to afford 4.4 as a white solid (5.23 g, 15.2 mmol, 83%). $^1$H NMR (300 MHz, CD$_3$OD) δ 7.61 (m, 2H), 7.33 (m, 1H), 5.18 (m, 1H), 4.85 (bs, 3H), 4.13 (q, J=7.2, 2H), 3.15 (ddd, 2H), 1.22 (t, J=7.5, 3H) LCMS m/z 292.0 (MH$^+$), $t_R$=1.97 min. To free base the HCL salt, 4.4 (50 mg) was dissolved in EtOAc (20 mL) and washed with 10% Na$_2$CO$_3$ (3×20 mL). The organics were dried (Na$_2$SO$_4$) and concentrated in vacuo to afford the free base. A racemic mixture of the final β-amino ester product was prepared and analyzed by chiral HPLC to confirm separation of the enantiomers (Chiralpak AD column, 1 mL/min, S, $t_R$=5.84; R, $t_R$=7.47 min)

Example 5

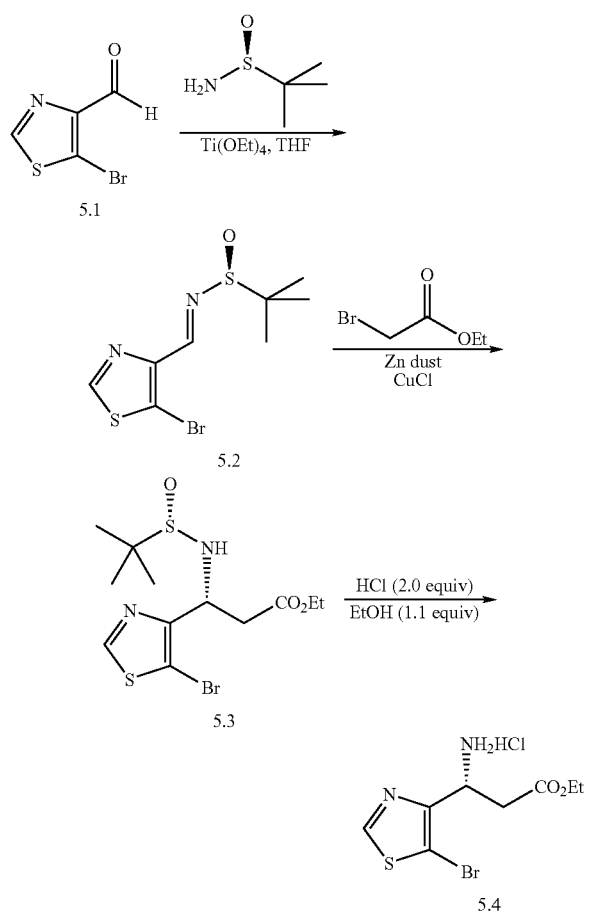

Step 1:

A 250 mL round-bottom flask was charged with dry THF (54 mL), titanium ethoxide (18.25 g, 3 equiv), (S)-(−)-tert-butanesulfinamide (4.85 g, 1.5 equiv), and 5-bromothiazole-4-carbaldehyde 5.1 (5.12 g, 1.0 equiv). The resulting reaction mixture was stirred under N$_2$ at rt. Upon reaction completion as monitored by LCMS, the reaction mixture was diluted with EtOAc (360 mL), and a mixture of brine (200 mL) with celite was added with vigorous stirring. The resulting emulsion was filtered through a pad of celite and washed with EtOAc (200 mL). The filtrate was transferred to a seperatory funnel, and the aqueous layer removed. The organics were washed with brine (200 mL), then dried (Na$_2$SO$_4$) and concentrated in vacuo to afford 5.2 as a yellowish oil (7.9 g, 100%). $^1$H NMR (300 MHz, CD$_3$Cl) 67 8.88 (s, 1H), 8.72 (s, 1H), 1.21 (s, 9H) LCMS m/z 296.9 (MH$^+$), $t_R$=2.35 min.

Step 2:

A three-necked 100 mL round-bottom flask, reflux condensor, and addition funnel were oven-dried overnight. Upon removal from the oven, they were assembled and put under positive N$_2$ pressure and cooled to room temperature. The flask was charged with Zn dust (25.4 g, 400.0 mmol, 15.0 equiv), CuCl (3.96 g, 40.mmol, 1.5 equiv), and dry THF (80 mL). The resulting reaction mixture was heated to reflux temperature (bath temperature approximately 90° C.) and stirred vigorously with an overhead stirrer for 30 min. The reaction was removed from the oil bath (maintaining vigorous stirring) and the addition funnel was then charged with ethylbromoacetate (6.68 g, 40 mmol, 1.5 equiv) and dry THF (40 mL). Addition of the ethylbromoacetate should be done at a rate to maintain gentle refluxing of the reaction mixture. Once addition is complete, the reaction mixture was stirred for an additional 30 min, then heated to 50° C. for 30 min. The reaction mixture was then cooled to 0° C., and the addition funnel charged with 5.2 (26.67 mmol, 1.0 equiv) and dry THF (27 mL). This solution was then added dropwise to the reaction mixture, which was stirred an additional 4 hours at 0° C. Once the reaction has gone to completion as judged by LCMS, the reaction mixture was filtered through a pad of celite, washing the Zn and the filter pad with Et$_2$O (2×100 mL). The filtrate was washed with 0.25 M citric acid (200 mL), sat. NaHCO$_{3(aq)}$ (2×200 mL), dried (Na$_2$SO$_4$), and concentrated in vacuo to afford 5.3 (10 g) as a clear oil.

Step 3:

A 500 mL round-bottom flask-was charged with 5.3 (10 g, 26.67 mmol, 1.0 equiv), Et$_2$O (27 mL), EtOH (1.7 mL) and 4M HCl in Et$_2$O (53 mL, 2.0 equiv). The reaction mixture was stirred at room temperature for 30 minutes. The resulting suspension was filtered and the solids triturated with Et$_2$O (3×40 mL) and hexanes (2×40 mL). The solid was dried under vacuum to afford 5.4 as a white solid (6.6 g, 88.7%). LCMS m/z 280.9 (MH$^+$), $t_R$=1.63 min.

Example 6

Preparation of (R)-2-amino-7-(2-(cyclopentyloxy)-4-fluorophenyl)-4-methyl-7,8-dihydropyrido[4,3-d]pyrimidin-5(6H)-one

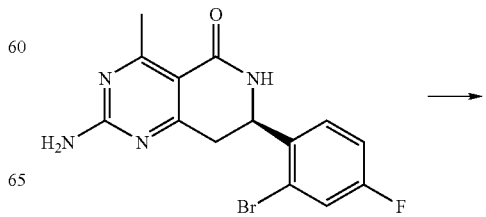

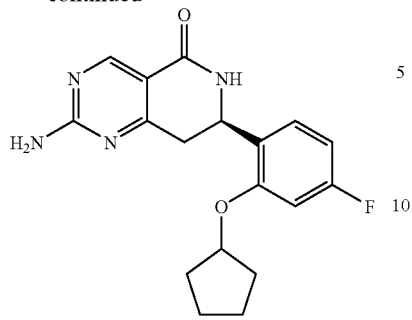

A microwave vial was charged with (R)-2-amino-7-(2-bromo-4-fluorophenyl)-4-methyl-7,8-dihydropyrido[4,3-d]pyrimidin-5(6H)-one, cesium carbonate (2 eq), copper (I) iodide (10 mol %), 1,10-phenanthroline (20 mol %), and cyclopentanol. The reaction mixture was heated with microwave irradiation to a temperature of 180° C. for 20 min. After cooling to RT, the reaction mixture was concentrated and purified by reverse phase HPLC to afford (R)-2-amino-7-(2-(cyclopentyloxy)-4-fluorophenyl)-4-methyl-7,8-dihydropyrido[4,3-d]pyrimidin-5(6H)-one (m/z=357 (M+H)).

Example 7

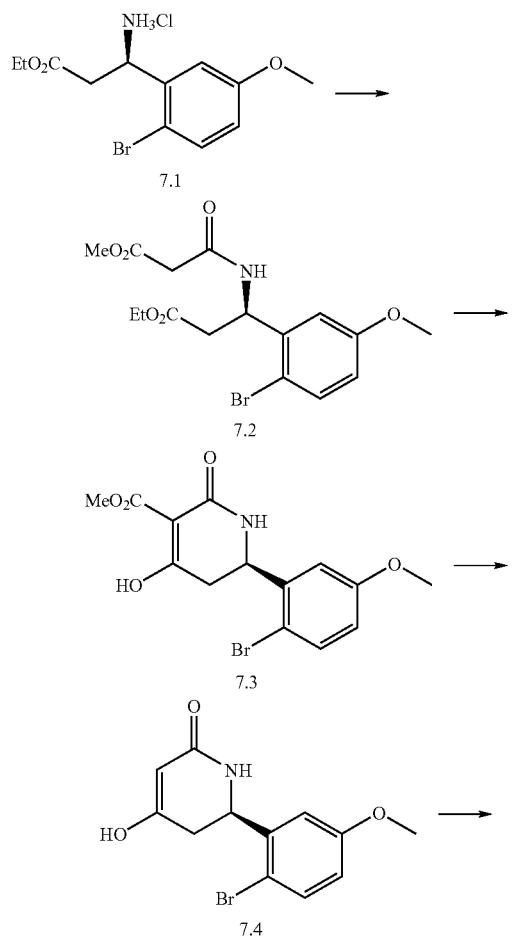

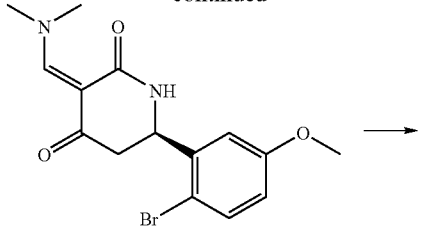

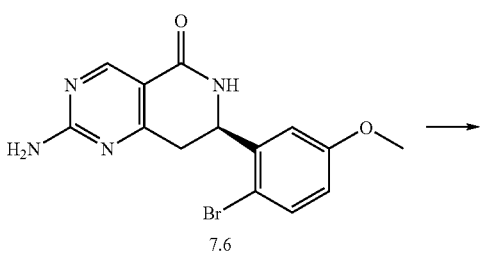

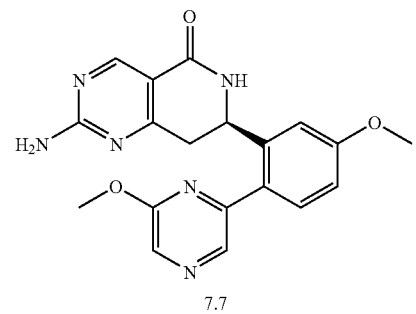

Aminoester hydrochloride 7.1 (prepared according to the general procedure of Example 1) was taken up in methylene chloride and the resulting solution was cooled to 0° C. Triethylamine (3 eq) was added followed by dropwise addition of methyl malonyl chloride (1.3 eq). The reaction was stirred for 2 h the partitioned between water and methylene chloride. The layers were separated and the organic layer was dried over anhydrous sodium sulfate and concentrated in vacuo to afford compound 7.2 in 71% yield.

Compound 7.2 was dissolved in methanol to which freshly prepared 4.2M sodium methoxide in methanol was added. The reaction vessel was sealed and heated for 10 min at 140° C. (microwave). The reaction mixture was cooled to room temperature and partitioned between 1M aqueous hydrochloric acid and methylene chloride. The organic and aqueous layers were separated and the organic layer was dried over anhydrous sodium sulfate and concentration in vacuo afforded compound 7.3 in 93% yield.

Compound 7.3 was taken up in acetonitrile containing 1% water. The reaction vessel was sealed and heated for 10 min at 120° C. (microwave). Concentration in vacuo provided compound 7.4 in a quantitative yield.

Compound 7.4 was taken up in dimethylacetamide dimethyl acetal and heated at 140° C. for 5 min. Cooling to room temperature and concentration in vacuo provided 7.5 as an orange solid, which was immediately taken up in a 5.0 M solution of dimethyl amine in ethanol. Acetyl guanidine (1.5 eq) was added and the resulting mixture was heated at 140° C. for 10 min. The crude reaction mixture was concentrated in vacuo and the resulting solid 7.6, used without purification.

Bromide 7.6 was taken up in a 1:1 mixture of dimethoxyethane and 2M aqueous sodium carbonate. Boronic acid 6-methoxy-pyrazin-2-yl boronic acid was added followed by Pd(dppf)Cl₂.CH₂Cl₂. The reaction mixture was heated at 120° C. for 10 min (microwave). After cooling to room temperature, the layers were separated and the organic layer was concentrated under a stream of nitrogen. Purification by reverse-phase HPLC afforded compound 7.7.

Example 8

Preparation of (R)-2-Amino-7-[5-(6-methoxy-pyrazin-2-yl)-thiazol-4-yl]-4-methyl-7,8-dihydro-6H-pyrido[4,3-d]pyrimidin-5-one

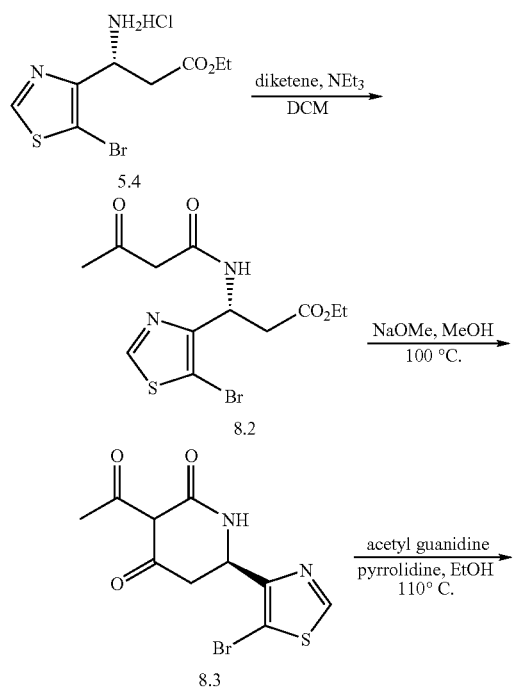

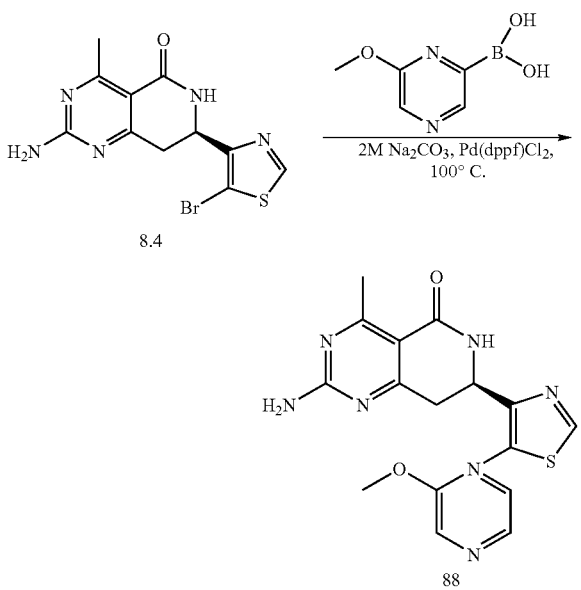

Compound 88 was prepared as shown above from 5.4, the synthesis of which is given in Example 5. Compound 5.4 is converted to 88 following the general procedure of Example 1 using the indicated reagents.

Example 9

Representative 2-amino-7,8-dihydro-6H-pyrido[4,3-d]pyrimidin-5-one Compounds

Representative 2-amino-7,8-dihydro-6H-pyrido[4,3-d]pyrimidin-5-one compounds are shown in Tables 1-5. In the tables, m/z refers to the molecular ion observed by mass spectrometry.

TABLE 1

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (µM) A ≧ 10 B < 10 |
|---|---|---|---|---|---|
| 1 | 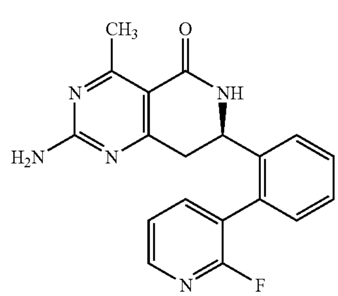 | (R)-2-Amino-7-[2-(2-fluoro-pyridin-3-yl)-phenyl]-4-methyl-7,8-dihydro-6H-pyrido[4,3-d]pyrimidin-5-one | 1.65 | 350.3 | B |

TABLE 1-continued

Representative 2-Amino-7,8-dihydro-6H-pyrido[4,3-d]pyrimidin-5-one Compounds.

| Cmpd. | Structure | Name | LC/MS $R_t$ (min) | observed m/z | IC50 (μM) A ≧ 10 B < 10 |
|---|---|---|---|---|---|
| 2 | 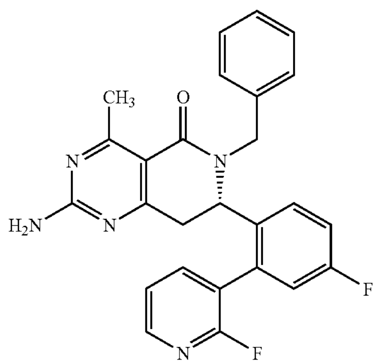 | (S)-2-Amino-6-benzyl-7-[4-fluoro-2-(2-fluoro-pyridin-3-yl)-phenyl]-4-methyl-7,8-dihydro-6H-pyrido[4,3-d]pyrimidin-5-one | 2.61 | 458.1 | A |
| 3 | 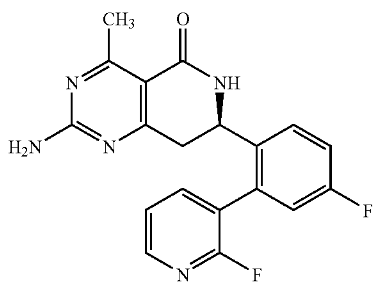 | (R)-2-Amino-7-[4-fluoro-2-(2-fluoro-pyridin-3-yl)-phenyl]-4-methyl-7,8-dihydro-6H-pyrido[4,3-d]pyrimidin-5-one | 1.73 | 368.1 | B |
| 4 | 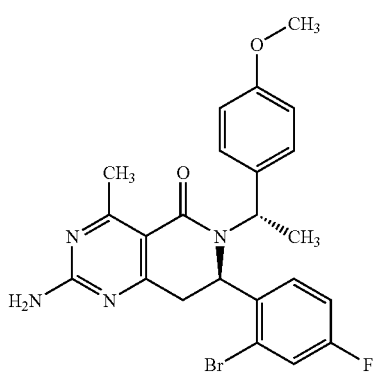 | (R)-2-Amino-7-(2-bromo-4-fluoro-phenyl)-6-[(S)-1-(4-methoxy-phenyl)-ethyl]-4-methyl-7,8-dihydro-6H-pyrido[4,3-d]pyrimidin-5-one | 2.61 | 485 | A |
| 5 | 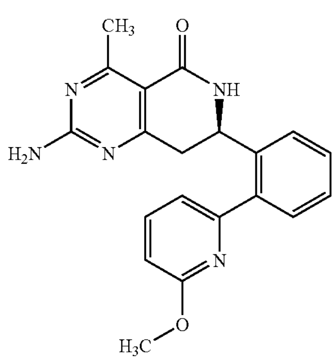 | (R)-2-Amino-7-[2-(6-methoxy-pyridin-2-yl)-phenyl]-4-methyl-7,8-dihydro-6H-pyrido[4,3-d]pyrimidin-5-one | 1.86 | 362 | B |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≥ 10 B < 10 |
|---|---|---|---|---|---|
| 6 | 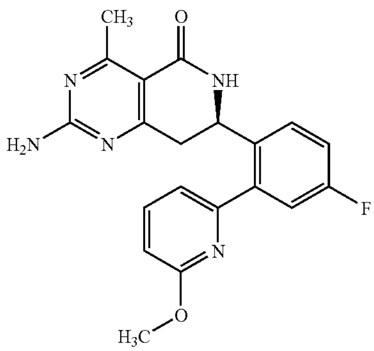 | (R)-2-Amino-7-[4-fluoro-2-(6-methoxy-pyridin-2-yl)-phenyl]-4-methyl-7,8-dihydro-6H-pyrido[4,3-d]pyrimidin-5-one | 2.07 | 380 | B |
| 7 | 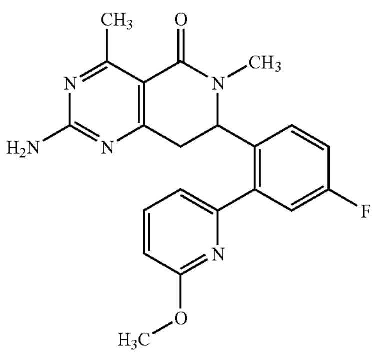 | 2-Amino-7-[4-fluoro-2-(6-methoxy-pyridin-2-yl)-phenyl]-4,6-dimethyl-7,8-dihydro-6H-pyrido[4,3-d]pyrimidin-5-one | 2.41 | 394.2 | B |
| 8 | 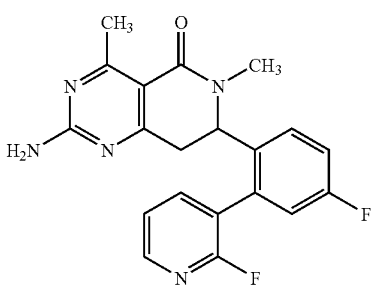 | 2-Amino-7-[4-fluoro-2-(2-fluoro-pyridin-3-yl)-phenyl]-4,6-dimethyl-7,8-dihydro-6H-pyrido[4,3-d]pyrimidin-5-one | 1.88 | 382 | B |
| 9 | 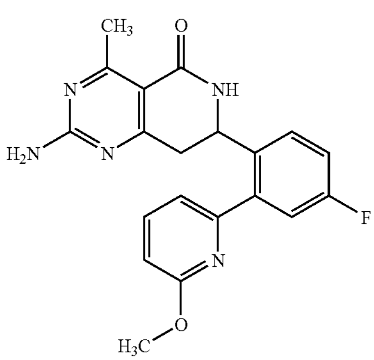 | 2-amino-7-[4-fluoro-2-(6-methoxypyridin-2-yl)phenyl]-4-methyl-7,8-dihydropyrido[4,3-d]pyrimidin-5(6H)-one | 1.97 | 380 | B |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≧ 10 B < 10 |
|---|---|---|---|---|---|
| 10 | 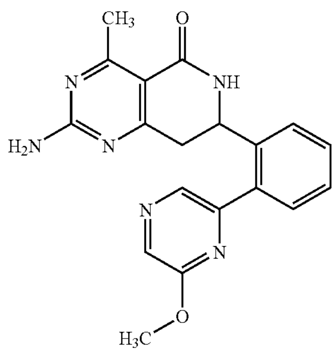 | 2-Amino-7-[2-(6-methoxy-pyrazin-2-yl)-phenyl]-4-methyl-7,8-dihydro-6H-pyrido[4,3-d]pyrimidin-5-one | 1.68 | 363 | B |
| 11 | 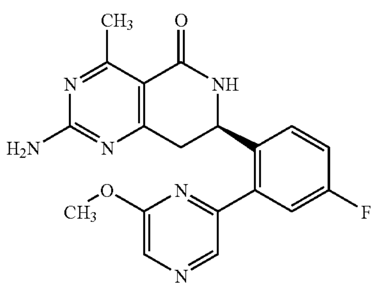 | (R)-2-Amino-7-[4-fluoro-2-(6-methoxy-pyrazin-2-yl)-phenyl]-4-methyl-7,8-dihydro-6H-pyrido[4,3-d]pyrimidin-5-one | 1.85 | 381.1 | B |
| 12 | 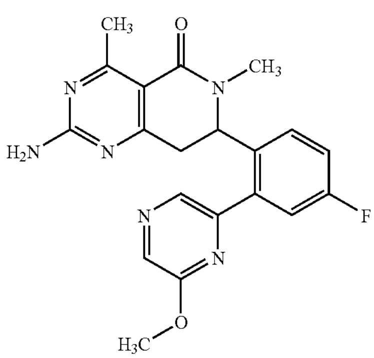 | 2-Amino-7-[4-fluoro-2-(6-methoxy-pyrazin-2-yl)-phenyl]-4,6-dimethyl-7,8-dihydro-6H-pyrido[4,3-d]pyrimidin-5-one | 2.19 | 395.1 | B |
| 13 | 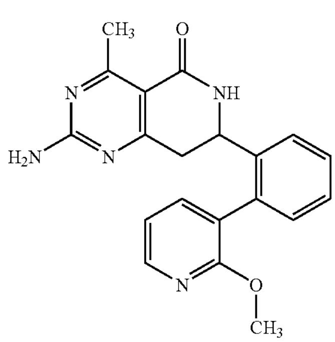 | 2-Amino-7-[2-(2-methoxy-pyridin-3-yl)-phenyl]-4-methyl-7,8-dihydro-6H-pyrido[4,3-d]pyrimidin-5-one | 2.01 | 362.1 | B |

TABLE 1-continued

Representative 2-Amino-7,8-dihydro-6H-pyrido[4,3-d]pyrimidin-5-one Compounds.

| Cmpd. | Structure | Name | LC/MS $R_t$ (min) | observed m/z | IC50 (μM) A ≥ 10 B < 10 |
|---|---|---|---|---|---|
| 14 | 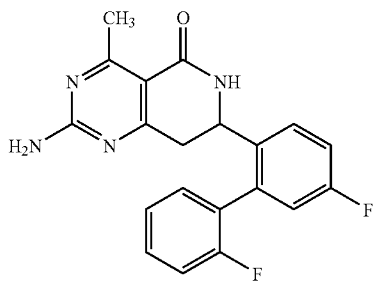 | 2-Amino-7-(5,2'-difluoro-biphenyl-2-yl)-4-methyl-7,8-dihydro-6H-pyrido[4,3-d]pyrimidin-5-one | 2.02 | 367.1 | B |
| 15 | 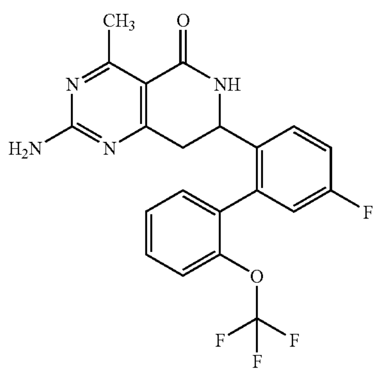 | 2-Amino-7-(5-fluoro-2'-trifluoromethoxy-biphenyl-2-yl)-4-methyl-7,8-dihydro-6H-pyrido[4,3-d]pyrimidin-5-one | 2.27 | 433.1 | B |
| 16 | 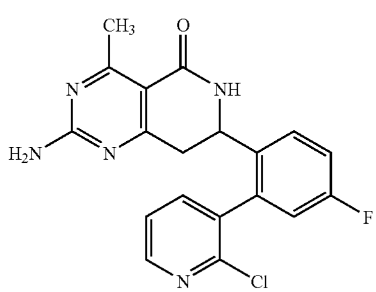 | 2-Amino-7-[2-(2-chloro-pyridin-3-yl)-4-fluoro-phenyl]-4-methyl-7,8-dihydro-6H-pyrido[4,3-d]pyrimidin-5-one | 1.75 | 384.1 | B |
| 17 | 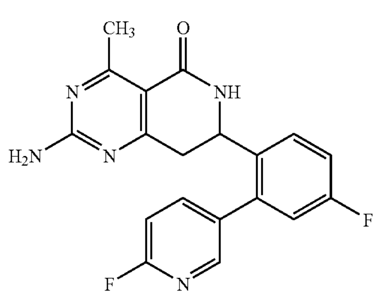 | 2-Amino-7-[4-fluoro-2-(6-fluoro-pyridin-3-yl)-phenyl]-4-methyl-7,8-dihydro-6H-pyrido[4,3-d]pyrimidin-5-one | 1.75 | 368.1 | B |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≧ 10 B < 10 |
|---|---|---|---|---|---|
| 18 | 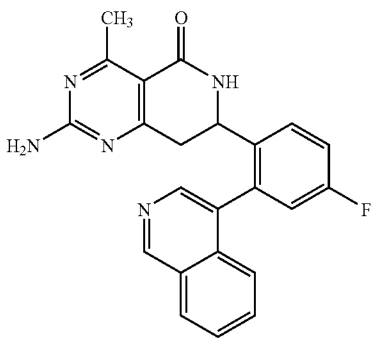 | 2-Amino-7-(4-fluoro-2-isoquinolin-4-yl-phenyl)-4-methyl-7,8-dihydro-6H-pyrido[4,3-d]pyrimidin-5-one | 1.46 | 400.1 | B |
| 19 | 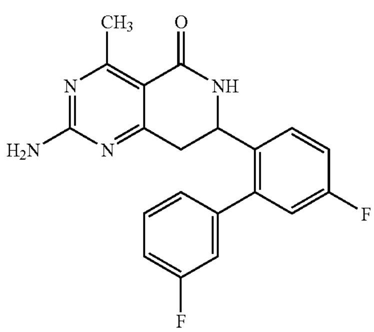 | 2-Amino-7-(5,3'-difluoro-biphenyl-2-yl)-4-methyl-7,8-dihydro-6H-pyrido[4,3-d]pyrimidin-5-one | 2.31 | 367.1 | B |
| 20 | 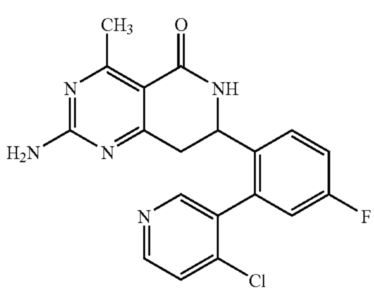 | 2-Amino-7-[2-(4-chloro-pyridin-3-yl)-4-fluoro-phenyl]-4-methyl-7,8-dihydro-6H-pyrido[4,3-d]pyrimidin-5-one | 2.09 | 384.1 | B |
| 21 | 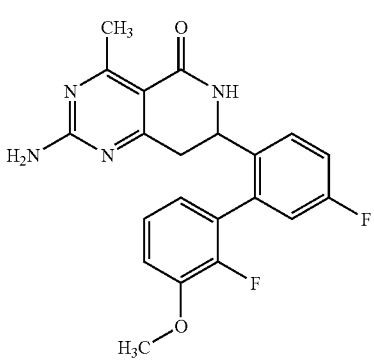 | 2-Amino-7-(5,2'-difluoro-3'-methoxy-biphenyl-2-yl)-4-methyl-7,8-dihydro-6H-pyrido[4,3-d]pyrimidin-5-one | 2.3 | 397.1 | A |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≥ 10 B < 10 |
|---|---|---|---|---|---|
| 22 | 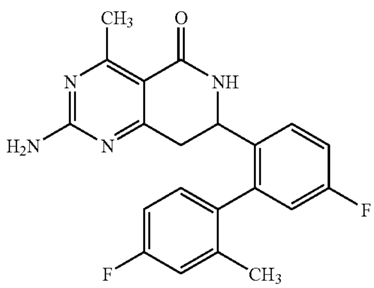 | 2-Amino-7-(5,4'-difluoro-2'-methyl-biphenyl-2-yl)-4-methyl-7,8-dihydro-6H-pyrido[4,3-d]pyrimidin-5-one | 2.44 | 381.1 | B |
| 23 | 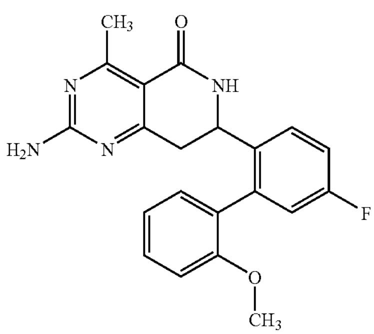 | 2-Amino-7-(5-fluoro-2'-methoxy-biphenyl-2-yl)-4-methyl-7,8-dihydro-6H-pyrido[4,3-d]pyrimidin-5-one | 2.29 | 379.1 | B |
| 24 | 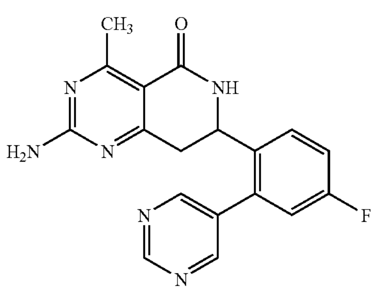 | 2-Amino-7-(4-fluoro-2-pyrimidin-5-yl-phenyl)-4-methyl-7,8-dihydro-6H-pyrido[4,3-d]pyrimidin-5-one | 1.66 | 351.1 | A |
| 25 | 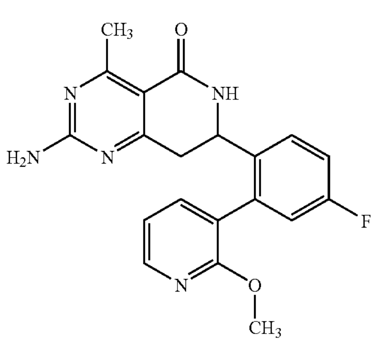 | 2-Amino-7-[4-fluoro-2-(2-methoxy-pyridin-3-yl)-phenyl]-4-methyl-7,8-dihydro-6H-pyrido[4,3-d]pyrimidin-5-one | 1.84 | 380 | A |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≧ 10 B < 10 |
|---|---|---|---|---|---|
| 26 | 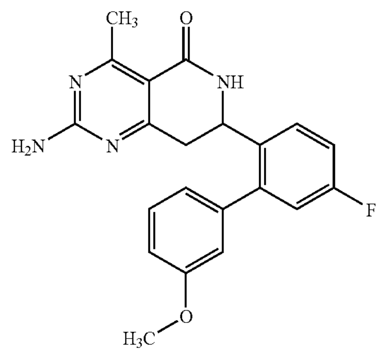 | 2-Amino-7-(5-fluoro-3'-methoxy-biphenyl-2-yl)-4-methyl-7,8-dihydro-6H-pyrido[4,3-d]pyrimidin-5-one | 2.11 | 379 | B |
| 27 | 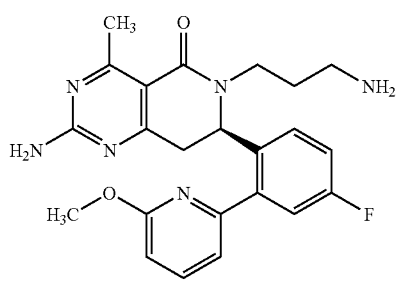 | (R)-2-Amino-6-(3-aminopropyl)-7-[4-fluoro-2-(6-methoxy-pyridin-2-yl)-phenyl]-4-methyl-7,8-dihydro-6H-pyrido[4,3-d]pyrimidin-5-one | 1.97 | 437.1 | B |
| 28 | 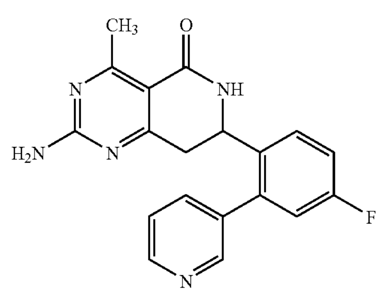 | 2-Amino-7-(4-fluoro-2-pyridin-3-yl-phenyl)-4-methyl-7,8-dihydro-6H-pyrido[4,3-d]pyrimidin-5-one | 1.24 | 350 | B |
| 29 | 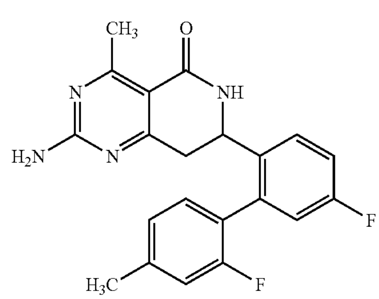 | 2-Amino-7-(5,2'-difluoro-4'-methyl-biphenyl-2-yl)-4-methyl-7,8-dihydro-6H-pyrido[4,3-d]pyrimidin-5-one | 2.43 | 381.1 | B |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (µM) A ≥ 10 B < 10 |
|---|---|---|---|---|---|
| 30 | 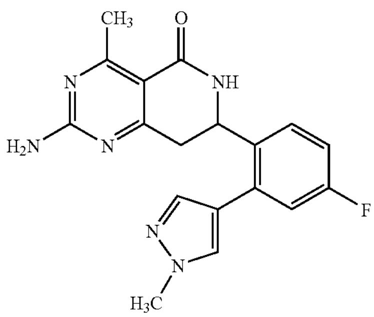 | 2-Amino-7-[4-fluoro-2-(1-methyl-1H-pyrazol-4-yl)-phenyl]-4-methyl-7,8-dihydro-6H-pyrido[4,3-d]pyrimidin-5-one | 1.87 | 353.1 | B |
| 31 | 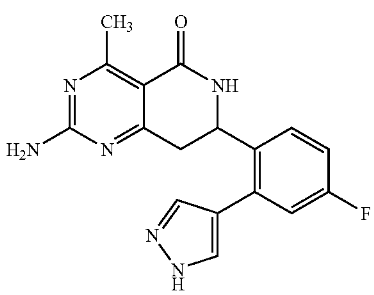 | 2-Amino-7-[4-fluoro-2-(1H-pyrazol-4-yl)-phenyl]-4-methyl-7,8-dihydro-6H-pyrido[4,3-d]pyrimidin-5-one | 2.68 | 339 | A |
| 32 | 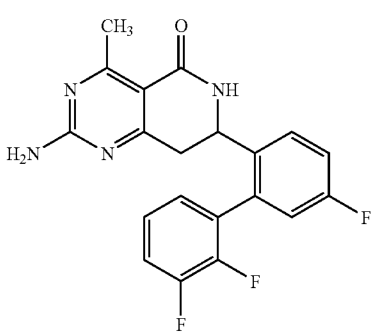 | 2-Amino-4-methyl-7-(5,2',3'-trifluoro-biphenyl-2-yl)-7,8-dihydro-6H-pyrido[4,3-d]pyrimidin-5-one | 2.08 | 385 | B |
| 33 | 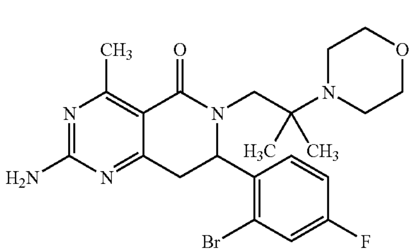 | 2-Amino-7-(2-bromo-4-fluoro-phenyl)-4-methyl-6-(2-methyl-2-morpholin-4-yl-propyl)-7,8-dihydro-6H-pyrido[4,3-d]pyrimidin-5-one | 2.08 | 492.1 | A |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≧ 10 B < 10 |
|---|---|---|---|---|---|
| 34 | 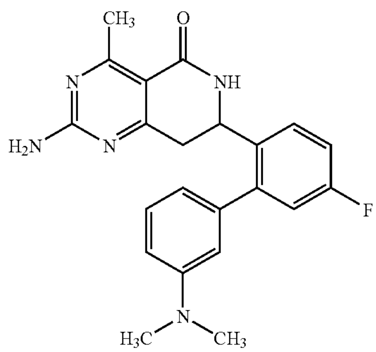 | 2-Amino-7-(3'-dimethylamino-5-fluoro-biphenyl-2-yl)-4-methyl-7,8-dihydro-6H-pyrido[4,3-d]pyrimidin-5-one | 1.54 | 392.1 | A |
| 35 | 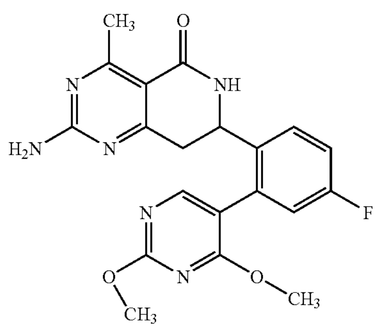 | 2-Amino-7-[2-(2,4-dimethoxy-pyrimidin-5-yl)-4-fluoro-phenyl]-4-methyl-7,8-dihydro-6H-pyrido[4,3-d]pyrimidin-5-one | 1.99 | 411.1 | A |
| 36 | 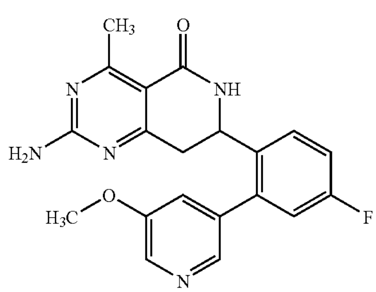 | 2-Amino-7-[4-fluoro-2-(5-methoxy-pyridin-3-yl)-phenyl]-4-methyl-7,8-dihydro-6H-pyrido[4,3-d]pyrimidin-5-one | 1.65 | 380.1 | B |
| 37 | 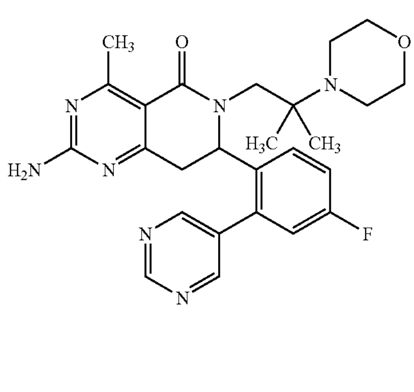 | 2-Amino-7-(4-fluoro-2-pyrimidin-5-yl-phenyl)-4-methyl-6-(2-methyl-2-morpholin-4-yl-propyl)-7,8-dihydro-6H-pyrido[4,3-d]pyrimidin-5-one | 1.8 | 492.2 | A |

TABLE 1-continued

Representative 2-Amino-7,8-dihydro-6H-pyrido[4,3-d]pyrimidin-5-one Compounds.

| Cmpd. | Structure | Name | LC/MS R$_t$ (min) | observed m/z | IC50 (μM) A ≧ 10 B < 10 |
|---|---|---|---|---|---|
| 38 | 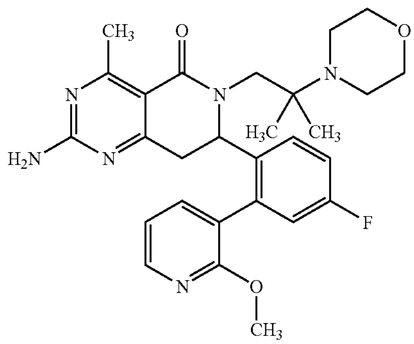 | 2-Amino-7-[4-fluoro-2-(2-methoxy-pyridin-3-yl)-phenyl]-4-methyl-6-(2-methyl-2-morpholin-4-yl-propyl)-7,8-dihydro-6H-pyrido[4,3-d]pyrimidin-5-one | 2.08 | 521.2 | A |
| 39 | 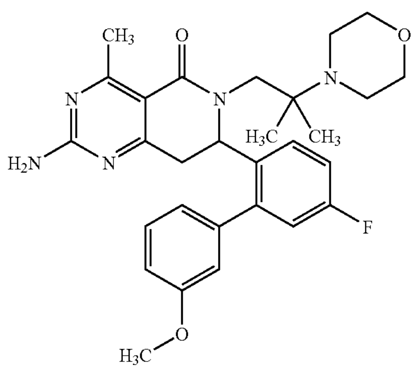 | 2-Amino-7-(5-fluoro-3'-methoxy-biphenyl-2-yl)-4-methyl-6-(2-methyl-2-morpholin-4-yl-propyl)-7,8-dihydro-6H-pyrido[4,3-d]pyrimidin-5-one | 2.25 | 520.2 | A |
| 40 | 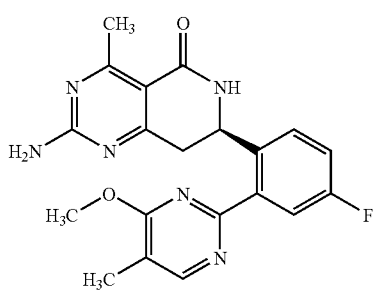 | (R)-2-Amino-7-[4-fluoro-2-(4-methoxy-5-methyl-pyrimidin-2-yl)-phenyl]-4-methyl-7,8-dihydro-6H-pyrido[4,3-d]pyrimidin-5-one | 3.11 | 395.1 | B |
| 41 | 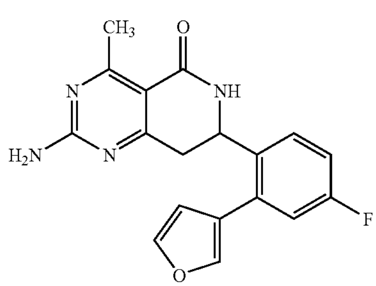 | 2-Amino-7-(4-fluoro-2-furan-3-yl-phenyl)-4-methyl-7,8-dihydro-6H-pyrido[4,3-d]pyrimidin-5-one | 1.84 | 339.1 | B |

TABLE 2

| Cmpd. | Structure | Name | LC/MS (Rt (min), m/z) | IC50 (μM) A ≥ 10 B < 10 |
|---|---|---|---|---|
| 42 | 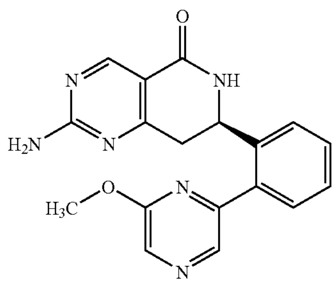 | (R)-2-Amino-7-[2-(6-methoxy-pyrazin-2-yl)-phenyl]-7,8-dihydro-6H-pyrido[4,3-d]pyrimidin-5-one | Rt = 1.87 m/z = 349.1 | B |
| 43 | 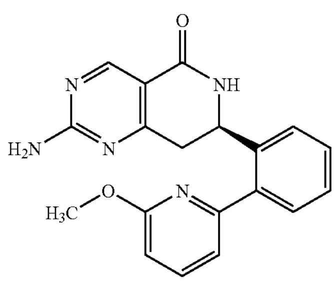 | (R)-2-Amino-7-[2-(6-methoxy-pyridin-2-yl)-phenyl]-7,8-dihydro-6H-pyrido[4,3-d]pyrimidin-5-one | Rt = 1.83 m/z = 348.1 | B |
| 44 | 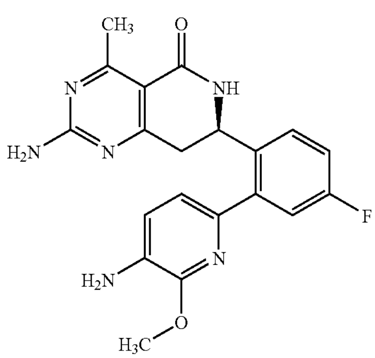 | (R)-2-Amino-7-[2-(5-amino-6-methoxy-pyridin-2-yl)-4-fluoro-phenyl]-4-methyl-7,8-dihydro-6H-pyrido[4,3-d]pyrimidin-5-one | Rt = 2.07; m/z = 395.1 | B |
| 45 | 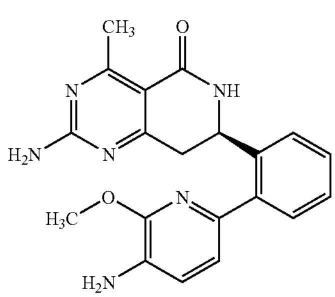 | (R)-2-Amino-7-[2-(5-amino-6-methoxy-pyridin-2-yl)-phenyl]-4-methyl-7,8-dihydro-6H-pyrido[4,3-d]pyrimidin-5-one | Rt = 1.85; m/z = 377.1 | B |

TABLE 2-continued

| Cmpd. | Structure | Name | LC/MS (Rt (min), m/z) | IC50 (μM) A ≧ 10 B < 10 |
|---|---|---|---|---|
| 46 | 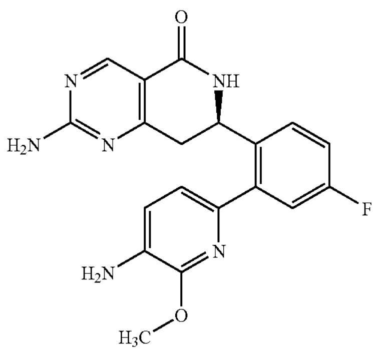 | (R)-2-Amino-7-[2-(5-amino-6-methoxy-pyridin-2-yl)-4-fluoro-phenyl]-7,8-dihydro-6H-pyrido[4,3-d]pyrimidin-5-one | Rt = 2.08; m/z = 381.1 | B |
| 47 | 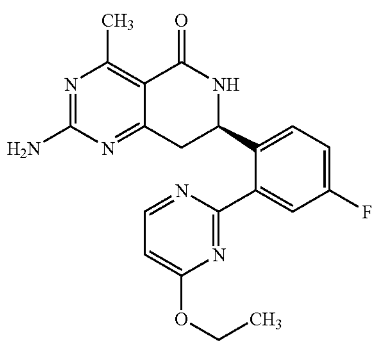 | (R)-2-Amino-7-[2-(4-ethoxy-pyrimidin-2-yl)-4-fluoro-phenyl]-4-methyl-7,8-dihydro-6H-pyrido[4,3-d]pyrimidin-5-one | Rt = 2.13; m/z = 395 | B |
| 48 | 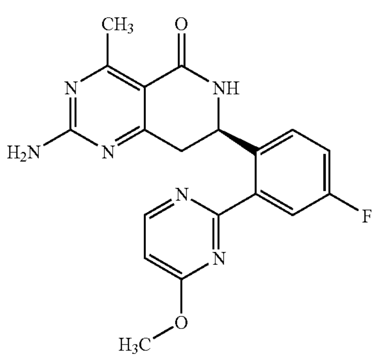 | (R)-2-Amino-7-[4-fluoro-2-(4-methoxy-pyrimidin-2-yl)-phenyl]-4-methyl-7,8-dihydro-6H-pyrido[4,3-d]pyrimidin-5-one | Rt = 2.00; m/z = 381 | B |
| 49 | 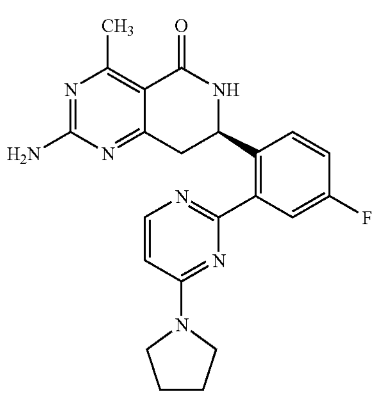 | (R)-2-Amino-7-[4-fluoro-2-(4-pyrrolidin-1-yl-pyrimidin-2-yl)-phenyl]-4-methyl-7,8-dihydro-6H-pyrido[4,3-d]pyrimidin-5-one | Rt = 1.72; m/z = 420 | A |

TABLE 2-continued

| Cmpd. | Structure | Name | LC/MS (Rt (min), m/z) | IC50 (μM) A ≧ 10 B < 10 |
|---|---|---|---|---|
| 50 | 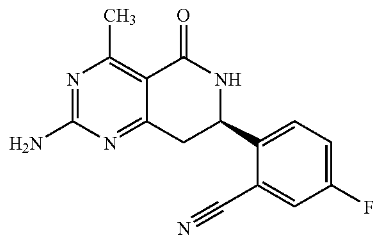 | 2-((R)-2-Amino-4-methyl-5-oxo-5,6,7,8-tetrahydro-pyrido[4,3-d]pyrimidin-7-yl)-5-fluoro-benzonitrile | Rt = 2.03; m/z = 298 | A |
| 51 | 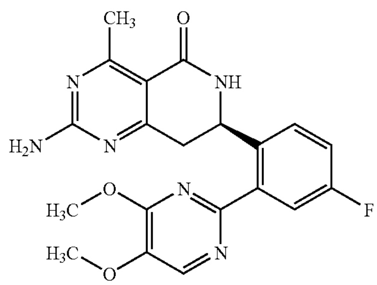 | (R)-2-Amino-7-[2-(4,5-4-methoxy-pyrimidin-2-yl)-4-fluoro-phenyl]-dimethyl-7,8-dihydro-6H-pyrido[4,3-d]pyrimidin-5-one | m/z = 411 | B |
| 52 | 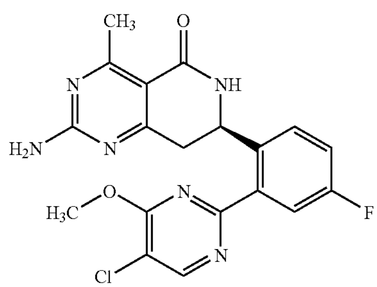 | (R)-2-Amino-7-[2-(5-chloro-4-methoxy-pyrimidin-2-yl)-4-fluoro-phenyl]-4-methyl-7,8-dihydro-6H-pyrido[4,3-d]pyrimidin5-one | Rt = 2.27; m/z = 415 | B |
| 53 | 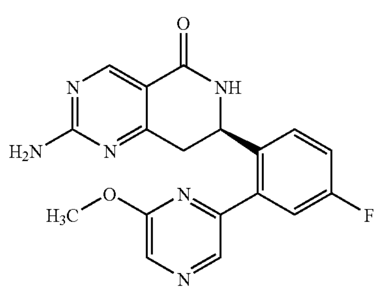 | (R)-2-Amino-7-[4-fluoro-2-(6-methoxy-pyrazin-2-yl)-phenyl]-7,8-dihydro-6H-pyrido[4,3-d]pyrimidin-5-one | Rt = 1.93; m/z = 367 | B |
| 54 | 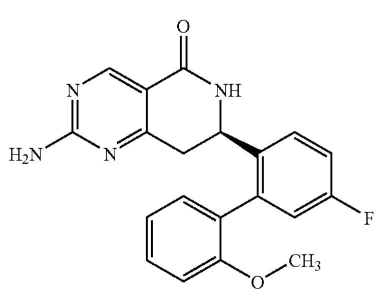 | (R)-2-Amino-7-(5-fluoro-2'-methoxy-biphenyl-2-yl)-7,8-dihydro-6H-pyrido[4,3-d]pyrimidin-5-one | Rt = 2.21; m/z = 365 | B |

TABLE 2-continued

| Cmpd. | Structure | Name | LC/MS (Rt (min), m/z) | IC50 (μM) A ≧ 10 B < 10 |
|---|---|---|---|---|
| 55 | 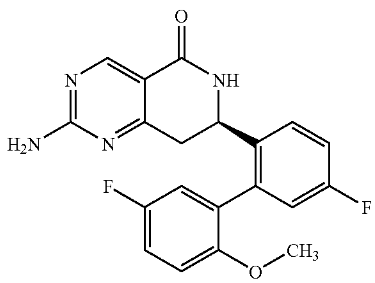 | (R)-2-Amino-7-(5,5'-difluoro-2'-methoxy-biphenyl-2-yl)-7,8-dihydro-6H-pyrido[4,3-d]pyrimidin-5-one | Rt = 2.27; m/z = 383 | B |
| 56 | 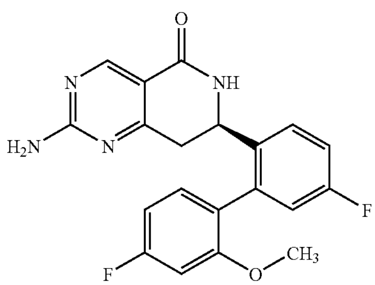 | (R)-2-Amino-7-(5,4'-difluoro-2'-methoxy-biphenyl-2-yl)-7,8-dihydro-6H-pyrido[4,3-d]pyrimidin-5-one | Rt = 2.28; m/z = 383 | B |
| 57 | 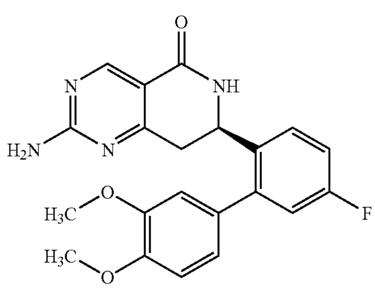 | (R)-2-Amino-7-(5-fluoro-3',4'-dimethoxy-biphenyl-2-yl)-7,8-dihydro-6H-pyrido[4,3-d]pyrimidin-5-one | Rt = 2.11; m/z = 395 | A |
| 58 | 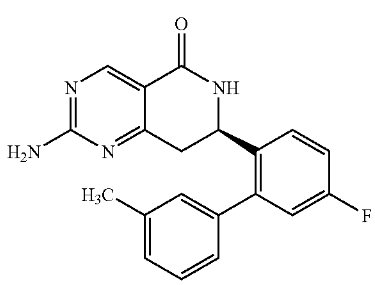 | (R)-2-Amino-7-(5-fluoro-3'-methyl-biphenyl-2-yl)-7,8-dihydro-6H-pyrido[4,3-d]pyrimidin-5-one | Rt = 2.35; m/z = 349 | B |
| 60 | 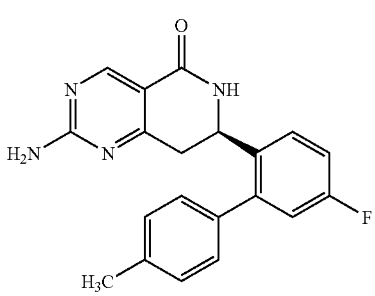 | (R)-2-Amino-7-(5-fluoro-4'-methyl-biphenyl-2-yl)-7,8-dihydro-6H-pyrido[4,3-d]pyrimidin-5-one | Rt = 2.36; m/z = 349 | B |

TABLE 2-continued

| Cmpd. | Structure | Name | LC/MS (Rt (min), m/z) | IC50 (μM) A ≧ 10 B < 10 |
|---|---|---|---|---|
| 61 | 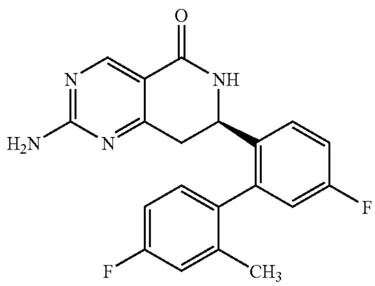 | (R)-2-Amino-7-(5,4'-difluoro-2'-methyl-biphenyl-2-yl)-7,8-dihydro-6H-pyrido[4,3-d]pyrimidin-5-one | Rt = 2.36; m/z = 367 | B |
| 62 | 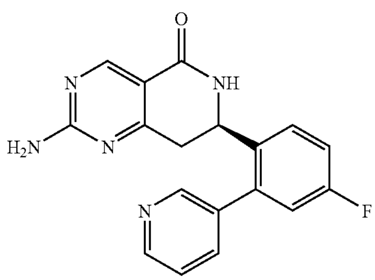 | (R)-2-Amino-7-(4-fluoro-2-pyridin-3-yl-phenyl)-7,8-dihydro-6H-pyrido[4,3-d]pyrimidin-5-one | Rt = 1.4 m/z = 336 | B |
| 63 | 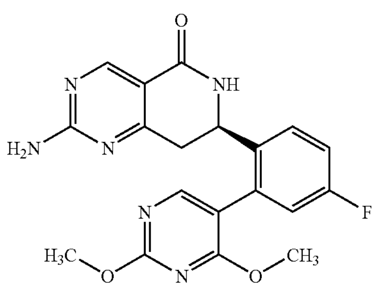 | (R)-2-Amino-7-[2-(2,4-dimethoxy-pyrimidin-5-yl)-4-fluoro-phenyl]-7,8-dihydro-6H-pyrido[4,3-d]pyrimidin-5-one | Rt = 1.95 m/z = 397 | A |
| 64 | 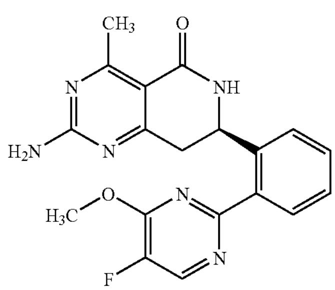 | (R)-2-Amino-7-[2-(5-fluoro-4-methoxy-pyrimidin-2-yl)-phenyl]-4-methyl-7,8-dihydro-6H-pyrido[4,3-d]pyrimidin-5-one | Rt = 1.971 m/z = 381.2 | B |
| 65 | 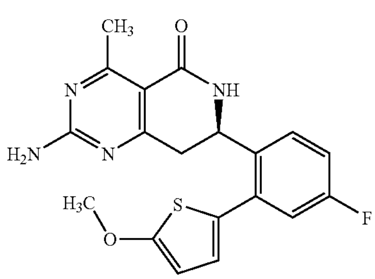 | (R)-2-Amino-7-[4-fluoro-2-(5-methoxy-thiophen-2-yl)-phenyl]-4-methyl-7,8-dihydro-6H-pyrido[4,3-d]pyrimidin-5-one | Rt = 2.064 m/z = 385.0 | B |

TABLE 2-continued

| Cmpd. | Structure | Name | LC/MS (Rt (min), m/z) | IC50 (μM) A ≧ 10 B < 10 |
|---|---|---|---|---|
| 66 | 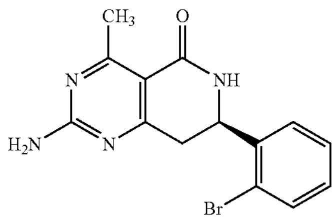 | (R)-2-Amino-7-(2-bromo-phenyl)-4-methyl-7,8-dihydro-6H-pyrido[4,3-d]pyrimidin-5-one | Rt = 1.85 m/z = 332.9/334.9 | A |
| 67 | 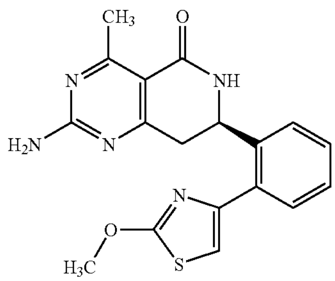 | (R)-2-Amino-7-[2-(2-methoxy-thiazol-4-yl)-phenyl]-4-methyl-7,8-dihydro-6H-pyrido[4,3-d]pyrimidin-5-one | Rt = 2.10 m/z = 368.0 | B |
| 68 | 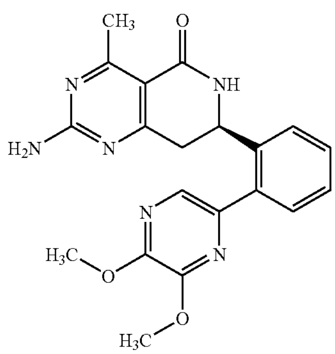 | (R)-2-Amino-7-[2-(5,6-dimethoxy-pyrazin-2-yl)-phenyl]-4-methyl-7,8-dihydro-6H-pyrido[4,3-d]pyrimidin-5-one | Rt = 2.11 m/z = 393.1 | B |
| 69 | 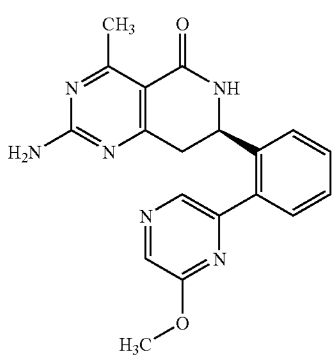 | (R)-2-Amino-7-[2-(6-methoxy-pyrazin-2-yl)-phenyl]-4-methyl-7,8-dihydro-6H-pyrido[4,3-d]pyrimidin-5-one | Rt = 1.94 m/z = 363.0 | B |
| 70 | 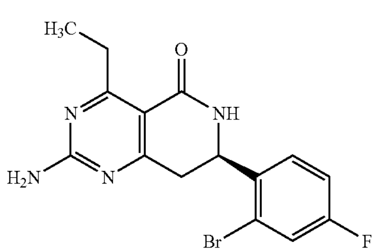 | (R)-2-Amino-7-(2-bromo-4-fluoro-phenyl)-4-ethyl-7,8-dihydro-6H-pyrido[4,3-d]pyrimidin-5-one | Rt = 2.05 m/z = 367.0 | A |

TABLE 2-continued

| Cmpd. | Structure | Name | LC/MS (Rt (min), m/z) | IC50 (μM) A ≧ 10 B < 10 |
|---|---|---|---|---|
| 71 | 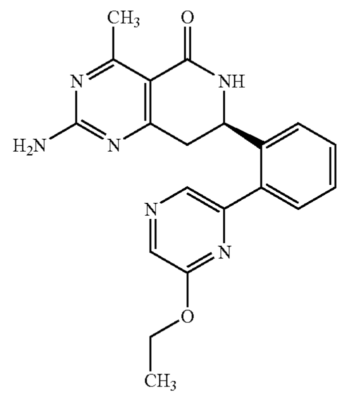 | (R)-2-Amino-7-[2-(6-ethoxy-pyrazin-2-yl)-phenyl]-4-methyl-7,8-dihydro-6H-pyrido[4,3-d]pyrimidin-5-one | Rt = 2.07 m/z = 377.1 | B |
| 72 | 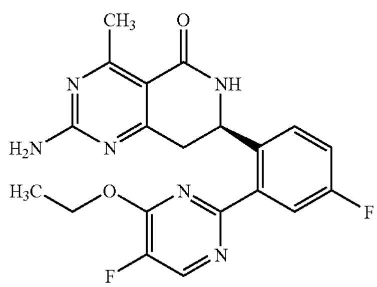 | (R)-2-Amino-7-[2-(4-ethoxy-5-fluoro-pyrimidin-2-yl)-4-fluoro-phenyl]-4-methyl-7,8-dihydro-6H-pyrido[4,3-d]pyrimidin-5-one | Rt = 2.33; m/z = 413.1 | B |
| 73 | 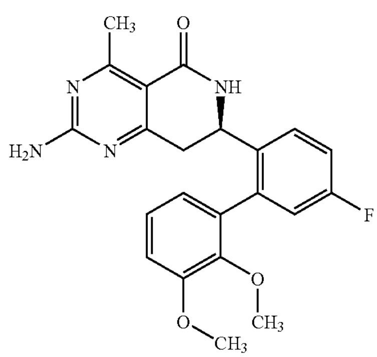 | (R)-2-Amino-7-(5-fluoro-2',3'-dimethoxy-biphenyl-2-yl)-4-methyl-7,8-dihydro-6H-pyrido[4,3-d]pyrimidin-5-one | Rt = 2.067; m/z = 409.1 | B |
| 74 | 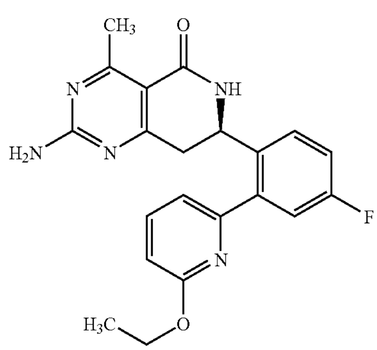 | (R)-2-Amino-7-[2-(6-ethoxy-pyridin-2-yl)-4-fluoro-phenyl]-4-methyl-7,8-dihydro-6H-pyrido[4,3-d]pyrimidin-5-one | Rt = 2.37; m/z = 394.0 | B |

TABLE 2-continued

| Cmpd. | Structure | Name | LC/MS (Rt (min), m/z) | IC50 (μM) A ≧ 10 B < 10 |
|---|---|---|---|---|
| 75 | 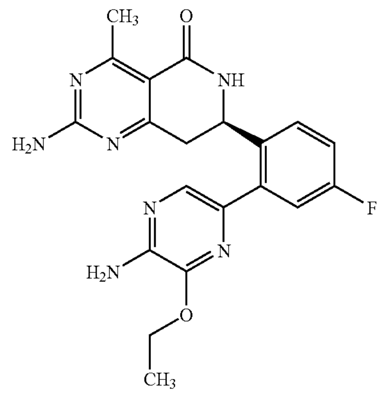 | (R)-2-Amino-7-[2-(5-amino-6-ethoxy-pyrazin-2-yl)-4-fluoro-phenyl]-4-methyl-7,8-dihydro-6H-pyrido[4,3-d]pyrimidin-5-one | Rt = 1.84; m/z = 410.1 | B |
| 76 | 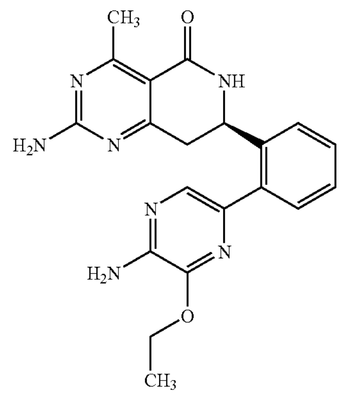 | (R)-2-Amino-7-[2-(5-amino-6-ethoxy-pyrazin-2-yl)-phenyl]-4-methyl-7,8-dihydro-6H-pyrido[4,3-d]pyrimidin-5-one | Rt = 1.76; m/z = 376.1 | B |
| 77 | 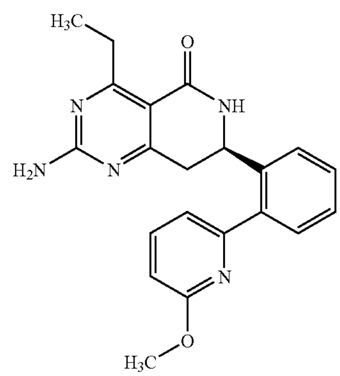 | (R)-2-Amino-4-ethyl-7-[2-(6-methoxy-pyridin-2-yl)-phenyl]-7,8-dihydro-6H-pyrido[4,3-d]pyrimidin-5-one | Rt = 2.24; m/z = 376.1 | B |
| 78 | 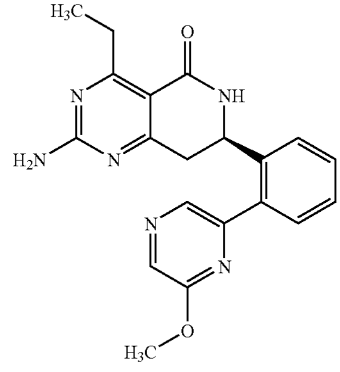 | (R)-2-Amino-4-ethyl-7-[2-(6-methoxy-pyrazin-2-yl)-phenyl]-7,8-dihydro-6H-pyrido[4,3-d]pyrimidin-5-one | Rt = 2.03; m/z = 377.1 | B |

TABLE 2-continued

| Cmpd. | Structure | Name | LC/MS (Rt (min), m/z) | IC50 (μM) A ≧ 10 B < 10 |
|---|---|---|---|---|
| 79 | 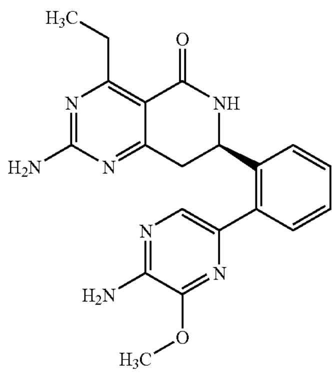 | (R)-2-Amino-7-[2-(5-amino-6-methoxy-pyrazin-2-yl)-phenyl]-4-ethyl-7,8-dihydro-6H-pyrido[4,3-d]pyrimidin-5-one | Rt = 1.76; m/z = 392.2 | B |
| 80 | 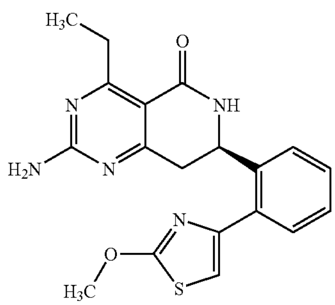 | (R)-2-Amino-4-ethyl-7-[2-(2-methoxy-thiazol-4-yl)-phenyl]-7,8-dihydro-6H-pyrido[4,3-d]pyrimidin-5-one | Rt = 2.24; m/z = 382.0 | A |
| 81 | 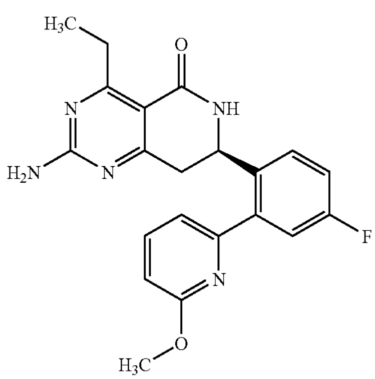 | (R)-2-Amino-4-ethyl-7-[4-fluoro-2-(6-methoxy-pyridin-2-yl)-phenyl]-7,8-dihydro-6H-pyrido[4,3-d]pyrimidin-5-one | Rt = 2.33; m/z = 394.1 | B |
| 82 | 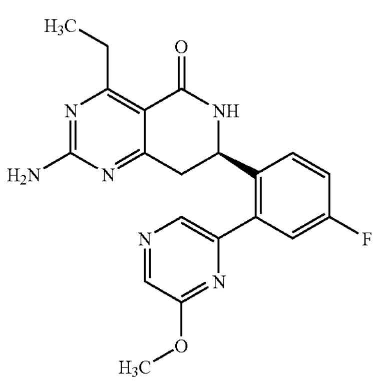 | (R)-2-Amino-4-ethyl-7-[4-fluoro-2-(6-methoxy-pyrazin-2-yl)-phenyl]-7,8-dihydro-6H-pyrido[4,3-d]pyrimidin-5-one | Rt = 2.11; m/z = 395.1 | B |

TABLE 2-continued

| Cmpd. | Structure | Name | LC/MS (Rt (min), m/z) | IC50 (μM) A ≧ 10 B < 10 |
|---|---|---|---|---|
| 83 | 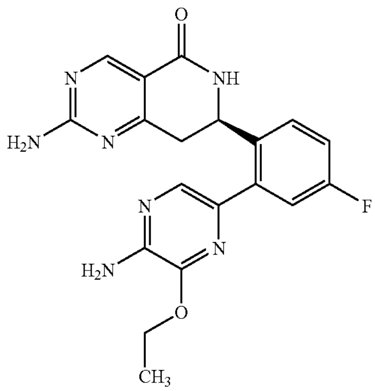 | (R)-2-Amino-7-[2-(5-amino-6-ethoxy-pyrazin-2-yl)-4-fluoro-phenyl]-7,8-dihydro-6H-pyrido[4,3-d]pyrimidin-5-one | Rt = 1.84; m/z = 396.1 | B |
| 84 | 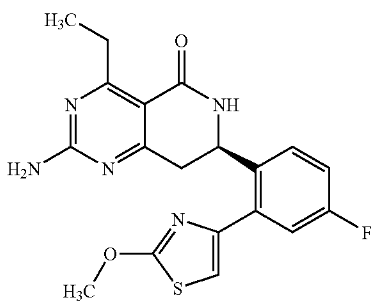 | (R)-2-Amino-4-ethyl-7-[4-fluoro-2-(2-methoxy-thiazol-4-yl)-pbenyl]-7,8-dihydro-6H-pyrido[4,3-d]pyrimidin-5-one | Rt = 2.07; m/z = 400.0 | B |
| 85 | 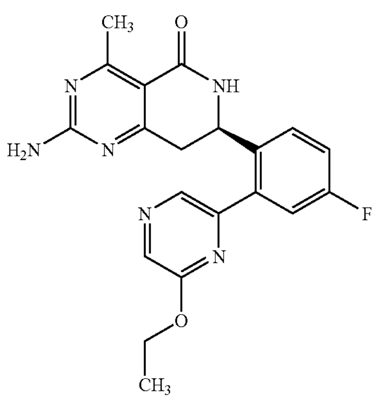 | (R)-2-Amino-7-[2-(6-ethoxy-pyrazin-2-yl)-4-fluoro-phenyl]-4-methyl-7,8-dihydro-6H-pyrido[4,3-d]pyrimidin-5-one | Rt = 1.92; m/z = 395.1 | B |
| 86 | 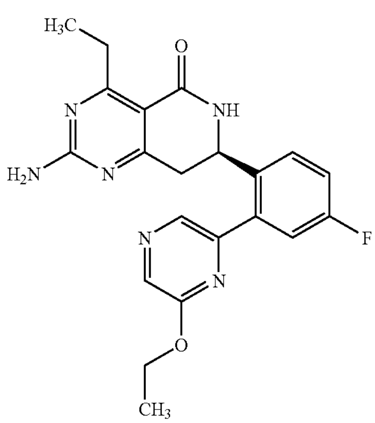 | (R)-2-Amino-7-[2-(6-ethoxy-pyrazin-2-yl)-4-fluoro-phenyl]-4-ethyl-7,8-dihydro-6H-pyrido[4,3-d]pyrimidin-5-one | Rt = 2.00; m/z = 409.1 | B |

TABLE 2-continued

| Cmpd. | Structure | Name | LC/MS (Rt (min), m/z) | IC50 (μM) A ≥ 10 B < 10 |
|---|---|---|---|---|
| 87 | 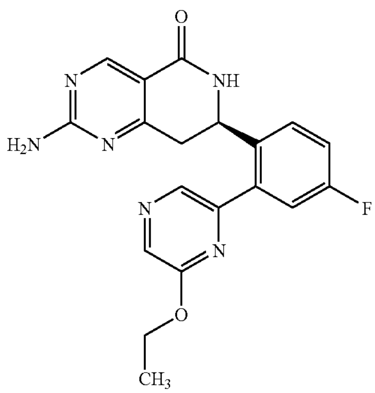 | (R)-2-Amino-7-[2-(6-ethoxy-pyrazin-2-yl)-4-fluoro-phenyl]-7,8-dihydro-6H-pyrido[4,3-d]pyrimidin-5-one | Rt = 2.15; m/z = 381.0 | B |
| 88 | 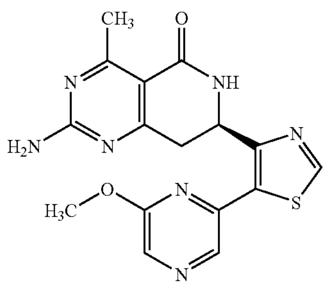 | (R)-2-Amino-7-[5-(6-methoxy-pyrazin-2-yl)-thiazol-4-yl]-4-methyl-7,8-dihydro-6H-pyrido[4,3-d]pyrimidin-5-one | Rt = 1.72; m/z = 370.0 | B |

TABLE 3

| Cmpd. | Structure | Name | LC/MS (Rt (min), m/z) | IC50 (μM) A ≥ 10 B < 10 |
|---|---|---|---|---|
| 89 | 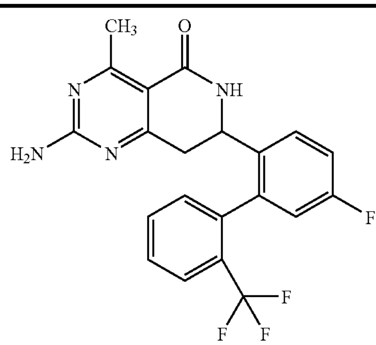 | 2-Amino-7-(5-fluoro-2'-trifluoromethyl-biphenyl-2-yl)-4-methyl-7,8-dihydro-6H-pyrido[4,3-d]pyrimidin-5-one | Rt = 2.2 m/z = 417.0 | B |
| 90 | 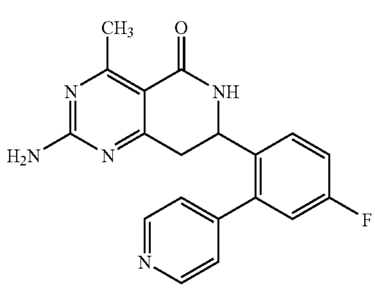 | 2-Amino-7-(4-fluoro-2-pyridin-4-yl-phenyl)-4-methyl-7,8-dihydro-6H-pyrido[4,3-d]pyrimidin-5-one | Rt = 2.63 m/z = 350.0 | A |

TABLE 3-continued

| Cmpd. | Structure | Name | LC/MS (Rt (min), m/z) | IC50 (μM) A ≧ 10 B < 10 |
|---|---|---|---|---|
| 91 | 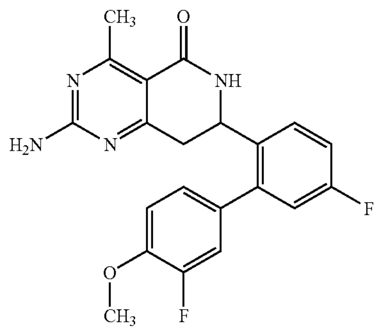 | 2-Amino-7-(5,3'-difluoro-4'-methoxy-biphenyl-2-yl)-4-methyl-7,8-dihydro-6H-pyrido[4,3-d]pyrimidin-5-one | Rt = 2.07 m/z = 397.0 | A |
| 92 | 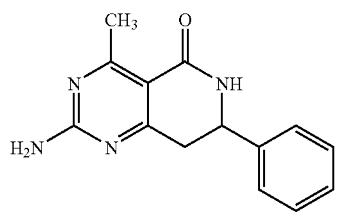 | 2-Amino-4-methyl-7-phenyl-7,8-dihydro-6H-pyrido[4,3-d]pyrimidin-5-one | Rt = 1.39 m/z = 255.0 | A |
| 93 | 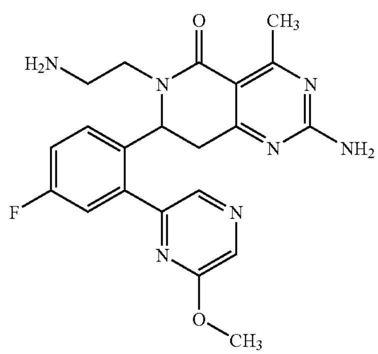 | 2-Amino-6-(2-amino-ethyl)-7-[4-fluoro-2-(6-methoxy-pyrazin-2-yl)-phenyl]-4-methyl-7,8-dihydro-6H-pyrido[4,3-d]pyrimidin-5-one | Rt = 1.87 m/z = 424.2 | B |
| 94 | 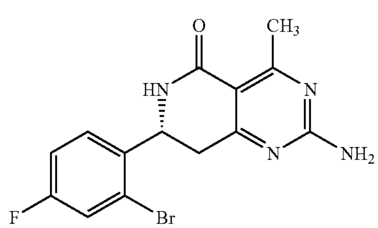 | (R)-2-Amino-7-(2-bromo-4-fluoro-phenyl)-4-methyl-7,8-dihydro-6H-pyrido[4,3-d]pyrimidin-5-one | Rt = 1.95 m/z = 350.9/353.0 | |
| 95 | 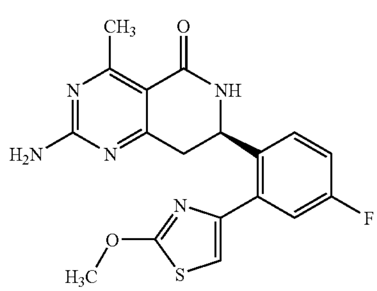 | (R)-2-Amino-7-[4-fluoro-2-(2-methoxy-thiazol-4-yl)-phenyl]-4-methyl-7,8-dihydro-6H-pyrido[4,3-d]pyrimidin-5-one | Rt = 2.19 m/z = 386.3 | B |

TABLE 3-continued

| Cmpd. | Structure | Name | LC/MS (Rt (min), m/z) | IC50 (μM) A ≧ 10 B < 10 |
|---|---|---|---|---|
| 96 | 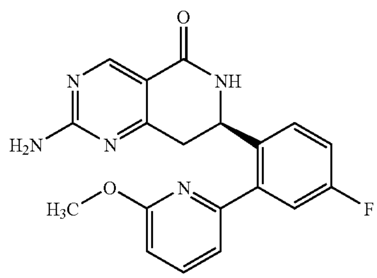 | (R)-2-Amino-7-[4-fluoro-2-(6-methoxy-pyridin-2-yl)-phenyl]-7,8-dihydro-6H-pyrido[4,3-d]pyrimidin-5-one | Rt = 2.09; m/z = 366 | B |
| 97 | 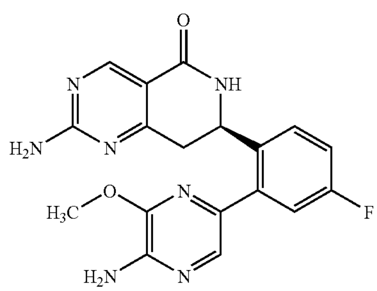 | (R)-2-Amino-7-[2-(5-amino-6-methoxy-pyrazin-2-yl)-4-fluoro-phenyl]-7,8-dihydro-6H-pyrido[4,3-d]pyrimidin-5-one | Rt = 1.61; m/z = 328 | B |
| 98 | 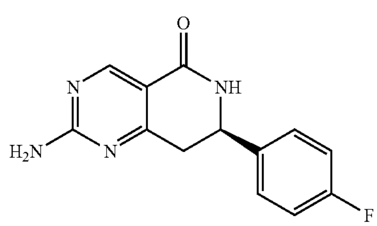 | (R)-2-Amino-7-(4-fluoro-phenyl)-7,8-dihydro-6H-pyrido[4,3-d]pyrimidin-5-one | | B |
| 99 | 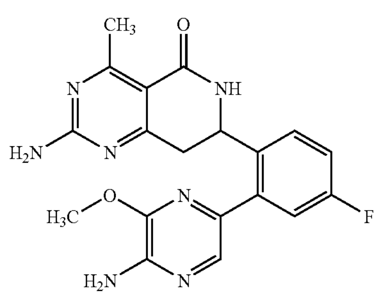 | 2-Amino-7-[2-(5-amino-6-methoxy-pyrazin-2-yl)-4-fluoro-phenyl]-4-methyl-7,8-dihydro-6H-pyrido[4,3-d]pyrimidin-5-one | Rt = 1.46 m/z = 396.0 | B |
| 100 | 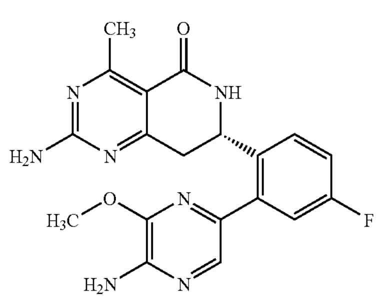 | (S)-2-Amino-7-[2-(5-amino-6-methoxy-pyrazin-2-yl)-4-fluoro-phenyl]-4-methyl-7,8-dihydro-6H-pyrido[4,3-d]pyrimidin-5-one | Rt = 1.46 m/z = 396.0 | A |

TABLE 3-continued

| Cmpd. | Structure | Name | LC/MS (Rt (min), m/z) | IC50 (μM) A ≧ 10 B < 10 |
|---|---|---|---|---|
| 101 | 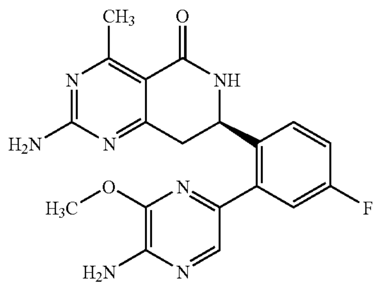 | (R)-2-Amino-7-[2-(5-amino-6-methoxy-pyrazin-2-yl)-4-fluoro-phenyl]-4-methyl-7,8-dihydro-6H-pyrido[4,3-d]pyrimidin-5-one | Rt = 1.46 m/z = 396.0 | B |
| 102 | 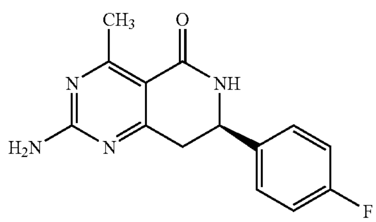 | (R)-2-Amino-7-(4-fluoro-phenyl)-4-methyl-7,8-dihydro-6H-pyrido[4,3-d]pyrimidin-5-one | Rt = 1.622 m/z = 273.1 | B |
| 103 | 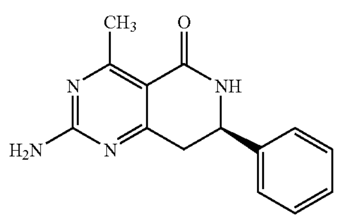 | (R)-2-Amino-4-methyl-7-phenyl-7,8-dihydro-6H-pyrido[4,3-d]pyrimidin-5-one | Rt = 1.534 m/z = 255.2 | B |
| 104 | 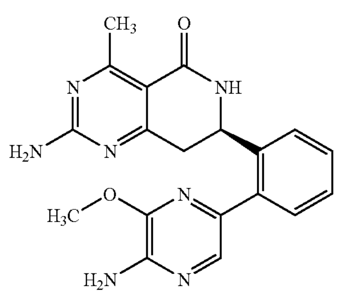 | (R)-2-Amino-7-[2-(5-amino-6-methoxy-pyrazin-2-yl)-phenyl]-4-methyl-7,8-dihydro-6H-pyrido[4,3-d]pyrimidin-5-one | Rt = 1.538 m/z = 378.2 | B |
| 105 | 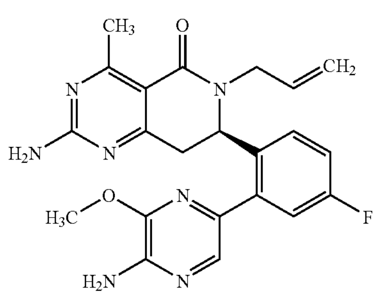 | (R)-6-Allyl-2-amino-7-[2-(5-amino-6-methoxy-pyrazin-2-yl)-4-fluoro-phenyl]-4-methyl-7,8-dihydro-6H-pyrido[4,3-d]pyrimidin-5-one | Rt = 1.917 m/z = 436.2 | B |

TABLE 3-continued

| Cmpd. | Structure | Name | LC/MS (Rt (min), m/z) | IC50 (μM) A ≧ 10 B < 10 |
|---|---|---|---|---|
| 106 | 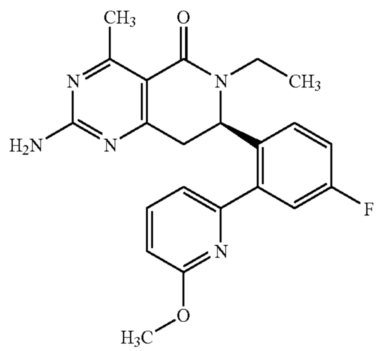 | (R)-2-Amino-6-ethyl-7-[4-fluoro-2-(6-methoxy-pyridin-2-yl)-phenyl]-4-methyl-7,8-dihydro-6H-pyrido[4,3-d]pyrimidin-5-one | Rt = 2.51 m/z = 408.1 | B |
| 107 | 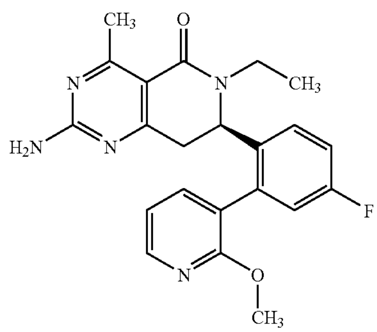 | (R)-2-Amino-6-ethyl-7-[4-fluoro-2-(2-methoxy-pyridin-3-yl)-phenyl]-4-methyl-7,8-dihydro-6H-pyrido[4,3-d]pyrimidin-5-one | Rt = 2.32 m/z = 408.1 | B |
| 108 | 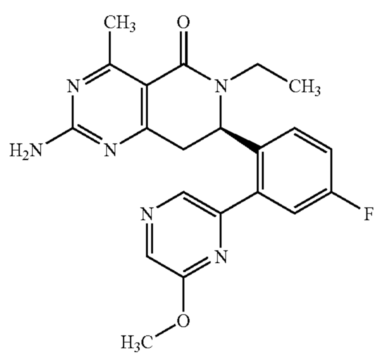 | (R)-2-Amino-6-ethyl-7-[4-fluoro-2-(6-methoxy-pyrazin-2-yl)-phenyl]-4-methyl-7,8-dihydro-6H-pyrido[4,3-d]pyrimidin-5-one | Rt = 2.29 m/z = 409.1 | B |
| 109 | 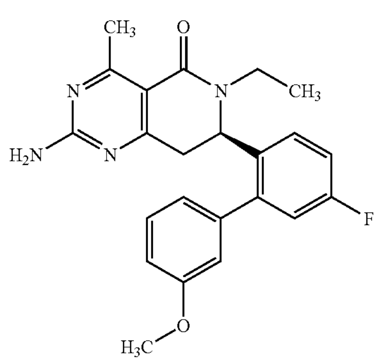 | (R)-2-Amino-6-ethyl-7-(5-fluoro-3'-methoxy-biphenyl-2-yl)-4-methyl-7,8-dihydro-6H-pyrido[4,3-d]pyrimidin-5-one | Rt = 2.58 m/z = 407.1 | B |

TABLE 3-continued

| Cmpd. | Structure | Name | LC/MS (Rt (min), m/z) | IC50 (μM) A ≥ 10 B < 10 |
|---|---|---|---|---|
| 110 | 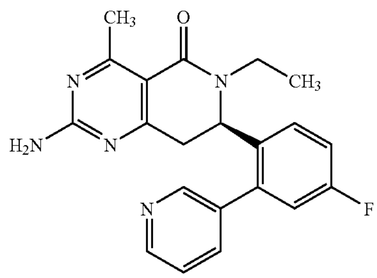 | (R)-2-Amino-6-ethyl-7-(4-fluoro-2-pyridin-3-yl-phenyl)-4-methyl-7,8-dihydro-6H-pyrido[4,3-d]pyrimidin-5-one | Rt = 1.74 m/z = 378.1 | B |
| 111 | 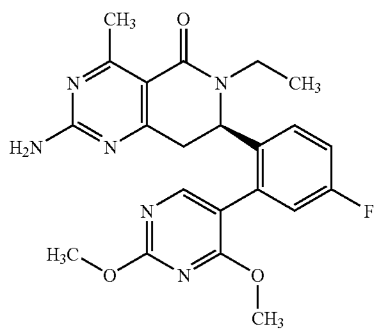 | (R)-2-Amino-7-[2-(2,4-dimethoxy-pyrimidin-5-yl)-4-fluoro-phenyl]-6-ethyl-4-methyl-7,8-dihydro-6H-pyrido[4,3-d]pyrimidin-5-one | Rt = 2.24 m/z = 439.1 | A |
| 112 | 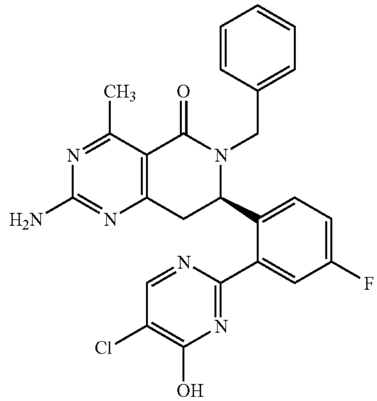 | (R)-2-Amino-6-benzyl-7-[2-(5-chloro-4-hydroxy-pyrimidin-2-yl)-4-fluoro-phenyl]-4-methyl-7,8-dihydro-6H-pyrido[4,3-d]pyrimidin-5-one | Rt = 2.29 m/z = 491.1 | A |
| 113 | 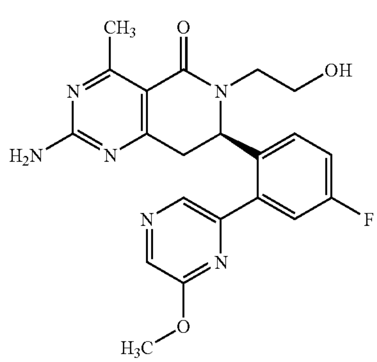 | (R)-2-Amino-7-[4-fluoro-2-(6-methoxy-pyrazin-2-yl)-phenyl]-6-(2-hydroxy-ethyl)-4-methyl-7,8-dihydro-6H-pyrido[4,3-d]pyrimidin-5-one | Rt = 2.01 m/z = 425.1 | B |

TABLE 3-continued

| Cmpd. | Structure | Name | LC/MS (Rt (min), m/z) | IC50 (μM) A ≧ 10 B < 10 |
|---|---|---|---|---|
| 114 | 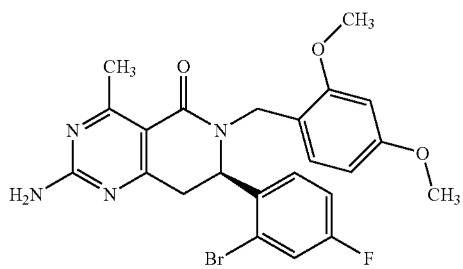 | (R)-2-Amino-7-(2-bromo-4-fluoro-phenyl)-6-(2,4-dimethoxy-benzyl)-4-methyl-7,8-dihydro-6H-pyrido[4,3-d]pyrimidin-5-one | Rt = 2.72 m/z = 501.0, 503.0 | A |
| 115 | 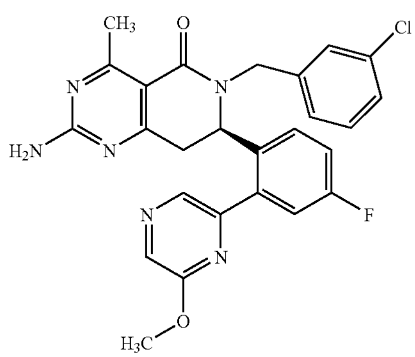 | (R)-2-Amino-6-(3-chloro-benzyl)-7-[4-fluoro-2-(6-methoxy-pyrazin-2-yl)-phenyl]-4-methyl-7,8-dihydro-6H-pyrido[4,3-d]pyrimidin-5-one | Rt = 2.79 m/z = 505.0 | B |
| 116 | 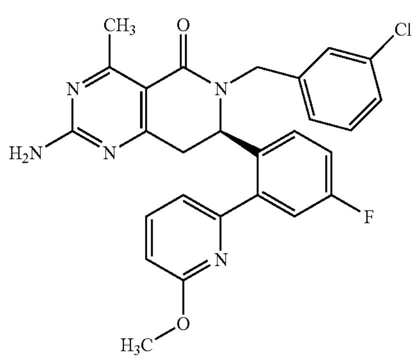 | (R)-2-Amino-6-(3-chloro-benzyl)-7-[4-fluoro-2-(6-methoxy-pyridin-2-yl)-phenyl]-4-methyl-7,8-dihydro-6H-pyrido[4,3-d]pyrimidin-5-one | Rt = 3.05 m/z = 504.0 | B |
| 117 | 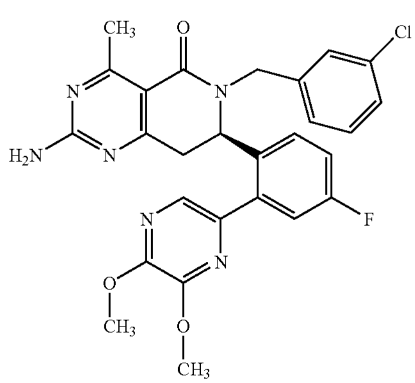 | (R)-2-Amino-6-(3-chloro-benzyl)-7-[2-(5,6-dimethoxy-pyrazin-2-yl)-4-fluoro-phenyl]-4-methyl-7,8-dihydro-6H-pyrido[4,3-d]pyrimidin-5-one | Rt = 2.94 m/z = 535.0 | B |

TABLE 3-continued

| Cmpd. | Structure | Name | LC/MS (Rt (min), m/z) | IC50 (μM) A ≧ 10 B < 10 |
|---|---|---|---|---|
| 118 | 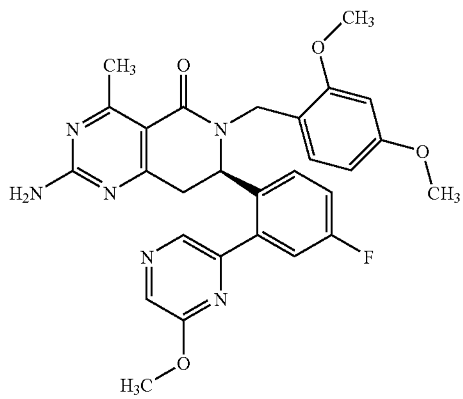 | (R)-2-Amino-6-(2,4-dimethoxy-benzyl)-7-[4-fluoro-2-(6-methoxy-pyrazin-2-yl)-phenyl]-4-methyl-7,8-dihydro-6H-pyrido[4,3-d]pyrimidin-5-one | Rt = 2.58 m/z = 531.1 | B |
| 119 | 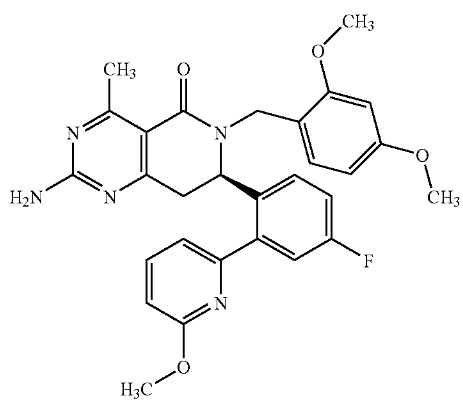 | (R)-2-Amino-6-(2,4-dimethoxy-benzyl)-7-[4-fluoro-2-(6-methoxy-pyridin-2-yl)-phenyl]-4-methyl-7,8-dihydro-6H-pyrido[4,3-d]pyrimidin-5-one | Rt = 2.82 m/z = 530.1 | B |
| 120 | 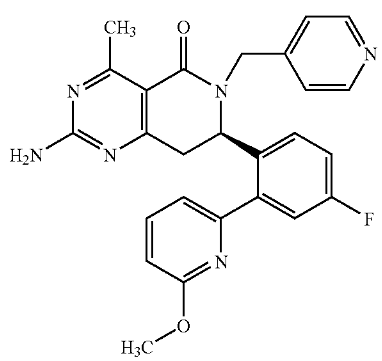 | (R)-2-Amino-7-[4-fluoro-2-(6-methoxy-pyridin-2-yl)-phenyl]-4-methyl-6-pyridin-4-ylmethyl-7,8-dihydro-6H-pyrido[4,3-d]pyrimidin-5-one | Rt = 2.01 m/z = 471.1 | B |
| 121 | 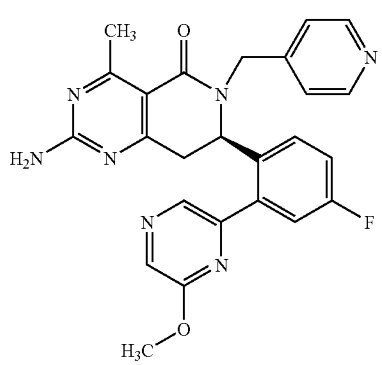 | (R)-2-Amino-7-[4-fluoro-2-(6-methoxy-pyrazin-2-yl)-phenyl]-4-methyl-6-pyridin-4-ylmethyl-7,8-dihydro-6H-pyrido[4,3-d]pyrimidin-5-one | Rt = 1.89 m/z = 472.1 | B |

TABLE 3-continued

| Cmpd. | Structure | Name | LC/MS (Rt (min), m/z) | IC50 (μM) A ≥ 10 B < 10 |
|---|---|---|---|---|
| 122 | 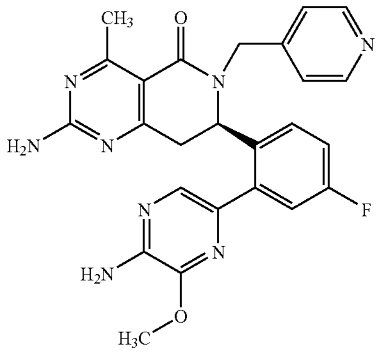 | (R)-2-Amino-7-[2-(5-amino-6-methoxy-pyrazin-2-yl)-4-fluoro-phenyl]-4-methyl-6-pyridin-4-ylmethyl-7,8-dihydro-6H-pyrido[4,3-d]pyrimidin-5-one | Rt = 1.72 m/z = 487.1 | B |
| 123 | 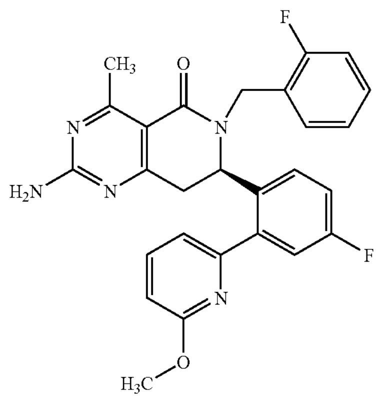 | (R)-2-Amino-6-(2-fluoro-benzyl)-7-[4-fluoro-2-(6-methoxy-pyridin-2-yl)-phenyl]-4-methyl-7,8-dihydro-6H-pyrido[4,3-d]pyrimidin-5-one | Rt = 2.90 m/z = 488.0 | B |
| 124 | 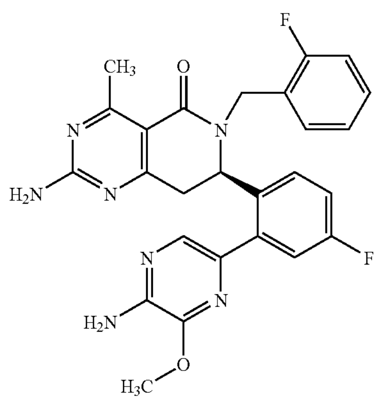 | (R)-2-Amino-7-[2-(5-amino-6-methoxy-pyrazin-2-yl)-4-fluoro-phenyl]-6-(2-fluoro-benzyl)-4-methyl-7,8-dihydro-6H-pyrido[4,3-d]pyrimidin-5-one | Rt = 2.27 m/z = 504.0 | B |
| 125 | 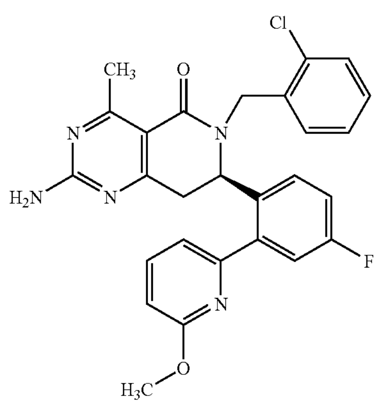 | (R)-2-Amino-6-(2-chloro-benzyl)-7-[4-fluoro-2-(6-methoxy-pyridin-2-yl)-phenyl]-4-methyl-7,8-dihydro-6H-pyrido[4,3-d]pyrimidin-5-one | Rt = 3.03 m/z = 504.0 | B |

TABLE 3-continued

| Cmpd. | Structure | Name | LC/MS (Rt (min), m/z) | IC50 (μM) A ≧ 10 B < 10 |
|---|---|---|---|---|
| 126 | 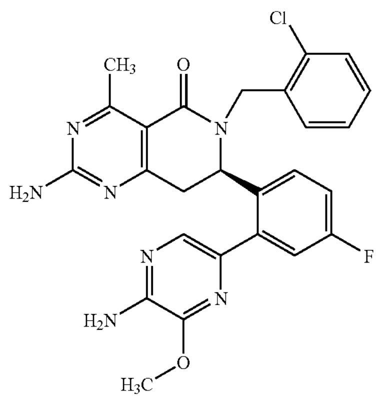 | (R)-2-Amino-7-[2-(5-amino-6-methoxy-pyrazin-2-yl)-4-fluoro-phenyl]-6-(2-chloro-benzyl)-4-methyl-7,8-dihydro-6H-pyrido[4,3-d]pyrimidin-5-one | Rt = 2.36 m/z = 520.1 | B |
| 127 | 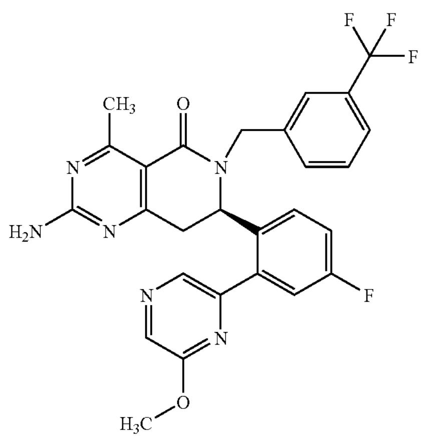 | (R)-2-Amino-7-[4-fluoro-2-(6-methoxy-pyrazin-2-yl)-phenyl]-4-methyl-6-(3-trifluoromethyl-benzyl)-7,8-dihydro-6H-pyrido[4,3-d]pyrimidin-5-one | Rt = 2.87 m/z = 539.1 | B |
| 128 | 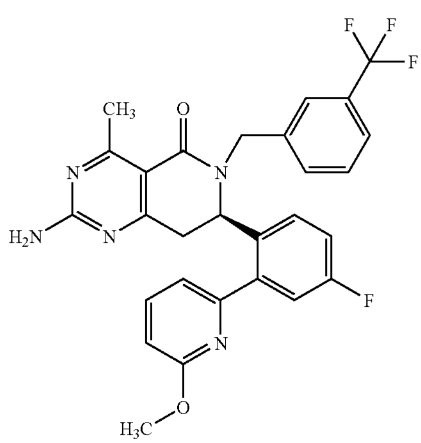 | (R)-2-Amino-7-[4-fluoro-2-(6-methoxy-pyridin-2-yl)-phenyl]-4-methyl-6-(3-trifluoromethyl-benzyl)-7,8-dihydro-6H-pyrido[4,3-d]pyrimidin-5-one | Rt = 3.11 m/z = 538.1 | B |

TABLE 3-continued

| Cmpd. | Structure | Name | LC/MS (Rt (min), m/z) | IC50 (μM) A ≧ 10 B < 10 |
|---|---|---|---|---|
| 129 | 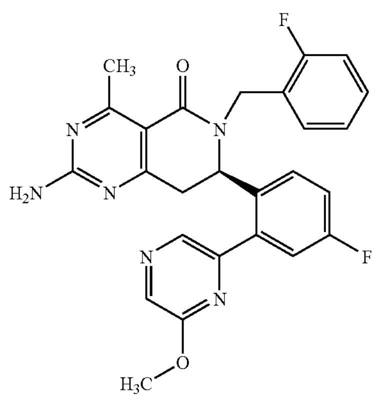 | (R)-2-Amino-6-(2-fluoro-benzyl)-7-[4-fluoro-2-(6-methoxy-pyrazin-2-yl)-phenyl]-4-methyl-7,8-dihydro-6H-pyrido[4,3-d]pyrimidin-5-one | Rt = 2.64 m/z = 489.0 | B |
| 130 | 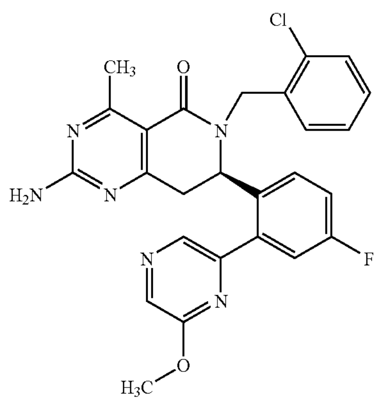 | (R)-2-Amino-6-(2-chloro-benzyl)-7-[4-fluoro-2-(6-methoxy-pyrazin-2-yl)-phenyl]-4-methyl-7,8-dihydro-6H-pyrido[4,3-d]pyrimidin-5-one | Rt = 2.73 m/z = 505.1 | B |
| 131 | 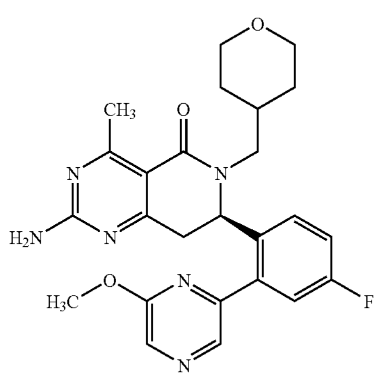 | (R)-2-Amino-7-[4-fluoro-2-(6-methoxy-pyrazin-2-yl)-phenyl]-4-methyl-6-(tetrahydro-pyran-4-ylmethyl)-7,8-dihydro-6H-pyrido[4,3-d]pyrimidin-5-one | Rt = 2.29 m/z = 479.1 | B |
| 132 | 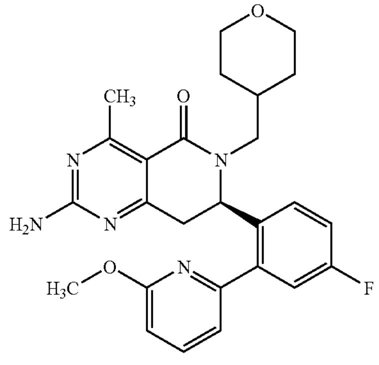 | (R)-2-Amino-7-[4-fluoro-2-(6-methoxy-pyridin-2-yl)-phenyl]-4-methyl-6-(tetrahydro-pyran-4-ylmethyl)-7,8-dihydro-6H-pyrido[4,3-d]pyrimidin-5-one | Rt = 2.51 m/z = 478.2 | B |

TABLE 3-continued

| Cmpd. | Structure | Name | LC/MS (Rt (min), m/z) | IC50 (μM) A ≧ 10 B < 10 |
|---|---|---|---|---|
| 133 | 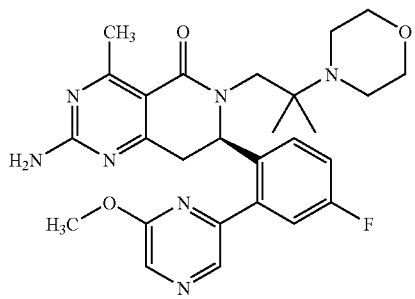 | (R)-2-Amino-7-[4-fluoro-2-(6-methoxy-pyrazin-2-yl)-phenyl]-4-methyl-6-(2-methyl-2-morpholin-4-yl-propyl)-7,8-dihydro-6H-pyrido[4,3-d]pyrimidin-5-one | Rt = 2.00 m/z = 522.2 | B |
| 134 | 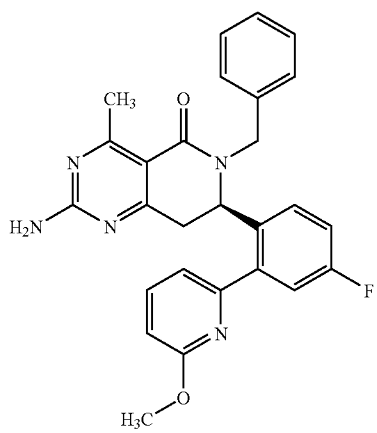 | (R)-2-Amino-6-benzyl-7-[4-fluoro-2-(6-methoxy-pyridin-2-yl)-phenyl]-4-methyl-7,8-dihydro-6H-pyrido[4,3-d]pyrimidin-5-one | Rt = 2.90 m/z = 470.2 | B |
| 135 | 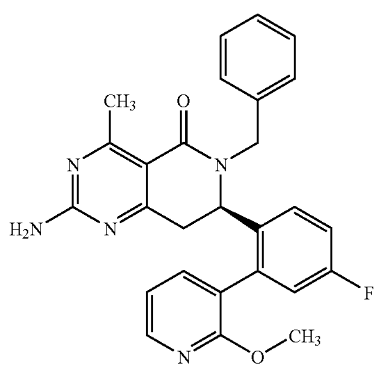 | (R)-2-Amino-6-benzyl-7-[4-fluoro-2-(2-methoxy-pyridin-3-yl)-phenyl]-4-methyl-7,8-dihydro-6H-pyrido[4,3-d]pyrimidin-5-one | Rt = 2.70 m/z = 470.1 | B |
| 136 | 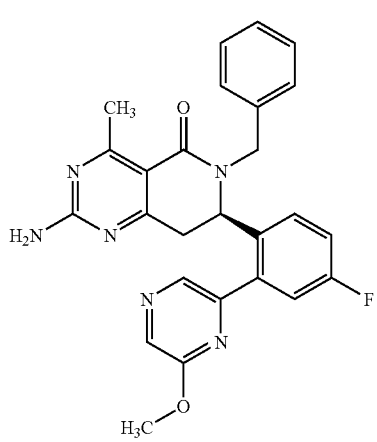 | (R)-2-Amino-6-benzyl-7-[4-fluoro-2-(6-methoxy-pyrazin-2-yl)-phenyl]-4-methyl-7,8-dihydro-6H-pyrido[4,3-d]pyrimidin-5-one | Rt = 2.64 m/z = 471.1 | B |

TABLE 3-continued

| Cmpd. | Structure | Name | LC/MS (Rt (min), m/z) | IC50 (μM) A ≧ 10 B < 10 |
|---|---|---|---|---|
| 137 | 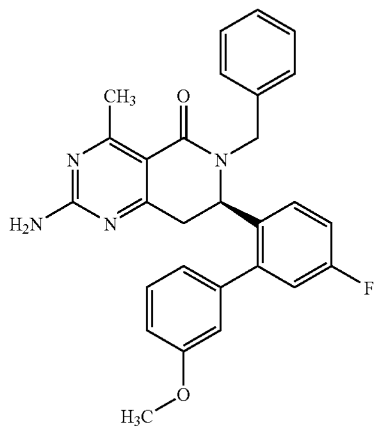 | (R)-2-Amino-6-benzyl-7-(5-fluoro-3'-methoxy-biphenyl-2-yl)-4-methyl-7,8-dihydro-6H-pyrido[4,3-d]pyrimidin-5-one | Rt = 2.94 m/z = 469.1 | A |
| 138 | 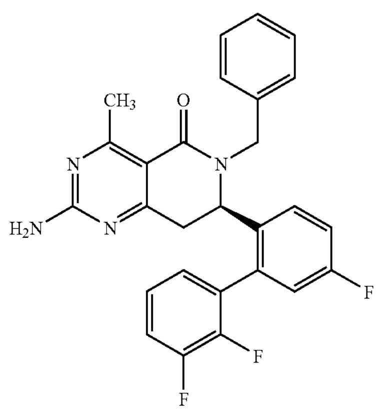 | (R)-2-Amino-6-benzyl-4-methyl-7-(5,2',3'-trifluoro-biphenyl-2-yl)-7,8-dihydro-6H-pyrido[4,3-d]pyrimidin-5-one | Rt = 2.94 m/z = 475.1 | B |
| 139 | 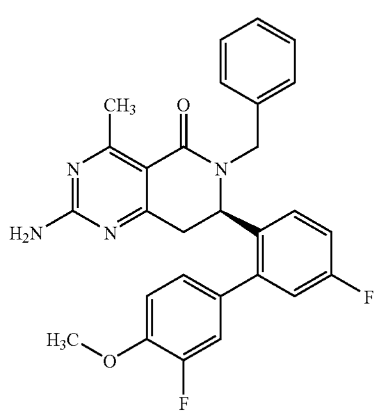 | (R)-2-Amino-6-benzyl-7-(5,3'-difluoro-4'-methoxy-biphenyl-2-yl)-4-methyl-7,8-dihydro-6H-pyrido[4,3-d]pyrimidin-5-one | Rt = 2.91 m/z = 487.1 | A |

TABLE 3-continued

| Cmpd. | Structure | Name | LC/MS (Rt (min), m/z) | IC50 (μM) A ≧ 10 B < 10 |
|---|---|---|---|---|
| 140 | 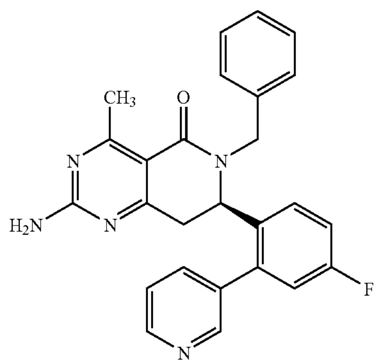 | (R)-2-Amino-6-benzyl-7-(4-fluoro-2-pyridin-3-yl-phenyl)-4-methyl-7,8-dihydro-6H-pyrido[4,3-d]pyrimidin-5-one | Rt = 2.07 m/z = 440.1 | B |
| 141 | 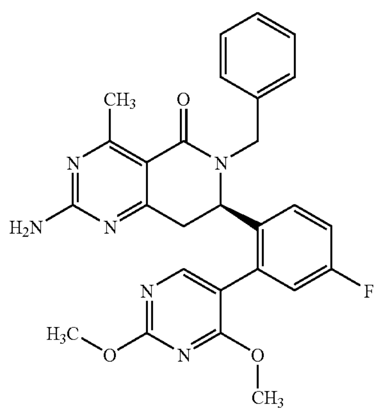 | (R)-2-Amino-6-benzyl-7-[2-(2,4-dimethoxy-pyrimidin-5-yl)-4-fluoro-phenyl]-4-methyl-7,8-dihydro-6H-pyrido[4,3-d]pyrimidin-5-one | Rt = 2.59 m/z = 501.1 | A |
| 142 | 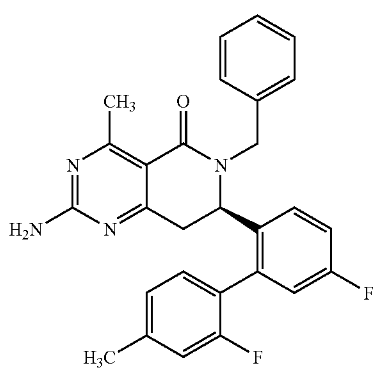 | (R)-2-Amino-6-benzyl-7-(5,2'-difluoro-4'-methyl-biphenyl-2-yl)-4-methyl-7,8-dihydro-6H-pyrido[4,3-d]pyrimidin-5-one | Rt = 3.08 m/z = 471.2 | A |
| 143 | 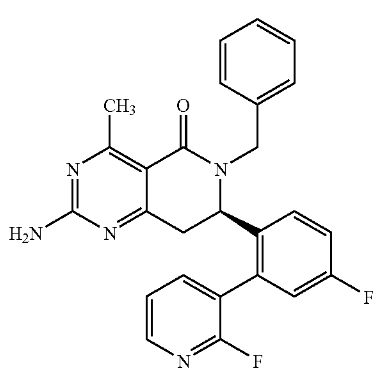 | (R)-2-Amino-6-benzyl-7-[4-fluoro-2-(2-fluoro-pyridin-3-yl)-phenyl]-4-methyl-7,8-dihydro-6H-pyrido[4,3-d]pyrimidin-5-one | Rt = 2.61 m/z = 458.1 | B |

TABLE 3-continued

| Cmpd. | Structure | Name | LC/MS (Rt (min), m/z) | IC50 (μM) A ≧ 10 B < 10 |
|---|---|---|---|---|
| 144 | 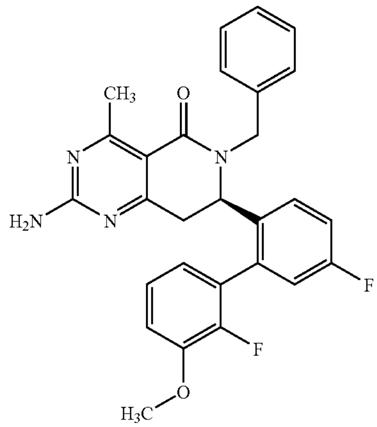 | (R)-2-Amino-6-benzyl-7-(5,2'-difluoro-3'-methoxy-biphenyl-2-yl)-4-methyl-7,8-dihydro-6H-pyrido[4,3-d]pyrimidin-5-one | Rt = 2.92<br>m/z = 487.2 | A |
| 145 | 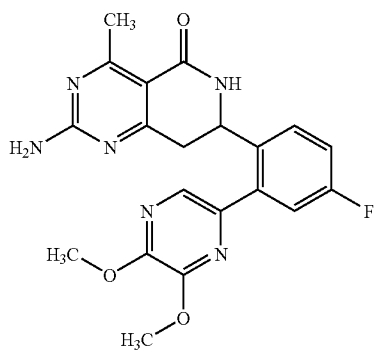 | 2-Amino-7-[2-(5,6-dimethoxy-pyrazin-2-yl)-4-fluoro-phenyl]-4-methyl-7,8-dihydro-6H-pyrido[4,3-d]pyrimidin-5-one | Rt = 2.18<br>m/z = 411.1 | B |
| 146 | 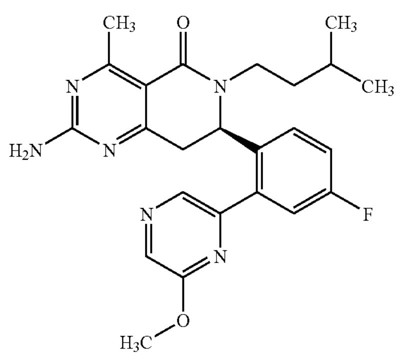 | (R)-2-Amino-7-[4-fluoro-2-(6-methoxy-pyrazin-2-yl)-phenyl]-4-methyl-6-(3-methyl-butyl)-7,8-dihydro-6H-pyrido[4,3-d]pyrimidin-5-one | Rt = 2.72<br>m/z = 451.2 | B |
| 147 | 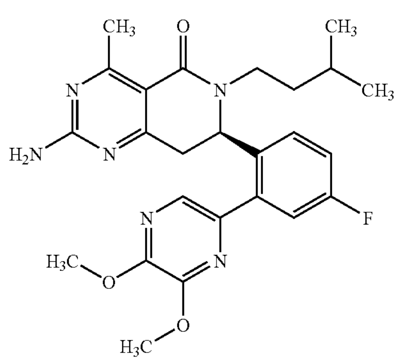 | (R)-2-Amino-7-[2-(5,6-dimethoxy-pyrazin-2-yl)-4-fluoro-phenyl]-4-methyl-6-(3-methyl-butyl)-7,8-dihydro-6H-pyrido[4,3-d]pyrimidin-5-one | Rt = 2.68<br>m/z = 481.1 | B |

TABLE 3-continued

| Cmpd. | Structure | Name | LC/MS (Rt (min), m/z) | IC50 (μM) A ≧ 10 B < 10 |
|---|---|---|---|---|
| 148 | 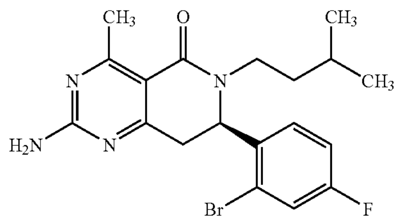 | (R)-2-Amino-7-(2-bromo-4-fluoro-phenyl)-4-methyl-6-(3-methyl-butyl)-7,8-dihydro-6H-pyrido[4,3-d]pyrimidin-5-one | Rt = 2.83 m/z = 421.1 | A |
| 149 | 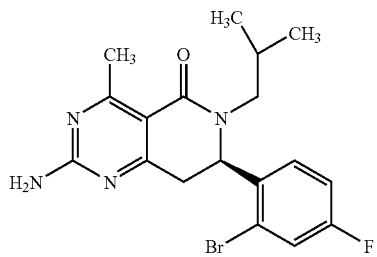 | (R)-2-Amino-7-(2-bromo-4-fluoro-phenyl)-6-isobutyl-4-methyl-7,8-dihydro-6H-pyrido[4,3-d]pyrimidin-5-one | Rt = 2.67 m/z = 407.0 | A |
| 150 | 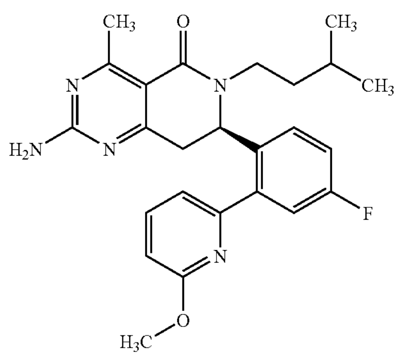 | (R)-2-Amino-7-[4-fluoro-2-(6-methoxy-pyridin-2-yl)-phenyl]-4-methyl-6-(3-methyl-butyl)-7,8-dihydro-6H-pyrido[4,3-d]pyrimidin-5-one | Rt = 2.98 m/z = 450.2 | B |
| 151 | 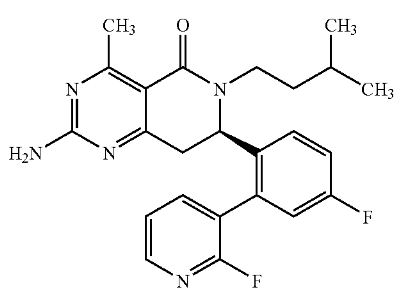 | (R)-2-Amino-7-[4-fluoro-2-(2-fluoro-pyridin-3-yl)-phenyl]-4-methyl-6-(3-methyl-butyl)-7,8-dihydro-6H-pyrido[4,3-d]pyrimidin-5-one | Rt = 2.68 m/z = 438.1 | B |
| 152 | 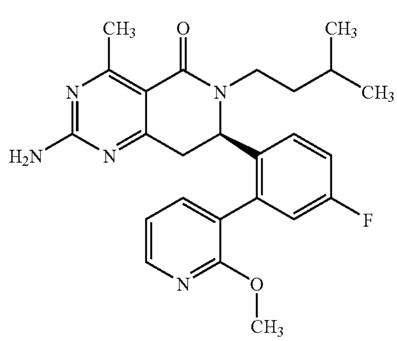 | (R)-2-Amino-7-[4-fluoro-2-(2-methoxy-pyridin-3-yl)-phenyl]-4-methyl-6-(3-methyl-butyl)-7,8-dihydro-6H-pyrido[4,3-d]pyrimidin-5-one | Rt = 2.79 m/z = 450.2 | B |

TABLE 3-continued

| Cmpd. | Structure | Name | LC/MS (Rt (min), m/z) | IC50 (μM) A ≥ 10 B < 10 |
|---|---|---|---|---|
| 153 | 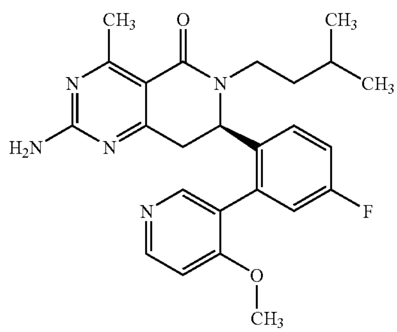 | (R)-2-Amino-7-[4-fluoro-2-(4-methoxy-pyridin-3-yl)-phenyl]-4-methyl-6-(3-methyl-butyl)-7,8-dihydro-6H-pyrido[4,3-d]pyrimidin-5-one | Rt = 2.11 m/z = 450.2 | B |
| 154 | 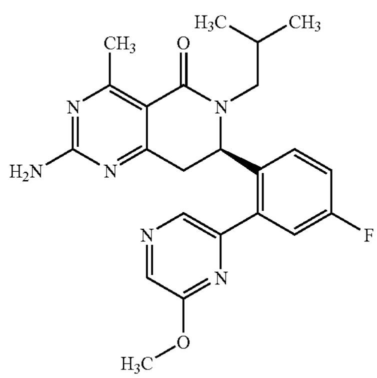 | (R)-2-Amino-7-[4-fluoro-2-(6-methoxy-pyrazin-2-yl)-phenyl]-6-isobutyl-4-methyl-7,8-dihydro-6H-pyrido[4,3-d]pyrimidin-5-one | Rt = 2.55 m/z = 437.1 | B |
| 155 | 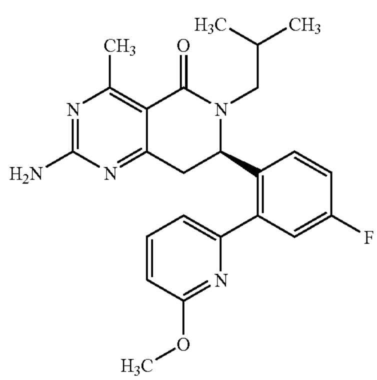 | (R)-2-Amino-7-[4-fluoro-2-(6-methoxy-pyridin-2-yl)-phenyl]-6-isobutyl-4-methyl-7,8-dihydro-6H-pyrido[4,3-d]pyrimidin-5-one | Rt = 2.79 m/z = 436.2 | B |
| 156 | 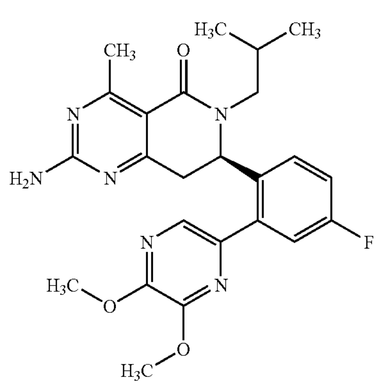 | (R)-2-Amino-7-[2-(5,6-dimethoxy-pyrazin-2-yl)-4-fluoro-phenyl]-6-isobutyl-4-methyl-7,8-dihydro-6H-pyrido[4,3-d]pyrimidin-5-one | Rt = 2.74 m/z = 467.1 | B |

TABLE 3-continued

| Cmpd. | Structure | Name | LC/MS (Rt (min), m/z) | IC50 (μM) A ≧ 10 B < 10 |
|---|---|---|---|---|
| 157 | 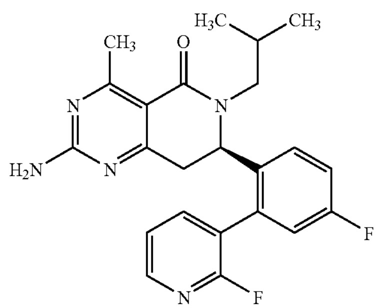 | (R)-2-Amino-7-[4-fluoro-2-(2-fluoro-pyridin-3-yl)-phenyl]-6-isobutyl-4-methyl-7,8-dihydro-6H-pyrido[4,3-d]pyrimidin-5-one | Rt = 2.57 m/z = 424.1 | B |
| 158 | 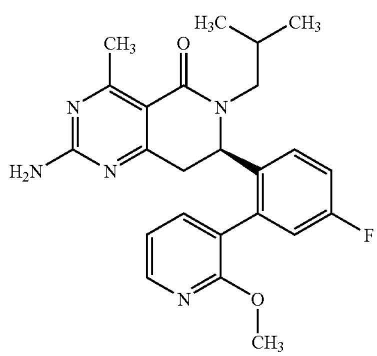 | (R)-2-Amino-7-[4-fluoro-2-(2-methoxy-pyridin-3-yl)-phenyl]-isobutyl-4-methyl-7,8-dihydro-6H-pyrido[4,3-d]pyrimidin-5-one | Rt = 2.61 m/z = 436.2 | B |
| 159 | 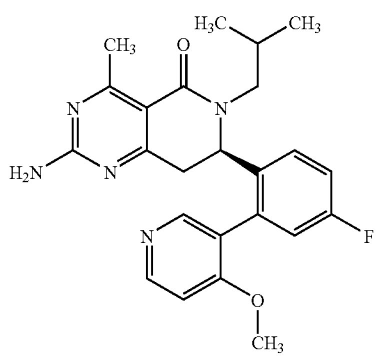 | (R)-2-Amino-7-[4-fluoro-2-(4-methoxy-pyridin-3-yl)-phenyl]-6-isobutyl-4-methyl-7,8-dihydro-6H-pyrido[4,3-d]pyrimidin-5-one | Rt = 1.98 m/z = 436.1 | A |
| 160 | 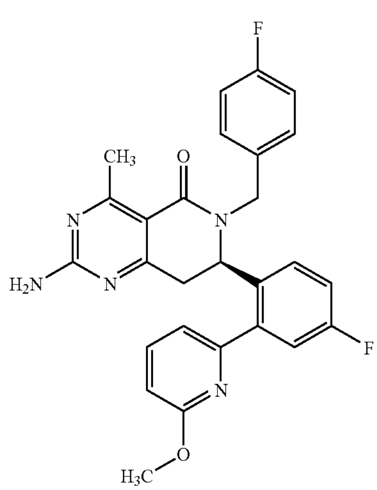 | (R)-2-Amino-6-(4-fluoro-benzyl)-7-[4-fluoro-2-(6-methoxy-pyridin-2-yl)-phenyl]-4-methyl-7,8-dihydro-6H-pyrido[4,3-d]pyrimidin-5-one | Rt = 2.92 m/z = 488.0 | B |

TABLE 3-continued

| Cmpd. | Structure | Name | LC/MS (Rt (min), m/z) | IC50 (μM) A ≧ 10 B < 10 |
|---|---|---|---|---|
| 161 | 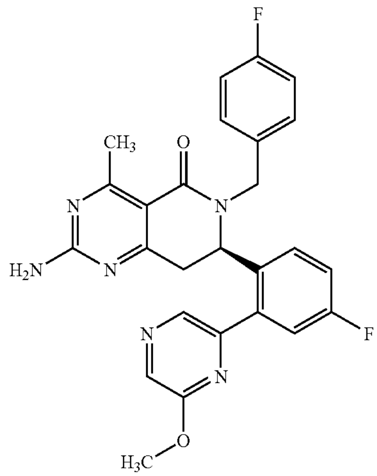 | (R)-2-Amino-6-(4-fluoro-benzyl)-7-[4-fluoro-2-(6-methoxy-pyrazin-2-yl)-phenyl]-4-methyl-7,8-dihydro-6H-pyrido[4,3-d]pyrimidin-5-one | Rt = 2.968 m/z = 489.1 | B |
| 162 | 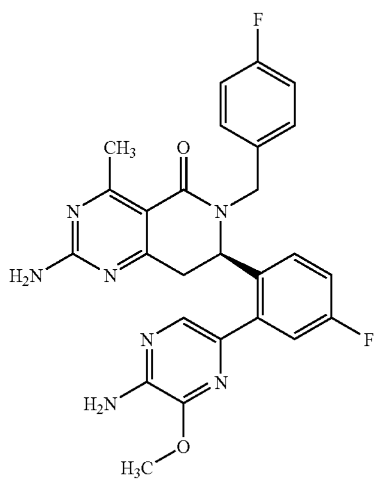 | (R)-2-Amino-7-[2-(5-amino-6-methoxy-pyrazin-2-yl)-4-fluoro-phenyl]-6-(4-fluoro-benzyl)-4-methyl-7,8-dihydro-6H-pyrido[4,3-d]pyrimidin-5-one | Rt = 2.30 m/z = 504.1 | B |
| 163 | 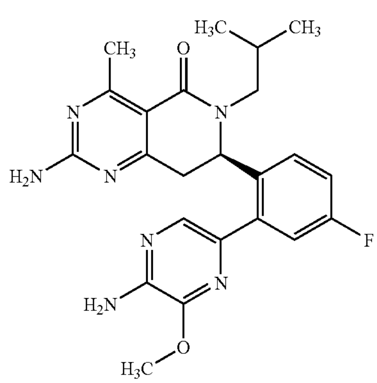 | (R)-2-Amino-7-[2-(5-amino-6-methoxy-pyrazin-2-yl)-4-fluoro-phenyl]-6-isobutyl-4-methyl-7,8-dihydro-6H-pyrido[4,3-d]pyrimidin-5-one | Rt = 2.21 m/z = 452.1 | B |

TABLE 3-continued

| Cmpd. | Structure | Name | LC/MS (Rt (min), m/z) | IC50 (μM) A ≧ 10 B < 10 |
|---|---|---|---|---|
| 164 | 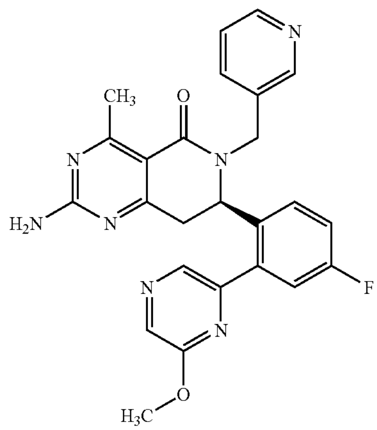 | (R)-2-Amino-7-[4-fluoro-2-(6-methoxy-pyrazin-2-yl)-phenyl]-4-methyl-6-pyridin-3-ylmethyl-7,8-dihydro-6H-pyrido[4,3-d]pyrimidin-5-one | Rt = 2.03 m/z = 471.1 | B |
| 165 | 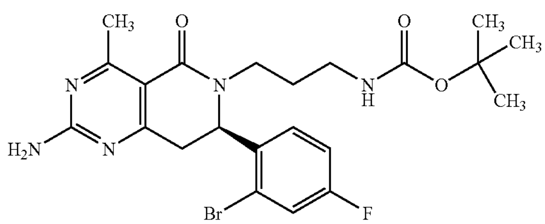 | {3-[(R)-2-Amino-7-(2-bromo-4-fluoro-phenyl)-4-methyl-5-oxo-7,8-dihydro-5H-pyrido[4,3-d]pyrimidin-6-yl]-propyl}-carbamic acid tert-butyl ester | Rt = 2.61 m/z = 510.1 | A |
| 166 | 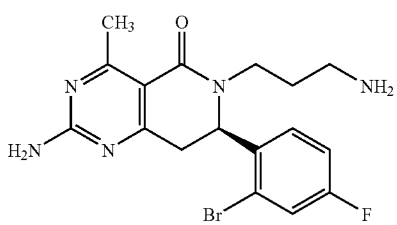 | (R)-2-Amino-6-(3-amino-propyl)-7-(2-bromo-4-fluoro-phenyl)-4-methyl-7,8-dihydro-6H-pyrido[4,3-d]pyrimidin-5-one | Rt = 1.76 m/z = 410.0 | A |
| 167 | 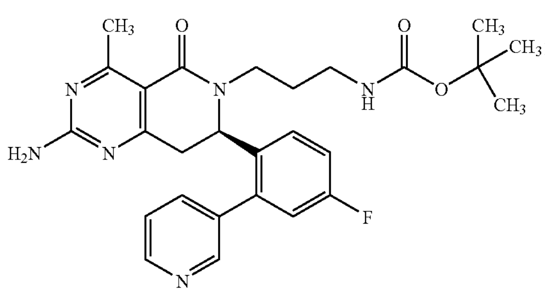 | {3-[(R)-2-Amino-7-(4-fluoro-2-pyridin-3-yl-phenyl)-4-methyl-5-oxo-7,8-dihydro-5H-pyrido[4,3-d]pyrimidin-6-yl]-propyl}-carbamic acid tert-butyl ester | Rt = 2.107 m/z = 507.2 | B |
| 168 | 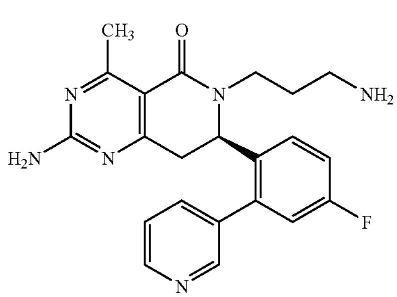 | (R)-2-Amino-6-(3-amino-propyl)-7-(4-fluoro-2-pyridin-3-yl-phenyl)-4-methyl-7,8-dihydro-6H-pyrido[4,3-d]pyrimidin-5-one | Rt = 1.48 m/z = 407.1 | B |

TABLE 3-continued

| Cmpd. | Structure | Name | LC/MS (Rt (min), m/z) | IC50 (μM) A ≧ 10 B < 10 |
|---|---|---|---|---|
| 169 | 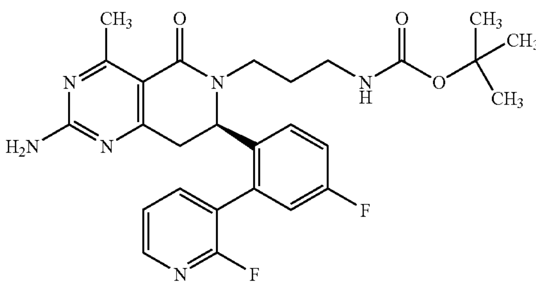 | (3-{(R)-2-Amino-7-[4-fluoro-2-(2-fluoro-pyridin-3-yl)-phenyl]-4-methyl-5-oxo-7,8-dihydro-5H-pyrido[4,3-d]pyrimidin-6-yl}-propyl)-carbamic acid tert-butyl ester | Rt = 2.55 m/z = 525.2 | B |
| 170 | 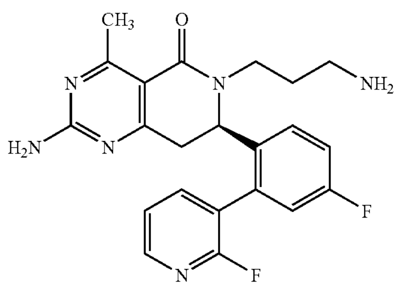 | (R)-2-Amino-6-(3-amino-propyl)-7-[4-fluoro-2-(2-fluoro-pyridin-3-yl)-phenyl]-4-methyl-7,8-dihydro-6H-pyrido[4,3-d]pyrimidin-5-one | Rt = 1.87 m/z = 425.2 | A |
| 171 | 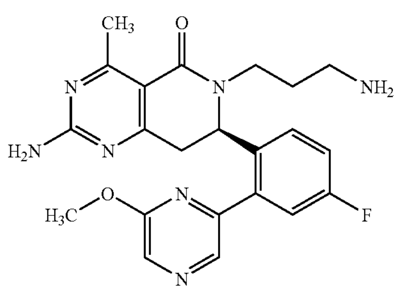 | (R)-2-Amino-6-(3-amino-propyl)-7-[4-fluoro-2-(6-methoxy-pyrazin-2-yl)-phenyl]-4-methyl-7,8-dihydro-6H-pyrido[4,3-d]pyrimidin-5-one | Rt = 1.89 m/z = 438.1 | B |
| 172 | 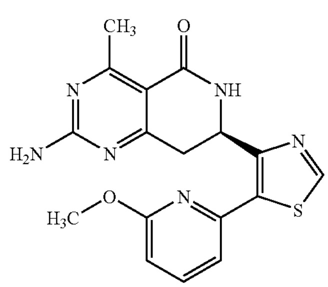 | (R)-2-Amino-7-[5-(6-methoxy-pyridin-2-yl)-thiazol-4-yl]-4-methyl-7,8-dihydro-6H-pyrido[4,3-d]pyrimidin-5-one | Rt = 1.96 m/z = 369.0 | B |
| 173 | 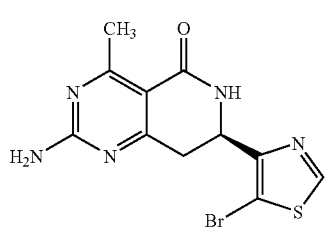 | (R)-2-Amino-7-(5-bromo-thiazol-4-yl)-4-methyl-7,8-dihydro-6H-pyrido[4,3-d]pyrimidin-5-one | Rt = 1.28 m/z = 341.9 | |

TABLE 4

| Cmpd. | Structure | Name | LC/MS (Rt, m/z) | IC$_{50}$ (μM) A ≧ 10 B < 10 |
|---|---|---|---|---|
| 174 | 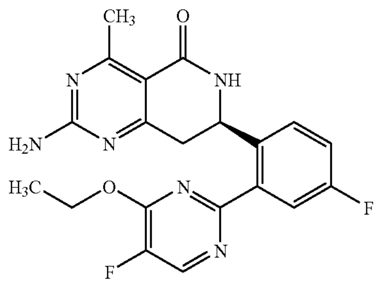 | (R)-2-Amino-7-[2-(4-ethoxy-5-fluoro-pyrimidin-2-yl)-4-fluoro-phenyl]-4-methyl-7,8-dihydro-6H-pyrido[4,3-d]pyrimidin-5-one | Rt = 2.33; m/z = 413.1 | B |
| 175 | 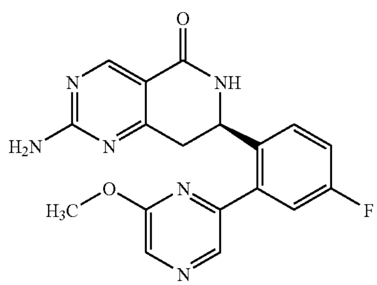 | (R)-2-Amino-7-[4-fluoro-2-(6-methoxy-pyrazin-2-yl)-phenyl]-7,8-dihydro-6H-pyrido[4,3-d]pyrimidin-5-one | Rt = 1.93; m/z = 367 | B |
| 176 | 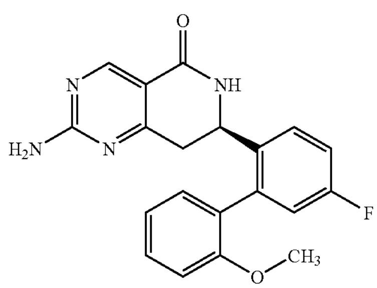 | (R)-2-Amino-7-(5-fluoro-2'-methoxy-biphenyl-2-yl)-7,8-dihydro-6H-pyrido[4,3-d]pyrimidin-5-one | Rt = 2.21; m/z = 365 | B |
| 177 | 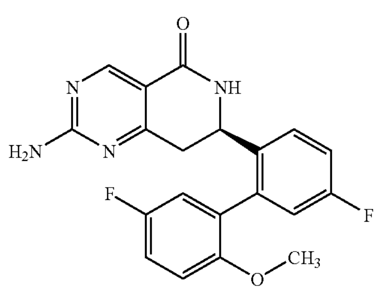 | (R)-2-Amino-7-(5,5'-difluoro-2'-methoxy-biphenyl-2-yl)-7,8-dihydro-6H-pyrido[4,3-d]pyrimidin-5-one | Rt = 2.27; m/z = 383 | B |
| 178 | 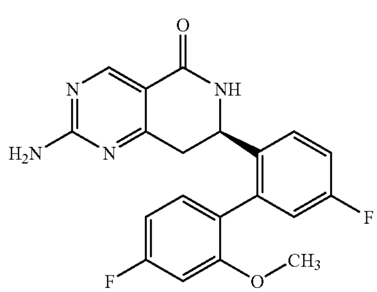 | (R)-2-Amino-7-(5,4'-difluoro-2'-methoxy-biphenyl-2-yl)-7,8-dihydro-6H-pyrido[4,3-d]pyrimidin-5-one | Rt = 2.28; m/z = 383 | |

TABLE 4-continued

| Cmpd. | Structure | Name | LC/MS (Rt, m/z) | IC$_{50}$ (μM) A ≧ 10 B < 10 |
|---|---|---|---|---|
| 179 | 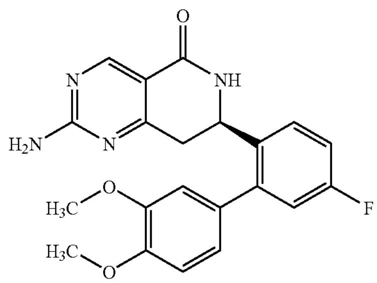 | (R)-2-Amino-7-(5-fluoro-3',4'-dimethoxy-biphenyl-2-yl)-7,8-dihydro-6H-pyrido[4,3-d]pyrimidin-5-one | Rt = 2.11; m/z = 395 | A |
| 180 | 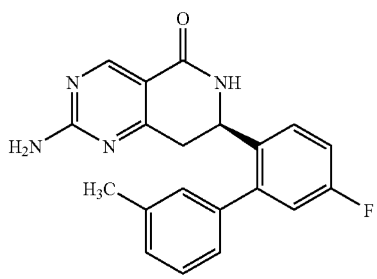 | (R)-2-Amino-7-(5-fluoro-3'-methyl-biphenyl-2-yl)-7,8-dihydro-6H-pyrido[4,3-d]pyrimidin-5-one | Rt = 2.35; m/z = 349 | B |
| 181 | 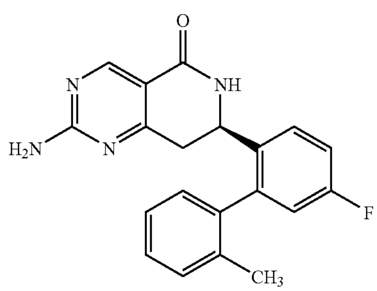 | (R)-2-Amino-7-(5-fluoro-2'-methyl-biphenyl-2-yl)-7,8-dihydro-6H-pyrido[4,3-d]pyrimidin-5-one | Rt = 2.31; m/z = 349 | B |
| 182 | 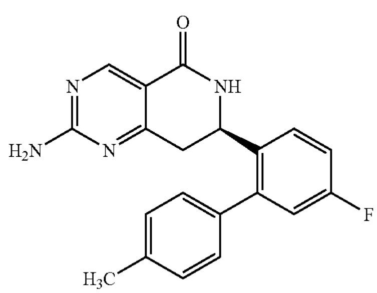 | (R)-2-Amino-7-(5-fluoro-4'-methyl-biphenyl-2-yl)-7,8-dihydro-6H-pyrido[4,3-d]pyrimidin-5-one | Rt = 2.36; m/z = 349 | B |
| 183 | 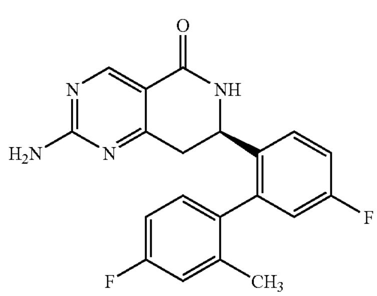 | (R)-2-Amino-7-(5,4'-difluoro-2'-methyl-biphenyl-2-yl)-7,8-dihydro-6H-pyrido[4,3-d]pyrimidin-5-one | Rt = 2.36; m/z = 367 | B |

TABLE 4-continued

| Cmpd. | Structure | Name | LC/MS (Rt, m/z) | IC$_{50}$ (μM) A ≧ 10 B < 10 |
|---|---|---|---|---|
| 184 | 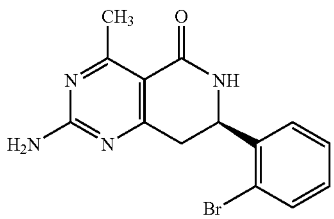 | (R)-2-Amino-7-(2-bromo-phenyl)-4-methyl-7,8-dihydro-6H-pyrido[4,3-d]pyrimidin-5-one | Rt = 1.85 m/z = 332.9/334.9 | A |
| 185 | 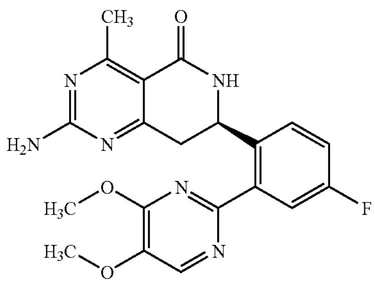 | (R)-2-Amino-7-[2-(4,5-dimethoxy-pyrimidin-2-yl)-4-fluoro-phenyl]-4-methyl-7,8-dihydro-6H-pyrido[4,3-d]pyrimidin-5-one | | B |
| 186 | 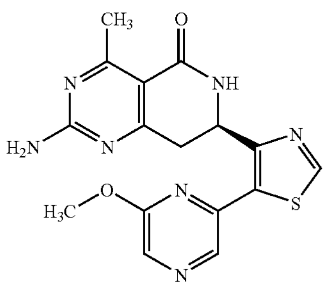 | (R)-2-Amino-7-[5-(6-methoxy-pyrazin-2-yl)-thiazol-4-yl]-4-methyl-7,8-dihydro-6H-pyrido[4,3-d]pyrimidin-5-one | Rt = 1.72; m/z = 370.0 | B |
| 187 | 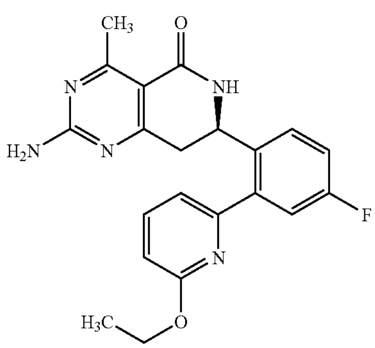 | (R)-2-Amino-7-[2-(6-ethoxy-pyridin-2-yl)-4-fluoro-phenyl]-4-methyl-7,8-dihydro-6H-pyrido[4,3-d]pyrimidin-5-one | Rt = 2.37; m/z = 394.0 | B |
| 188 | 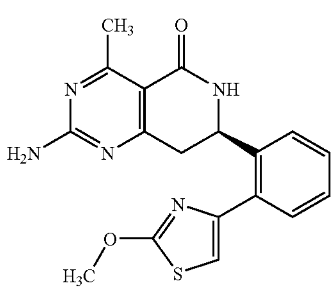 | (R)-2-Amino-7-[2-(2-methoxy-thiazol-4-yl)-phenyl]-4-methyl-7,8-dihydro-6H-pyrido[4,3-d]pyrimidin-5-one | Rt = 2.10 m/z = 368.0 | B |

TABLE 4-continued

| Cmpd. | Structure | Name | LC/MS (Rt, m/z) | IC$_{50}$ (μM) A ≧ 10 B < 10 |
|---|---|---|---|---|
| 189 | 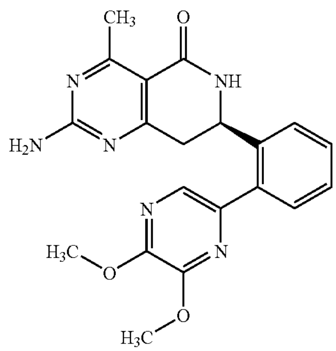 | (R)-2-Amino-7-[2-(5,6-dimethoxy-pyrazin-2-yl)-phenyl]-4-methyl-7,8-dihydro-6H-pyrido[4,3-d]pyrimidin-5-one | Rt = 2.11 m/z = 393.1 | B |
| 190 | 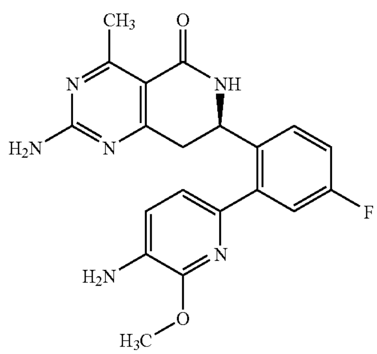 | (R)-2-Amino-7-[2-(5-amino-6-methoxy-pyridin-2-yl)-4-fluoro-phenyl]-4-methyl-7,8-dihydro-6H-pyrido[4,3-d]pyrimidin-5-one | Rt = 2.07; m/z = 395.1 (M + H) | B |
| 191 | 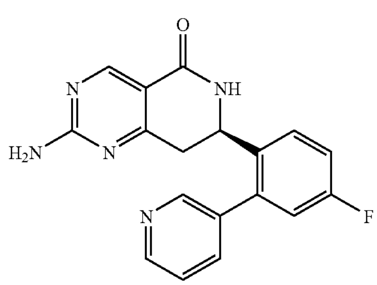 | (R)-2-Amino-7-(4-fluoro-2-pyridin-3-yl-phenyl)-7,8-dihydro-6H-pyrido[4,3-d]pyrimidin-5-one | Rt = 1.4 m/z = 336 | B |
| 192 | 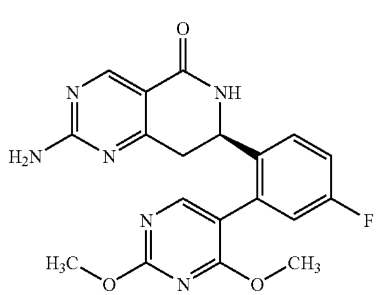 | (R)-2-Amino-7-[2-(2,4-dimethoxy-pyrimidin-5-yl)-4-fluoro-phenyl]-7,8-dihydro-6H-pyrido[4,3-d]pyrimidin-5-one | Rt = 1.95 m/z = 397 | A |

TABLE 4-continued

| Cmpd. | Structure | Name | LC/MS (Rt, m/z) | IC$_{50}$ (µM) A ≧ 10 B < 10 |
|---|---|---|---|---|
| 193 | 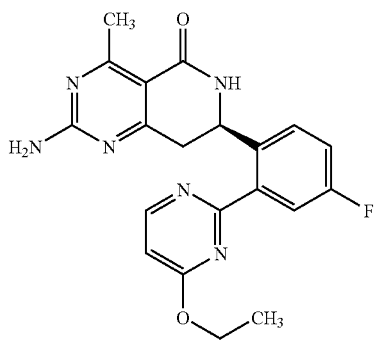 | (R)-2-Amino-7-[2-(4-ethoxy-pyrimidin-2-yl)-4-fluoro-phenyl]-4-methyl-7,8-dihydro-6H-pyrido[4,3-d]pyrimidin-5-one | Rt = 2.13; m/z = 395 | B |
| 194 | 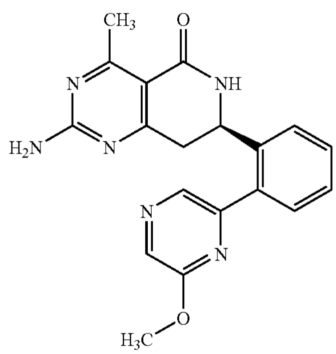 | (R)-2-Amino-7-[2-(6-methoxy-pyrazin-2-yl)-phenyl]-4-methyl-7,8-dihydro-6H-pyrido[4,3-d]pyrimidin-5-one | Rt = 1.94 m/z = 363.0 | B |
| 195 | 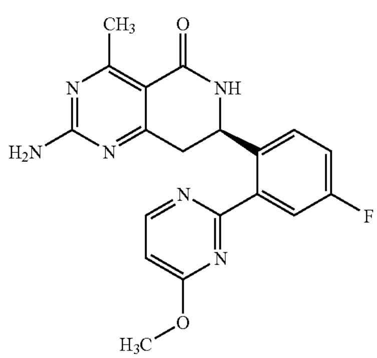 | (R)-2-Amino-7-[4-fluoro-2-(4-methoxy-pyrimidin-2-yl)-phenyl]-4-methyl-7,8-dihydro-6H-pyrido[4,3-d]pyrimidin-5-one | Rt = 2.00; m/z = 381 | B |
| 196 | 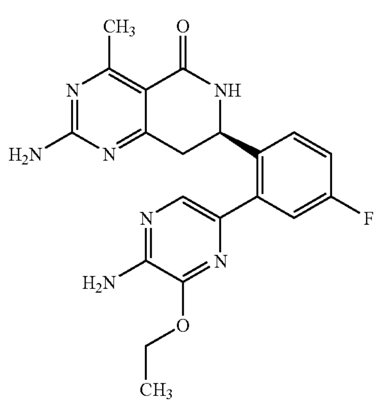 | (R)-2-Amino-7-[2-(5-amino-6-ethoxy-pyrazin-2-yl)-4-fluoro-phenyl]-4-methyl-7,8-dihydro-6H-pyrido[4,3-d]pyrimidin-5-one | Rt = 1.84; m/z = 410.1 | B |

TABLE 4-continued

| Cmpd. | Structure | Name | LC/MS (Rt, m/z) | IC$_{50}$ (μM) A ≧ 10 B < 10 |
|---|---|---|---|---|
| 197 | 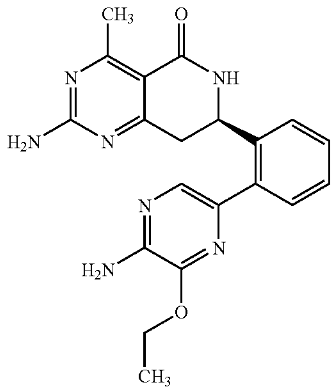 | (R)-2-Amino-7-[2-(5-amino-6-ethoxy-pyrazin-2-yl)-phenyl]-4-methyl-7,8-dihydro-6H-pyrido[4,3-d]pyrimidin-5-one | Rt = 1.76; m/z = 392.1 | B |
| 198 | 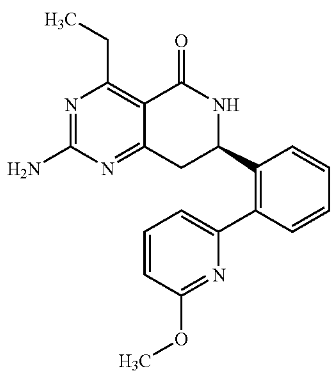 | (R)-2-Amino-4-ethyl-7-[2-(6-methoxy-pyridin-2-yl)-phenyl]-7,8-dihydro-6H-pyrido[4,3-d]pyrimidin-5-one | Rt = 2.24; m/z = 376.1 | B |
| 199 | 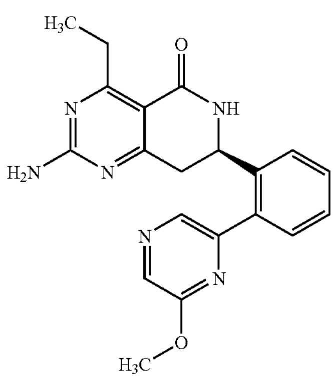 | (R)-2-Amino-4-ethyl-7-[2-(6-methoxy-pyrazin-2-yl)-phenyl]-7,8-dihydro-6H-pyrido[4,3-d]pyrimidin-5-one | Rt = 2.03; m/z 377.1 | B |
| 200 | 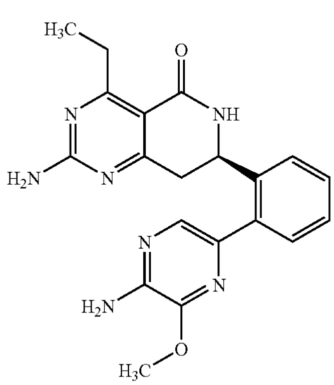 | (R)-2-Amino-7-[2-(5-amino-6-methoxy-pyrazin-2-yl)-phenyl]-4-ethyl-7,8-dihydro-6H-pyrido[4,3-d]pyrimidin-5-one | Rt = 1.76; m/z = 392.2 | B |

TABLE 4-continued

| Cmpd. | Structure | Name | LC/MS (Rt, m/z) | IC$_{50}$ (μM) A ≥ 10 B < 10 |
|---|---|---|---|---|
| 201 | 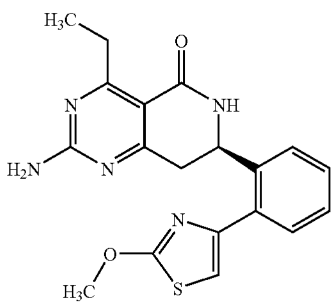 | (R)-2-Amino-4-ethyl-7-[2-(2-methoxy-thiazol-4-yl)-phenyl]-7,8-dihydro-6H-pyrido[4,3-d]pyrimidin-5-one | Rt = 2.24; m/z = 382.0 | A |
| 202 | 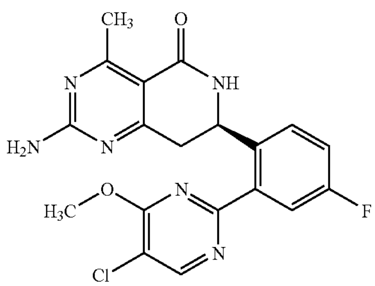 | (R)-2-Amino-7-[2-(5-chloro-4-methoxy-pyrimidin-2-yl)-4-fluoro-phenyl]-4-methyl-7,8-dihydro-6H-pyrido[4,3-d]pyrimidin-5-one | | B |
| 203 | 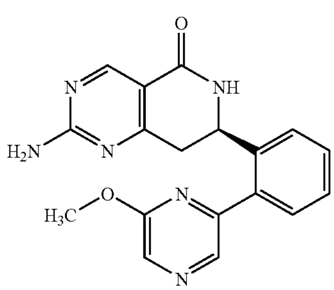 | (R)-2-Amino-7-[2-(6-methoxy-pyrazin-2-yl)-phenyl]-7,8-dihydro-6H-pyrido[4,3-d]pyrimidin-5-one | rt = 1.87 m/z = 349.1 | B |
| 204 | 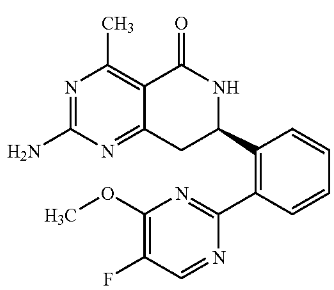 | (R)-2-Amino-7-[2-(5-fluoro-4-methoxy-pyrimidin-2-yl)-phenyl]-4-methyl-7,8-dihydro-6H-pyrido[4,3-d]pyrimidin-5-one | Rt = 1.971 m/z = 381.2 | B |
| 205 | 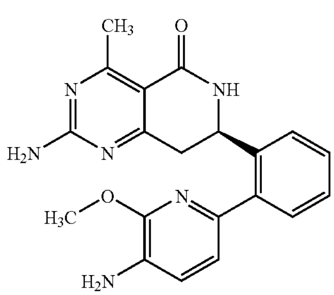 | (R)-2-Amino-7-[2-(5-amino-6-methoxy-pyridin-2-yl)-phenyl]-4-methyl-7,8-dihydro-6H-pyrido[4,3-d]pyrimidin-5-one | Rt = 1.85; m/z = 377.1 (M + H) | B |

TABLE 4-continued

| Cmpd. | Structure | Name | LC/MS (Rt, m/z) | IC$_{50}$ (μM) A ≧ 10 B < 10 |
|---|---|---|---|---|
| 206 | 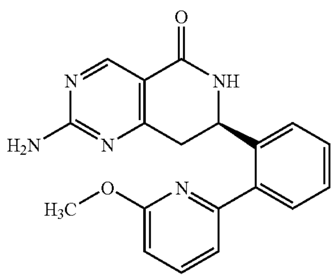 | (R)-2-Amino-7-[2-(6-methoxy-pyridin-2-yl)-phenyl]-7,8-dihydro-6H-pyrido[4,3-d]pyrimidin-5-one | Rt = 1.83 m/z = 348.1 | B |
| 207 | 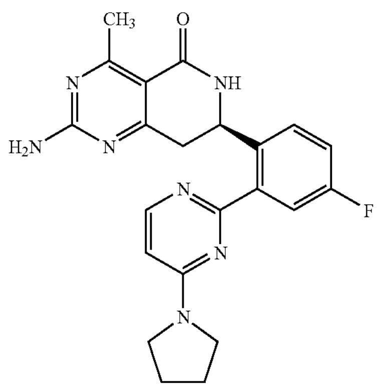 | (R)-2-Amino-7-[4-fluoro-2-(4-pyrrolidin-1-yl-pyrimidin-2-yl)-phenyl]-4-methyl-7,8-dihydro-6H-pyrido[4,3-d]pyrimidin-5-one | Rt = 1.72 min; m/z = 420 | A |
| 208 | 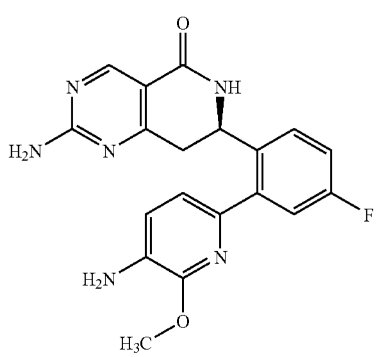 | (R)-2-Amino-7-[2-(5-amino-6-methoxy-pyridin-2-yl)-4-fluoro-phenyl]-7,8-dihydro-6H-pyrido[4,3-d]pyrimidin-5-one | Rt = 2.08 min; m/z = 381.1 (M + H) | B |
| 209 | 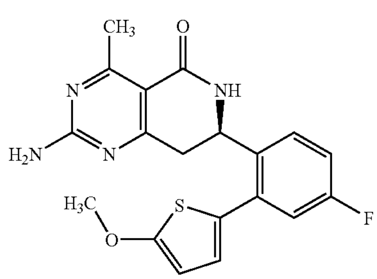 | (R)-2-Amino-7-[4-fluoro-2-(5-methoxy-thiophen-2-yl)-phenyl]-4-methyl-7,8-dihydro-6H-pyrido[4,3-d]pyrimidin-5-one | Rt = 2.064 m/z = 385.0 | B |

TABLE 4-continued

| Cmpd. | Structure | Name | LC/MS (Rt, m/z) | IC$_{50}$ (μM) A ≧ 10 B < 10 |
|---|---|---|---|---|
| 210 | 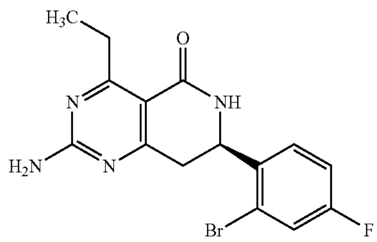 | (R)-2-Amino-7-(2-bromo-4-fluoro-phenyl)-4-ethyl-7,8-dihydro-6H-pyrido[4,3-d]pyrimidin-5-one | Rt = 2.05 m/z = 367.0 | A |
| 211 | 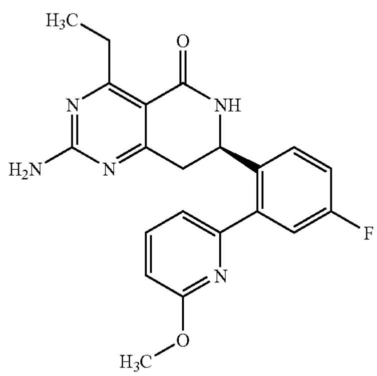 | (R)-2-Amino-4-ethyl-7-[4-fluoro-2-(6-methoxy-pyridin-2-yl)-phenyl]-7,8-dihydro-6H-pyrido[4,3-d]pyrimidin-5-one | Rt = 2.33; m/z = 394.1 | B |
| 212 | 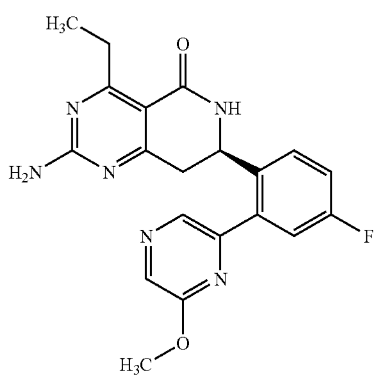 | (R)-2-Amino-4-ethyl-7-[4-fluoro-2-(6-methoxy-pyrazin-2-yl)-phenyl]-7,8-dihydro-6H-pyrido[4,3-d]pyrimidin-5-one | Rt = 2.11; m/z = 395.1 | B |
| 213 | 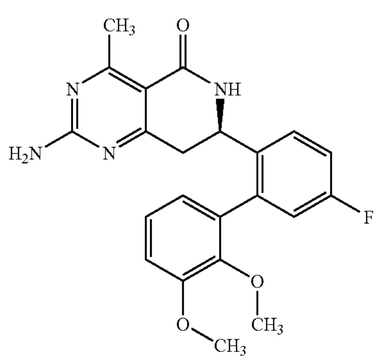 | (R)-2-Amino-7-(5-fluoro-2',3'-dimethoxy-biphenyl-2-yl)-4-methyl-7,8-dihydro-6H-pyrido[4,3-d]pyrimidin-5-one | Rt = 2.067; m/z = 409.1 | B |

TABLE 4-continued

| Cmpd. | Structure | Name | LC/MS (Rt, m/z) | IC$_{50}$ (μM) A ≧ 10 B < 10 |
|---|---|---|---|---|
| 214 | 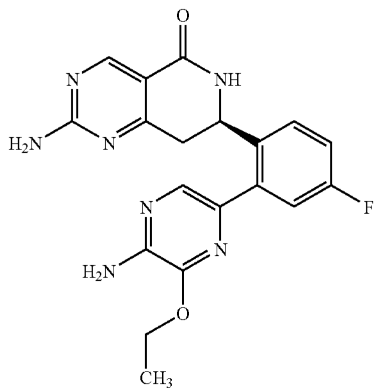 | (R)-2-Amino-7-[2-(5-amino-6-ethoxy-pyrazin-2-yl)-4-fluoro-phenyl]-7,8-dihydro-6H-pyrido[4,3-d]pyrimidin-5-one | Rt = 1.84; m/z = 396.1 | B |
| 215 | 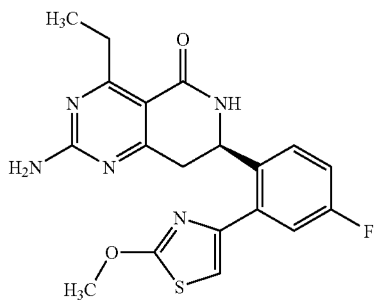 | (R)-2-Amino-4-ethyl-7-[4-fluoro-2-(2-methoxy-thiazol-4-yl)-phenyl]-7,8-dihydro-6H-pyrido[4,3-d]pyrimidin-5-one | Rt = 2.07; m/z = 400.0 | B |
| 216 | 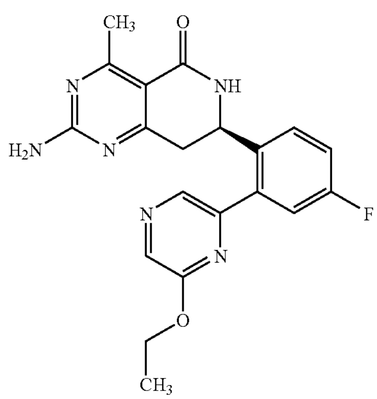 | (R)-2-Amino-7-[2-(6-ethoxy-pyrazin-2-yl)-4-fluoro-phenyl]-4-methyl-7,8-dihydro-6H-pyrido[4,3-d]pyrimidin-5-one | Rt = 1.92; m/z = 395.1 | B |
| 217 | 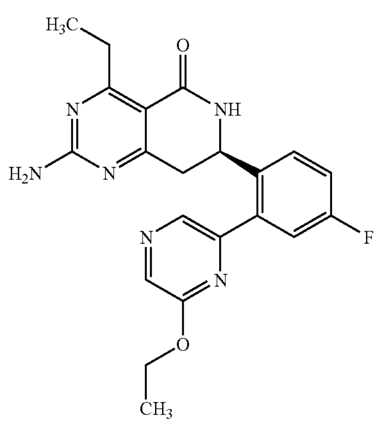 | (R)-2-Amino-7-[2-(6-ethoxy-pyrazin-2-yl)-4-fluoro-phenyl]-4-ethyl-7,8-dihydro-6H-pyrido[4,3-d]pyrimidin-5-one | Rt = 2.00; m/z = 409.1 | B |

TABLE 4-continued

| Cmpd. | Structure | Name | LC/MS (Rt, m/z) | IC$_{50}$ (μM) A ≧ 10 B < 10 |
|---|---|---|---|---|
| 218 | 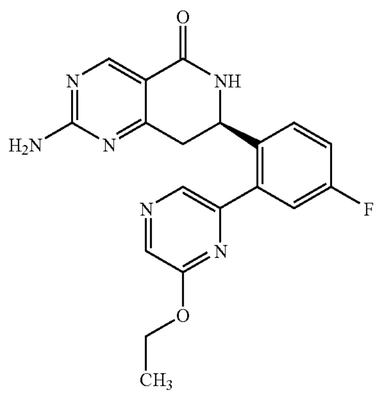 | (R)-2-Amino-7-[2-(6-ethoxy-pyrazin-2-yl)-4-fluoro-phenyl]-7,8-dihydro-6H-pyrido[4,3-d]pyrimidin-5-one | Rt = 2.15; m/z = 381.0 | B |
| 219 | 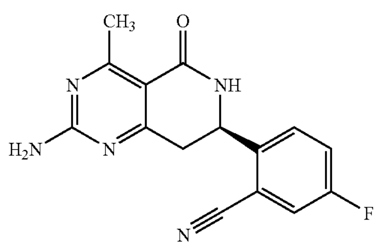 | 2-((R)-2-Amino-4-methyl-5-oxo-5,6,7,8-tetrahydro-pyrido[4,3-d]pyrimidin-7-yl)-5-fluoro-benzonitrile | Rt = 2.03; m/z = 298 | A |
| 220 | 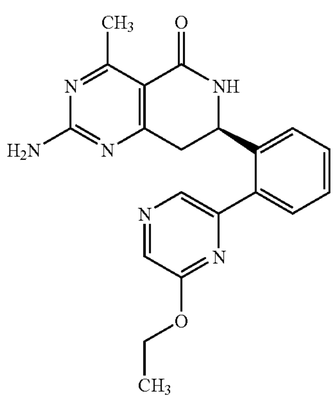 | (R)-2-Amino-7-[2-(6-ethoxy-pyrazin-2-yl)-phenyl]-4-methyl-7,8-dihydro-6H-pyrido[4,3-d]pyrimidin-5-one | Rt = 2.07 m/z = 377.1 | B |
| 221 | 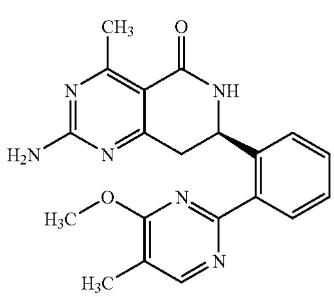 | (R)-2-Amino-7-[2-(4-methoxy-5-methyl-pyrimidin-2-yl)-phenyl]-4-methyl-7,8-dihydro-6H-pyrido[4,3-d]pyrimidin-5-one | Rt = 1.553 m/z = 377.1 | B |

TABLE 4-continued

| Cmpd. | Structure | Name | LC/MS (Rt, m/z) | IC$_{50}$ (μM) A ≥ 10 B < 10 |
|---|---|---|---|---|
| 222 | 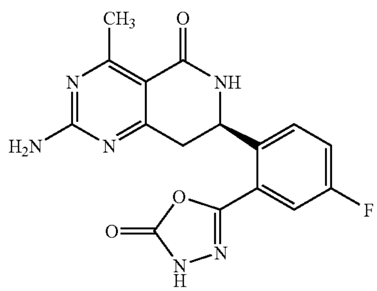 | (R)-2-Amino-7-[4-fluoro-2-(5-oxo-4,5-dihydro-[1,3,4]oxadiazol-2-yl)-phenyl]-4-methyl-7,8-dihydro-6H-pyrido[4,3-d]pyrimidin-5-one | Rt = 1.72; m/z = 357 | A |
| 223 | 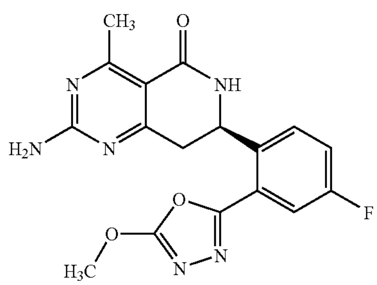 | (R)-2-Amino-7-[4-fluoro-2-(5-methoxy-[1,3,4]oxadiazol-2-yl)-phenyl]-4-methyl-7,8-dihydro-6H-pyrido[4,3-d]pyrimidin-5-one | Rt = 2.22; m/z = 371 | B |
| 224 | 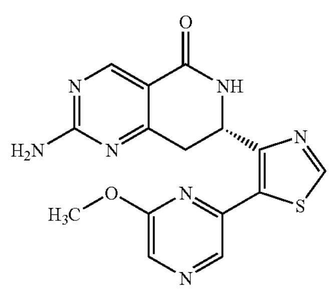 | (S)-2-Amino-7-[5-(6-methoxy-pyrazin-2-yl)-thiazol-4-yl]-7,8-dihydro-6H-pyrido[4,3-d]pyrimidin-5-one | Rt = 1.72 m/z = 356.1 | B |
| 225 | 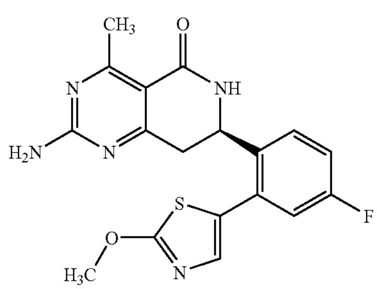 | (R)-2-Amino-7-[4-fluoro-2-(2-methoxy-thiazol-5-yl)-phenyl]-4-methyl-7,8-dihydro-6H-pyrido[4,3-d]pyrimidin-5-one | Rt = 1.834 m/z = 386.0 | B |
| 226 | 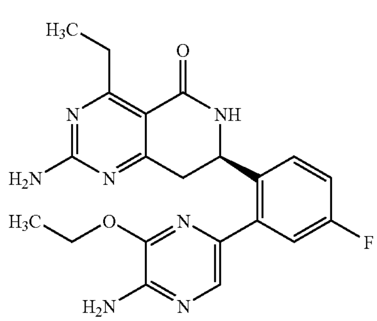 | (R)-2-Amino-7-[2-(5-amino-6-ethoxy-pyrazin-2-yl)-4-fluoro-phenyl]-4-ethyl-7,8-dihydro-6H-pyrido[4,3-d]pyrimidin-5-one | Rt = 1.91 m/z = 424.1 | B |

TABLE 4-continued

| Cmpd. | Structure | Name | LC/MS (Rt, m/z) | IC$_{50}$ (μM) A ≥ 10 B < 10 |
|---|---|---|---|---|
| 227 | 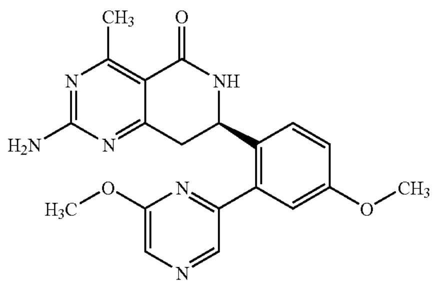 | (R)-2-Amino-7-[4-methoxy-2-(6-methoxy-pyrazin-2-yl)-phenyl]-4-methyl-7,8-dihydro-6H-pyrido[4,3-d]pyrimidin-5-one | Rt = 1.98; m/z = 393.1 | B |
| 228 | 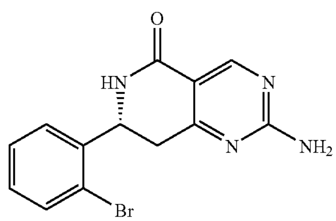 | (R)-2-Amino-7-(2-bromo-phenyl)-7,8-dihydro-6H-pyrido[4,3-d]pyrimidin-5-one | Rt = 1.74, 322.9 | |
| 229 | 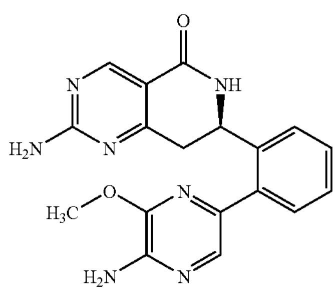 | (R)-2-Amino-7-[2-(5-amino-6-methoxy-pyrazin-2-yl)-phenyl]-7,8-dihydro-6H-pyrido[4,3-d]pyrimidin-5-one | Rt = 1.65, m/z = 364.0 | B |
| 230 | 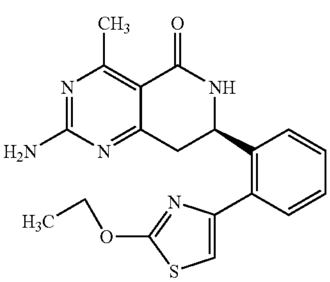 | (R)-2-Amino-7-[2-(2-ethoxy-thiazol-4-yl)-phenyl]-4-methyl-7,8-dihydro-6H-pyrido[4,3-d]pyrimidin-5-one | Rt = 2.63, m/z = 383 | B |
| 231 | 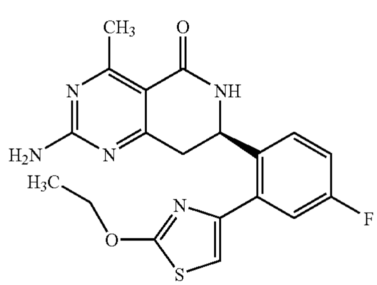 | (R)-2-Amino-7-[2-(2-ethoxy-thiazol-4-yl)-4-fluoro-phenyl]-4-methyl-7,8-dihydro-6H-pyrido[4,3-d]pyrimidin-5-one | Rt = 2.87, m/z = 400 | B |

TABLE 4-continued

| Cmpd. | Structure | Name | LC/MS (Rt, m/z) | IC$_{50}$ (μM) A ≧ 10 B < 10 |
|---|---|---|---|---|
| 232 | 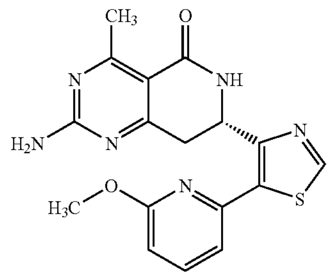 | (S)-2-Amino-7-[5-(6-methoxy-pyridin-2-yl)-thiazol-4-yl]-4-methyl-7,8-dihydro-6H-pyrido[4,3-d]pyrimidin-5-one | Rt = 1.96, m/z = 369.0 | B |
| 233 | 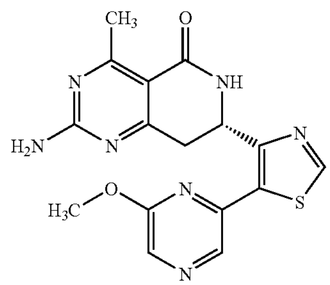 | (S)-2-Amino-7-[5-(6-methoxy-pyrazin-2-yl)-thiazol-4-yl]-4-methyl-7,8-dihydro-6H-pyrido[4,3-d]pyrimidin-5-one | Rt = 1.72, m/z = 370.0 | B |
| 234 | 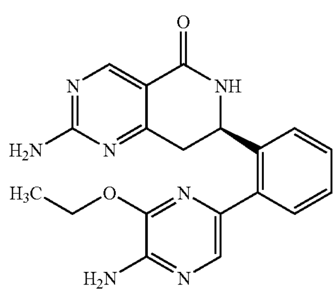 | (R)-2-Amino-7-[2-(5-amino-6-ethoxy-pyrazin-2-yl)-phenyl]-7,8-dihydro-6H-pyrido[4,3-d]pyrimidin-5-one | Rt = 1.72, m/z = 378.1 | B |
| 235 | 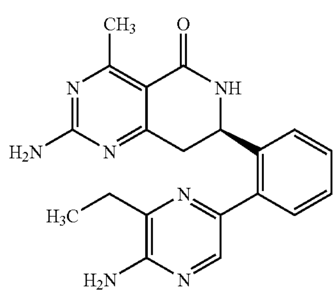 | (R)-2-Amino-7-[2-(5-amino-6-ethyl-pyrazin-2-yl)-phenyl]-4-methyl-7,8-dihydro-6H-pyrido[4,3-d]pyrimidin-5-one | Rt = 1.68; m/z = 376 | B |
| 236 | 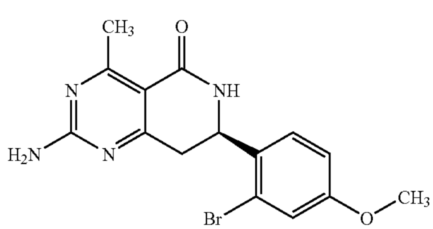 | (R)-2-Amino-7-(2-bromo-4-methoxy-phenyl)-4-methyl-7,8-dihydro-6H-pyrido[4,3-d]pyrimidin-5-one | Rt = 1.95 min; m/z = 365.0 | A |

TABLE 4-continued

| Cmpd. | Structure | Name | LC/MS (Rt, m/z) | IC$_{50}$ (μM) A ≥ 10 B < 10 |
|---|---|---|---|---|
| 237 | 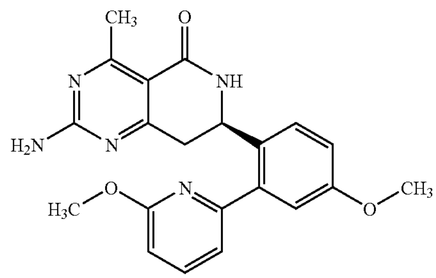 | (R)-2-Amino-7-[4-methoxy-2-(6-methoxy-pyridin-2-yl)-phenyl]-4-methyl-7,8-dihydro-6H-pyrido[4,3-d]pyrimidin-5-one | Rt = 2.15 min; m/z = 392.1 | B |
| 238 | 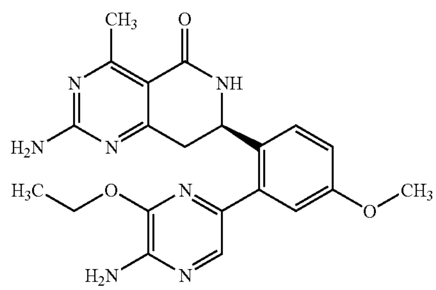 | (R)-2-Amino-7-[2-(5-amino-6-ethoxy-pyrazin-2-yl)-4-methoxy-phenyl]-4-methyl-7,8-dihydro-6H-pyrido[4,3-d]pyrimidin-5-one | Rt = 1.79 min; m/z = 422.1 | B |
| 239 | 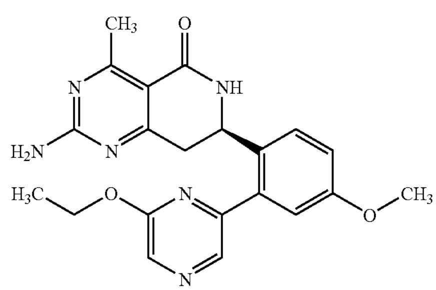 | (R)-2-Amino-7-[2-(6-ethoxy-pyrazin-2-yl)-4-methoxy-phenyl]-4-methyl-7,8-dihydro-6H-pyrido[4,3-d]pyrimidin-5-one | Rt = 2.11 min; m/z = 407.1 | B |

TABLE 5

| Cmpd | Structure | Name | LC/MS (Rt, m/z) | IC50 (nM) A ≥ 10 B < 10 |
|---|---|---|---|---|
| 240 | 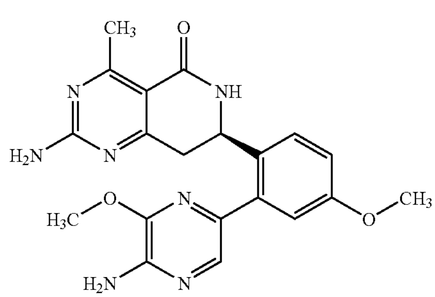 | (R)-2-Amino-7-[2-(5-amino-6-methoxy-pyrazin-2-yl)-4-methoxy-phenyl]-4-methyl-7,8-dihydro-6H-pyrido[4,3-d]pyrimidin-5-one | Rt = 1.69 m/z = 408.1 | B |

TABLE 5-continued

| Cmpd | Structure | Name | LC/MS (Rt, m/z) | IC50 (nM) A ≧ 10 B < 10 |
|---|---|---|---|---|
| 241 | 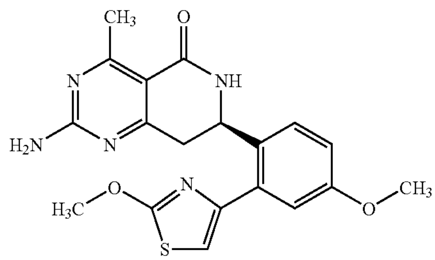 | (R)-2-Amino-7-[4-methoxy-2-(2-methoxy-thiazol-4-yl)-phenyl]-4-methyl-7,8-dihydro-6H-pyrido[4,3-d]pyrimidin-5-one | Rt = 2.14 m/z = 398.1 | |
| 242 | 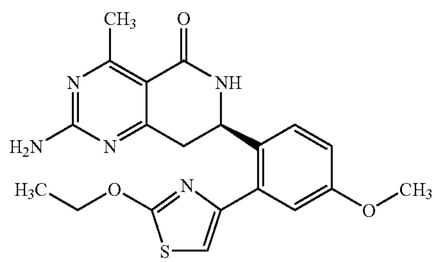 | (R)-2-Amino-7-[2-(2-ethoxy-thiazol-4-yl)-4-methoxy-phenyl]-4-methyl-7,8-dihydro-6H-pyrido[4,3-d]pyrimidin-5-one | Rt = 2.31 m/z = 412.0 | A |
| 243 | 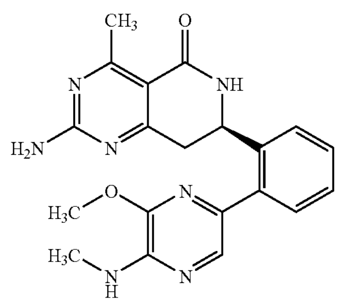 | (R)-2-Amino-7-[2-(6-methoxy-5-methylamino-pyrazin-2-yl)-phenyl]-4-methyl-7,8-dihydro-6H-pyrido[4,3-d]pyrimidin-5-one | Rt = 1.40 m/z = 392.1 | B |
| 244 | 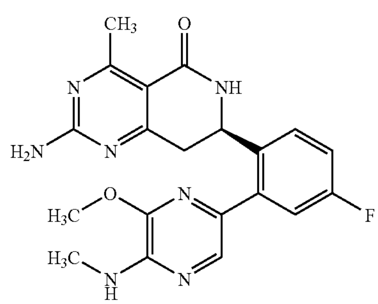 | (R)-2-Amino-7-[4-fluoro-2-(6-methoxy-5-methylamino-pyrazin-2-yl)-phenyl]-4-methyl-7,8-dihydro-6H-pyrido[4,3-d]pyrimidin-5-one | Rt = 1.49 m/z = 410.1 | B |
| 245 | 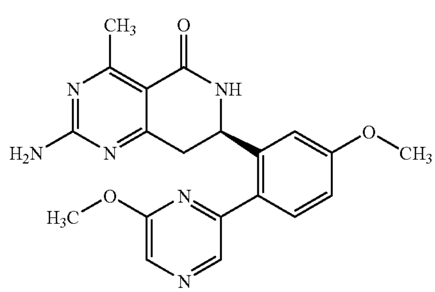 | (R)-2-Amino-7-[5-methoxy-2-(6-methoxy-pyrazin-2-yl)-phenyl]-4-methyl-7,8-dihydro-6H-pyrido[4,3-d]pyrimidin-5-one | Rt = 1.78 m/z = 393 | B |

TABLE 5-continued

| Cmpd | Structure | Name | LC/MS (Rt, m/z) | IC50 (nM) A ≧ 10 B < 10 |
|---|---|---|---|---|
| 246 | 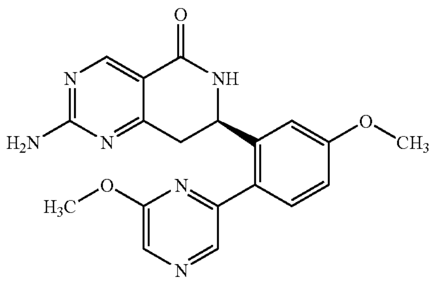 | (R)-2-Amino-7-[5-methoxy-2-(6-methoxy-pyrazin-2-yl)-phenyl]-7,8-dihydro-6H-pyrido[4,3-d]pyrimidin-5-one | Rt = 1.75 m/z = 379 | B |
| 247 | 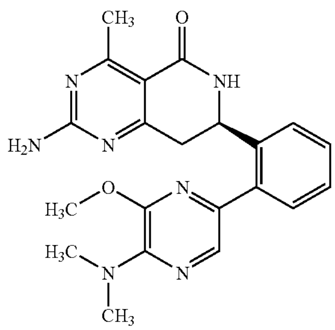 | (R)-2-Amino-7-[2-(5-dimethylamino-6-methoxy-pyrazin-2-yl)-phenyl]-4-methyl-7,8-dihydro-6H-pyrido[4,3-d]pyrimidin-5-one | Rt = 1.63 m/z = 406.1 | B |
| 248 | 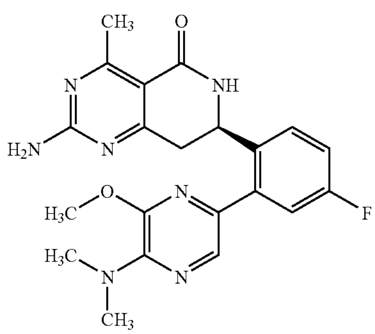 | (R)-2-Amino-7-[2-(5-dimethylamino-6-methoxy-pyrazin-2-yl)-4-fluoro-phenyl]-4-methyl-7,8-dihydro-6H-pyrido[4,3-d]pyrimidin-5-one | Rt = 1.77 m/z = 424.1 | B |
| 249 | 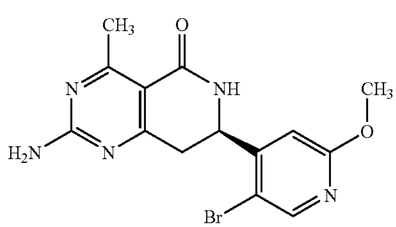 | (R)-2-Amino-7-(5-bromo-2-methoxy-pyridin-4-yl)-4-methyl-7,8-dihydro-6H-pyrido[4,3-d]pyrimidin-5-one | Rt = 1.76 m/z = 364 | B |
| 250 | 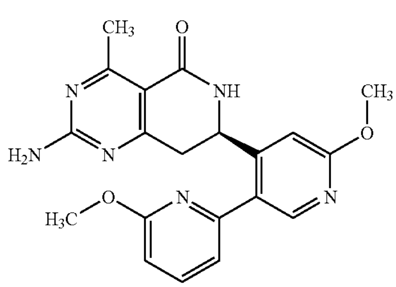 | (R)-2-Amino-7-(6,6'-dimethoxy-[2,3']bipyridinyl-4'-yl)-4-methyl-7,8-dihydro-6H-pyrido[4,3-d]pyrimidin-5-one | Rt = 1.98 m/z = 393 | B |

TABLE 5-continued

| Cmpd | Structure | Name | LC/MS (Rt, m/z) | IC50 (nM) A ≧ 10 B < 10 |
|---|---|---|---|---|
| 251 | 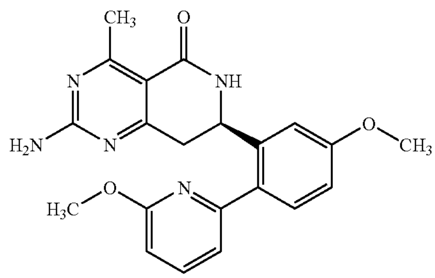 | (R)-2-Amino-7-[5-methoxy-2-(6-methoxy-pyridin-2-yl)-phenyl]-4-methyl-7,8-dihydro-6H-pyrido[4,3-d]pyrimidin-5-one | Rt = 1.95 m/z = 392 | A |
| 252 | 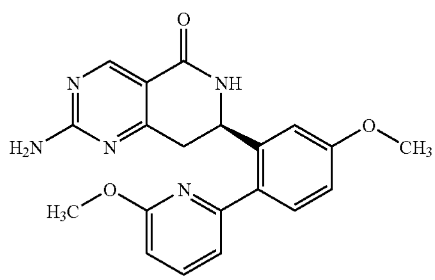 | (R)-2-Amino-7-[5-methoxy-2-(6-methoxy-pyridin-2-yl)-phenyl]-7,8-dihydro-6H-pyrido[4,3-d]pyrimidin-5-one | Rt = 1.94 m/z = 378 | B |
| 253 | 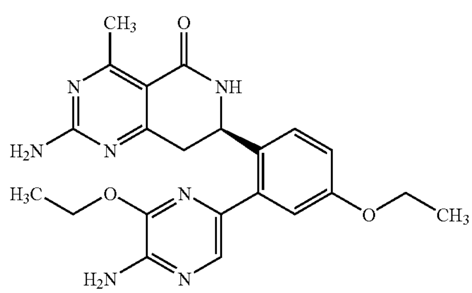 | (R)-2-Amino-7-[2-(5-amino-6-ethoxy-pyrazin-2-yl)-4-ethoxy-phenyl]-4-methyl-7,8-dihydro-6H-pyrido[4,3-d]pyrimidin-5-one | Rt = 1.91 m/z = 436.1 | B |
| 254 | 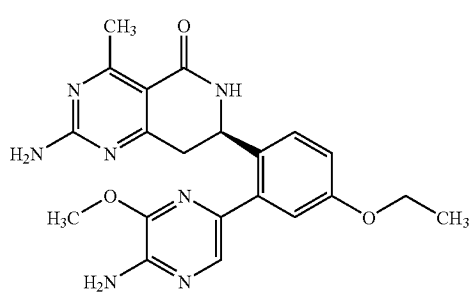 | (R)-2-Amino-7-[2-(5-amino-6-methoxy-pyrazin-2-yl)-4-ethoxy-phenyl]-4-methyl-7,8-dihydro-6H-pyrido[4,3-d]pyrimidin-5-one | Rt = 1.79 m/z = 422.1 | B |
| 255 | 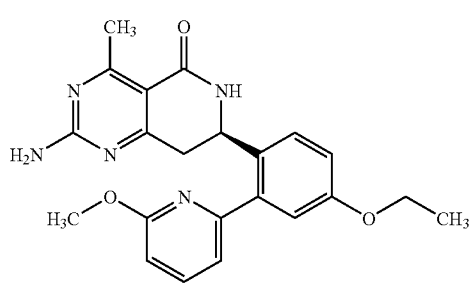 | (R)-2-Amino-7-[4-ethoxy-2-(6-methoxy-pyridin-2-yl)-phenyl]-4-methyl-7,8-dihydro-6H-pyrido[4,3-d]pyrimidin-5-one | Rt = 2.29 m/z = 406.1 | B |

TABLE 5-continued

| Cmpd | Structure | Name | LC/MS (Rt, m/z) | IC50 (nM) A ≧ 10 B < 10 |
|---|---|---|---|---|
| 256 | 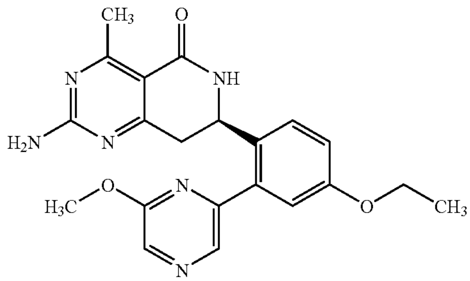 | (R)-2-Amino-7-[4-ethoxy-2-(6-methoxy-pyrazin-2-yl)-phenyl]-4-methyl-7,8-dihydro-6H-pyrido[4,3-d]pyrimidin-5-one | Rt = 2.13 m/z = 407.1 | B |
| 257 | Chiral | (R)-2-amino-7-(2-(cyclopentyloxy)-4-fluorophenyl)-4-methyl-7,8-dihydropyrido[4,3-d]pyrimidin-5(6H)-one | Rt = 2.1 m/z = 357 | B |
| 258 | Chiral | (R)-2-amino-7-(2-(cyclopentyloxy)phenyl)-4-methyl-7,8-dihydropyrido[4,3-d]pyrimidin-5(6H)-one | Rt = 2.03 m/z = 339 | B |
| 259 | Chiral | (R)-2-amino-7-(4-fluoro-2-isopropoxyphenyl)-4-methyl-7,8-dihydropyrido[4,3-d]pyrimidin-5(6H)-one | Rt = 1.87 m/z = 331 | B |
| 260 | Chiral | (R)-2-amino-7-((R)-5-fluoro-2-(6-methoxypyridin-2-yl)phenyl)-4-methyl-7,8-dihydropyrido[4,3-d]pyrimidin-5(6H)-one | Rt = 2.51 min, MH+ = 380.1 | B |

TABLE 5-continued

| Cmpd | Structure | Name | LC/MS (Rt, m/z) | IC50 (nM) A ≧ 10 B < 10 |
|---|---|---|---|---|
| 261 | Chiral | (R)-2-amino-7-((R)-2-(6-methoxypyridin-2-yl)-4-methylphenyl)-4-methyl-7,8-dihydropyrido[4,3-d]pyrimidin-5(6H)-one | Rt = 2.31 m/z = 376.2 | B |
| 262 | Chiral | (R)-2-amino-7-((R)-5-fluoro-2-(6-methoxypyrazin-2-yl)phenyl)-4-methyl-7,8-dihydropyrido[4,3-d]pyrimidin-5(6H)-one | Rt = 2.20 min, MH+ = 381.1 | B |
| 263 | Chiral | (R)-2-amino-7-((R)-2-(6-methoxypyrazin-2-yl)-4-methylphenyl)-4-methyl-7,8-dihydropyrido[4,3-d]pyrimidin-5(6H)-one | Rt = 2.11 m/z = 377.2 | B |
| 264 | Chiral | (R)-2-amino-7-(2-((R)-5-amino-6-(2,2,2-trifluoroethoxy)pyrazin-2-yl)-4-fluorophenyl)-4-methyl-7,8-dihydropyrido[4,3-d]pyrimidin-5(6H)-one | Rt = 1.79 m/z = 463.9 | B |
| 265 | Chiral | (R)-2-amino-7-((R)-5-fluoro-2-(2-methoxythiazol-4-yl)phenyl)-4-methyl-7,8-dihydropyrido[4,3-d]pyrimidin-5(6H)-one | Rt = 2.18 m/z = 386.1 | B |

TABLE 5-continued

| Cmpd | Structure | Name | LC/MS (Rt, m/z) | IC50 (nM) A ≥ 10 B < 10 |
|---|---|---|---|---|
| 266 | Chiral | (R)-2-amino-7-((R)-2-(5-amino-6-methoxypyrazin-2-yl)-5-fluorophenyl)-4-methyl-7,8-dihydropyrido[4,3-d]pyrimidin-5(6H)-one | Rt = 1.73 m/z = 396.1 | B |
| 267 | 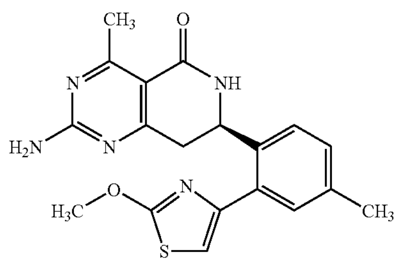 | (R)-2-amino-7-((R)-2-(2-methoxythiazol-4-yl)-4-methylphenyl)-4-methyl-7,8-dihydropyrido[4,3-d]pyrimidin-5(6H)-one | Rt = 2.29 m/z = 382.1 | B |
| 268 | Chiral | (R)-2-amino-7-((R)-2-(5-amino-6-methoxypyrazin-2-yl)-4-methylphenyl)-4-methyl-7,8-dihydropyrido[4,3-d]pyrimidin-5(6H)-one | Rt = 1.80 m/z = 392.2 | B |
| 269 | Chiral | (R)-2-amino-7-(2-(cyclopentyloxy)-4-fluorophenyl)-7,8-dihydropyrido[4,3-d]pyrimidin-5(6H)-one | Rt = 2.4 min m/z = 343 | B |
| 270 | Chiral | (R)-2-amino-7-(2-((R)-5-amino-6-(2,2,2-trifluoroethoxy)pyrazin-2-yl)phenyl)-7,8-dihydropyrido[4,3-d]pyrimidin-5(6H)-one | Rt = 1.68 m/z = 431.9 | A |

TABLE 5-continued

| Cmpd | Structure | Name | LC/MS (Rt, m/z) | IC50 (nM) A ≧ 10 B < 10 |
|---|---|---|---|---|
| 271 | Chiral | (R)-2-amino-7-(2-((R)-5-amino-6-(2,2,2-trifluoroethoxy)pyrazin-2-yl)phenyl)-4-methyl-7,8-dihydropyrido[4,3-d]pyrimidin-5(6H)-one | Rt = 1.67 m/z = 445.9 | B |
| 272 | Chiral | (R)-2-amino-7-(2-((R)-5-amino-6-(2,2,2-trifluoroethoxy)pyrazin-2-yl)-4-fluorophenyl)-7,8-dihydropyrido[4,3-d]pyrimidin-5(6H)-one | Rt = 1.79 m/z = 449.9 | A |
| 273 | Chiral | (R)-2-amino-7-((S)-2-(5-amino 6-methoxypyrazin-2-yl)-4-fluoro-5-methoxyphenyl)-4-methyl-7,8-dihydropyrido[4,3-d]pyrimidin-5(6H)-one | Rt = 1.75 m/z = 426.1 | B |
| 274 | Chiral | (R)-2-amino-7-((S)-4-fluoro-5-methoxy-2-(6-methoxypyrazin-2-yl)phenyl)-4-methyl-7,8-dihydropyrido[4,3-d]pyrimidin-5(6H)-one | Rt = 2.06 m/z = 411.1 | B |

TABLE 5-continued

| Cmpd | Structure | Name | LC/MS (Rt, m/z) | IC50 (nM) A ≧ 10 B < 10 |
|---|---|---|---|---|
| 275 | Chiral | (R)-2-amino-7-(4-fluoro-5-methoxy-2-((S)-6-methoxypyridin-2-yl)phenyl)-4-methyl-7,8-dihydropyrido[4,3-d]pyrimidin-5(6H)-one | Rt = 2.30 m/z = 410.1 | B |
| 276 | Chiral | (R)-2-amino-7-((R)-4-fluoro-5-methoxy-2-(2-methoxythiazol-4-yl)phenyl)-4-methyl-7,8-dihydropyrido[4,3-d]pyrimidin-5(6H)-one | Rt = 2.25 m/z = 416.1 | B |
| 277 | Chiral | (R)-2-amino-7-((S)-2-(5-amino-6-methoxypyrazin-2-yl)-4-isopropoxy-5-methoxyphenyl)-4-methyl-7,8-dihydropyrido[4,3-d]pyrimidin-5(6H)-one | Rt = 1.87, m/z = 466.2 | B |
| 278 | Chiral | (R)-2-amino-7-((S)-4-isopropoxy-5-methoxy-2-(6-methoxypyrazin-2-yl)phenyl)-4-methyl-7,8-dihydropyrido[4,3-d]pyrimidin-5(6H)-one | Rt = 2.19 m/z = 451.1 | B |

TABLE 5-continued

| Cmpd | Structure | Name | LC/MS (Rt, m/z) | IC50 (nM) A ≥ 10 B < 10 |
|---|---|---|---|---|
| 279 | 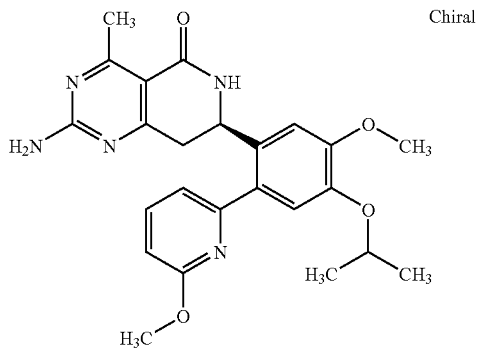 | Chiral (R)-2-amino-7-(4-isopropoxy-5-methoxy-2-((S)-6-methoxypyridin-2-yl)phenyl)-4-methyl-7,8-dihydropyrido[4,3-d]pyrimidin-5(6H)-one | Rt = 2.37 m/z = 450.1 | B |
| 280 | 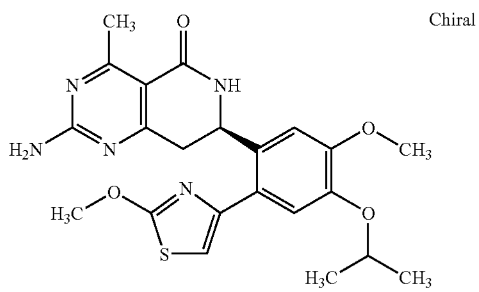 | Chiral (R)-2-amino-7-((R)-4-isopropoxy-5-methoxy-2-(2-methoxythiazol-4-yl)phenyl)-4-methyl-7,8-dihydropyrido[4,3-d]pyrimidin-5(6H)-one | Rt = 2.36, m/z = 456.1 | A |
| 281 | 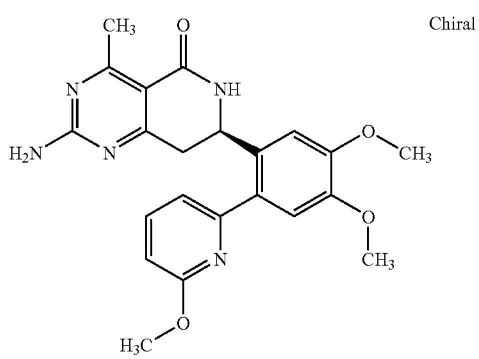 | Chiral (R)-2-amino-7-((S)-4,5-dimethoxy-2-(6-methoxypyridin-2-yl)phenyl)-4-methyl-7,8-dihydropyrido[4,3-d]pyrimidin-5(6H)-one | Rt = 2.12 m/z = 422.1 | B |
| 282 | 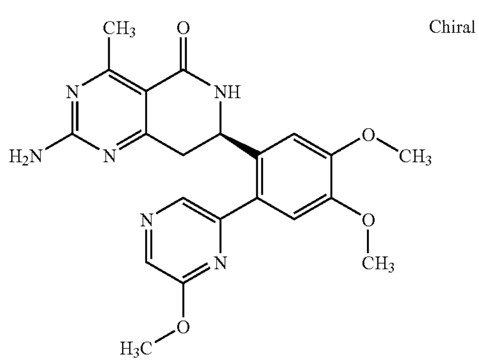 | Chiral (R)-2-amino-7-((S)-4,5-dimethoxy-2-(6-methoxypyrazin-2-yl)phenyl)-4-methyl-7,8-dihydropyrido[4,3-d]pyrimidin-5(6H)-one | Rt = 1.94 m/z = 423.1 | B |

TABLE 5-continued

| Cmpd | Structure | Name | LC/MS (Rt, m/z) | IC50 (nM) A ≧ 10 B < 10 |
|---|---|---|---|---|
| 283 | 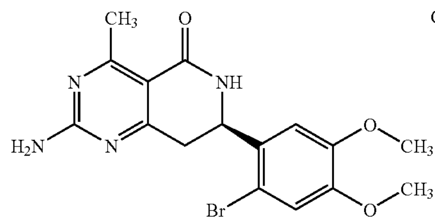 | Chiral (R)-2-amino-7-(2-bromo-4,5-dimethoxyphenyl)-4-methyl-7,8-dihydropyrido[4,3-d]pyrimidin-5(6H)-one | Rt = 1.90 m/z = 395.1 | A |
| 284 | 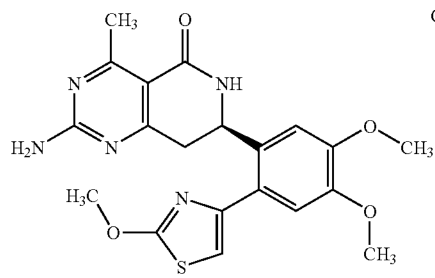 | Chiral (R)-2-amino-7-((R)-4,5-dimethoxy-2-(2-methoxythiazol-4-yl)phenyl)-4-methyl-7,8-dihydropyrido[4,3-d]pyrimidin-5(6H)-one | Rt = 1.969 m/z = 428.1 | B |
| 285 | 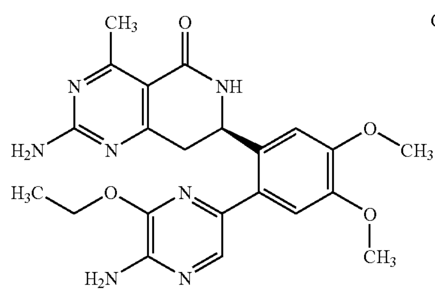 | Chiral (R)-2-amino-7-((R)-2-(5-amino-6-ethoxypyrazin-2-yl)-4,5-dimethoxyphenyl)-4-methyl-7,8-dihydropyrido[4,3-d]pyrimidin-5(6H)-one | Rt = 1.45 m/z = 452.1 | A |
| 286 | 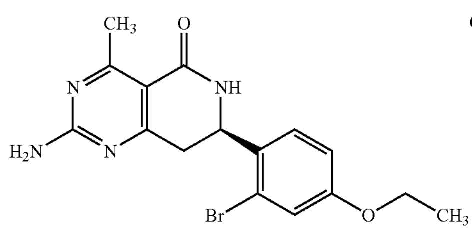 | Chiral (R)-2-amino-7-(2-bromo-4-ethoxyphenyl)-4-methyl-7,8-dihydropyrido[4,3-d]pyrimidin-5(6H)-one | Rt = 2.13 m/z = 377.0 | A |
| 287 | 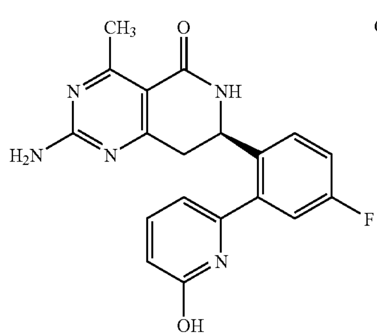 | Chiral (R)-2-amino-7-((S)-4-fluoro-2-(6-hydroxypyridin-2-yl)phenyl)-4-methyl-7,8-dihydropyrido[4,3-d]pyrimidin-5(6H)-one | Rt = 1.382 m/z = 366.1 | B |

TABLE 5-continued

| Cmpd | Structure | Name | LC/MS (Rt, m/z) | IC50 (nM) A ≥ 10 B < 10 |
|---|---|---|---|---|
| 288 | Chiral | (R)-2-amino-7-((R)-4-fluoro-2-(6-hydroxypyrazin-2-yl)phenyl)-4-methyl-7,8-dihydropyrido[4,3-d]pyrimidin-5(6H)-one | Rt = 1.35 m/z = 367.1 | B |
| 289 | 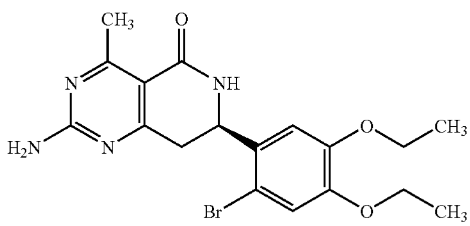 | (R)-2-amino-7-(2-bromo-4,5-diethoxyphenyl)-4-methyl-7,8-dihydropyrido[4,3-d]pyrimidin-5(6H)-one | Rt = 2.20 m/z = 423.0 | A |
| 290 | 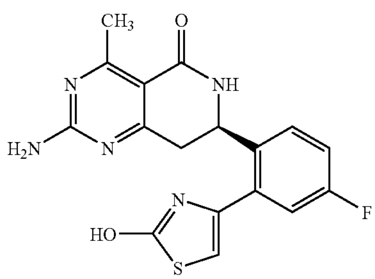 | (R)-2-amino-7-((R)-4-fluoro-2-(2-hydroxythiazol-4-yl)phenyl)-4-methyl-7,8-dihydropyrido[4,3-d]pyrimidin-5(6H)-one | Rt = 1.89 m/z = 377.2 | A |

Using the procedure described in Example 10, certain compounds in Tables 1-5 were shown to have HSP90 inhibitory activity at an $IC_{50}$ of less than 25 µM. Some of the compounds have an $IC_{50}$ of less than about 10 µM.

Example 10

HSP90 Inhibitor Binding Potency: TRF Binding Assay

In this example, the binding potency of HSP90 inhibitors as measured by a TRF binding assay is described.

TRF competition binding assays were performed to determine the binding potency ($IC_{50}$ values) of HSP90 inhibitors. Purified His-tagged N-terminal ATP binding domain (amino acid residues 9-236) of HSP90α (HSP90α GeneID: 3320; mRNA Sequence NM_005348) was incubated for two hours at room temperature in binding buffer (50 mM HEPES, 6 mM $MgCl_2$, 20 mM KCl and 0.1% BSA) with biotinylated radicicol and progressively higher concentrations of the competing compounds. A fraction of the mixture was transferred to capture plates (coated with streptavidin) and incubated for one hour at room temperature. After washing with DELFIA wash buffer, europium-labeled anti-his antibody was added and incubated for two hours at room temperature, followed by washing with DELFIA buffer. DELFIA enhancement solution was then added. After gentle shaking for 10 minutes, the plates were read in VICTOR for europium counts.

Note: $IC_{50}$ values can also be determined using published methods in the following references:

1. Carreras, C. W., A. Schirmer, et al. (2003). "Filter binding assay for the geldanamycin-heat shock protein 90 interaction." Anal Biochem 317(1): 40-6;
2. Kim, J., S. Felts, et al. (2004). "Development of a fluorescence polarization assay for the molecular chaperone HSP90." J Biomol Screen 9(5): 375-81; and
3. Zhou, V., S. Han, et al. (2004). "A time-resolved fluorescence resonance energy transfer-based HTS assay and a surface plasmon resonance-based binding assay for heat shock protein 90 inhibitors." Anal Biochem 331(2): 349-57.

While the preferred embodiment of the invention has been illustrated and described, it will be appreciated that various changes can be made therein without departing from the spirit and scope of the invention.

DOCUMENTS CITED

The following publications were referred to in the specification:

1. Beliakoff J, Bagatell R, Paine-Murrieta G, et al (2003) Hormone-refractory breast cancer remains sensitive to the antitumor activity of heat shock protein 90 inhibitors. Clin Cancer Res, 9, 4961-71.

2. Smith V, Hobbs S, Court W, et al (2002) ErbB2 overexpression in an ovarian cancer cell line confers sensitivity to the HSP90 inhibitor geldanamycin. Anticancer Res, 22, 1993-9.
3. Solit D B, Zheng F F, Drobnjak M, et al (2002) 17-Allylamino-17-demethoxygeldanamycin induces the degradation of androgen receptor and HER-2/neu and inhibits the growth of prostate cancer xenografts. Clin Cancer Res, 8, 986-93.
4. Blagosklonny M V, Fojo T, Bhalla K N, et al (2001) The Hsp90 inhibitor geldanamycin selectively sensitizes Bcr-Abl-expressing leukemia cells to cytotoxic chemotherapy. Leukemia, 15, 1537-43
5. Burger A M, Fiebig H H, Stinson S F, et al (2004) 17-(Allylamino)-17-demethoxygeldanamycin activity in human melanoma models. Anticancer Drugs, 15, 377-87.
6. Nakatani H, Kobayashi M, Jin T, et al (2005) ST1571 (Glivec) inhibits the interaction between c-KIT and heat shock protein 90 of the gastrointestinal stromal tumor cell line, GIST-T1. Cancer Sci, 96, 116-9.
7. Fumo G, Akin C, Metcalfe D D, et al (2004) 17-Allylamino-17-demethoxygeldanamycin (17-AAG) is effective in down-regulating mutated, constitutively activated KIT protein in human mast cells. Bloood, 103, 1078-84.
8. George P, Bali P, Annavarapu S, et al (2005) Combination of the histone deacetylase inhibitor LBH589 and the hsp90 inhibitor 17-AAG is highly active against human CML-BC cells and AML cells with activating mutation of FLT-3. Blood, 105, 1768-76.
9. George P, Bali P, Cohen P, et al (2004) Cotreatment with 17-allylamino-demethoxygeldanamycin and FLT-3 kinase inhibitor PKC412 is highly effective against human acute myelogenous leukemia cells with mutant FLT-3. Cancer Res, 64, 3645-52.
10. Heideman D A, Snijders P J, Bloemena E, Meijer C J, Offerhaus G J, Meuwissen S G, Gerritsen W R, Craanen M E (2001) Absence of tpr-met and expression of c-met in human gastric mucosa and carcinoma. J Pathol. 194 (4):428-35
11. Nguyen D M, Lorang D, Chen G A, et al (2001) Enhancement of paclitaxel-mediated cytotoxicity in lung cancer cells by 17-allylamino geldanamycin: in vitro and in vivo analysis. Ann Thorac Surg, 72, 371-8; discussion 378-9.
12. Yin X, Zhang H, Burrows F, et al (2005) Potent activity of a novel dimeric heat shock protein 90 inhibitor against head and neck squamous cell carcinoma in vitro and in vivo. Clin Cancer Res, 11, 3889-96.
13. Yang J, Yang J M, Iannone M, et al (2001) Disruption of the EF-2 kinase/Hsp90 protein complex: a possible mechanism to inhibit glioblastoma by geldanamycin. Cancer Res, 61, 4010-6.
14. Chung Y L, Troy H, Banerji U, Jackson L E, Walton M I, Stubbs M, Griffiths J R, Judson I R, Leach M O, Workman P, Ronen S M. Magnetic resonance spectroscopic pharmacodynamic markers of the heat shock protein 90 inhibitor 17-allylamino, 17-demethoxygeldanamycin (17AAG) in human colon cancer models. J Natl Cancer Inst. 2003 Nov. 5;95(21):1624-33.
15. Park J W, Yeh M W, Wong M G, Lobo M, Hyun W C, Duh Q Y, Clark O H. The heat shock protein 90-binding geldanamycin inhibits cancer cell proliferation, down-regulates oncoproteins, and inhibits epidermal growth factor-induced invasion in thyroid cancer cell lines. J Clin Endocrinol Metab. 2003 July;88(7):3346-53.
16. Mitsiades C S, Mitsiades N S, McMullan C J, Poulaki V, Kung A L, Davies F E, Morgan G, Akiyama M, Shringarpure R, Munshi N C, Richardson P G, Hideshima T, Chauhan D, Gu X, Bailey C, Joseph M, Libermann T A, Rosen N S, Anderson K C. Antimyeloma activity of heat shock protein-90 inhibition. Blood 2006 Feb. 1;107(3):1092-100.
17. Isaacs J S, Jung Y J, Mimnaugh E G, Martinez A, Cuttitta F, Neckers LMHsp90 regulates a von Hippel Lindau-independent hypoxia-inducible factor-1 alpha-degradative pathway. J Biol Chem. 2002 Aug. 16;277 (33):29936-44
18. Bonvini P, Gastaldi T, Falini B, Rosolen A. Nucleophosmin-anaplastic lymphoma kinase (NPM-ALK), a novel Hsp90-client tyrosine kinase: down-regulation of NPM-ALK expression and tyrosine phosphorylation in ALK(+) CD30(+) lymphoma cells by the Hsp90 antagonist 17-allylamino, 17-demethoxygeldanamycin. Cancer Res. 2002 Mar., 1;62(5):1559-66
19. Georgakis G V, Li Y, Rassidakis G Z, Martinez-Valdez H, Medeiros L J, Younes A. Inhibition of heat shock protein 90 function by 17-allylamino-17-demethoxy-geldanamycin in Hodgkin's lymphoma cells down-regulates Akt kinase, dephosphorylates extracellular signal-regulated kinase, and induces cell cycle arrest and cell death. Clin. Cancer Res. 2006 Jan. 15;12(2):584-90
20. Neckers L, Ivy, S. P. Heat shock protein 90. Current Opinion in Onclology 2003 Jan. 15:419-424.
21. Bagatell R., Whitesell L. Altered Hsp90 function in cancer: A unique therapeutic opportunity. Molecular Cancer Therapeutics 2004 3(8):1021-1030.
22. Machajewski T., Lin X. D., Jefferson A. B., Gao, Z. AKT kinase and Hsp90 inhibitors as novel anti-cancer therapeutics. Annual Reports in Medicinal Chemistry 2005 40: 263-276.
23. Gao Z., Harrison S., and Duhl D. Beyond kinases for anticancer discovery: purine-binding enzymes and ATPases. Annual Reports in Medicinal Chemistry 2003 38: 194-202.

What is claimed is:
1. A compound of formula (I):

or a stereoisomer, tautomer, pharmaceutically acceptable salt, or prodrug thereof, wherein
$R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkyithiol,
(7) substituted or unsubstituted $C_1$-$C_6$ alkyl,
(8) amino or substituted amino,
(9) substituted or unsubstituted aryl,
(10) substituted or unsubstituted heteroaryl, and
(11) substituted or unsubstituted heterocyclyl;

R is selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl;
$R^b$ is selected from the group consisting of
(1) substituted or unsubstituted $C_3$-$C_7$ cycloalkyl,
(2) substituted or unsubstituted $C_5$-$C_7$ cycloalkenyl,
(3) substituted or unsubstituted aryl,
(4) substituted or unsubstituted heteroaryl, and
(5) substituted or unsubstituted heterocyclyl; and
with the proviso that when $R^a$ is amino, then $R^b$ is not phenyl, 4-alkyl-phenyl, 4-alkoxy-phenyl, or 4-halo-phenyl.

2. A compound of claim 1 having formula (Ia)

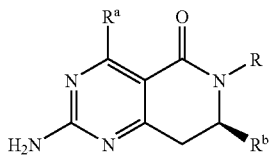

(Ia)

wherein R, $R^a$, and $R^b$ are previously defined for formula (I).

3. A compound of claim 1 having formula (II):

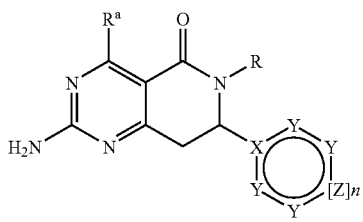

(II)

or a stereoisomer, tautomer, pharmaceutically acceptable salt, or prodrug thereof, wherein
n is 0 or 1,
wherein $R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkyithiol,
(7) substituted or unsubstituted $C_1$-$C_6$ alkyl,
(8) amino or substituted amino,
(9) substituted or unsubstituted aryl,
(10) substituted or unsubstituted heteroaryl, and
(11) substituted or unsubstituted heterocyclyl;
wherein R is selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl,
wherein when n is 1, X is C, Y is at each position independently selected from $CQ^1$ and N, and Z is selected from $CR^2$ and N with the proviso that no more than 3 Y and Z groups are N, and wherein when n is 0, X is C or N, Y is at each position independently selected from $CQ^1$, N, $NQ^2$, O, and S with the proviso that no more than 4 X and Y groups are N and $NQ^2$ and no more than 1 Y group is S or O;
wherein $Q^1$ is at each position independently selected from the group consisting of
(1) hydrogen,
(2) halogen,
(3) substituted or unsubstituted $C_1$-$C_6$ alkyl,
(4) substituted or unsubstituted $C_2$-$C_6$ alkenyl,
(5) substituted or unsubstituted $C_2$-$C_6$ alkynyl,
(6) substituted or unsubstituted $C_3$-$C_7$ cycloalkyl,
(7) substituted or unsubstituted $C_5$-$C_7$ cycloalkenyl,
(8) substituted or unsubstituted aryl,
(9) substituted or unsubstituted heteroaryl,
(10) substituted or unsubstituted heterocyclyl,
(11) substituted or unsubstituted amino,
(12) —$OR^3$ or —$SR^3$
(13) —$C(O)R^3$, —$CO_2R^3$, —$C(O)N(R^3)_2$, —$S(O)R^3$, —$SO_2R^3$, or —$SO_2N(R^3)_2$,
(14) —$OC(O)R^3$, —$N(R^3)C(O)R^3$, or —$N(R^3)SO_2R^3$,
(15) —CN, and
(16) —$NO_2$;
wherein $Q^2$ is at each position independently selected from the group consisting of
(1) hydrogen,
(3) substituted or unsubstituted $C_1$-$C_6$ alkyl,
(4) substituted or unsubstituted $C_2$-$C_6$ alkenyl,
(5) substituted or unsubstituted $C_2$-$C_6$ alkynyl,
(6) substituted or unsubstituted $C_3$-$C_7$ cycloalkyl,
(7) substituted or unsubstituted $C_5$-$C_7$ cycloalkenyl,
(8) substituted or unsubstituted aryl,
(9) substituted or unsubstituted heteroaryl, and
(10) substituted or unsubstituted heterocyclyl;
wherein $R^2$ is selected from the group consisting of
(1) hydrogen,
(2) halogen,
(3) substituted or unsubstituted $C_1$-$C_3$ alkyl, and
(4) —$OR^3$, or —$NHR^3$; —$SR^3$,
wherein $R^3$ is at each position independently selected from the group consisting of
(1) hydrogen,
(2) substituted or unsubstituted $C_1$-$C_6$ alkyl,
(3) substituted or unsubstituted $C_2$-$C_6$ alkenyl,
(4) substituted or unsubstituted $C_2$-$C_6$ alkynyl,
(5) substituted or unsubstituted $C_3$-$C_7$ cycloalkyl,
(6) substituted or unsubstituted $C_5$-$C_7$ cycloalkenyl,
(7) substituted or unsubstituted aryl,
(8) substituted or unsubstituted heteroaryl, and
(9) substituted or unsubstituted heterocyclyl,
with the proviso that when $R^a$ is amino, then X, Y, Z, and n together do not form a phenyl, 4-alkyl-phenyl, 4-alkoxy-phenyl, or 4-halo-phenyl group.

4. A compound of claim 3 having formula (IIa):

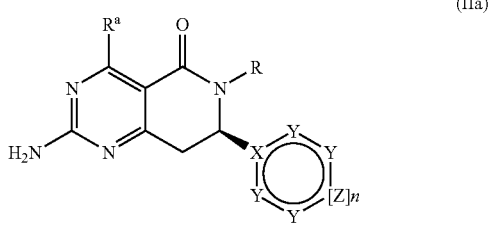

or a tautomer, pharmaceutically acceptable salt, or prodrug thereof, wherein $R^a$, R, X, Y, Z, and n are previously defined for formula (II).

5. A compound of claim 4 having formula (III):

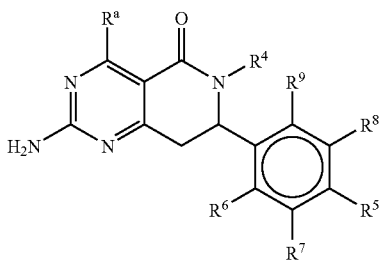

or a stereoisomer, tautomer, pharmaceutically acceptable salt, or prodrug thereof, wherein
$R^a$ is selected from the group consisting of
(1) hydrogen,
(2) halogen,
(3) hydroxyl,
(4) $C_1$-$C_6$ alkoxy,
(5) thiol,
(6) $C_1$-$C_6$ alkylthiol,
(7) substituted or unsubstituted $C_1$-$C_6$ alkyl,
(8) amino or substituted amino
(9) substituted or unsubstituted aryl,
(10) substituted or unsubstituted heteroaryl, and
(11) substituted or unsubstituted heterocyclyl;
$R^4$ is hydrogen or substituted or unsubstituted $C_1$-$C_6$ alkyl;
$R^5$ is hydrogen, alkyl, alkoxy, or halo;
each of $R^6$, $R^7$, $R^8$, and $R^9$ are independently selected from the group consisting of hydrogen, alkyl, alkoxy, halo, substituted or unsubstituted aryl, and substituted or unsubstituted heteroaryl; or
a stereoisomer, tautomer, pharmaceutically acceptable salt, or prodrug thereof, and with the proviso that when $R^a$ is amino and $R^6$, $R^7$, $R^8$ and $R^9$ are hydrogen, then $R^5$ is not hydrogen, alkyl, alkoxy, or halo.

6. A compound of claim 5 wherein $R^a$ is hydrogen.

7. A compound of claim 5 wherein $R^a$ is substituted or unsubstituted $C_1$-$C_6$ alkyl.

8. A compound of claim 7 wherein $R^a$ is methyl.

9. A compound of claim 5, wherein $R^4$ is selected from the group consisting of hydrogen, benzyl, 1-(4-methoxyphenyl) ethyl, methyl, 3-aminopropyl, and 2-methyl-2-morpholinopropyl.

10. A compound of claim 9, wherein $R^4$ is hydrogen.

11. A compound of claim 5, wherein $R^5$ is hydrogen or fluoro.

12. A compound of claim 5, wherein $R^7$, $R^8$, and $R^9$ are each hydrogen.

13. A compound of claim 5, wherein $R^6$ is selected from the group consisting of substituted aryl and substituted heteroaryl.

14. A compound of claim 13, wherein said aryl and heteroaryl is selected from the group consisting of furanyl, pyrrolyl, phenyl, pyridyl, pyrazinyl, pyrimidinyl, pyridazinyl, pyrazolyl, imidazolyl, triazolyl, indolyl, oxadiazole, thiadiazole, quinolinyl, isoquinolinyl, isoxazolyl, oxazolyl, thiazolyl, and thienyl.

15. A compound of claim 14, wherein $R^6$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol-4-yl, 2-(5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-aminocarbonylphenyl, 2-aminopyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethyl-phenyl, 2-ethoxy-thiazol-4-yl, 2-fluoro-3-methoxy-phenyl, 2-fluoro-3-methylphenyl, 2-fluoro-4-methyl-phenyl, 2-fluoro-5-methoxy-phenyl, 2-fluoro-5-methylphenyl, 2-fluorophenyl, 2-fluoro-pyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethoxy-phenyl, 3,4-dimethoxy-phenyl, 3,5-dimethyl-isoxazol-4-yl, 3,6-dimethyl-pyrazin-2-yl, 3-acetamidophenyl, 3-aminocarbonylphenyl, 3-bromo-phenyl, 3-chloro-pyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6-methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxypyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-amino-6-methoxy-pyridin-2-yl, 5-chloro-4methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6-ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2- yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy)pyrazin-2-yl, and 6-trifluoromethyl-pyridin-2-yl.

16. A compound of claim 5 having formula (IIIa):

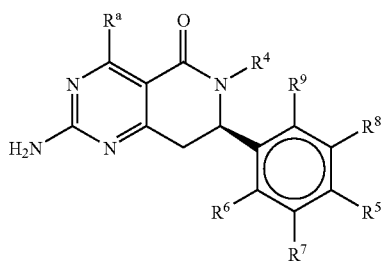

(IIIa)

or a tautomer, pharmaceutically acceptable salt, or prodrug thereof, wherein $R^a$, $R^4$, X, Y, Z, and n are as previously defined for formula (III) and with the proviso that when $R^a$ is amino and $R^6$, $R^7$, $R^8$, and $R^9$ are hydrogen, then $R^5$ is not hydrogen, alkyl, alkoxy, or halo.

17. A compound of claim 5 having formula (IV):

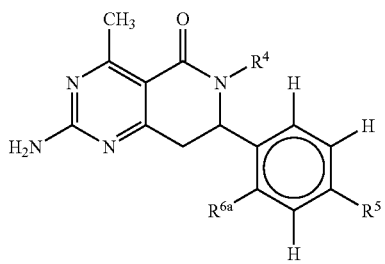

(IV)

or a stereoisomer, tautomer, pharmaceutically acceptable salt, or prodrug thereof, wherein
$R^4$ is hydrogen or substituted or unsubstituted $C_1$-$C_6$ alkyl,
$R^5$ is hydrogen or halo,
$R^{6a}$ is selected from the group consisting of hydrogen, halo, substituted or unsubstituted aryl, and substituted or unsubstituted heteroaryl.

18. A compound of claim 17 having formula (IVa):

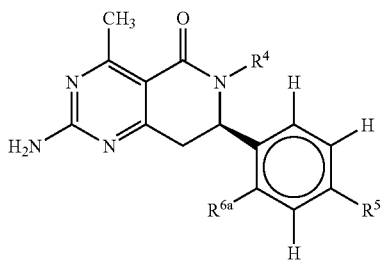

(IVa)

or a tautomer, pharmaceutically acceptable salt, or prodrug thereof, wherein
$R^4$, $R^5$, and $R^{6a}$ are as previously defined for formula (IV).

19. A compound of claim 3 having formula (V):

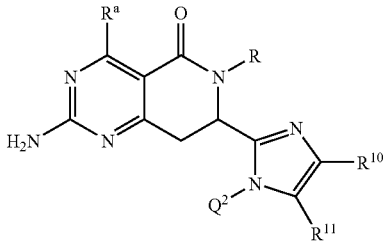

(V)

wherein $R^{10}$ and $R^{11}$ are independently $Q^1$, and $R^a$, R, $Q^1$, and $Q^2$ are as previously defined for formula (II).

20. A compound of claim 19 having formula (Va):

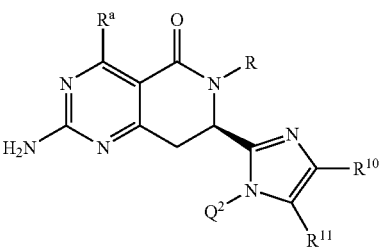

(Va)

wherein $R^{10}$ and $R^{11}$ are independently $Q^1$, and $R^a$, R, $Q^1$, and $Q^2$ are as previously defined for formula (V).

21. A compound of claim 1 selected from the group consisting of
(R)-2-Amino-7-[2-(2-fluoro-pyridin-3-yl)-phenyl]-4-methyl-7,8-dihydro-6H-pyrido[4,3-d]pyrimidin-5-one;
(S)-2-Amino-6-benzyl-7-[4-fluoro-2-(2-fluoro-pyridin-3-yl)-phenyl]-4-methyl-7,8-dihydro-6H-pyrido[4,3-d]pyrimidin-5-one;
(R)-2-Amino-7-[4-fluoro-2-(2-fluoro-pyridin-3-yl)-phenyl]-4-methyl-7,8-dihydro-6H-pyrido[4,3-d]pyrimidin-5-one;
(R)-2-Amino-7-(2-bromo-4-fluoro-phenyl)-6-[(S)-1-(4-methoxy-phenyl)-ethyl]-4-methyl-7,8-dihydro-6H-pyrido[4,3-d]pyrimidin-5-one;
(R)-2-Amino-7-[2-(6-methoxy-pyridin-2-yl)-phenyl]-4-methyl-7,8-dihydro-6H-pyrido[4,3-d]pyrimidin-5-one;
(R)-2-Amino-7-[4-fluoro-2-(6-methoxy-pyridin-2-yl)-phenyl]-4-methyl-7,8-dihydro-6H-pyrido[4,3-d]pyrimidin-5-one;
2-Amino-7-[4-fluoro-2-(6-methoxy-pyridin-2-yl)-phenyl]-4,6-dimethyl-7,8-dihydro-6H-pyrido[4,3-d]pyrimidin-5-one;
2-Amino-7-[4-fluoro-2-(2-fluoro-pyridin-3-yl)-phenyl]-4,6-dimethyl-7,8-dihydro-6H-pyrido[4,3-d]pyrimidin-5-one;
2-Amino-7-[4-fluoro-2-(6-methoxypyridin-2-yl)phenyl]-4-methyl-7,8-dihydropyrido[4,3-d]pyrimidin-5(6H)-one;
2-Amino-7-[2-(6-methoxy-pyrazin-2-yl)-phenyl]-4-methyl-7,8-dihydro-6H-pyrido[4,3-d]pyrimidin-5-one;
(R)-2-Amino-7-[4-fluoro-2-(6-methoxy-pyrazin-2-yl)-phenyl]-4-methyl-7,8-dihydro-6H-pyrido[4,3-d]pyrimidin-5-one;

2-Amino-7-[4-fluoro-2-(6-methoxy-pyrazin-2-yl)-phenyl]-4,6-dimethyl-7,8-dihydro-6H-pyrido[4,3-d]pyrimidin-5-one;
2-Amino-7-[2-(2-methoxy-pyridin-3-yl)-phenyl]-4-methyl-7,8-dihydro-6H-pyrido[4,3-d]pyrimidin-5-one;
2-Amino-7-(5,2'-difluoro-biphenyl-2-yl)-4-methyl-7,8-dihydro-6H-pyrido[4,3-d]pyrimidin-5-one;
2-Amino-7-(5-fluoro-2'-trifluoromethoxy-biphenyl-2-yl)-4-methyl-7,8-dihydro-6H-pyrido[4,3-d]pyrimidin-5-one;
2-Amino-7-[2-(2-chloro-pyridin-3-yl)-4-fluoro-phenyl]-4-methyl-7,8-dihydro-6H-pyrido[4,3-d]pyrimidin-5-one;
2-Amino-7-[4-fluoro-2-(6-fluoro-pyridin-3-yl)-phenyl]-4-methyl-7,8-dihydro-6H-pyrido[4,3-d]pyrimidin-5-one;
2-Amino-7-(4-fluoro-2-isoquinolin-4-yl-phenyl)-4-methyl-7,8-dihydro-6H-pyrido[4,3-d]pyrimidin-5-one;
2-Amino-7-(5,3'-difluoro-biphenyl-2-yl)-4-methyl-7,8-dihydro-6H-pyrido[4,3-d]pyrimidin-5-one;
2-Amino-7-[2-(4-chloro-pyridin-3-yl)-4-fluoro-phenyl]-4-methyl-7,8-dihydro-6H-pyrido[4,3-d]pyrimidin-5-one;
2-Amino-7-(5,2'-difluoro-3'-methoxy-biphenyl-2-yl)-4-methyl-7,8-dihydro-6H-pyrido[4,3-d]pyrimidin-5-one;
2-Amino-7-(5,4'-difluoro-2'-methyl-biphenyl-2-yl)-4-methyl-7,8-dihydro-6H-pyridol[4,3-d]pyrimidin-5-one;
2-Amino-7-(5-fluoro-2'-methoxy-biphenyl-2-yl)-4-methyl-7,8-dihydro-6H-pyrido[4,3-d]pyrimidin-5-one;
2-Amino-7-(4-fluoro-2-pyrimidin-5-yl-phenyl)-4-methyl-7,8-dihydro-6H-pyrido[4,3-d]pyrimidin-5-one;
2-Amino-7-[4-fluoro-2-(2-methoxy-pyridin-3-yl)-phenyl]-4-methyl-7,8-dihydro-6H-pyrido[4,3-d]pyrimidin-5-one;
2-Amino-7-(5-fluoro-3'-methoxy-biphenyl-2-yl)-4-methyl-7,8-dihydro-6H-pyrido[4,3-d]pyrimidin-5-one;
(R)-2-Amino-6-(3-amino-propyl)-7-[4-fluoro-2-(6-methoxy-pyridin-2-yl)-phenyl]-4-methyl-7,8-dihydro-6H-pyrido[4,3-d]pyrimidin-5-one;
2-Amino-7-(4-fluoro-2-pyridin-3-yl-phenyl)-4-methyl-7,8-dihydro-6H-pyrido[4,3-d]pyrimidin-5-one;
2-Amino-7-(5,2'-difluoro-4'-methyl-biphenyl-2-yl)-4-methyl-7,8-dihydro-6H-pyrido[4,3-d]pyrimidin-5-one;
2-Amino-7-[4-fluoro-2-(1-methyl-1H-pyrazol-4-yl)-phenyl]-4-methyl-7,8-dihydro-6H-pyrido[4,3-d]pyrimidin-5-one;
2-Amino-7-[4-fluoro-2-(1H-pyrazol-4-yl)-phenyl]-4-methyl-7,8-dihydro-6H-pyrido[4,3-d]pyrimidin-5-one;
2-Amino-4-methyl-7-(5,2',3'-trifluoro-biphenyl-2-yl)-7,8-dihydro-6H-pyrido[4,3-d]pyrimidin-5-one;
2-Amino-7-(2-bromo-4-fluoro-phenyl)-4-methyl-6-(2-methyl-2-morpholin-4-yl-propyl)-7,8-dihydro-6H-pyrido[4,3-d]pyrimidin-5-one;
2-Amino-7-(3'-dimethylamino-5-fluoro-biphenyl-2-yl)-4-methyl-7,8-dihydro-6H-pyrido[4,3-d]pyrimidin-5-one;
2-Amino-7-[2-(2,4-dimethoxy-pyrimidin-5-yl)-4-fluoro-phenyl]-4-methyl-7,8-dihydro-6H-pyrido[4,3-d]pyrimidin-5-one;
2-Amino-7-[4-fluoro-2-(5-methoxy-pyridin-3-yl)-phenyl]-4-methyl-7,8-dihydro-6H-pyrido[4,3-d]pyrimidin-5-one;
2-Amino-7-(4-fluoro-2-pyrimidin-5-yl-phenyl)-4-methyl-6-(2-methyl-2-morpholin-4-yl-propyl)-7,8-dihydro-6H-pyrido[4,3-d]pyrimidin-5-one;
2-Amino-7-[4-fluoro-2-(2-methoxy-pyridin-3-yl)-phenyl]-4-methyl-6-(2-methyl-2-morpholin-4-yl-propyl)-7,8-dihydro-6H-pyrido[4,3-d]pyrimidin-5-one;
2-Amino-7-(5-fluoro-3'-methoxy-biphenyl-2-yl)-4-methyl-6-(2-methyl-2-morpholin-4-yl-propyl)-7,8-dihydro-6H-pyrido[4,3-d]pyrimidin-5-one;
(R)-2-Amino-7-[4-fluoro-2-(4-methoxy-5-methyl-pyrimidin-2-yl)-phenyl]-4-methyl-7,8-dihydro-6H-pyrido[4,3-d]pyrimidin-5-one;
2-Amino-7-(4-fluoro-2-furan-3-yl-phenyl)-4-methyl-7,8-dihydro-6H-pyrido[4,3-d]pyrimidin-5-one;
(R)-2-Amino-7-[2-(6-methoxy-pyrazin-2-yl)-phenyl]-7,8-dihydro-6H-pyrido[4,3-d]pyrimidin-5-one;
(R)-2-Amino-7-[2-(6-methoxy-pyridin-2-yl)-phenyl]-7,8-dihydro-6H-pyrido[4,3-d]pyrimidin-5-one;
(R)-2-Amino-7-[2-(5-amino-6-methoxy-pyridin-2-yl)-4-fluoro-phenyl]-4-methyl-7,8-dihydro-6H-pyrido[4,3-d]pyrimidin-5-one;
(R)-2-Amino-7-[2-(5-amino-6-methoxy-pyridin-2-yl)-phenyl]-4-methyl-7,8-dihydro-6H-pyrido[4,3-d]pyrimidin-5-one;
(R)-2-Amino-7-[2-(5-amino-6-methoxy-pyridin-2-yl)-4-fluoro-phenyl]-7,8-dihydro-6H-pyrido[4,3-d]pyrimidin-5-one;
(R)-2-Amino-7-[2-(4-ethoxy-pyrimidin-2-yl)-4-fluoro-phenyl]-4-methyl-7,8-dihydro-6H-pyrido[4,3-d]pyrimidin-5-one;
(R)-2-Amino-7-[4-fluoro-2-(4-methoxy-pyrimidin-2-yl)-phenyl]-4-methyl-7,8-dihydro-6H-pyrido[4,3-d]pyrimidin-5-one;
(R)-2-Amino-7-[4-fluoro-2-(4-pyrrolidin-1-yl-pyrimidin-2-yl)-phenyl]-4-methyl-7,8-dihydro-6H-pyrido[4,3-d]pyrimidin-5-one;
2-((R)-2-Amino-4-methyl-5-oxo-5,6,7,8-tetrahydro-pyrido[4,3-d]pyrimidin-7-yl)-5-fluoro-benzonitrile;
(R)-2-Amino-7-[2-(4,5-dimethoxy-pyrimidin-2-yl)-4-fluoro-phenyl]-4-methyl-7,8-dihydro-6H-pyrido[4,3-d]pyrimidin-5-one;
(R)-2-Amino-7-[2-(5-chloro-4-methoxy-pyrimidin-2-yl)-4-fluoro-phenyl]-4-methyl-7,8-dihydro-6H-pyrido[4,3-d]pyrimidin-5-one;
(R)-2-Amino-7-[4-fluoro-2-(6-methoxy-pyrazin-2-yl)-phenyl]-7,8-dihydro-6H-pyrido[4,3-d]pyrimidin-5-one;
(R)-2-Amino-7-(5-fluoro-2'-methoxy-biphenyl-2-yl)-7,8-dihydro-6H-pyrido[4,3-d]pyrimidin-5-one;
(R)-2-Amino-7-(5,5'-difluoro-2'-methoxy-biphenyl-2-yl)-7,8-dihydro-6H-pyrido[4,3-d]pyrimidin-5-one;
(R)-2-Amino-7-(5,4'-difluoro-2'-methoxy-biphenyl-2-yl)-7,8-dihydro-6H-pyrido[4,3-d]pyrimidin-5-one;
(R)-2-Amino-7-(5-fluoro-3',4'-dimethoxy-biphenyl-2-yl)-7,8-dihydro-6H-pyrido[4,3-d]pyrimidin-5-one;
(R)-2-Amino-7-(5-fluoro-3'-methyl-biphenyl-2-yl)-7,8-dihydro-6H-pyrido[4,3-d]pyrimidin-5-one;
(R)-2-Amino-7-(5-fluoro-4'-methyl-biphenyl-2-yl)-7,8-dihydro-6H-pyrido[4,3-d]pyrimidin-5-one;
(R)-2-Amino-7-(5,4'-difluoro-2'-methyl-biphenyl-2-yl)-7,8-dihydro-6H-pyrido[4,3-d]pyrimidin-5-one;
(R)-2-Amino-7-(4-fluoro-2-pyridin-3-yl-phenyl)-7,8-dihydro-6H-pyrido[4,3-d]pyrimidin-5-one;
(R)-2-Amino-7-[2-(2,4-dimethoxy-pyrimidin-5-yl)-4-fluoro-phenyl]-7,8-dihydro-6H-pyrido[4,3-d]pyrimidin-5-one;
(R)-2-Amino-7-[2-(5-fluoro-4-methoxy-pyrimidin-2-yl)-phenyl]-4-methyl-7,8-dihydro-6H-pyrido[4,3-d]pyrimidin-5-one;

(R)-2-Amino-7-[4-fluoro-2-(5-methoxy-thiophen-2-yl)-phenyl]-4-methyl-7,8-dihydro-6H-pyrido[4,3-d]pyrimidin-5-one;

(R)-2-Amino-7-(2-bromo-phenyl)-4-methyl-7,8-dihydro-6H-pyrido[4,3-d]pyrimidin-5-one;

(R)-2-Amino-7-[2-(2-methoxy-thiazol-4-yl)-phenyl]-4-methyl-7,8-dihydro-6H-pyrido[4,3-d]pyrimidin-5-one;

(R)-2-Amino-7-[2-(5,6-dimethoxy-pyrazin-2-yl)-phenyl]-4-methyl-7,8-dihydro-6H-pyrido[4,3-d]pyrimidin-5-one;

(R)-2-Amino-7-[2-(6-methoxy-pyrazin-2-yl)-phenyl]-4-methyl-7,8-dihydro-6H-pyrido[4,3-d]pyrimidin-5-one;

(R)-2-Amino-7-(2-bromo-4-fluoro-phenyl)-4-ethyl-7,8-dihydro-6H-pyrido[4,3-d]pyrimidin-5-one;

(R)-2-Amino-7-[2-(6-ethoxy-pyrazin-2-yl)-phenyl]-4-methyl-7,8-dihydro-6H-pyrido[4,3-d]pyrimidin-5-one;

(R)-2-Amino-7-[2-(4-ethoxy-5-fluoro-pyrimidin-2-yl)-4-fluoro-phenyl]-4-methyl-7,8-dihydro-6H-pyrido[4,3-d]pyrimidin-5-one;

(R)-2-Amino-7-(5-fluoro-2',3'-dimethoxy-biphenyl-2-yl)-4-methyl-7,8-dihydro-6H-pyrido[4,3-d]pyrimidin-5-one;

(R)-2-Amino-7-[2-(6-ethoxy-pyridin-2-yl)-4-fluoro-phenyl]-4-methyl-7,8-dihydro-6H-pyrido[4,3-d]pyrimidin-5-one;

(R)-2-Amino-7-[2-(5-amino-6-ethoxy-pyrazin-2-yl)-4-fluoro-phenyl]-4-methyl-7,8-dihydro-6H-pyrido[4,3-d]pyrimidin-5-one;

(R)-2-Amino-7-[2-(5-amino-6-ethoxy-pyrazin-2-yl)-phenyl]-4-methyl-7,8-dihydro-6H-pyrido[4,3-d]pyrimidin-5-one;

(R)-2-Amino-4-ethyl-7-[2-(6-methoxy-pyridin-2-yl)-phenyl]-7,8-dihydro-6H-pyrido[4,3-d]pyrimidin-5-one;

(R)-2-Amino-4-ethyl-7-[2-(6-methoxy-pyrazin-2-yl)-phenyl]-7,8-dihydro-6H-pyrido[4,3-d]pyrimidin-5-one;

(R)-2-Amino-7-[2-(5-amino-6-methoxy-pyrazin-2-yl)-phenyl]-4-ethyl-7,8-dihydro-6H-pyrido[4,3-d]pyrimidin-5-one;

(R)-2-Amino-4-ethyl-7-[2-(2-methoxy-thiazol-4-yl)-phenyl]-7,8-dihydro-6H-pyrido[4,3-d]pyrimidin-5-one;

(R)-2-Amino-4-ethyl-7-[4-fluoro-2-(6-methoxy-pyridin-2-yl)-phenyl]-7,8-dihydro-6H-pyrido[4,3-d]pyrimidin-5-one;

(R)-2-Amino-4-ethyl-7-[4-fluoro-2-(6-methoxy-pyrazin-2-yl)-phenyl]-7,8-dihydro-6H-pyrido[4,3-d]pyrimidin-5-one;

(R)-2-Amino-7-[2-(5-amino-6-ethoxy-pyrazin-2-yl)-4-fluoro-phenyl]-7,8-dihydro-6H-pyrido[4,3-d]pyrimidin-5-one;

(R)-2-Amino-4-ethyl-7-[4-fluoro-2-(2-methoxy-thiazol-4-yl)-phenyl]-7,8-dihydro-6H-pyrido[4,3-d]pyrimidin-5-one;

(R)-2-Amino-7-[2-(6-ethoxy-pyrazin-2-yl)-4-fluoro-phenyl]-4-methyl-7,8-dihydro-6H-pyrido[4,3-d]pyrimidin-5-one;

(R)-2-Amino-7-[2-(6-ethoxy-pyrazin-2-yl)-4-fluoro-phenyl]-4-ethyl-7,8-dihydro-6H-pyrido[4,3-d]pyrimidin-5-one;

(R)-2-Amino-7-[2-(6-ethoxy-pyrazin-2-yl)-4-fluoro-phenyl]-7,8-dihydro-6H-pyrido[4,3-d]pyrimidin-5-one;

(R)-2-Amino-7-[5-(6-methoxy-pyrazin-2-yl)-thiazol-4-yl]-4-methyl-7,8-dihydro-6H-pyrido[4,3-d]pyrimidin-5-one;

2-Amino-7-(5-fluoro-2'-trifluoromethyl-biphenyl-2-yl)-4-methyl-7,8-dihydro-6H-pyrido[4,3-d]pyrimidin-5-one;

2-Amino-7-(4-fluoro-2-pyridin-4-yl-phenyl)-4-methyl-7,8-dihydro-6H-pyrido[4,3-d]pyrimidin-5-one;

2-Amino-7-(5,3'-difluoro-4'-methoxy-biphenyl-2-yl)-4-methyl-7,8-dihydro-6H-pyrido[4,3-d]pyrimidin-5-one;

2-Amino-4-methyl-7-phenyl-7,8-dihydro-6H-pyrido[4,3-d]pyrimidin-5-one;

2-Amino-6-(2-amino-ethyl)-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-7-(2-bromo-4-fluoro-phenyl)-4-methyl-7,8-dihydro-6H-pyrido[4,3-d]pyrimidin-5-one;

(R)-2-Amino-7-[4-fluoro-2-(2-methoxy-thiazol-4-yl)-phenyl]-4-methyl-7,8-dihydro-6H-pyrido[4,3-d]pyrimidin-5-one;

(R)-2-Amino-7-[4-fluoro-2-(6-methoxy-pyridin-2-yl)-phenyl]-7,8-dihydro-6H-pyrido[4,3-d]pyrimidin-5-one;

(R)-2-Amino-7-[2-(5-amino-6-methoxy-pyrazin-2-yl)-4-fluoro-phenyl]-7,8-dihydro-6H-pyrido[4,3-d]pyrimidin-5-one;

(R)-2-Amino-7-(4-fluoro-phenyl)-7,8-dihydro-6H-pyrido[4,3-d]pyrimidin-5-one;

2-Amino-7-[2-(5-amino-6-methoxy-pyrazin-2-yl)-4-fluoro-phenyl]-4-methyl-7,8-dihydro-6H-pyrido[4,3-d]pyrimidin-5-one;

(S)-2-Amino-7-[2-(5-amino-6-methoxy-pyrazin-2-yl)-4-fluoro-phenyl]-4-methyl-7,8-dihydro-6H-pyrido[4,3-d]pyrimidin-5-one;

(R)-2-Amino-7-[2-(5-amino-6-methoxy-pyrazin-2-yl)-4-fluoro-phenyl]-4-methyl-7,8-dihydro-6H-pyrido[4,3-d]pyrimidin-5-one;

(R)-2-Amino-7-(4-fluoro-phenyl)-4-methyl-7,8-dihydro-6H-pyrido[4,3-d]pyrimidin-5-one;

(R)-2-Amino-4-methyl-7-phenyl-7,8-dihydro-6H-pyrido[4,3-d]pyrimidin-5-one;

(R)-2-Amino-7-[2-(5-amino-6-methoxy-pyrazin-2-yl)-phenyl]-4-methyl-7,8-dihydro-6H-pyrido[4,3-d]pyrimidin-5-one;

(R)-6-Allyl-2-amino-7-[2-(5-amino-6-methoxy-pyrazin-2-yl)-4-fluoro-phenyl]-4-methyl-7,8-dihydro-6H-pyrido[4,3-d]pyrimidin-5-one;

(R)-2-Amino-6-ethyl-7-[4-fluoro-2-(6-methoxy-pyridin-2-yl)-phenyl]-4-methyl-7,8-dihydro-6H-pyrido[4,3-d]pyrimidin-5-one;

(R)-2-Amino-6-ethyl-7-[4-fluoro-2-(2-methoxy-pyridin-3-yl)-phenyl]-4-methyl-7,8-dihydro-6H-pyrido[4,3-d]pyrimidin-5-one;

(R)-2-Amino-6-ethyl-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-6-ethyl-7-(5-fluoro-3'-methoxy-biphenyl-2-yl)-4-methyl-7,8-dihydro-6H-pyrido[4,3-d]pyrimidin-5-one;

(R)-2-Amino-6-ethyl-7-(4-fluoro-2-pyridin-3-yl-phenyl)-4-methyl-7,8-dihydro-6H-pyrido[4,3-d]pyrimidin-5-one;

(R)-2-Amino-7-[2-(2,4-dimethoxy-pyrimidin-5-yl)-4-fluoro-phenyl]-6-ethyl-4-methyl-7,8-dihydro-6H-pyrido[4,3-d]pyrimidin-5-one;

(R)-2-Amino-6-benzyl-7-[2-(5-chloro-4-hydroxy-pyrimidin-2-yl)-4-fluoro-phenyl]-4-methyl-7,8-dihydro-6H-pyrido[4,3-d]pyrimidin-5-one;

(R)-2-Amino-7-[4-fluoro-2-(6-methoxy-pyrazin-2-yl)-phenyl]-6-(2-hydroxy-ethyl)-4-methyl-7,8-dihydro-6H-pyrido[4,3-d]pyrimidin-5-one;

(R)-2-Amino-7-(2-bromo-4-fluoro-phenyl)-6-(2,4-dimethoxy-benzyl)-4-methyl-7,8-dihydro-6H-pyrido[4,3-d]pyrimidin-5-one;

(R)-2-Amino-6-(3-chloro-benzyl)-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-6-(3-chloro-benzyl)-7-[4-fluoro-2-(6-methoxy-pyridin-2-yl)-phenyl]-4-methyl-7,8-dihydro-6H-pyrido[4,3-d]pyrimidin-5-one;

(R)-2-Amino-6-(3-chloro-benzyl)-7-[2-(5,6-dimethoxy-pyrazin-2-yl)-4-fluoro-phenyl]-4-methyl-7,8-dihydro-6H-pyrido[4,3-d]pyrimidin-5-one;

(R)-2-Amino-6-(2,4-dimethoxy-benzyl)-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-6-(2,4-dimethoxy-benzyl)-7-[4-fluoro-2-(6-methoxy-pyridin-2-yl)-phenyl]-4-methyl-7,8-dihydro-6H-pyrido[4,3-d]pyrimidin-5-one;

(R)-2-Amino-7-[4-fluoro-2-(6-methoxy-pyridin-2-yl)-phenyl]-4-methyl-6-pyridin-4-ylmethyl-7,8-dihydro-6H-pyrido[4,3-d]pyrimidin-5-one;

(R)-2-Amino-7-[4-fluoro-2-(6-methoxy-pyrazin-2-yl)-phenyl]-4-methyl-6-pyridin-4-ylmethyl-7,8-dihydro-6H-pyrido[4,3-d]pyrimidin-5-one;

(R)-2-Amino-7-[2-(5-amino-6-methoxy-pyrazin-2-yl)-4-fluoro-phenyl]-4-methyl-6-pyridin-4-ylmethyl-7,8-dihydro-6H-pyrido[4,3-d]pyrimidin-5-one;

(R)-2-Amino-6-(2-fluoro-benzyl)-7-[4-fluoro-2-(6-methoxy-pyridin-2-yl)-phenyl]-4-methyl-7,8-dihydro-6H-pyrido[4,3-d]pyrimidin-5-one;

(R)-2-Amino-7-[2-(5-amino-6-methoxy-pyrazin-2-yl)-4-fluoro-phenyl]-6-(2-fluoro-benzyl)-4-methyl-7,8-dihydro-6H-pyrido[4,3-d]pyrimidin-5-one;

(R)-2-Amino-6-(2-chloro-benzyl)-7-[4-fluoro-2-(6-methoxy-pyridin-2-yl)-phenyl]-4-methyl-7,8-dihydro-6H-pyrido[4,3-d]pyrimidin-5-one;

(R)-2-Amino-7-[2-(5-amino-6-methoxy-pyrazin-2-yl)-4-fluoro-phenyl]-6-(2-chloro-benzyl)-4-methyl-7,8-dihydro-6H-pyrido[4,3-d]pyrimidin-5-one;

(R)-2-Amino-7-[4-fluoro-2-(6-methoxy-pyrazin-2-yl)-phenyl]-4-methyl-6-(3-trifluoromethyl-benzyl)-7,8-dihydro-6H-pyrido[4,3-d]pyrimidin-5-one;

(R)-2-Amino-7-[4-fluoro-2-(6-methoxy-pyridin-2-yl)-phenyl]-4-methyl-6-(3-trifluoromethyl-benzyl)-7,8-dihydro-6H-pyrido[4,3-d]pyrimidin-5-one;

(R)-2-Amino-6-(2-fluoro-benzyl)-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-6-(2-chloro-benzyl)-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-7-[4-fluoro-2-(6-methoxy-pyrazin-2-yl)-phenyl]-4-methyl-6-(tetrahydro-pyran-4-ylmethyl)-7,8-dihydro-6H-pyrido[4,3-d]pyrimidin-5-one;

(R)-2-Amino-7-[4-fluoro-2-(6-methoxy-pyridin-2-yl)-phenyl]-4-methyl-6-(tetrahydro-pyran-4-ylmethyl)-7,8-dihydro-6H-pyrido[4,3-d]pyrimidin-5-one;

(R)-2-Amino-7-[4-fluoro-2-(6-methoxy-pyrazin-2-yl)-phenyl]-4-methyl-6-(2-methyl-2-morpholin-4-yl-propyl)-7,8-dihydro-6H-pyrido[4,3-d]pyrimidin-5-one;

(R)-2-Amino-6-benzyl-7-[4-fluoro-2-(6-methoxy-pyridin-2-yl)-phenyl]-4-methyl-7,8-dihydro-6H-pyrido[4,3-d]pyrimidin-5-one;

(R)-2-Amino-6-benzyl-7-[4-fluoro-2-(2-methoxy-pyridin-3-yl)-phenyl]-4-methyl-7,8-dihydro-6H-pyrido[4,3-d]pyrimidin-5-one;

(R)-2-Amino-6-benzyl-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-6-benzyl-7-(5-fluoro-3'-methoxy-biphenyl-2-yl)-4-methyl-7,8-dihydro-6H-pyrido[4,3-d]pyrimidin-5-one;

(R)-2-Amino-6-benzyl-4-methyl-7-(5,2',3'-trifluoro-biphenyl-2-yl)-7,8-dihydro-6H-pyrido[4,3-d]pyrimidin-5-one;

(R)-2-Amino-6-benzyl-7-(5,3'-difluoro-4'-methoxy-biphenyl-2-yl)-4-methyl-7,8-dihydro-6H-pyrido[4,3-d]pyrimidin-5-one;

(R)-2-Amino-6-benzyl-7-(4-fluoro-2-pyridin-3-yl-phenyl)-4-methyl-7,8-dihydro-6H-pyrido[4,3-d]pyrimidin-5-one;

(R)-2-Amino-6-benzyl-7-[2-(2,4-dimethoxy-pyrimidin-5-yl)-4-fluoro-phenyl]-4-methyl-7,8-dihydro-6H-pyrido[4,3-d]pyrimidin-5-one;

(R)-2-Amino-6-benzyl-7-(5,2'-difluoro-4'-methyl-biphenyl-2-yl)-4-methyl-7,8-dihydro-6H-pyrido[4,3-d]pyrimidin-5-one;

(R)-2-Amino-6-benzyl-7-[4-fluoro-2-(2-fluoro-pyridin-3-yl)-phenyl]-4-methyl-7,8-dihydro-6H-pyrido[4,3-d]pyrimidin-5-one;

(R)-2-Amino-6-benzyl-7-(5,2'-difluoro-3'-methoxy-biphenyl-2-yl)-4-methyl-7,8-dihydro-6H-pyrido[4,3-d]pyrimidin-5-one;

2-Amino-7-[2-(5,6-dimethoxy-pyrazin-2-yl)-4-fluoro-phenyl]-4-methyl-7,8-dihydro-6H-pyrido[4,3-d]pyrimidin-5-one;

(R)-2-Amino-7-[4-fluoro-2-(6-methoxy-pyrazin-2-yl)-phenyl]-4-methyl-6-(3-methyl-butyl)-7,8-dihydro-6H-pyrido[4,3-d]pyrimidin-5-one;

(R)-2-Amino-7-[2-(5,6-dimethoxy-pyrazin-2-yl)-4-fluoro-phenyl]-4-methyl-6-(3-methyl-butyl)-7,8-dihydro-6H-pyrido[4,3-d]pyrimidin-5-one;

(R)-2-Amino-7-(2-bromo-4-fluoro-phenyl)-4-methyl-6-(3-methyl-butyl)-7,8-dihydro-6H-pyrido[4,3-d]pyrimidin-5-one;

(R)-2-Amino-7-(2-bromo-4-fluoro-phenyl)-6-isobutyl-4-methyl-7,8-dihydro-6H-pyrido[4,3-d]pyrimidin-5-one;

(R)-2-Amino-7-[4-fluoro-2-(6-methoxy-pyridin-2-yl)-phenyl]-4-methyl-6-(3-methyl-butyl)-7,8-dihydro-6H-pyrido[4,3-d]pyrimidin-5-one;

(R)-2-Amino-7-[4-fluoro-2-(2-fluoro-pyridin-3-yl)-phenyl]-4-methyl-6-(3-methyl-butyl)-7,8-dihydro-6H-pyrido[4,3-d]pyrimidin-5-one;

(R)-2-Amino-7-[4-fluoro-2-(2-methoxy-pyridin-3-yl)-phenyl]-4-methyl-6-(3-methyl-butyl)-7,8-dihydro-6H-pyrido[4,3-d]pyrimidin-5-one;

(R)-2-Amino-7-[4-fluoro-2-(4-methoxy-pyridin-3-yl)-phenyl]-4-methyl-6-(3-methyl-butyl)-7,8-dihydro-6H-pyrido[4,3-d]pyrimidin-5-one;

(R)-2-Amino-7-[4-fluoro-2-(6-methoxy-pyrazin-2-yl)-phenyl]-6-isobutyl-4-methyl-7,8-dihydro-6H-pyrido[4,3-d]pyrimidin-5-one;

(R)-2-Amino-7-[4-fluoro-2-(6-methoxy-pyridin-2-yl)-phenyl]-6-isobutyl-4-methyl-7,8-dihydro-6H-pyrido[4,3-d]pyrimidin-5-one;

(R)-2-Amino-7-[2-(5,6-dimethoxy-pyrazin-2-yl)-4-fluoro-phenyl]-6-isobutyl-4-methyl-7,8-dihydro-6H-pyrido[4,3-d]pyrimidin-5-one;

(R)-2-Amino-7-[4-fluoro-2-(2-fluoro-pyridin-3-yl)-phenyl]-6-isobutyl-4-methyl-7,8-dihydro-6H-pyrido[4,3-d]pyrimidin-5-one;
(R)-2-Amino-7-[4-fluoro-2-(2-methoxy-pyridin-3-yl)-phenyl]-6-isobutyl-4-methyl-7,8-dihydro-6H-pyrido[4,3-d]pyrimidin-5-one;
(R)-2-Amino-7-[4-fluoro-2-(4-methoxy-pyridin-3-yl)-phenyl]-6-isobutyl-4-methyl-7,8-dihydro-6H-pyrido[4,3-d]pyrimidin-5-one;
(R)-2-Amino-6-(4-fluoro-benzyl)-7-[4-fluoro-2-(6-methoxy-pyridin-2-yl)-phenyl]-4-methyl-7,8-dihydro-6H-pyrido[4,3-d]pyrimidin-5-one;
(R)-2-Amino-6-(4-fluoro-benzyl)-7-[4-fluoro-2-(6-methoxy-pyrazin-2-yl)-phenyl]-4-methyl-7,8-dihydro-6H-pyrido[4,3-d]pyrimidin-5-one;
(R)-2-Amino-7-[2-(5-amino-6-methoxy-pyrazin-2-yl)-4-fluoro-phenyl]-6-(4-fluoro-benzyl)-4-methyl-7,8-dihydro-6H-pyrido[4,3-d]pyrimidin-5-one;
(R)-2-Amino-7-[2-(5-amino-6-methoxy-pyrazin-2-yl)-4-fluoro-phenyl]-6-isobutyl-4-methyl-7,8-dihydro-6H-pyrido[4,3-d]pyrimidin-5-one;
(R)-2-Amino-7-[4-fluoro-2-(6-methoxy-pyrazin-2-yl)-phenyl]-4-methyl-6-pyridin-3-ylmethyl-7,8-dihydro-6H-pyrido[4,3-d]pyrimidin-5-one;
{3-[(R)-2-Amino-7-(2-bromo-4-fluoro-phenyl)-4-methyl-5-oxo-7,8-dihydro-5H-pyrido[4,3-d]pyrimidin-6-yl]-propyl}-carbamic acid tert-butyl ester;
(R)-2-Amino-6-(3-amino-propyl)-7-(2-bromo-4-fluoro-phenyl)-4-methyl-7,8-dihydro-6H-pyrido[4,3-d]pyrimidin-5-one;
{3-[(R)-2-Amino-7-(4-fluoro-2-pyridin-3-yl-phenyl)-4-methyl-5-oxo-7,8-dihydro-5H-pyrido[4,3-d]pyrimidin-6-yl]-propyl}-carbamic acid tert-butyl ester;
(R)-2-Amino-6-(3-amino-propyl)-7-(4-fluoro-2-pyridin-3-yl-phenyl)-4-methyl-7,8-dihydro-6H-pyrido[4,3-d]pyrimidin-5-one;
(3-{(R)-2-Amino-7-[4-fluoro-2-(2-fluoro-pyridin-3-yl)-phenyl]-4-methyl-5-oxo-7,8-dihydro-5H-pyrido[4,3-d]pyrimidin-6-yl}-propyl)-carbamic acid tert-butyl ester;
(R)-2-Amino-6-(3-amino-propyl)-7-[4-fluoro-2-(2-fluoro-pyridin-3-yl)-phenyl]-4-methyl-7,8-dihydro-6H-pyrido[4,3-d]pyrimidin-5-one;
(R)-2-Amino-6-(3-amino-propyl)-7-[4-fluoro-2-(6-methoxy-pyrazin-2-yl)-phenyl]-4-methyl-7,8-dihydro-6H-pyrido[4,3-d]pyrimidin-5-one;
(R)-2-Amino-7-[5-(6-methoxy-pyridin-2-yl)-thiazol-4-yl]-4-methyl-7,8-dihydro-6H-pyrido[4,3-d]pyrimidin-5-one;
(R)-2-Amino-7-(5-bromo-thiazol-4-yl)-4-methyl-7,8-dihydro-6H-pyrido[4,3-d]pyrimidin-5-one;
(R)-2-Amino-7-[2-(4-ethoxy-5-fluoro-pyrimidin-2-yl)-4-fluoro-phenyl]-4-methyl-7,8-dihydro-6H-pyrido[4,3-d]pyrimidin-5-one;
(R)-2-Amino-7-[4-fluoro-2-(6-methoxy-pyrazin-2-yl)-phenyl]-7,8-dihydro-6H-pyrido[4,3-d]pyrimidin-5-one;
(R)-2-Amino-7-(5-fluoro-2'-methoxy-biphenyl-2-yl)-7,8-dihydro-6H-pyrido[4,3-d]pyrimidin-5-one;
(R)-2-Amino-7-(5,5'-difluoro-2'-methoxy-biphenyl-2-yl)-7,8-dihydro-6H-pyrido[4,3-d]pyrimidin-5-one;
(R)-2-Amino-7-(5,4'-difluoro-2'-methoxy-biphenyl-2-yl)-7,8-dihydro-6H-pyrido[4,3-d]pyrimidin-5-one;
(R)-2-Amino-7-(5-fluoro-3',4'-dimethoxy-biphenyl-2-yl)-7,8-dihydro-6H-pyrido[4,3-d]pyrimidin-5-one;
(R)-2-Amino-7-(5-fluoro-3'-methyl-biphenyl-2-yl)-7,8-dihydro-6H-pyrido[4,3-d]pyrimidin-5-one;
(R)-2-Amino-7-(5-fluoro-2'-methyl-biphenyl-2-yl)-7,8-dihydro-6H-pyrido[4,3-d]pyrimidin-5-one;
(R)-2-Amino-7-(5-fluoro-4'-methyl-biphenyl-2-yl)-7,8-dihydro-6H-pyrido[4,3-d]pyrimidin-5-one;
(R)-2-Amino-7-(5,4'-difluoro-2'-methyl-biphenyl-2-yl)-7,8-dihydro-6H-pyrido[4,3-d]pyrimidin-5-one;
(R)-2-Amino-7-(2-bromo-phenyl)-4-methyl-7,8-dihydro-6H-pyrido[4,3-d]pyrimidin-5-one;
(R)-2-Amino-7-[2-(4,5-dimethoxy-pyrimidin-2-yl)-4-fluoro-phenyl]-4-methyl-7,8-dihydro-6H-pyrido[4,3-d]pyrimidin-5-one;
(R)-2-Amino-7-[5-(6-methoxy-pyrazin-2-yl)-thiazol-4-yl]-4-methyl-7,8-dihydro-6H-pyrido[4,3-d]pyrimidin-5-one;
(R)-2-Amino-7-[2-(6-ethoxy-pyridin-2-yl)-4-fluoro-phenyl]-4-methyl-7,8-dihydro-6H-pyrido[4,3-d]pyrimidin-5-one;
(R)-2-Amino-7-[2-(2-methoxy-thiazol-4-yl)-phenyl]-4-methyl-7,8-dihydro-6H-pyrido[4,3-d]pyrimidin-5-one;
(R)-2-Amino-7-[2-(5,6-dimethoxy-pyrazin-2-yl)-phenyl]-4-methyl-7,8-dihydro-6H-pyrido[4,3-d]pyrimidin-5-one;
(R)-2-Amino-7-[2-(5-amino-6-methoxy-pyridin-2-yl)-4-fluoro-phenyl]-4-methyl-7,8-dihydro-6H-pyrido[4,3-d]pyrimidin-5-one;
(R)-2-Amino-7-(4-fluoro-2-pyridin-3-yl-phenyl)-7,8-dihydro-6H-pyrido[4,3-d]pyrimidin-5-one;
(R)-2-Amino-7-[2-(2,4-dimethoxy-pyrimidin-5-yl)-4-fluoro-phenyl]-4-methyl-7,8-dihydro-6H-pyrido[4,3-d]pyrimidin-5-one;
(R)-2-Amino-7-[2-(4-ethoxy-pyrimidin-2-yl)-4-fluoro-phenyl]-4-methyl-7,8-dihydro-6H-pyrido[4,3-d]pyrimidin-5-one;
(R)-2-Amino-7-[2-(6-methoxy-pyrazin-2-yl)-phenyl]-4-methyl-7,8-dihydro-6H-pyrido[4,3-d]pyrimidin-5-one;
(R)-2-Amino-7-[4-fluoro-2-(4-methoxy-pyrimidin-2-yl)-phenyl]-4-methyl-7,8-dihydro-6H-pyrido[4,3-d]pyrimidin-5-one;
(R)-2-Amino-7-[2-(5-amino-6-ethoxy-pyrazin-2-yl)-4-fluoro-phenyl]-4-methyl-7,8-dihydro-6H-pyrido[4,3-d]pyrimidin-5-one;
(R)-2-Amino-7-[2-(5-amino-6-ethoxy-pyrazin-2-yl)-phenyl]-4-methyl-7,8-dihydro-6H-pyrido[4,3-d]pyrimidin-5-one;
(R)-2-Amino-4-ethyl-7-[2-(6-methoxy-pyridin-2-yl)-phenyl]-7,8-dihydro-6H-pyrido[4,3-d]pyrimidin-5-one;
(R)-2-Amino-4-ethyl-7-[2-(6-methoxy-pyrazin-2-yl)-phenyl]-7,8-dihydro-6H-pyrido[4,3-d]pyrimidin-5-one;
(R)-2-Amino-7-[2-(5-amino-6-methoxy-pyrazin-2-yl)-phenyl]-4-ethyl-7,8-dihydro-6H-pyrido[4,3-d]pyrimidin-5-one;
(R)-2-Amino-4-ethyl-7-[2-(2-methoxy-thiazol-4-yl)-phenyl]-7,8-dihydro-6H-pyrido[4,3-d]pyrimidin-5-one;
(R)-2-Amino-7-[2-(5-chloro-4-methoxy-pyrimidin-2-yl)-4-fluoro-phenyl]-4-methyl-7,8-dihydro-6H-pyrido[4,3-d]pyrimidin-5-one;
(R)-2-Amino-7-[2-(6-methoxy-pyrazin-2-yl)-phenyl]-7,8-dihydro-6H-pyrido[4,3-d]pyrimidin-5-one;
(R)-2-Amino-7-[2-(5-fluoro-4-methoxy-pyrimidin-2-yl)-phenyl]-4-methyl-7,8-dihydro-6H-pyrido[4,3-d]pyrimidin-5-one;
(R)-2-Amino-7-[2-(5-amino-6-methoxy-pyridin-2-yl)-phenyl]-4-methyl-7,8-dihydro-6H-pyrido[4,3-d]pyrimidin-5-one;

(R)-2-Amino-7-[2-(6-methoxy-pyridin-2-yl)-phenyl]-7,8-dihydro-6H-pyrido[4,3-d]pyrimidin-5-one;
(R)-2-Amino-7-[4-fluoro-2-(4-pyrrolidin-1-yl-pyrimidin-2-yl)-phenyl]-4-methyl-7,8-dihydro-6H-pyrido[4,3-d]pyrimidin-5-one;
(R)-2-Amino-7-[2-(5-amino-6-methoxy-pyridin-2-yl)-4-fluoro-phenyl]-7,8-dihydro-6H-pyrido[4,3-d]pyrimidin-5-one;
(R)-2-Amino-7-[4-fluoro-2-(5-methoxy-thiophen-2-yl)-phenyl]-4-methyl-7,8-dihydro-6H-pyrido[4,3-d]pyrimidin-5-one;
(R)-2-Amino-7-(2-bromo-4-fluoro-phenyl)-4-ethyl-7,8-dihydro-6H-pyrido[4,3-d]pyrimidin-5-one;
(R)-2-Amino-4-ethyl-7-[4-fluoro-2-(6-methoxy-pyridin-2-yl)-phenyl]-7,8-dihydro-6H-pyrido[4,3-d]pyrimidin-5-one;
(R)-2-Amino-4-ethyl-7-[4-fluoro-2-(6-methoxy-pyrazin-2-yl)-phenyl]-7,8-dihydro-6H-pyrido[4,3-d]pyrimidin-5-one;
(R)-2-Amino-7-(5-fluoro-2',3'-dimethoxy-biphenyl-2-yl)-4-methyl-7,8-dihydro-6H-pyrido[4,3-d]pyrimidin-5-one;
(R)-2-Amino-7-[2-(5-amino-6-ethoxy-pyrazin-2-yl)-4-fluoro-phenyl]-7,8-dihydro-6H-pyrido[4,3-d]pyrimidin-5-one;
(R)-2-Amino-4-ethyl-7-[4-fluoro-2-(2-methoxy-thiazol-4-yl)-phenyl]-7,8-dihydro-6H-pyrido[4,3-d]pyrimidin-5-one;
(R)-2-Amino-7-[2-(6-ethoxy-pyrazin-2-yl)-4-fluoro-phenyl]-4-methyl-7,8-dihydro-6H-pyrido[4,3-d]pyrimidin-5-one;
(R)-2-Amino-7-[2-(6-ethoxy-pyrazin-2-yl)-4-fluoro-phenyl]-4-ethyl-7,8-dihydro-6H-pyrido[4,3-d]pyrimidin-5-one;
(R)-2-Amino-7-[2-(6-ethoxy-pyrazin-2-yl)-4-fluoro-phenyl]-7,8-dihydro-6H-pyrido[4,3-d]pyrimidin-5-one;
2-((R)-2-Amino-4-methyl-5-oxo-5,6,7,8-tetrahydro-pyrido[4,3-d]pyrimidin-7-yl)-5-fluoro-benzonitrile;
(R)-2-Amino-7-[2-(6-ethoxy-pyrazin-2-yl)-phenyl]-4-methyl-7,8-dihydro-6H-pyrido[4,3-d]pyrimidin-5-one;
(R)-2-Amino-7-[2-(4-methoxy-5-methyl-pyrimidin-2-yl)-phenyl]-4-methyl-7,8-dihydro-6H-pyrido[4,3-d]pyrimidin-5-one;
(R)-2-Amino-7-[4-fluoro-2-(5-oxo-4,5-dihydro-[1,3,4]oxadiazol-2-yl)-phenyl]-4-methyl-7,8-dihydro-6H-pyrido[4,3-d]pyrimidin-5-one;
(R)-2-Amino-7-[4-fluoro-2-(5-methoxy-[1,3,4]oxadiazol-2-yl)-phenyl]-4-methyl-7,8-dihydro-6H-pyrido[4,3-d]pyrimidin-5-one;
(S)-2-Amino-7-[5-(6-methoxy-pyrazin-2-yl)-thiazol-4-yl]-7,8-dihydro-6H-pyrido[4,3-d]pyrimidin-5-one;
(R)-2-Amino-7-[4-fluoro-2-(2-methoxy-thiazol-5-yl)-phenyl]-4-methyl-7,8-dihydro-6H-pyrido[4,3-d]pyrimidin-5-one;
(R)-2-Amino-7-[2-(5-amino-6-ethoxy-pyrazin-2-yl)-4-fluoro-phenyl]-4-ethyl-7,8-dihydro-6H-pyrido[4,3-d]pyrimidin-5-one;
(R)-2-Amino-7-[4-methoxy-2-(6-methoxy-pyrazin-2-yl)-phenyl]-4-methyl-7,8-dihydro-6H-pyrido[4,3-d]pyrimidin-5-one;
(R)-2-Amino-7-(2-bromo-phenyl)-7,8-dihydro-6H-pyrido[4,3-d]pyrimidin-5-one;
(R)-2-Amino-7-[2-(5-amino-6-methoxy-pyrazin-2-yl)-phenyl]-7,8-dihydro-6H-pyrido[4,3-d]pyrimidin-5-one;
(R)-2-Amino-7-[2-(2-ethoxy-thiazol-4-yl)-phenyl]-4-methyl-7,8-dihydro-6H-pyrido[4,3-d]pyrimidin-5-one;
(R)-2-Amino-7-[2-(2-ethoxy-thiazol-4-yl)-4-fluoro-phenyl]-4-methyl-7,8-dihydro-6H-pyrido[4,3-d]pyrimidin-5-one;
(S)-2-Amino-7-[5-(6-methoxy-pyridin-2-yl)-thiazol-4-yl]-4-methyl-7,8-dihydro-6H-pyrido[4,3-d]pyrimidin-5-one;
(S)-2-Amino-7-[5-(6-methoxy-pyrazin-2-yl)-thiazol-4-yl]-4-methyl-7,8-dihydro-6H-pyrido[4,3-d]pyrimidin-5-one;
(R)-2-Amino-7-[2-(5-amino-6-ethoxy-pyrazin-2-yl)-phenyl]-7,8-dihydro-6H-pyrido[4,3-d]pyrimidin-5-one;
(R)-2-Amino-7-[2-(5-amino-6-ethyl-pyrazin-2-yl)-phenyl]-4-methyl-7,8-dihydro-6H-pyrido[4,3-d]pyrimidin-5-one;
(R)-2-Amino-7-(2-bromo-4-methoxy-phenyl)-4-methyl-7,8-dihydro-6H-pyrido[4,3-d]pyrimidin-5-one;
(R)-2-Amino-7-[4-methoxy-2-(6-methoxy-pyridin-2-yl)-phenyl]-4-methyl-7,8-dihydro-6H-pyrido[4,3-d]pyrimidin-5-one;
(R)-2-Amino-7-[2-(5-amino-6-ethoxy-pyrazin-2-yl)-4-methoxy-phenyl]-4-methyl-7,8-dihydro-6H-pyrido[4,3-d]pyrimidin-5-one;
(R)-2-Amino-7-[2-(6-ethoxy-pyrazin-2-yl)-4-methoxy-phenyl]-4-methyl-7,8-dihydro-6H-pyrido[4,3-d]pyrimidin-5-one;
(R)-2-Amino-7-[2-(5-amino-6-methoxy-pyrazin-2-yl)-4-methoxy-phenyl]-4-methyl-7,8-dihydro-6H-pyrido[4,3-d]pyrimidin-5-one;
(R)-2-Amino-7-[4-methoxy-2-(2-methoxy-thiazol-4-yl)-phenyl]-4-methyl-7,8-dihydro-6H-pyrido[4,3-d]pyrimidin-5-one;
(R)-2-Amino-7-[2-(2-ethoxy-thiazol-4-yl)-4-methoxy-phenyl]-4-methyl-7,8-dihydro-6H-pyrido[4,3-d]pyrimidin-5-one;
(R)-2-Amino-7-[2-(6-methoxy-5-methylamino-pyrazin-2-yl)-phenyl]-4-methyl-7,8-dihydro-6H-pyrido[4,3-d]pyrimidin-5-one;
(R)-2-Amino-7-[4-fluoro-2-(6-methoxy-5-methylamino-pyrazin-2-yl)-phenyl]-4-methyl-7,8-dihydro-6H-pyrido[4,3-d]pyrimidin-5-one;
(R)-2-Amino-7-[5-methoxy-2-(6-methoxy-pyrazin-2-yl)-phenyl]-4-methyl-7,8-dihydro-6H-pyrido[4,3-d]pyrimidin-5-one;
(R)-2-Amino-7-[5-methoxy-2-(6-methoxy-pyrazin-2-yl)-phenyl]-7,8-dihydro-6H-pyrido[4,3-d]pyrimidin-5-one;
(R)-2-Amino-7-[2-(5-dimethylamino-6-methoxy-pyrazin-2-yl)-phenyl]-4-methyl-7,8-dihydro-6H-pyrido[4,3-d]pyrimidin-5-one;
(R)-2-Amino-7-[2-(5-dimethylamino-6-methoxy-pyrazin-2-yl)-4-fluoro-phenyl]-4-methyl-7,8-dihydro-6H-pyrido[4,3-d]pyrimidin-5-one;
(R)-2-Amino-7-(5-bromo-2-methoxy-pyridin-4-yl)-4-methyl-7,8-dihydro-6H-pyrido[4,3-d]pyrimidin-5-one;
(R)-2-Amino-7-(6,6'-dimethoxy-[2,3']bipyridinyl-4'-yl)-4-methyl-7,8-dihydro-6H-pyrido[4,3-d]pyrimidin-5-one;
(R)-2-Amino-7-[5-methoxy-2-(6-methoxy-pyridin-2-yl)-phenyl]-4-methyl-7,8-dihydro-6H-pyrido[4,3-d]pyrimidin-5-one;
(R)-2-Amino-7-[5-methoxy-2-(6-methoxy-pyridin-2-yl)-phenyl]-7,8-dihydro-6H-pyrido[4,3-d]pyrimidin-5-one;
(R)-2-Amino-7-[2-(5-amino-6-ethoxy-pyrazin-2-yl)-4-ethoxy-phenyl]-4-methyl-7,8-dihydro-6H-pyrido[4,3-d]pyrimidin-5-one;

(R)-2-Amino-7-[2-(5-amino-6-methoxy-pyrazin-2-yl)-4-ethoxy-phenyl]-4-methyl-7,8-dihydro-6H-pyrido[4,3-d]pyrimidin-5-one;

(R)-2-Amino-7-[4-ethoxy-2-(6-methoxy-pyridin-2-yl)-phenyl]-4-methyl-7,8-dihydro-6H-pyrido[4,3-d]pyrimidin-5-one;

(R)-2-Amino-7-[4-ethoxy-2-(6-methoxy-pyrazin-2-yl)-phenyl]-4-methyl-7,8-dihydro-6H-pyrido[4,3-d]pyrimidin-5-one;

(R)-2-Amino-7-(2-(cyclopentyloxy)-4-fluorophenyl)-4-methyl-7,8-dihydropyrido[4,3-d]pyrimidin-5(6H)-one;

(R)-2-Amino-7-(2-(cyclopentyloxy)phenyl)-4-methyl-7,8-dihydropyrido[4,3-d]pyrimidin-5(6H)-one;

(R)-2-Amino-7-(4-fluoro-2-isopropoxyphenyl)-4-methyl-7,8-dihydropyrido[4,3-d]pyrimidin-5(6H)-one;

(R)-2-Amino-7-((R)-5-fluoro-2-(6-methoxypyridin-2-yl)phenyl)-4-methyl-7,8-dihydropyrido[4,3-d]pyrimidin-5(6H)-one;

(R)-2-Amino-7-((R)-2-(6-methoxypyridin-2-yl)-4-methylphenyl)-4-methyl-7,8-dihydropyrido[4,3-d]pyrimidin-5(6H)-one;

(R)-2-Amino-7-((R)-5-fluoro-2-(6-methoxypyrazin-2-yl)phenyl)-4-methyl-7,8-dihydropyrido[4,3-d]pyrimidin-5(6H)-one;

(R)-2-Amino-7-((R)-2-(6-methoxypyrazin-2-yl)-4-methylphenyl)-4-methyl-7,8-dihydropyrido[4,3-d]pyrimidin-5(6H)-one;

(R)-2-Amino-7-(2-((R)-5-amino-6-(2,2,2-trifluoroethoxy)pyrazin-2-yl)-4-fluorophenyl)-4-methyl-7,8-dihydropyrido[4,3-d]pyrimidin-5(6H)-one;

(R)-2-Amino-7-((R)-5-fluoro-2-(2-methoxythiazol-4-yl)phenyl)-4-methyl-7,8-dihydropyrido[4,3-d]pyrimidin-5(6H)-one;

(R)-2-Amino-7-((R)-2-(5-amino-6-methoxypyrazin-2-yl)-5-fluorophenyl)-4-methyl-7,8-dihydropyrido[4,3-d]pyrimidin-5(6H)-one;

(R)-2-Amino-7-((R)-2-(2-methoxythiazol-4-yl)-4-methylphenyl)-4-methyl-7,8-dihydropyrido[4,3-d]pyrimidin-5(6H)-one;

(R)-2-Amino-7-((R)-2-(5-amino-6-methoxypyrazin-2-yl)-4-methylphenyl)-4-methyl-7,8-dihydropyrido[4,3-d]pyrimidin-5(6H)-one;

(R)-2-Amino-7-(2-(cyclopentyloxy)-4-fluorophenyl)-7,8-dihydropyrido[4,3-d]pyrimidin-5(6H)-one;

(R)-2-Amino-7-(2-((R)-5-amino-6-(2,2,2-trifluoroethoxy)pyrazin-2-yl)phenyl)-7,8-dihydropyrido[4,3-d]pyrimidin-5(6H)-one;

(R)-2-Amino-7-(2-((R)-5-amino-6-(2,2,2-trifluoroethoxy)pyrazin-2-yl)phenyl)-4-methyl-7,8-dihydropyrido[4,3-d]pyrimidin-5(6H)-one;

(R)-2-Amino-7-(2-((R)-5-amino-6-(2,2,2-trifluoroethoxy)pyrazin-2-yl)-4-fluorophenyl)-7,8-dihydropyrido[4,3-d]pyrimidin-5(6H)-one;

(R)-2-Amino-7-((S)-2-(5-amino-6-methoxypyrazin-2-yl)-4-fluoro-5-methoxyphenyl)-4-methyl-7,8-dihydropyrido[4,3-d]pyrimidin-5(6H)-one;

(R)-2-Amino-7-((S)-4-fluoro-5-methoxy-2-(6-methoxypyrazin-2-yl)phenyl)-4-methyl-7,8-dihydropyrido[4,3-d]pyrimidin-5(6H)-one;

(R)-2-Amino-7-(4-fluoro-5-methoxy-2-((S)-6-methoxypyridin-2-yl)phenyl)-4-methyl-7,8-dihydropyrido[4,3-d]pyrimidin-5(6H)-one;

(R)-2-Amino-7-((R)-4-fluoro-5-methoxy-2-(2-methoxythiazol-4-yl)phenyl)-4-methyl-7,8-dihydropyrido[4,3-d]pyrimidin-5(6H)-one;

(R)-2-Amino-7-((S)-2-(5-amino-6-methoxypyrazin-2-yl)-4-isopropoxy-5-methoxyphenyl)-4-methyl-7,8-dihydropyrido[4,3-d]pyrimidin-5(6H)-one;

(R)-2-Amino-7-((S)-4-isopropoxy-5-methoxy-2-(6-methoxypyrazin-2-yl)phenyl)-4-methyl-7,8-dihydropyrido[4,3-d]pyrimidin-5(6H)-one;

(R)-2-Amino-7-(4-isopropoxy-5-methoxy-2-((S)-6-methoxypyridin-2-yl)phenyl)-4-methyl-7,8-dihydropyrido[4,3-d]pyrimidin-5(6H)-one;

(R)-2-Amino-7-((R)-4-isopropoxy-5-methoxy-2-(2-methoxythiazol-4-yl)phenyl)-4-methyl-7,8-dihydropyrido[4,3-d]pyrimidin-5(6H)-one;

(R)-2-Amino-7-((S)-4,5-dimethoxy-2-(6-methoxypyridin-2-yl)phenyl)-4-methyl-7,8-dihydropyrido[4,3-d]pyrimidin-5(6H)-one;

(R)-2-Amino-7-((S)-4,5-dimethoxy-2-(6-methoxypyrazin-2-yl)phenyl)-4-methyl-7,8-dihydropyrido[4,3-d]pyrimidin-5(6H)-one;

(R)-2-Amino-7-(2-bromo-4,5-dimethoxyphenyl)-4-methyl-7,8-dihydropyrido[4,3-d]pyrimidin-5(6H)-one;

(R)-2-Amino-7-((R)-4,5-dimethoxy-2-(2-methoxythiazol-4-yl)phenyl)-4-methyl-7,8-dihydropyrido[4,3-d]pyrimidin-5(6H)-one;

(R)-2-Amino-7-((R)-2-(5-amino-6-ethoxypyrazin-2-yl)-4,5-dimethoxyphenyl)-4-methyl-7,8-dihydropyrido[4,3-d]pyrimidin-5(6H)-one;

(R)-2-Amino-7-(2-bromo-4-ethoxyphenyl)-4-methyl-7,8-dihydropyrido[4,3-d]pyrimidin-5(6H)-one;

(R)-2-Amino-7-((S)-4-fluoro-2-(6-hydroxypyridin-2-yl)phenyl)-4-methyl-7,8-dihydropyrido[4,3-d]pyrimidin-5(6H)-one;

(R)-2-Amino-7-((R)-4-fluoro-2-(6-hydroxypyrazin-2-yl)phenyl)-4-methyl-7,8-dihydropyrido[4,3-d]pyrimidin-5(6H)-one;

(R)-2-Amino-7-(2-bromo-4,5-diethoxyphenyl)-4-methyl-7,8-dihydropyrido[4,3-d]pyrimidin-5(6H)-one; and (R)-2-Amino-7-((R)-4-fluoro-2-(2-hydroxythiazol-4-yl)phenyl)-4-methyl-7,8-dihydropyrido[4,3-d]pyrimidin-5(6H)-one or a stereoisomer, tautomer, or pharmaceutically acceptable salt thereof.

22. A composition comprising a pharmaceutically acceptable carrier and a compound of claim 1.

23. A compound selected from the group consisting of (R)-2-Amino-7-[4-fluoro-2-(6-methoxy-pyridin-2-yl)-phenyl]-4-methyl-7,8-dihydro-6H-pyrido[4,3-d]pyrimidin-5-one;

(R)-2-Amino-7-[4-fluoro-2-(6-methoxy-pyrazin-2-yl)-phenyl]-4-methyl-7,8-dihydro-6H-pyrido[4,3-d]pyrimidin-5-one;

(R)-2-Amino-7-(2-bromo-4-fluoro-phenyl)-4-methyl-7,8-dihydro-6H-pyrido[4,3-d]pyrimidin-5-one;

(R)-2-Amino-7-[4-fluoro-2-(2-methoxy-thiazol-4-yl)-phenyl]-4-methyl-7,8-dihydro-6H-pyrido[4,3-d]pyrimidin-5-one;

(R)-2-Amino-7-((R)-2-(5-amino-6-methoxypyrazin-2-yl)-4-methylphenyl)-4-methyl-7,8-dihydropyrido[4,3-d]pyrimidin-5(6H)-one;

(R)-2-Amino-7-((S)-4-fluoro-2-(6-hydroxypyridin-2-yl)phenyl)-4-methyl-7,8-dihydropyrido[4,3-d]pyrimidin-5(6H)-one; and (R)-2-Amino-7-((R)-4-fluoro-2-(6-hydroxypyrazin-2-yl)phenyl)-4-methyl-7,8-dihydropyrido[4,3-d]pyrimidin-5(6H)-one, or a pharmaceutically acceptable salt thereof.

24. A composition comprising a pharmaceutically acceptable carrier and a compound selected from the group consisting of
- (R)-2-Amino-7-[4-fluoro-2-(6-methoxy-pyridin-2-yl)-phenyl]-4-methyl-7,8-dihydro-6H-pyrido[4,3-d]pyrimidin-5-one;
- (R)-2-Amino-7-[4-fluoro-2-(6-methoxy-pyrazin-2-yl)-phenyl]-4-methyl-7,8-dihydro-6H-pyrido[4,3-d]pyrimidin-5-one;
- (R)-2-Amino-7-(2-bromo-4-fluoro-phenyl)-4-methyl-7,8-dihydro-6H-pyrido[4,3-d]pyrimidin-5-one;
- (R)-2-Amino-7-[4-fluoro-2-(2-methoxy-thiazol-4-yl)-phenyl]-4-methyl-7,8-dihydro-6H-pyrido[4,3-d]pyrimidin-5-one;
- (R)-2-Amino-7-((R)-2-(5-amino-6-methoxypyrazin-2-yl)-4-methylphenyl)-4-methyl-7,8-dihydropyrido[4,3-d]pyrimidin-5(6H)-one;
- (R)-2-Amino-7-((S)-4-fluoro-2-(6-hydroxypyridin-2-yl)phenyl)-4-methyl-7,8-dihydropyrido[4,3-d]pyrimidin-5(6H)-one; and
- (R)-2-Amino-7-((R)-4-fluoro-2-(6-hydroxypyrazin-2-yl)phenyl)-4-methyl-7,8-dihydropyrido[4,3-d]pyrimidin-5(6H)-one, or a pharmaceutically acceptable salt thereof.

25. A compound that is (R)-2-Amino-7-[4-fluoro-2-(6-methoxy-pyridin-2-yl)-phenyl]-4-methyl-7,8-dihydro-6H-pyrido[4,3-d]pyrimidin-5-one or a pharmaceutically acceptable salt thereof.

26. A composition comprising a pharmaceutically acceptable carrier and (R)-2-Amino-7-[4-fluoro-2-(6-methoxy-pyridin-2-yl)-phenyl]-4-methyl-7,8-dihydro-6H-pyrido[4,3-d]pyrimidin-5-one or a pharmaceutically acceptable salt thereof.

* * * * *